(12) United States Patent
Peschke et al.

(10) Patent No.: US 6,919,315 B1
(45) Date of Patent: Jul. 19, 2005

(54) COMPOUNDS WITH GROWTH HORMONE RELEASING PROPERTIES

(75) Inventors: Bernd Peschke, Malov (DK); Lutz Richter, deceased, late of St. James (JM); by Birgit Richter, legal representative, St. James (JM); Thomas Hansen Kruse, Herlev (DK); Michael Ankersen, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/356,313

(22) Filed: Jul. 16, 1999

Related U.S. Application Data

(63) Continuation-in-part of application No. 09/337,809, filed on Jun. 21, 1999, now abandoned.
(60) Provisional application No. 60/108,369, filed on Nov. 13, 1998, and provisional application No. 60/091,786, filed on Jul. 6, 1998.

(30) Foreign Application Priority Data

Jun. 30, 1998 (DK) .......... 1998 00857
Nov. 9, 1998 (DK) .......... 1998 01440

(51) Int. Cl.$^7$ .................. C07K 5/06
(52) U.S. Cl. .......... 514/19; 514/18; 514/183; 530/331
(58) Field of Search .................. 514/18, 19

(56) References Cited

U.S. PATENT DOCUMENTS

| | | | |
|---|---|---|---|
| 5,767,085 A | 6/1998 | Johansen et al. | 514/17 |
| 5,798,337 A | 8/1998 | Somers et al. | 514/19 |
| 6,127,354 A | * 10/2000 | Peschke et al. | 514/183 |
| 6,127,391 A | 10/2000 | Hansen et al. | 514/343 |

FOREIGN PATENT DOCUMENTS

| | | |
|---|---|---|
| EP | 18072 | 10/1980 |
| EP | 83864 | 5/1987 |
| WO | WO 8302272 | 7/1983 |
| WO | WO 09780 | 12/1988 |
| WO | WO 8901711 | 2/1989 |
| WO | WO 8907110 | 10/1989 |
| WO | WO 8910933 | 11/1989 |
| WO | WO 9118016 | 11/1991 |
| WO | WO 9201711 | 2/1992 |
| WO | WO 9304081 | 3/1993 |
| WO | WO 9413696 | 6/1994 |
| WO | WO 9514666 | 6/1995 |
| WO | WO 9517423 | 6/1995 |
| WO | WO 9615148 | 5/1996 |
| WO | WO 9622997 | 8/1996 |
| WO | WO 9635713 | 11/1996 |
| WO | WO 9700894 | 1/1997 |
| WO | WO 9722620 | 6/1997 |
| WO | WO 97/23508 | 7/1997 |
| WO | WO 9740023 | 10/1997 |
| WO | WO 98/03473 | 1/1998 |
| WO | WO 9810653 | 3/1998 |
| WO | WO 98/58950 | 12/1998 |

* cited by examiner

Primary Examiner—Christopher S. F. Low
Assistant Examiner—David Lukton
(74) Attorney, Agent, or Firm—Rosemarie R. Wilk-Drescan; Reza Green; Richard W. Bork

(57) ABSTRACT

Disclosed are compounds of formula I formula I wherein $R^1$, $R^2$, $R^5$, $R^6$, $R^7$, $R^8$, G, J, L, M, a, b, c, d, e, and f are as defined in the specification, and compositions containing them. These compounds are useful for treating medical disorders resulting from a deficiency in growth hormone.

17 Claims, No Drawings

COMPOUNDS WITH GROWTH HORMONE RELEASING PROPERTIES

CROSS REFERENCE TO RELATED APPLICATIONS

This application is a continuation-in-part of U.S. Application No. 09/337,809, filed on Jun. 21, 1999, now abandoned, which claims the benefit under 35 U.S.C. 119 of U.S. Provisional Application No. 60/091,786, filed Jul. 6, 1998, and U.S. Provisional Application No. 60/108,369, filed Nov. 13, 1998, and which claims priority of Danish Application No. PA 1998 00857, filed Jun. 30, 1998, and Danish Application No. PA 1998 01440, filed Nov. 9, 1998, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 8302272, WO 8907110, WO 8901711, WO 8910933, WO 8809780, WO 9118016, WO 9201711, WO 9304081, WO 9413698, WO 9517423, WO 9514666, WO 9615148, WO 9622997, WO 9635713, WO 9700894, WO 9722620, WO 9723508, WO 9740023, and WO 9810653.

The composition of growth hormone releasing compounds is important for their growth hormone releasing potency as well as their bioavailability. It is therefore an object of the present invention to provide novel compounds with growth hormone releasing properties. Moreover, it is an object to provide novel growth hormone releasing compounds (growth hormone secretagogues) which are specific and/or selective and have no or substantially no side-effects, such as e.g. release of LH, FSH, TSH, ACTH, vasopressin, oxytocin, cortisol and/or prolactin. It is also an object to provide compounds which have good oral bioavailability.

SUMMARY OF THE INVENTION

In accordance with the present invention there is provided novel compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase endogenous growth hormone release.

DESCRIPTION OF THE INVENTION

Accordingly, the present invention relates to a compound of the general formula I

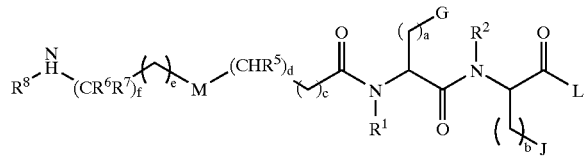

formula I wherein $R^1$ is hydrogen or $C_{1-6}$-alkyl;

$R^2$ is hydrogen or $C_{1-6}$-alkyl;

L is

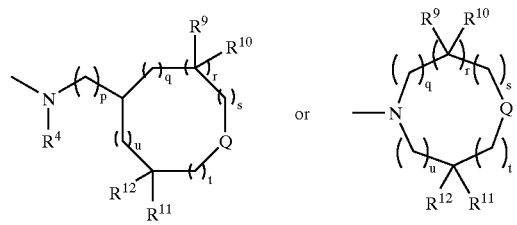

wherein $R^4$ is hydrogen or $C_{1-6}$ alkyl;

p is 0 or 1;

q, s, t, u are independently from each other 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

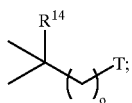

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl;

$R^{14}$ is hydrogen, aryl or hetaryl;

G is —O—$(CH_2)_k$—$R^{17}$,

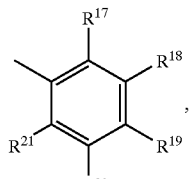 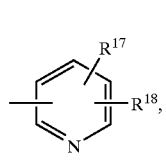

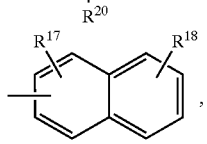 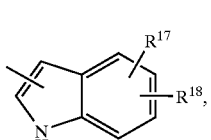

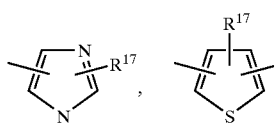  or

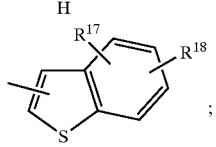

wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy;

k is 0, 1 or 2;

J is —O—$(CH_2)_l$—$R^{22}$,

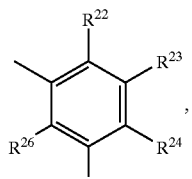 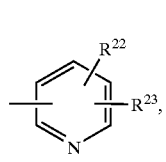

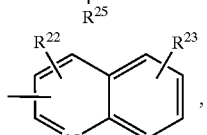 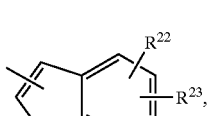

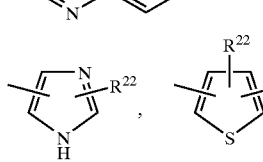 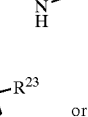 or

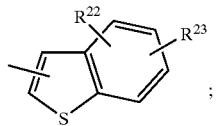 ;

wherein $R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy;

l is 0, 1 or 2;

a is 0, 1, or 2;

b is 0, 1, or 2;

c is 0, 1, or 2;

d is 0 or 1;

e is 0, 1, 2, or 3;

f is 0 or 1;

$R^5$ is hydrogen or $C_{1-6}$-alkyl optionally substituted with one or more hydroxyl, aryl or hetaryl;

$R^6$ and $R^7$ are independently from each other hydrogen or $C_{1-6}$-alkyl, optionally substituted with one or more halogen, amino, hydroxyl, aryl, or hetaryl;

$R^8$ is hydrogen or $C_{1-6}$-alkyl, optionally substituted with one or more halogen, amino, hydroxyl, aryl, or hetaryl;

$R^6$ and $R^7$ or $R^6$ and $R^8$ or $R^7$ and $R^8$ may optionally form —$(CH_2)_i$—U—$(CH_2)_j$—, wherein i and j independently from each other are 1, 2 or 3 and U is —O—, —S—, or a valence bond;

M is arylene, hetarylene, —O—, —S— or —$CR^{27}$=$CR^{28}$—;

$R^{27}$ and $R^{28}$ are independently from each other hydrogen or $C_{1-6}$-alkyl, optionally substituted with one or more aryl or hetaryl;

or a pharmaceutically acceptable salt thereof.

Moreover, the compounds of formula I may comprise any optical isomers thereof, in the form of separated, pure or partially purified optical isomers or racemic mixtures thereof. Whenever one or more chiral carbon atoms are present such chiral center or centers may be in the R- and/or S-configuration, or a mixture of R and S.

Furthermore, the compounds of formula I may have one or more carbon-carbon double bonds with the possibility of geometric isomer, and it is intended that possible stereoisomers (E or Z isomers) are included in the scope of the invention, unless a special geometric isomer is specified.

In one embodiment of the compound of formula I $R^1$ is $C_{1-6}$-alkyl, such as $C_{1-6}$-alkyl, in particular methyl. In a second embodiment $R^1$ is hydrogen.

In a further embodiment of the compound of formula I $R^2$ is $C_{1-6}$-alkyl, such as $C_{1-6}$-alkyl, in particular methyl.

In a still further embodiment of the compound of formula I L is

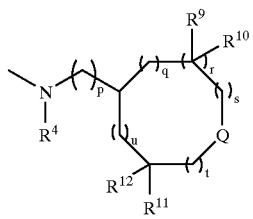

wherein $R^1$ is hydrogen or $C_{1-6}$ alkyl;

p is 0 or 1;

q, s, t, u are independently from each other 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

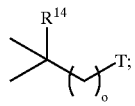

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl;

$R^{14}$ is hydrogen, aryl or hetaryl. In one embodiment $R^4$ is hydrogen. In a second embodiment $R^4$ is $C_{1-6}$-alkyl, such as $C_{1-4}$-alkyl, in particular methyl. In a third embodiment p is 0. In a further embodiment q is 0. In a still further embodiment q is 1. In a further embodiment s is 0. In a still further embodiment s is 1. In a further embodiment t is 0. In a still further embodiment t is 1. In a further embodiment u is 0. In a still further embodiment u is 1. In a further embodiment r is 0. In a still further embodiment r is 1. In a further embodiment $R^9$ is hydrogen. In a still further embodiment $R^9$ is $C_{1-6}$-alkyl, such as $C_{1-4}$-alkyl, in particular methyl. In a further embodiment $R^{10}$ is hydrogen. In a still further embodiment $R^{10}$ is $C_{1-6}$-alkyl, such as $C_{1-4}$-alkyl, in particular methyl. In a further embodiment $R^{11}$ is hydrogen. In a still further embodiment $R^{11}$ is $C_{1-6}$-alkyl, such as $C_{1-4}$-alkyl, in particular methyl. In a further embodiment $R^{12}$ is hydrogen. In a still further embodiment $R^{12}$ is $C_{1-6}$-alkyl, such as $C_{1-4}$-alkyl, in particular methyl. In a further embodiment Q is >N—$R^{13}$. In a still further embodiment $R^{13}$ is hydrogen. In a further embodiment $R^{13}$ is $C_{1-6}$-alkyl, such as $C_{1-4}$-alkyl, in particular methyl. In a still further embodiment Q is

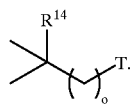

In a still further embodiment $R^{14}$ is hetaryl, In particular thiazolyl. In a further embodiment $R^{14}$ is hydrogen. In a still further embodiment o is 0. In a further embodiment o is 1. In a still further embodiment T is hydroxyl. In a further embodiment T is —N($R^{15}$)($R^{16}$). In a still further embodiment $R^{15}$ is $C_{1-6}$-alkyl, such as $C_{1-4}$-alkyl, in particular methyl. In a further embodiment $R^{16}$ is $C_{1-6}$-alkyl, such as $C_{1-4}$-alkyl, in particular methyl.

In a further embodiment of the compound of formula I L is

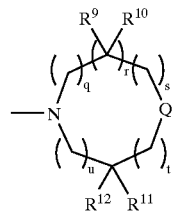

wherein q, s, t, u independently from each other are 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

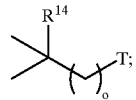

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl;

$R^{14}$ is hydrogen, aryl or hetaryl. In one embodiment q is 0. In a second embodiment q is 1. In a third embodiment s is 0. In a further embodiment s is 1. In a still further embodiment t is 0. In a further embodiment t is 1. In a further embodiment u is 0. In a further embodiment u is 1. In a still further embodiment r is 0. In a further embodiment r is 1. In a still further embodiment $R^9$ is hydrogen. In a still further embodiment $R^9$ is $C_{1-6}$-alkyl, such as $C_{1-4}$-alkyl, in particular methyl. In a further embodiment $R^{10}$ is hydrogen. In a still further embodiment $R^{10}$ is $C_{1-6}$-alkyl, such as $C_{1-4}$-alkyl, in particular methyl. In a further embodiment $R^{11}$ is hydrogen. In a still further embodiment $R^{11}$ is $C_{1-6}$-alkyl, such as $C_{1-4}$-alkyl, in particular methyl. In a further embodiment $R^{12}$ is hydrogen. In a still further embodiment $R^{12}$ is $C_{1-6}$-alkyl, such as $C_{1-4}$-alkyl, in particular methyl. In a further embodiment Q is >N—$R^{13}$. In a still further embodiment $R^{13}$ is hydrogen. In a still further embodiment $R^{13}$ is $C_{1-6}$-alkyl, such as $C_{1-4}$-alkyl, in particular methyl. In a further embodiment Q is

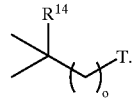

In a still further embodiment $R^{14}$ is hetaryl, in particular thiazolyl. In a further embodiment $R^{14}$ is hydrogen. In a still further embodiment o is 0. In a further embodiment o is 1. In a still further embodiment T is hydroxyl. In a further embodiment T is —N($R^{15}$)($R^{16}$). In a still further embodiment $R^{15}$ is $C_{1-6}$-alkyl, such as $C_{1-4}$-alkyl, in particular methyl. In a further embodiment $R^{16}$ is $C_{1-6}$-alkyl, such as $C_{1-4}$-alkyl, in particular methyl.

In the compound of the above formula I L is preferably 4-hydroxy-4-(2-thienyl)piperidino, (3-hydroxycyclohexyl)

amino, 4-(N,N-dimethylamino)piperidino, N-methyl-N-(1-methylpiperidin-4-yl)amino), 4-((N,N-dimethylamino)methyl)piperidino, 4-methylpiperazino, (2,2,6,6-tetramethylpiperidine-4-yl)amino, 4-hydroxypiperidino, (3S)-3-((N,N-dimethylamino)methyl)piperidino, (2S)-2-((N,N-dimethylamino)methyl)pyrrolidino.

In a still further embodiment of the compound of formula I G is wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy. In one embodiment $R^{17}$ is hydrogen. In a second embodiment $R^{18}$ is hydrogen. In a third embodiment $R^{19}$ is hydrogen. In a further embodiment $R^{19}$ is aryl, in particular phenyl. In a still further embodiment $R^{20}$ is hydrogen. In a further embodiment $R^{21}$ is hydrogen. In the compound of the above formula I G is preferably 2-naphthyl or biphenyl-4-yl.

In a further embodiment of the compound of formula I J is wherein $R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy. In one embodiment $R^{22}$ is hydrogen. In a second embodiment $R^{23}$ is hydrogen. In a third embodiment $R^{24}$ is hydrogen. In a further embodiment $R^{24}$ is halogen, in particular fluorine. In a still further embodiment $R^{25}$ is hydrogen. In a further embodiment $R^{26}$ is hydrogen. In the compound of the above formula I J is preferably phenyl, 4-fluorophenyl or 2-thienyl.

In a still further embodiment of the compound of formula I a is 1.

In a further embodiment of the compound of formula I b is 1.

In a still further embodiment of the compound of formula I c is 0.

In a further embodiment of the compound of formula I d is 0.

In a still further embodiment of the compound of formula I M is arylene or —$CR^{27}$=$CR^{28}$—, wherein $R^{27}$ and $R^{28}$ independently from each other are hydrogen or $C_{1-6}$-alkyl, optionally substituted with aryl or hetaryl. In one embodiment M is arylene, in particular phenylene. In another embodiment M is —$CR^{27}$=$CR^{28}$—, wherein $R^{27}$ and $R^{28}$ are independently hydrogen or $C_{1-6}$-alkyl. In a further embodiment $R^{21}$ is hydrogen. In a still further embodiment $R^{27}$ is $C_{1-6}$-alkyl, in particular methyl. In a further embodiment $R^{28}$ is hydrogen. In a further embodiment M is the E-isomer of $CR^{27}$=$CR^{28}$—. In the compound of the above formula I M is preferably ethenylene, 1,3-phenylene or 1,2-propenylene.

In a further embodiment of the compound of formula I e is 0.

In a still further embodiment of the compound of formula I e is 0.

In a further embodiment of the compound of formula I f is 0.

In a still further embodiment of the compound of formula I f is 1.

In a further embodiment of the compound of formula I $R^6$ and $R^7$ are independently from each other hydrogen or $C_{1-6}$-alkyl. In one embodiment $R^6$ is hydrogen. In a second embodiment $R^6$ is $C_{1-6}$-alkyl, in particular methyl. In a third embodiment $R^7$ is hydrogen. In a further embodiment $R^7$ is $C_{1-6}$-alkyl, in particular methyl.

In a still further embodiment of the compound of formula I $R^6$ and $R^7$ or $R^6$ and $R^8$ or $R^7$ and $R^8$ may optionally form —$(CH_2)_i$—U—$(CH_2)_j$—, wherein i and j independently from each other are 1 or 2 and U is —O—, —S—, or a valence bond.

In a further embodiment of the compound of formula I $R^6$ and $R^7$ form —$(CH_2)_i$—U—$(CH_2)_j$—, wherein i and j independently from each other are 1, 2 or 3 and U is —O—, —S—, or a valence bond. In one embodiment the sum i+j is 3. In a second embodiment U is a valence bond. In a particular embodiment ($CR^6R^7$) is cyclobutyl.

In a still further embodiment of the compound of formula I $R^6$ and $R^7$ form —$(CH_2)_i$—U—$(CH_2)_j$—, wherein i and j independently from each other are 1 or 2 and U is —O—, —S—, or a valence bond. In one embodiment the sum i+j is 3. In a second embodiment U is a valence bond. In a particular embodiment ($CR^6R^7$) is cyclobutyl.

In a further embodiment of the compound of formula I $R^8$ is hydrogen. In a second embodiment $R^8$ is $C_{1-6}$-alkyl, in particular methyl.

In a special embodiment the present invention relates to a compound of the general formula I formula I wherein $R^1$ is hydrogen or $C_{1-6}$-alkyl;

$R^2$ is $C_{1-6}$-alkyl;

L is wherein $R^4$ is hydrogen or $C_{1-6}$ alkyl;

p is 0 or 1;

q, s, t, u are independently from each other 0, 1, 2, 3 or 4;

r is 0 or 1;

the sum q+r+s+t+u is 0, 1, 2, 3, or 4;
R$^9$, R$^{10}$, R$^{11}$, and R$^{12}$ are independently from each other hydrogen or C$_{1-6}$ alkyl;
Q is >N—R$^{13}$ or

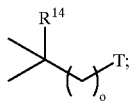

wherein o is 0, 1 or 2;
T is —N(R$^{15}$)(R$^{16}$) or hydroxyl;
R$^{13}$, R$^{15}$, and R$^{16}$ are independently from each other hydrogen or C$_{1-6}$ alkyl;
R$^{14}$ is hydrogen, aryl or hetaryl;
G is

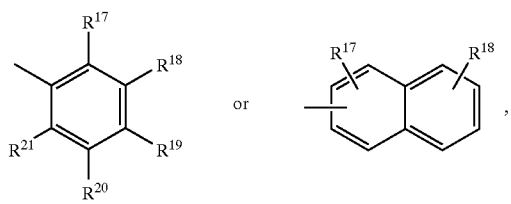

wherein R$^{17}$, R$^{18}$, R$^{19}$, R$^{20}$ and R$^{21}$ independently from each other are hydrogen, halogen, aryl, hetaryl, C$_{1-6}$-alkyl or C$_{1-6}$-alkoxy;
J is

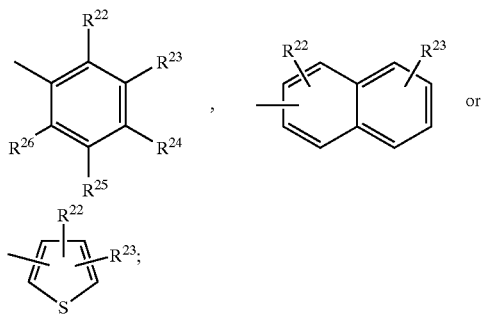

wherein R$^{22}$, R$^{23}$, R$^{24}$, R$^{25}$ and R$^{26}$ independently from each other are hydrogen, halogen, aryl, hetaryl, C$_{1-6}$-alkyl or C$_{1-6}$-alkoxy;
a is 0, 1, or 2;
b is 0, 1, or 2;
c is 0, 1, or 2;
d is 0 or 1;
e is 0, 1, 2, or 3;
f is 0 or 1;
R$^5$ is hydrogen or C$_{1-6}$-alkyl optionally substituted with one or more hydroxyl, aryl or hetaryl;
R$^6$ and R$^7$ are independently from each other hydrogen or C$_{1-6}$-alkyl, optionally substituted with one or more halogen, amino, hydroxyl, aryl, or hetaryl;
R$^8$ is hydrogen or C$_{1-6}$-alkyl, optionally substituted with one or more halogen, amino, hydroxyl, aryl, or hetaryl;
R$^6$ and R$^7$ or R$^6$ and R$^8$ or R$^7$ and R$^8$ may optionally form —(CH$_2$)$_i$—U—(CH$_2$)$_j$—, wherein i and j independently from each other are 1, 2 or 3 and U is —O—, —S—, or a valence bond;

M is arylene or —CR$^{27}$=CR$^{28}$—;
R$^{27}$ and R$^{28}$ are independently from each other hydrogen or C$_{1-6}$-alkyl, optionally substituted with one or more aryl or hetaryl;
or a pharmaceutically acceptable salt thereof.
Preferred compounds of formula I of the invention are:
(2E)-5-Amino-5-methylhex-2-enoic acid N-((1R)-1-{N-[(1R)-1-benzyl-2-(4-(dimethylamino)methyl)piperidin-1-yl)-2-oxoethyl]-N-methylcarbamoyl}-2-(2-naphthyl)ethyl)-N-methylamide

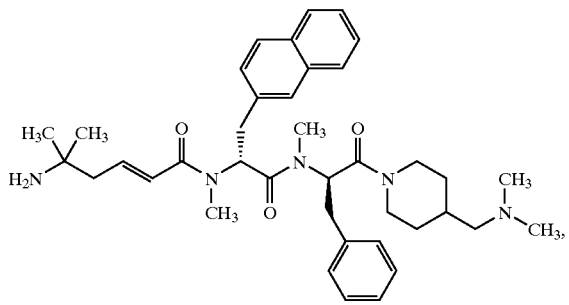

(2E)-5-Amino-5-methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

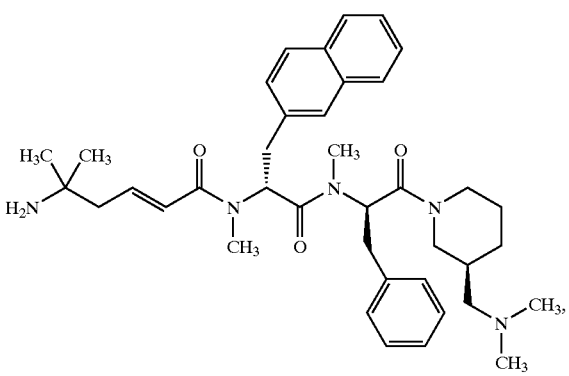

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

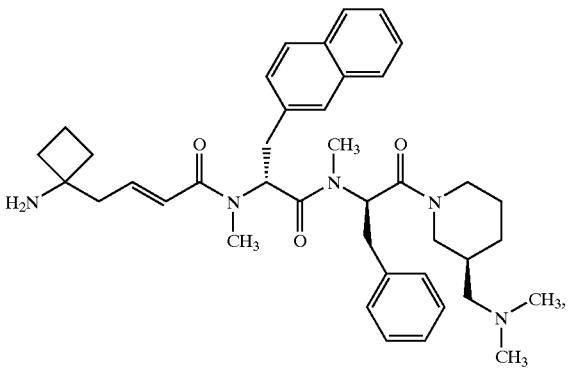

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

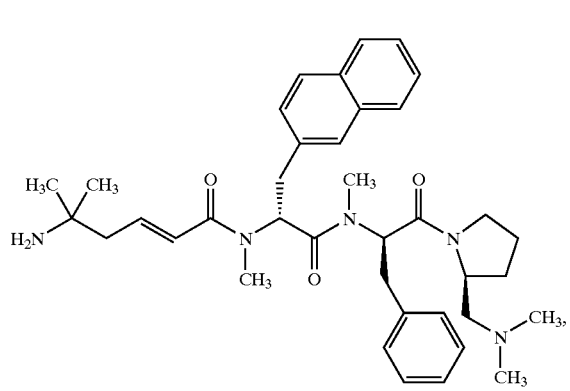

N-((1R)-1-{N-[(1R)-1-Benzyl-2-((2S)-2-(dimethylamino)methyl)pyrrolidin-1-yl)-2-oxoethyl]-N-methylcarbamoyl}-2-(2-naphthyl)ethyl)-N-methyl-3-((methylamino)methyl)benzamide

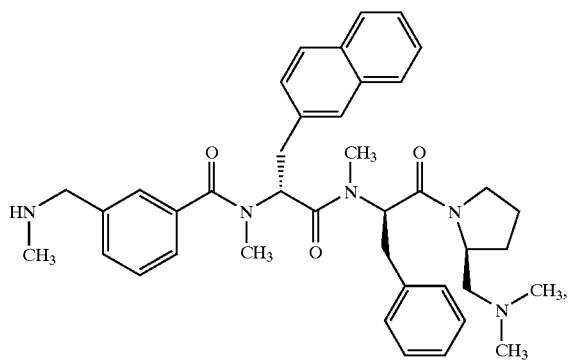

(2E)-5-Amino-5-methylhex-2-enoic acid N-((1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide.

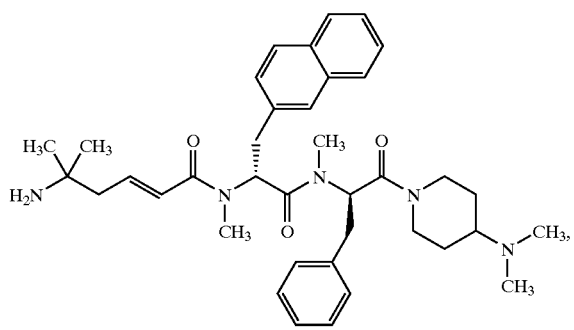

(2E)-5-Amino-5-methylhex-2-enoic acid N-methyl-N-[(1R)-1-(N-methyl-N-{(1R)-1-[N-methyl-N-(1-methylpiperidin-4-yl)carbamoyl]-2-phenylethyl}carbamoyl)-2-(2-naphthyl)ethyl]amide

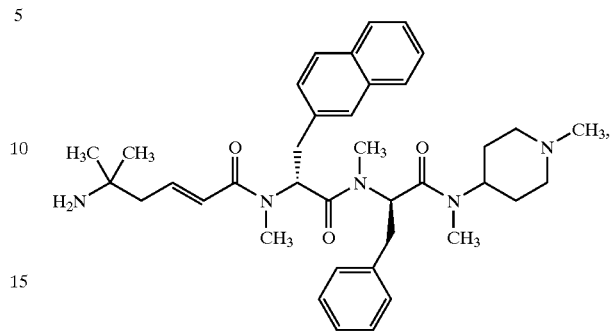

3-Aminomethyl-N-((1R)-1-{N-[(1R)-1-benzyl-2-(4-methylpiperazin-1-yl)-2-oxoethyl]-N-methylcarbamoyl}-2-(2-naphthyl)ethyl)-N-methylbenzamide

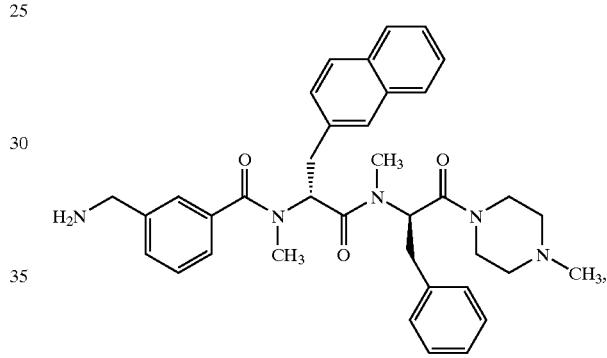

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

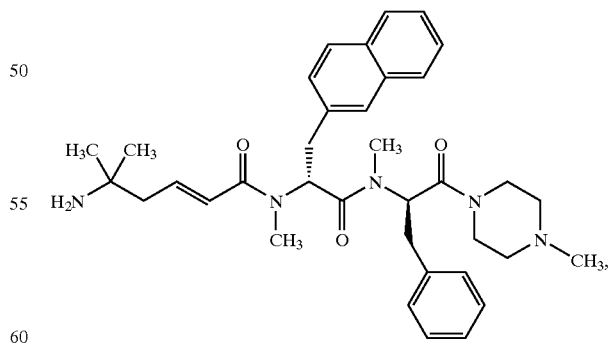

(2E)-5-Amino-5-methylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

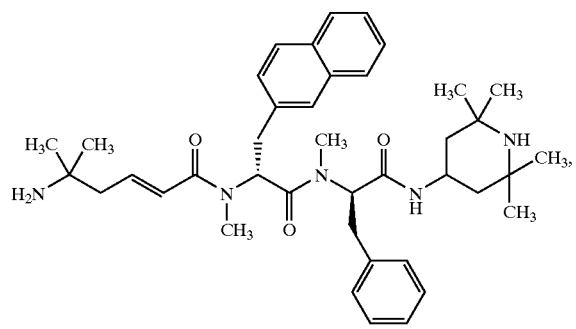

3-Aminomethyl-N-methyl-N-((1R)1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide

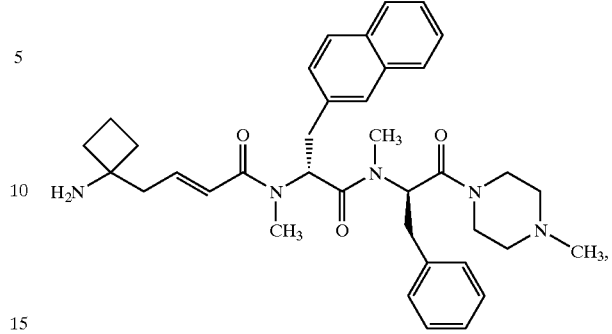

(2E)-5-Amino-3,5-dimethylhex-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

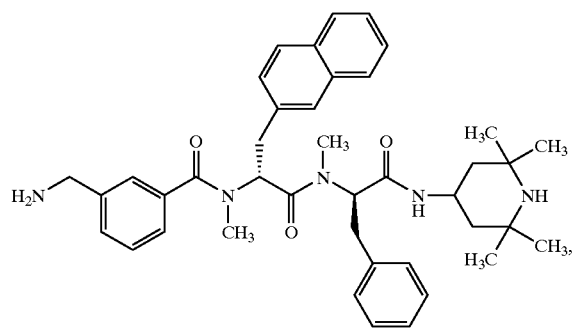

(2E)-5-Amino-3,5-dimethylhex-2-enoic acid N-methyl-N-((1R)-1-{N-methyl-N-[(1R)-2-phenyl-1-((2 2,6,6-tetramethylpiperdin-4-yl)carbamoyl)ethyl]carbamoyl}-2-(2-naphthyl)ethyl)amide

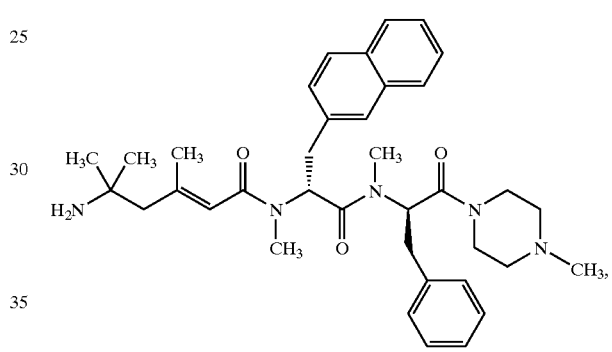

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

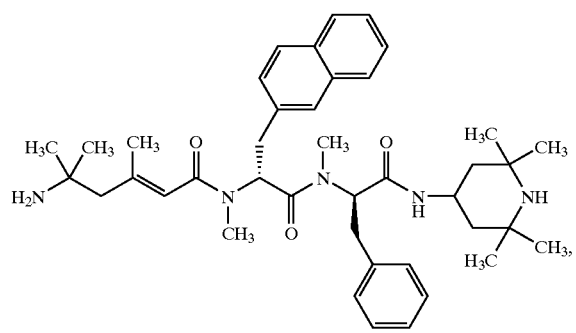

(2E)4-(1-Aminocyclobutyl)but-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

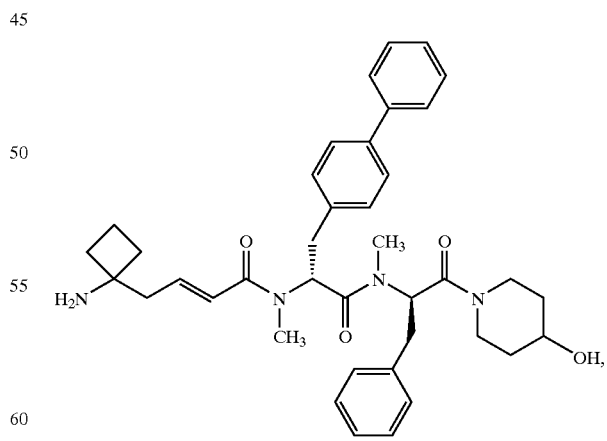

(2E)-5-Amino-5-methylhex-2-enoic acid N-((1R)-1-{N-[(1R)-1-benzyl-2-(4-hydroxypiperidin-1-yl)-2-oxoethyl]-

N-methylcarbamoyl}-2-(biphenyl-4-yl)ethyl)-N-methylamide

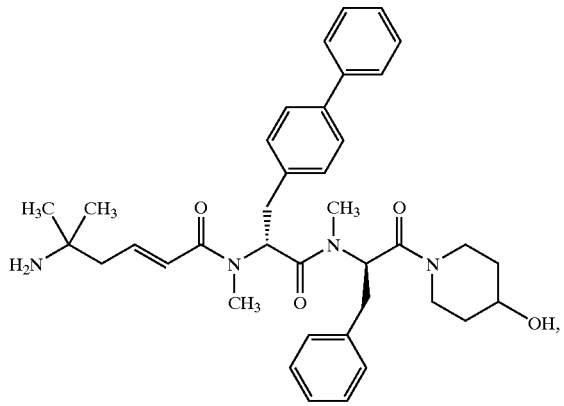

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

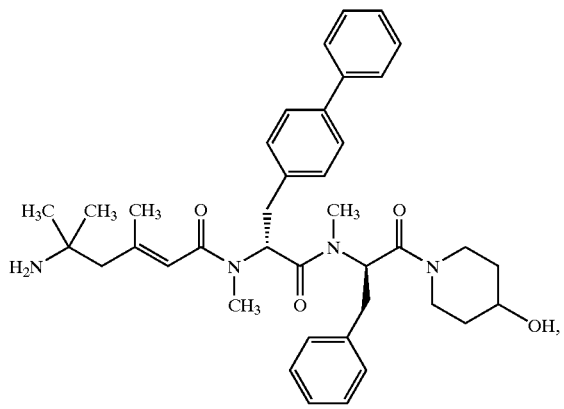

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

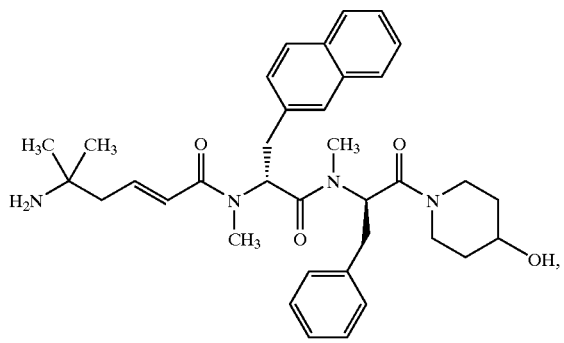

(2E)-5-Amino-3,5-dimethylhex-2-enoic acid N-((1R)-1-{N-[(1R)-1-benzyl-2-(4-hydroxypiperidin-1-yl)-2-oxoethyl]-

N-methylcarbamoyl}-2-(2-naphthyl)ethyl)-N-methylamide

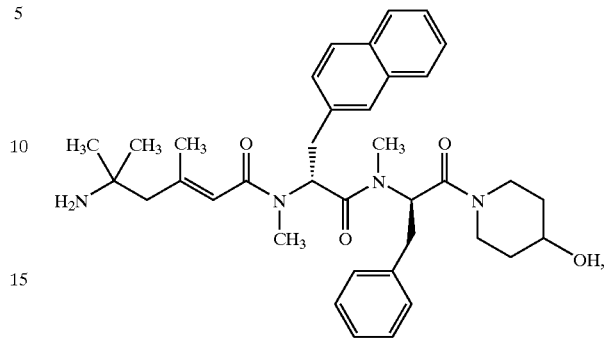

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

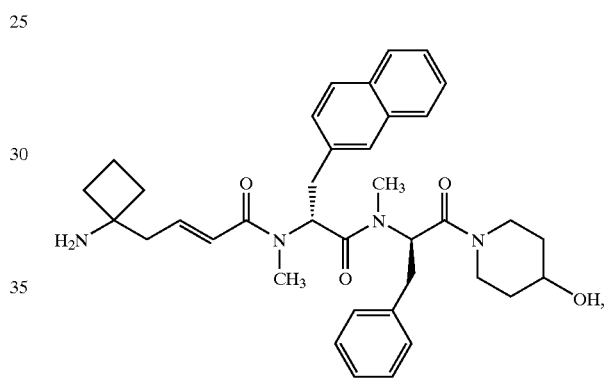

(2E)-5-Amino-5-methylhex-2-enoic acid N-((1R)-1-{N[(1R)-1-(4-fluorobenzyl)-2-(4-hydroxypiperidin-1-yl)-2-oxoethyl]-N-methylcarbamoyl}-2-(2-naphthyl)ethyl)-N-methylamide

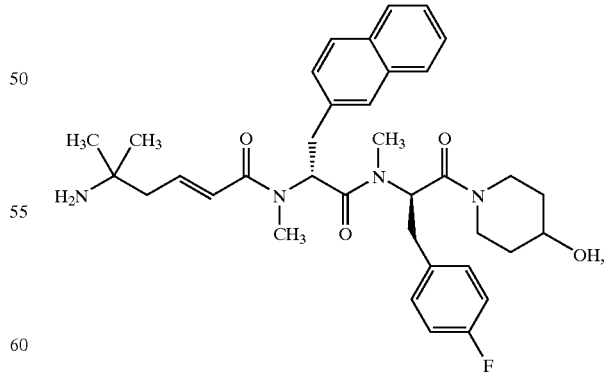

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

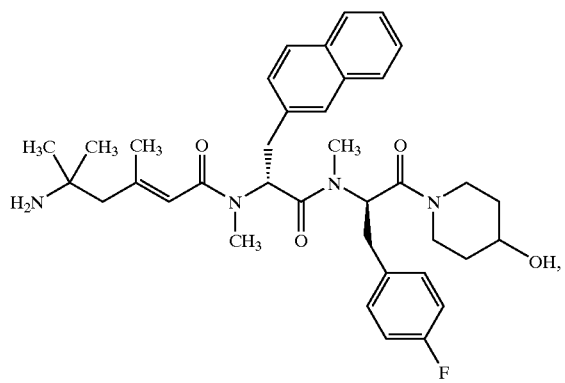

(2E)-5-Amino-5-methylhex-2-enoic acid N-((1R)-1-{N-[(1R)-1-benzyl-2-(4-hydroxy-4-(2-thienyl)piperidin-1-yl)-2-oxoethyl]-N-methylcarbamoyl}-2-(2-naphthyl)ethyl)-N-methylamide

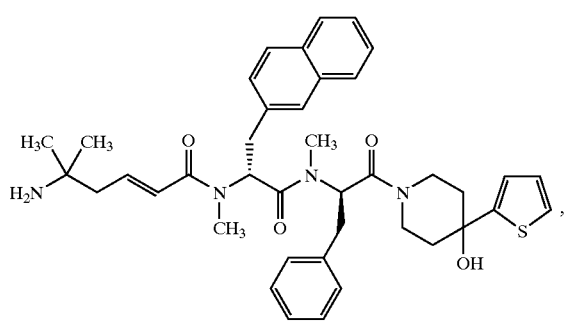

(2E)5-Amino-5-methylhex-2-enoic acid N-((1R)-1-{N-[(1R)-1-(3-hydroxycyclohexylcarbamoyl)-2-phenylethyl]-N-methylcarbamoyl}-2-(2-naphthyl)ethyl)-N-methylamide

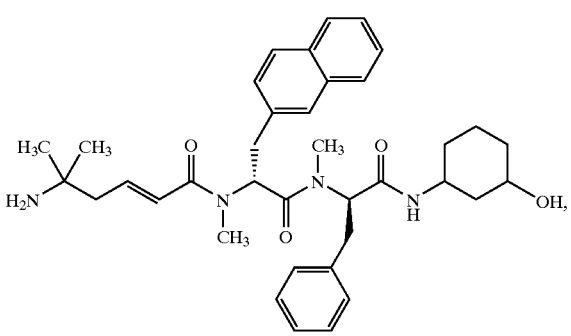

(2E)4-(1-Aminocyclobutyl)but-2-enoic acid N-((1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide

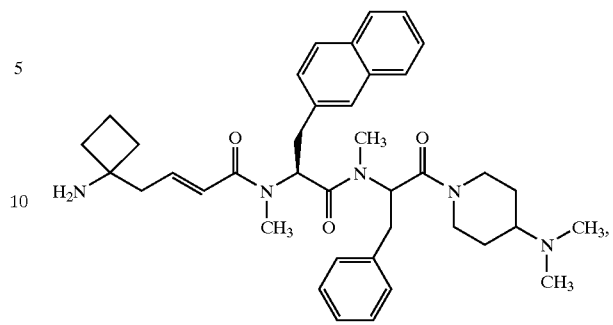

(2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide (2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide (2E)-5-Amino-5-methylhex-2-enoic acid N-((1R)-2-(biphenyl-4-yl)-1-{N-[(2R)-2-(4-hydroxypiperidin-1-yl)-2-oxo-1-((2-thienyl)methyl)ethyl]-N-methylcarbamoyl}ethyl)-N-methylamide

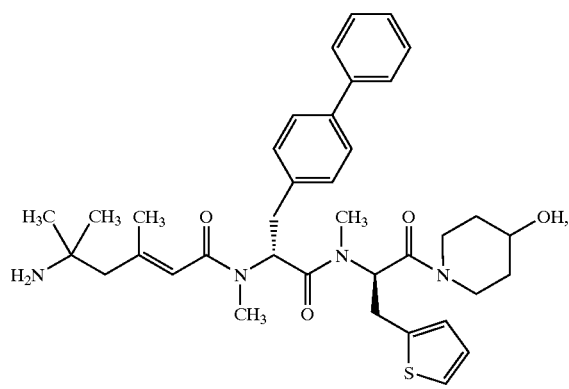

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide (2E)-5-Methyl-5-methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

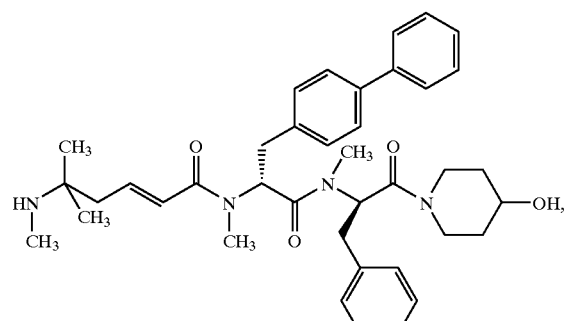

(2E)74-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide

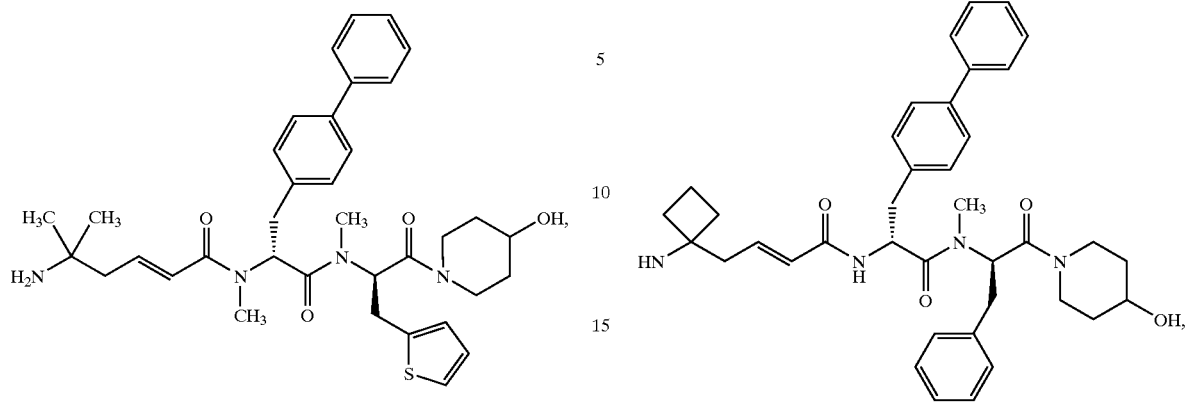

and pharmaceutically acceptable salts thereof.

General Methods

The methods illustrated in below schemes I–III are by no mean intended to limit the present invention in any aspect, but should only be seen as a guidance for how the present compounds may be prepared.

Scheme I

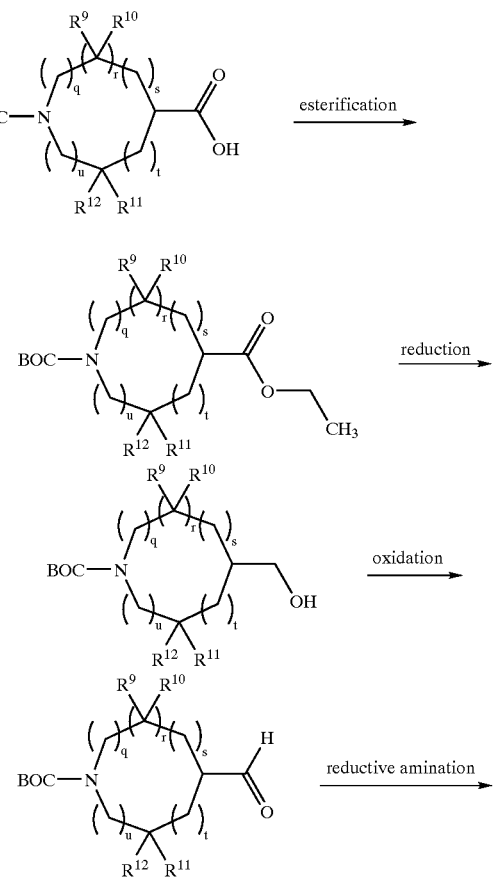

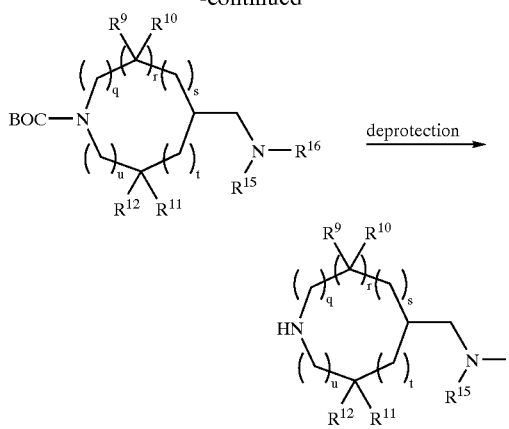

Amines of Type

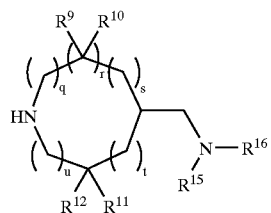

may be synthesized from a BOC-protected amino acid (cf. scheme I). The acid is transformed into an ester by reaction with or without a reagent such as e. g. 1-hydroxybenzotriazole, 1-hydroxy-7-azabenzotriazole, or 3-hydroxy-1,2,3-benzotriazole-4(3H)-one and a reagent such e.g. as N-3-dimethylaminopropyl)-N'-ethylcarbodiimide hydrochloride or diisopropylcarbodiimide and a catalyst such as N,N-dimethylaminopyridine. The ester may be reduced by a suitable reagent, such as diisobutylaluminum hydride in a appropriate solvent such as e.g. toluene, dichloromethane, ether, or tetrahydrofuran to give the BOC-protected aldehyde or alcohol. If the alcohol is obtained, the alcohol may be oxidized to the corresponding aldehyde, by a suitable method, such as e.g. dimethylsulfoxide/oxalyl chloride/triethylamine or dimethylsufloxide/sulfotrioxide/pyridine, pyridinium dichromate, or pyridinium chlorochromate. A reductive amination with an appropriate amine $N(R^{15})(R^{16})$ and a suitable reagent, such as sodium cyanoborohydride or sodium triacetoxyborohydride in a suitable solvent such as e.g. alcohols may yield the BOC-protected amine. If at least one of $R^{15}$ or $R^{16}$ is hydrogen, the amino group may be protected by a method known to those skilled in the art and described in the literature as e.g. T. W. Greene, P. G. M. Wuts Protective groups in organic synthesis, $2^{nd}$ edition, Wiley, New York, before carrying out the following steps. The removal of the BOC-protection group can be achieved by a method known to those skilled in the art as described in T. W. Greene, P. G. M. Wuts Protective groups in organic synthesis, $2^{nd}$ edition, Wiley, New York, such as e.g. hydrogen chloride in ethyl acetate, or trifluoroacetic acid in dichloromethane.

Scheme II

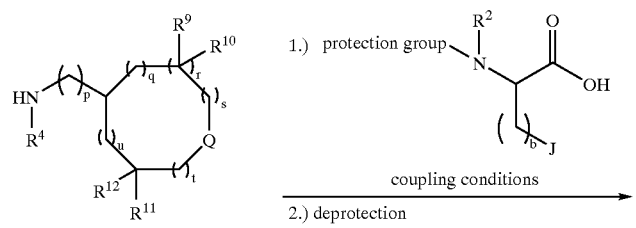

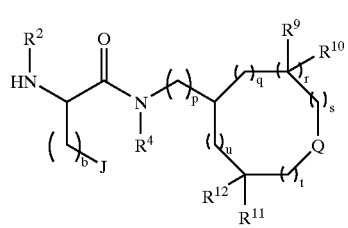

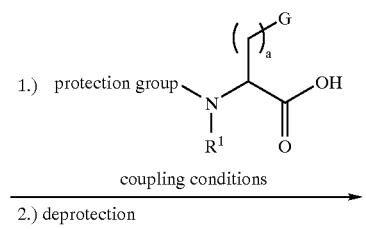

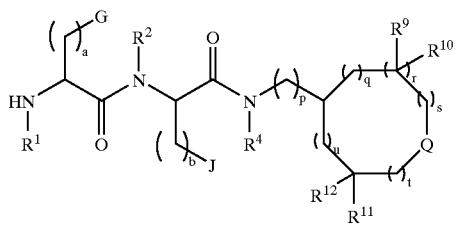

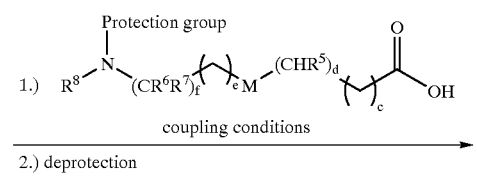

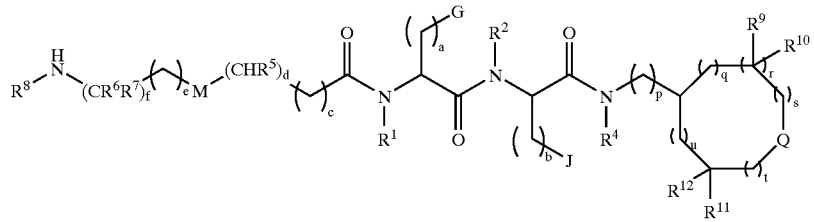

Compounds of the type of formula I may be synthesized by coupling of an amine of type

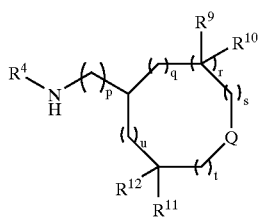

and a suitable protected acid with or without a coupling reagent such as e.g. 1-hydroxybenzotriazole, 1 hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane (cf. scheme II). The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. All protection groups may be removed by a method known for a person skilled in the art and described in the literature e.g. in T. W. Greene, P. G. M. Wuts Protective groups in organic synthesis, $2^{nd}$ edition, Wiley, New York.

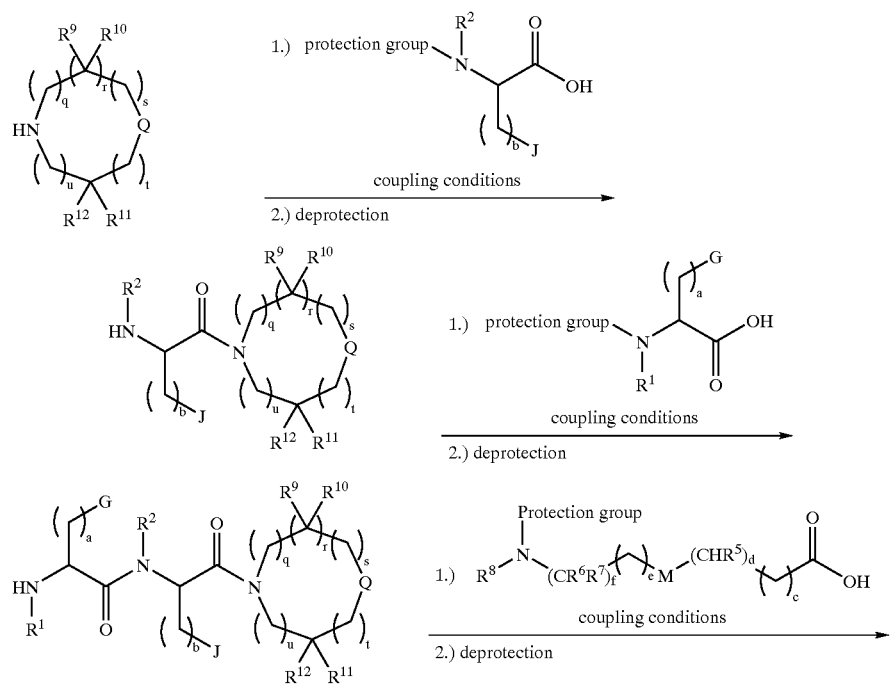

Scheme III

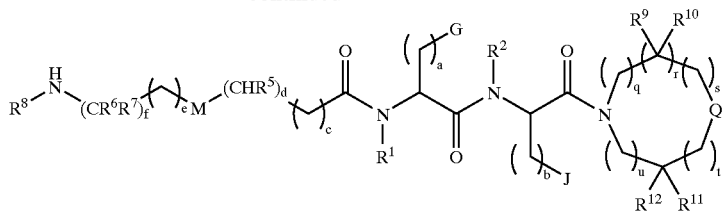

Compounds of the type of formula I may be synthesized by coupling of an amine of type

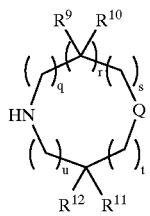

and a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane (cf. scheme III). The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as (3-dimethylaminopropyl)-N'-ethylcarbodiimide hydrochloride or diisopropylcarbodiimide in a suitable solvent, such as N,N-dimethylformamide or dichloromethane. The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. All protection groups may be removed by a method known for a person skilled in the art and described in the literature e.g. in T. W. Greene, P. G. M. Wuts Protective groups in organic synthesis, $2^{nd}$ edition, Wiley, New York.

The compounds of formula I exhibit an improved resistance to proteolytic degradation by enzymes because they are non-natural, in particular because the natural amide bonds are replaced by non-natural amide bond mimetics. The increased resistance to proteolytic degradation of the compounds of the invention in comparison with known hormone releasing peptides is expected to improve their bioavailability compared to that of the peptides suggested in the prior literature.

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$ cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are $C_{3-6}$-cycloalkoxy such as cyclopropyloxy, cyclobutyloxy, cyclopentyloxy and cyclohexyloxy.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and naphthylene, optionally substituted with one or more $C_{1-6}$-alkyl, $C_{1-6}$-alkoxy, halogen, amino or aryl.

In the present context, the term "hetaryl" is intended to Include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted with one or more $C_{1-6}$-alkyl, $C_{1-6}$-alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted with one or more $C_{1-6}$-alkyl, $C_{1-6}$-alkoxy, halogen, amino or aryl.

In the present context, the term "heterocyclic system" is intended to include aromatic as well as non-aromatic ring moieties, which may be monocyclic, bicyclic or polycyclic, and contain in their ring structure at least one, such as one, two or three, nitrogen atom(s), and optionally one or more, such as one or two, other hetero atoms, e.g. sulpher or oxygen atoms. The heterocyclic system is preferably selected from pyrazole, pyridazine, triazine, indazole, phthalazine, cinnoline, pyrazolidine, pyrazoline, aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine, optionally substituted with one or more $C_{1-6}$-alkyl, $C_{1-6}$-alkoxy, halogen, amino, oxy or aryl.

The term "halogen" is intended to include chlorine (Cl), fluorine (F), bromine (Br) and iodine (I).

In the context of the present application, the term "growth hormone secretagogue" is intended to include any compound which has the capacity, directly or indirectly, of inducing (i.e. stimulating or increasing) the release of growth hormone from the pituitary gland. The term "growth hormone secretagogue" includes growth hormone releasing peptides, growth hormone releasing peptidomimetics, and growth hormone releasing compounds of a nonpeptidyl nature.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, malic, maleic, mandelic phthalic, citric, glutaric, gluconic, methanesulfonic, salicylic, succinic, tartaric, toluenesulfonic, trifluoracetic, sulfamic or fumaric acid and/or water.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 10 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacet: 940 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to a method of treating growth retardation in connection with asthma, the method comprising administering to a subject in need thereof an effective amount of a growth hormone secretagogue or a pharmaceutically acceptable salt thereof. In a particular embodiment, the present invention relates to a method of treating growth retardation in connection with asthma, the method comprising administering to a subject in need thereof an effective amount of a compound of the general formula I or a pharmaceutically acceptable salt thereof.

In a still further aspect, the present invention relates to a method of treating growth retardation in connection with juvenile rheumatic arthritis or systic fibrosis, the method comprising administering to a subject in need thereof an effective amount of a growth hormone secretagogue or a pharmaceutically acceptable salt thereof. In one embodiment, the present invention relates to a method of treating growth retardation in connection with juvenile rheumatic arthritis, the method comprising administering to a subject in need thereof an effective amount of a growth hormone secretagogue or a pharmaceutically acceptable salt thereof. In a second embodiment, the present invention relates to a method of treating growth retardation in connection with systic fibrosis, the method comprising administering to a subject in need thereof an effective amount of a growth hormone secretagogue or a pharmaceutically acceptable salt thereof. In a particular embodiment, the present invention relates to a method of treating growth retardation in connection with Juvenile rheumatic arthritis, the method comprising administering to a subject in need thereof an effective amount of a compound of the general formula I or a pharmaceutically acceptable salt thereof. In another particular embodiment, the present invention relates to a method of treating growth retardation In connection with systic fibrosis, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. Compounds of formula I are useful for stimulation of growth hormone release in the elderly, prevention of catabolic side effects of glucocorticoids, prevention and treatment of osteoporosis, treatment of chronic fatigue syndrom (CFS), treatment of acute fatigue syndrom and muscle loss following elective surgery, stimulation of the immune system, acceleration of wound healing, accelerating bone fracture repair, accelerating complicated fractures, e.g. disctraction osteogenesis, treatment of wasting secondary to fractures, treatment of growth retardation, treating growth retardation resulting from renal failure or insufficiency, treatment of cardiomyopathy, treatment of wasting in connection with chronic liver disease, treatment of thrombocytopenia, treatment of growth retardation in connection with Crohn's disease, treatment of short bowel syndrome, treatment of wasting in connection with chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treatment of growth retardation associated with the Prader-Willi syndrome and Turner's syndrome; increasing the growth rate of a patient having partial growth hormone insensitive syndrome, accelerating the recovery and reducing hospitalization of bum patients; treatment of intrauterine growth retardation, skeletal dysplasia, hypercortisolism and Cushing's syndrome; induction of pulsatile growth hormone release; replacement of growth hormone in stressed patents, treatment of osteochondrodysplasias, Noonan's syndrome, schizophrenia, depressions, Alzheimer's disease, delayed wound healing and psychosocial deprivation, treatment of catabolism in connection with pulmonary dysfunction and ventilator dependency; treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperihsulinemia including nesidioblastosis, adjuvant treatment for ovulation induction; stimulation of thymic development and prevention of the age related decline of thyme function, treatment of immunosuppressed patients; treatments of sarcopenia, treatment of wasting in connection with AIDS; improvement in muscle strength, mobility, maintenance of skin thickness, treatment of metabolic homeostasis and renal homeostasis in the frail elderly, stimulation of osteoblasts, bone remodelling and cartilage growth; regulation of food intake; stimulation of the immune system in companion animals and treatment of disorder of aging in companion animals, promoting growth in livestock and stimulation of wool growth in sheep, increasing milk production in livestock, treatment of metabolic syndrom (syndrome X), treatment of insulin resistance, including NIDDM, in mammals, e.g. humans, treatment of insulin resistance in the heart, improvement of sleep quality and correction of the relative hyposomatotropism of senescence due to high increase in REM sleep and a decrease in REM latency, treatment of hypothermia, treatment of frailty associated with aging, treatment of congestive heart failure, treatment of hip fractures, treatment of immune deficiency in individuals with a depressed T4/T8 cell ratio, treatment of muscular atrophy, treatment of musculoskeletal impairment in elderly, enhancing the activity of protein kinase B (PKB), improvement of the overall pulmonary function, and treatment of sleep disorders.

Within the context of the present application, the term "treatment" is also intended to include prophylactic treatment.

In a further aspect the present invention relates to the use of a growth hormone secretagogue or a pharmaceutically acceptable salt thereof for the preparation of a medicament for the treatment of growth retardation in connection with asthma. In one particular embodiment the invention relates to the use of a compound of the general formula I or a pharmaceutically acceptable salt thereof for the treatment of growth retardation in connection with asthma. In a second particular embodiment the invention relates to the use of growth hormone releasing peptides, growth hormone releasing peptidomimetics, or growth hormone releasing compounds of a nonpeptidyl nature or a pharmaceutically acceptable salt thereof for the treatment of growth retardation in connection with asthma.

In a still further aspect the present invention relates to the use of a growth hormone secretagogue or a pharmaceutically acceptable salt thereof for the preparation of a medicament for the treatment of growth retardation in connection with juvenile rheumatic arthritis or systic fibrosis. In one embodiment the invention relates to the use of a growth hormone secretagogue or a pharmaceutically acceptable salt thereof for the preparation of a medicament for the treatment of growth retardation in connection with juvenile rheumatic arthritis. In a second embodiment the invention relates to the use of a growth hormone secretagogue or a pharmaceutically acceptable salt thereof for the preparation of a medicament for the treatment of growth retardation in connection with systic fibrosis. In one particular embodiment the invention relates to the use of a compound of the general formula or a pharmaceutically acceptable salt thereof for the treatment of growth retardation in connection with juvenile rheumatic arthritis. In another particular embodiment the invention relates to the use of a compound of the general formula I or a pharmaceutically acceptable salt thereof for the treatment of growth retardation in connection with systic fibrosis. In a further particular embodiment the invention relates to the use of growth hormone releasing peptides, growth hormone releasing peptidomimetics, or growth hormone releasing compounds of a nonpeptidyl nature or a pharmaceutically acceptable salt thereof for the treatment of growth retardation in connection with juvenile rheumatic arthritis. In a still further particular embodiment the invention relates to the use of growth hormone releasing peptides, growth hormone releasing peptidomimetics, or growth hormone releasing compounds of a nonpeptidyl nature or a pharmaceutically acceptable salt thereof for the treatment of growth retardation in connection with systic fibrosis.

For the above indications the dosage will vary depending on the growth hormone secretagogue employed, e.g. on the compound of formula I employed, on the mode of administration and on the therapy desired. However, generally dosage levels between 0.0001 and 100 mg/kg body weight daily are administered to patients and animals to obtain effective release of endogenous growth hormone. Moreover the compounds of formula I have no or substantially no side-effects, 30 when administered in the above dosage levels, such side-effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

The dosage of the compounds according to this invention is suitably 0.01–500 mg/day, e.g. from about 5 to about 50 mg, such as about 10 mg per dose, when administered to patients, e.g. humans, as a drug.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk and wool production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures, and such evaluation may be performed as described below.

The isolation of rat pituitary cells is a modification of O. Sartor et al. *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium: DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D-4902) pH 7.3, to a density of $2\times10^5$ cells/ml. The cells were seeded into microtiter plates (Nunc, Denmark), 200 ml/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability using the procedure described below:

Compounds is dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, MO, USA).

Enzymes (trypsin, chymotrypsin, elastase aminopeptidase M and carboxypeptidase Y and B) were all purchased from Boehringer Mannheim GmbH (Mannheim, Germany).

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0.

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. enzyme mix |
|---|---|---|---|
| Standards | | | |
| ACTH 4–10 | 1124.5/562.8 | + | − |
| Glucagon | 3483/871.8 | − | − |
| Insulin (B23–29) | 859.1/430.6 | | |
| Angiotensin 1–14 | 1760.1/881.0 | − | − |
| GHRP-2 | 817.4/409.6 | − | − |
| GHRP-6 | 872.6/437.4 | − | − |

+: Stable (less than 20% decrease in SIM signal after 24 h in degradation solution)
−: Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in ° C. Column chromatography was carried out using the technique described by W. C. Still et al, J. Org. Chem. 1978, 43, 2923–2925 on silica gel 60. Compounds used as starting materials are either known compounds or compounds which can readily be prepared by methods known per se.

HPLC-Analysis:
Method A1.

The RP-analysis was performed using UV detections at 214, 254, 276, and 301 nm on a 218TP54 4.6 mm×250 mm 5 m C-18 silica column (The Seperations Group, Hesperia), a which was eluted at 1 mL/min at 42° C. The column was equilibrated with 5% acetonitrile in a buffer consisting of 0.1 M ammonium sulfate, which was adjusted to pH 2.5 with 4M sulfuric acid. After injection the sample was eluted by a gradient of 5% to 60% acetonitrile in the same buffer during 50 min.

Method B1.

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% (acetonitrile+0.1% TFA) in an aqueous solution of TFA in water (0.1%). After injection the sample was eluted by a gradient of 5% to 60% (acetonitrile+0.1% TFA) in the same aqueous buffer during 50 min.

Abbreviations:

| TLC: | thin layer chromatography |
|---|---|
| DMSO: | dimethylsulfoxide |
| min: | minutes |
| h: | hours |

Boc: tert butyloxycarbonyl
DMF: dimethylformamide
THF: tetrahydrofuran
EDAC: N-ethyl-N'-dimethylaminopropylcarbodiimide hydrochloride
HOAt: 1-hydroxy-7-azabenzotrazole
DIEA: diisopropylethylamine
TFA: trifluoroacetic acid Buildingblocks:
N-methylated amino acids used in the following examples were prepared as in Can. J. Chem. 1977, 55, 906.
3-Hydroxy-1,1-dimethylpropylcarbamic acid tert-butyl ester:

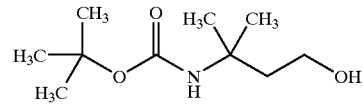

At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature over a period of 4 h. It was cooled to 0° C. Methanol (5 mL) was added carefully. 1N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetate/heptane 1:2 to give 1.84 g of 3hydroxy-1,1-dimethylpropylcarbamic acid tert-butyl ester.

¹H-NMR (CDCl₃): d 1.33 (s, 6H); 1.44 (s, 9H); 1.88 (t, 2H); 1.94 (br, 1H); 3.75 (q, 2H); 4.98 (br, 1H).

3-(tert-Butoxycarbonylamino)-3-methylbutanal:

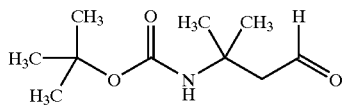

DMSO (1.22 mL, 17.2 mmol) was added to a solution of oxalyl chloride (1.1 mL, 12.9 mmol) at −78° C. in dichloromethane (I 5 mL). The mixture was stirred for 15 min at −78° C. A solution of 3-hydroxy-1,1-dimethylpropylcarbamic acid tert-butyl ester (1.75 g, 8.6 mmol) in dichloromethane (10 mL) was added dropwise over a period of 15 min. The solution was stirred at −78° C. for another 15 min. Triethylamine (6.0 mL, 43 mmol) was added. The solution was stirred at −78° C. for 5 min and then warmed to room temperature. The solution was diluted with dichloromethane (100 mL) and extracted with 1 N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

MHz-¹H-NMR (CDCl₃): d 1.39 (s, 6H); 1.45 (s, 9H); 2.85 (d, 2H); 4.73 (br, 1H); 9.80 (t, 1H).

Ethyl (2E)-5-(tert-Butoxycarbonylamino)-5-methylhex-2-enoate:

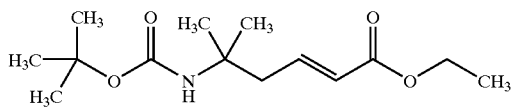

Triethylphoshonoacetate (1.96 ml, 9.8 mmol) was dissolved in tetrahydrofuran (30 ml). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 ml) was added. The solution was stirred at room temperature for 75 min. It was diluted with ethyl acetate (100 ml) and 1N hydrochloric acid (100 ml). The phases were separated. The aqueous phase was extracted with ethyl acetate (2×50 ml). The combined organic phases were washed with saturated sodium hydrogen carbonate solution (60 ml) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

¹H-NMR (CDCl₃): d 1.30 (s, 6H); 1.30 (t, 3H); 1.46 (s, 9H); 2.62 (d, 2H); 4.27 (q, 2H); 4.42 (br, 1H); 5.88 (d, 1H); 6.94 (td, 1H).

(2E)-5-(tert-Butoxycarbonylamino)-5-methylhex-2-enoic acid:

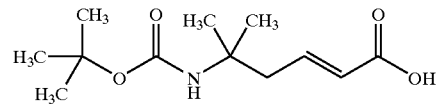

Ethyl (2E)-5-(tert-butoxycarbonylamino)-5-methylhex-2-enoate (1.233 g, 4.54 mmol) was dissolved in dioxane (20 ml). Lithium hydroxide (0.120 g, 5.00 mmol) was added as a solid. Water (10 ml) was added, until a clear solution was reached. The solution was stirred 16 h at room temperature. The solution was diluted with water (70 ml) and was extracted with tert-butyl methyl ether (2×100 ml). The aqueous phase was acidified with 1N sodium hydrogensulfate solution (pH=1) and was extracted with tert-butylmethylether (3×70 ml). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.

¹H-NMR (DMSO d₆): d 1.15 (s, 6H); 1.35 (s, 9H); 2.53 (d, 2H); 5.75 (d, 1H); 6.57 (br, 1H); 6.75 (td, 1H); 12.15 (s, 1H).

1-Aza-spiro[3.3]heptan-2-one:

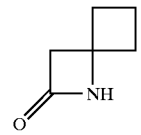

Methylenecyclobutane (40.0g, 0.587 mol) was dissolved in diethylether (250 ml). At −40° C. chlorosulfonylisocyanate (26 ml, 0.294 mol) was added dropwise. The reaction mixture was warmed to 10° C., An exothermic reaction was observed, and precipitation was formed. The reaction mixture was cooled to −20° C. It was stirred for 16 h, while it was warming up to room temperature. A saturated aqueous solution of sodium sulfite (100 ml) was added dropwise. The reaction mixture was stirred vigorously for 1 h. Another saturated aqueous solution of sodium sulfite (100 ml) was added dropwise. Solid sodium hydrogen carbonate was added, until pH 7. Dichloromethane (500 ml) was added. The phases were separated. The organic layer was dried over magnesium sulfate. The solvent was removed in vacuo, to give 23.59 g of 1-aza-spiro[3.3]heptan-2-one.

¹H-NMR (CDCl₃): d 1.75 (m, 2H); 2.26 (m, 2H); 2.39 (m, 2H); 2.96 (s, 2H); 6.55 (br, 1H).

2-Oxo-1-azaspiro[3.3]heptane-1-carboxylic acid tert-butylester

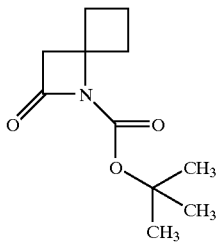

A solution of di-tert-butyl dicarbonate (55.7 g. 0.211 mol) in dichloromethane (100 ml) was added dropwise to a solution of 1-aza-spiro[3.3]heptan-2-one, triethylamine (36 ml, 0.255 mol), and 4-dimethylaminopyridiene (2.6 g, 0.021 mol) in dichloromethane (100 ml). The reaction mixture was stirred for 16 h at room temperature. It was washed with a 10% aqueous solution of ammonium chloride (100 ml), water (100 ml) and a saturated aqueous solution of sodium hydrogen carbonate (100 ml). The organic layer was dried over magnesium sulfate. The solvent was removed in vacuo to give 48.24 g of crude 2-oxo-1-azaspiro[3.3]heptane-1-carboxylic acid tert-butylester, which was used for the next step without purification.

$^1$H-NMR (CDCl$_3$): d 1.55 (s, 9H); 1.78 (m, 1H); 1.92 (m, 1H); 2.18 (m, 2H); 2.90 (m, 2H); 3,04 (s, 1H).

(1-(tert-Butoxycarbonylamino)cyclobutyl)acetic acid:

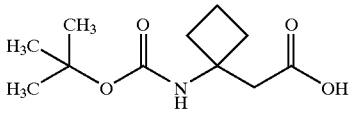

An 1 N aqueous solution of lithium hydroxide (227 ml, 227 mmol) was added to a solution of 2-oxo-1-azaspiro[3.3]heptane-1-carboxylic acid tert-butylester (48 g, 0.227 mmol) in tetrahydrofuran (200 ml). The reaction mixture was stirred for 2 h. Diethyl ether (200 ml) and water (200 ml) were added. The mixture was stirred for 16 h. The organic layer was isolated. The aqueous phase was extracted with diethyl ether (200 ml). The aqueous phase was acidified with a 10% aqueous solution of sodium hydrogen sulfate until pH 3. The formed precipitation was filtered off, washed with water, and dried in vacuo, to give 38.84 g of (1-(tert-butoxycarbonylamino)cyclobutyl)acetic acid.

$^1$H-NMR (CDCl$_3$): d 1.45 (s, 9H); 1.85 (m, 1H); 1.95 (m, 1H); 2.25 (m, 4H); 2.87 (m, 2H); 5.15 and 6.20 (both br, together 1H).

(2E)-4-(1-(tert-Butoxycarbonylamino)cyclobutyl)but-2-enoic acid:

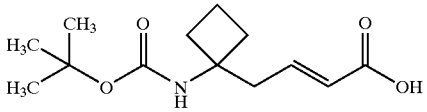

(2E)4-(1-(tert-Butoxycarbonylamino)cyclobutyl)but-2-enoic acid was synthesized starting with (1-tert-butoxycarbonylamino)cyclobutyl)acetic acid analogously to the synthesis of (2E)-5-(tert-butoxycarbonylamino)-5-methylhex-2-enoic acid starting with 3-tert-butoxycarbonylamino-3-methylbutanoic acid.

$^1$H-NMR (CDCl$_3$): d 1.43 (s, 9H); 1.84 (m, 1H); 1.95 (m, 1H); 2.10 (m, 2H); 2.20 (m, 2H); 2.70 (m, 2H); 4.75 (br, 0.5H); 5.90 (m, 1H); 6.35 (br, 0.5H); 6.95 (m, 1H).

(2E)-5-tert-Butoxycarbonylamino-3,5-dimethylhex-2-enoic acid ethyl ester

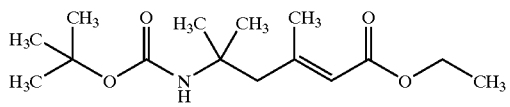

Diacetonamine hydrogen oxalate (30.0 g; 146 mmol) was suspended in tetrahydrofuran (400 ml). An aqueous solution of sodium hydroxide (1 N; 146 ml) was added. Di-tert-butyl dicarbonate (38.3 g; 175 mmol) was dissolved in tetrahydrofuran (100 ml) and added dropwise to the reaction mixture. The reaction mixture was stirred for 2 h at room temperature. Sodium hydroxide (1 N; 146 ml) was added and the reaction mixture was stirred for 12 h at room temperature. Water (200 ml) and ethyl acetate (200 ml) were added. The aqueous phase was extracted with ethyl acetate (4×200 ml). The combined organic phases were dried over magnesium sulfate, and the solvent was removed in vacuo. The residue was purified by flash chromatography on silica (200 g), using ethyl acetate/heptane (1:3) as eluent, to afford 28.4 g of (1,1-dimethyl-3-oxobutyl)carbamic acid tert-butyl ester.

Triethyl phosphonoacetate (4.7 g; 20.9 mmol) was dissolved in tetrahydrofuran (36 ml). Potassium tert-butoxide (2.3 g; 20.9 mmol) was added and the reaction mixture was stirred for 40 min at room temperature. (1,1-Dimethyl-3-oxobutyl)carbamic acid tert-butyl ester (2.5 g; 11.6 mmol) was dissolved in tetrahydrofuran (15 ml) and added dropwise to the reaction mixture which was heated to reflux for 12 h. Ethyl acetate (100 ml) and hydrochloric acid (1 N; 100 ml) were added and the phases were separated. The aqueous phase was extracted with ethyl acetate (3×50 ml). The combined organic phases were washed with an aqueous solution of sodium hydrogen carbonate (saturated; 100 ml), dried (magnesium sulfate) and evaporated in vacuo. The residue was purified by flash chromatography on silica (120 g) using ethyl acetate/heptane (1:2) as eluent to afford 2.0 g of (2E)-5-tert-butoxycarbonylamino-3,5-dimethylhex-2-enoic acid ethyl ester.

$^1$H-NMR (CDCl$_3$) d 1.25 (t, 3H); 1.30 (s, 6H); 1.44 (s, 9H); 2.21 (s, 3H); 2.58 (s, 2H); 4.14 (q, 2H); 4.48 (s, 1H); 5.65 (s, 1H).

(2E)-5-tert-Butoxycarbonylamino-3,5-dimethylhex-2-enoic acid:

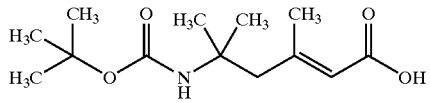

(2E)-5-tert-Butoxycarbonylamino-3,5-dimethylhex-2-enoic acid ethyl ester (1.95 g; 6.83 mmol) was dissolved in 1,4-dioxane (25 ml) and water (15 ml). Lithium hydroxide (0.18 g; 7.52 mmol) was added and the reaction mixture was stirred for 12 h at room temperature. Water (150 ml) and tert-butyl methyl ether (150 ml) was added. The aqueous phase was diluted with a 10% aqueous solution of sodium hydrogensulfate until pH 2.5 and extracted with tert-butyl methyl ether (3×100 ml). The combined organic phases were dried over magnesium sulfate and evaporated in vacuo. The residue was recrystallized from heptane (20 ml) to afford 0.6 g of (2E)-tert-Butoxycarbonylamino-3,5-dimethylhex-2-enoic acid.

$^1$H-NMR (CDCl$_3$) d 1.29 (s, 6H); 1.44 (s, 9H); 2.23 (s, 3H); 2.62 (s, 2H); 4.45 (s, 1H); 5.66 (s, 1H).

(2E)-5-(N-(tert Butoxycarbonyl)-N-methylamino)-5-methylhex-2-enoic acid.

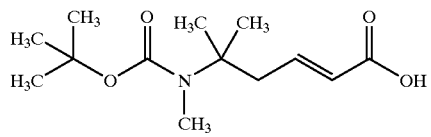

(2E)-5-(tert-Butyloxycarbonylamino)-5-methylhex-2-enoic acid (5.00 g; 20.6 mmol) was dissolved in tetrahydrofuran (70 ml). Methyliodide (10.3 ml; 164 mmol) was added and the solution was cooled to 0° C. Sodium hydride (60% in oil) (2.07 g; 61.6 mmol) was added in portions and the solution was stirred at room temperature for four days. Ethyl acetate (70 ml) and water (60 ml) was added dropwise and the solvent was removed in vacuo. The crude product was dissolved in water (40 ml) and ether (40 ml). The organic phase was washed with a saturated aqueous solution of sodium hydrogencarbonate (30 ml). The aqueous phases were mixed and 5% aqueous citric acid was added to pH 3. The aqueous phase was extracted with ethylacetate (4×50 ml). The organic phase was washed with water (2×40 ml), an aqueous solution of sodium thiosulfate (5%; 40 ml), water (40 ml), dried over MgSO₄ and the solvent was removed in vacuo. The residue was dissolved in ethylacetate (45 ml) and washed with an aqueous solution of sodium hydrogensulfate (10%; 3×30 ml), dried over MgSO₄ and concentrated in vacuo to give 4.00 g of (2E)-5-(N-(tert Butoxycarbonyl)-N-methylamino)-5-methylhex-2-enoic acid.

$^1$H-NMR (CDCl₃) δ 1.38 (s, 6H), 1.45 (s, 9H); 2.80 (d, 2H); 2.85 (s, 3H); 5.88 (d, 1H); 7.01 (q, 1H).

Example 1

(2E)-5-Amino-5-methylhex-2-enoic acid N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylamide

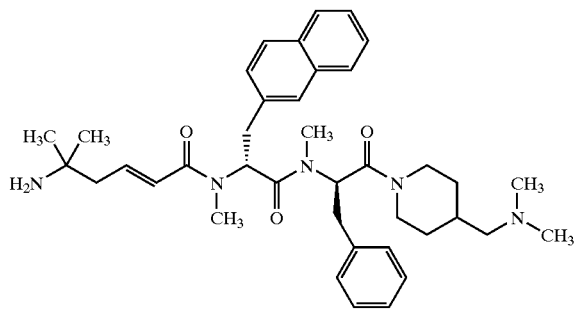

4-(Dimethylcarbamoyl)piperidine-1-carboxylic acid tert-butyl ester

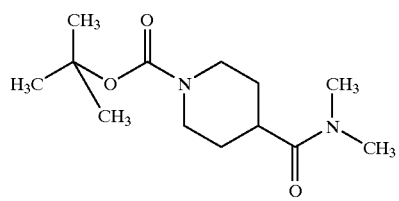

1-(tert-Butoxycarbonyl)piperidine-4-carboxylic acid (8.0 g, 35 mmol) was dissolved in dichloromethane (70 ml) and N,N-dimethylformamide (35 ml). 1-Hydroxy-7-azabenzotriazole (4.75 g, 35 mmol) was added. The solution was cooled to 0° C. N-3-dimethylaminopropyl)-N'-ethylcarbodiimide hydrochloride (6.69 g, 35 mmol) was added. The reaction mixture was stirred for 20 min at 0° C. A 5.6 M solution of dimethylamine in ethanol (37 ml, 209 mmol) was added. The reaction mixture was stirred for 3 days, while it was warming up to room temperature. It was diluted with ethyl acetate (400 ml) and washed with a 10% aqueous solution of sodium hydrogen sulfate (400 ml). The aqueous phase was extracted with ethyl acetate (2×200 ml). The combined organic layers were washed with a saturated aqueous solution of sodium hydrogen carbonate (300 ml) and dried over magnesium sulfate. The solvent was removed in vacua. The crude product was purified by flash chromatography on silica (300 g), using dichloromethane/methanol 20:1 as eluent, to give 4.56 g of 4-(dimethylcarbamoyl)piperidine-1-carboxylic acid tert-butyl ester.

$^1$H-NMR (CDCl₃): δ 1.47 (s, 9H); 1.70 (m, 4H); 2.60–2.90 (m, 3H); 2.96 (s, 3H); 3.08 (s, 3H); 4.17(m, 2H).

4-((Dimethylamino)methyl)piperidine-1-carboxylic acid tert-butyl ester

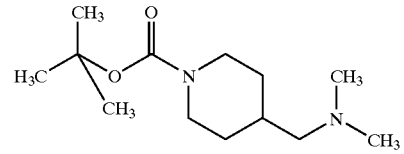

At 0° C. a solution of 4-((dimethylamino)methyl)piperidine-1-carboxylic acid tert-butyl ester (4.56 g, 18 mmol) in tetrahyrofuran (80 ml) was added dropwise to a suspension of sodium borohydride (1.61 g, 43 mmol) in tetrahydrofuran (80 ml). The reaction mixture was stirred for 20 min at 0° C. A solution of iodine 4.51 g, 18 mmol) in tetrahydrofuran (80 ml) was added dropwise at 0° C. The reaction mixture was heated to reflux for 16 h. It was cooled to 4° C. Methanol (200 ml) was added dropwise. The solvent was removed in vacuo. The residue was dissolved in a 20% aqueous solution of sodium hydroxide (200 ml) and tert-butyl methyl ether (150 ml). The phases were separated. The aqueous phase was extracted with tert-butyl methyl ether (3×100 ml). The combined organic layers were dried over magnesium sulfate. The solvent was removed in vacua. The crude product was purified by flash chromatography on silica (100 g), using dichloromethane/methanol/25% aqueous ammonia (100:10:1) as eluent, to give 4.07 g of 4-((dimethylamino)methyl)piperidine-1-carboxylic acid tert-butyl ester.

$^1$H-NMR (CDCl₃): δ 1.22 (m, 2H); 1.44 (s, 9H); 1.85 (d, 2H); 2.09 (m, 1H); 2.61 (s, 6H); 2.65 (m, 2H); 2.78 (t, 2H); 4.05 (d, 2H).

N,N-Dimethyl-N-((piperidin-4-yl)methyl)amine

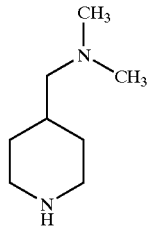

A 3 M solution of hydrogen chloride in ethyl acetate (120 ml, 360 mmol) was added to a solution of 4-((dimethylamino)methyl)piperidine-1-carboxylic acid tert-butyl ester (2.0 g, 14 mmol) in ethyl acetate (50 ml). The reaction mixture was stirred for 30 min at room temperature. The solvent was removed in vacuo to give 2.3 g of the crude dihydrochloride salt of N,N-dimethyl-N-((piperidin-4-yl)methyl)amine, which was used without purification for the next step.

¹H-NMR (CDCl₃, selected values): δ 1.48 (m, 2H); 1.92 (s, 6H); 3.22 (d, 2H).

N-[(1R)-1-Benzyl-2-(4-((dimethylamino)methyl)piperidin-1-yl)-2-oxoethyl]-N-methylcarbamic acid tert-butyl ester

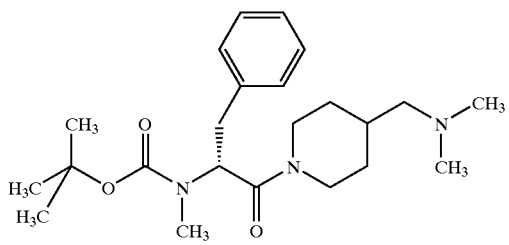

At 0° C., N-(3-dimethylaminopropyl)-N'-ethylcarbodiimide hydrochloride (1.158,g, 6.04 mmol) was added to a solution of (2R)-2-(N-(tert-butoxycarbonyl)-N-methylamino)-3-phenylpropionic acid (149 g, 6.04 mmol) and 1-hydroxy-7-azabenzotriazole (0.822 g, 6.04 mmol) in dichloromethane (25 ml) and N,N-dimethylformamide (12 ml). The reaction mixture was stirred for 20 min at 0° C. A solution of the crude dihydrochloride salt of N,N-dimethyl-N-((piperidin-4-yl)methyl)amine (1.3 g, 6.04 mmol) in N,N-dimethylformamide (10 ml) and dichloromethane (5 ml) and ethyldiisopropylamine (6.2 ml, 36.25 mmol) were added successively. The reaction mixture was stirred for 16 h, while it was warming up to room temperature. It was diluted with ethyl acetate (100 ml) and washed with a saturated aqueous solution of sodium hydrogen carbonate (100 ml). The organic layer was dried over magnesium sulfate. The solvent was removed in vacuo. The crude product was purified by flash chromatography on silica (100 g), using dichloromethane/methanol/25% aqueous ammonia (200:10:1) as eluent, to give 1.22 g of N-[(1R)-1-benzyl-2-(4-((dimethylamino)methyl)piperidin-1-yl)-2-oxoethyl]-N-methylcarbamic acid tert-butyl ester.

¹H-NMR (CDCl₃, selected values): δ 1.28, 1.11, 1.37, and 1.38 (all s, together 9H); 4.00 (m, 1H); 4.57 (m, 1H); 4.97 and 5.28 (both t, together 1H); 7.10–7.40 (m, 5H).

MS: 404 [M+1]⁺.

(2R)-1-(4-((Dimethylamino)methyl)piperidin-1-yl)-2-(methylamino)-3-phenylpropan-1-one

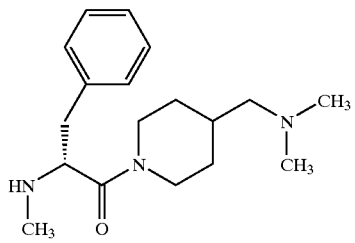

At 0° C., trifluoroacetic acid (20 ml) was added to a solution of N-[(1R)-1-benzyl-2-(4-((dimethylamino)methyl)piperidin-1-yl)-2-oxoethyl]-N-methylcarbamic acid tert-butyl ester (1.22 g, 3.02 mmol) in dichloromethane (20 ml). The reaction mixture was stirred for 1 h at 0° C. The solvents were removed in vacuo. The residue was dissolved in dichloromethane (70 ml) and the solvent was removed in vacuo. The latter procedure was repeated two times. The crude product was purified by flash chromatography on silica (100 g), using dichloromethane/methanol/25% aqueous ammonia (100:10:1), to give 659 mg of (2R)-1-(4-((dimethylamino)methyl)piperidin-1-yl)-2-(methylamino)-3-phenylpropan-1-one.

¹H-NMR (CDCl₃, selected values): δ 0.91 and 1.47 (m and d, together 1H); 1.27 (m, 1H); 4.62 (t, 1H).

N-((1R)-1-{N-[(1R)-1-Benzyl-2-(4-((dimethylamino)methyl)piperidin-1-yl)-2-oxoethyl]-N-methylcarbamoyl}-2-(2-naphthyl)ethyl)-N-methylcarbamic acid tert-butyl ester

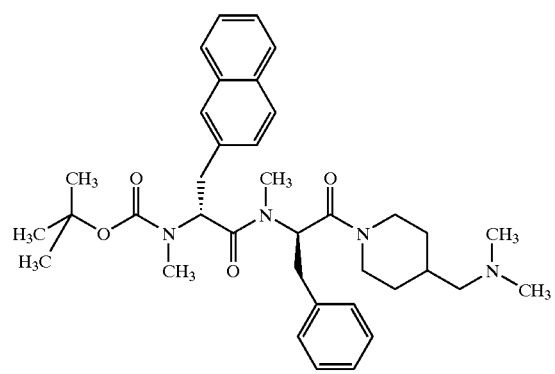

At 0° C., N-3-dimethylaminopropyl)-N'-ethylcarbodiimide hydrochloride (416 mg, 2.17 mmol) was added to a solution of (2R)-2-(N-(tert-butoxycarbonyl)-N-methylamino)-3-(2-naphthyl)-propioni acid (715 mg, 2.17 mmol) and 1-hydroxy-7-azabenzotriazole (296 mg, 2.17 mmol) in dichloromethane (20 ml) and N,N-dimethyformamide (10 ml). The reaction mixture was stirred for 20 min at 0° c. A solution of (2R)-1-(4-((dimethylamino)methyl)piperidin-1-yl)-2-(methylamino)-3-phenylpropan-1-one (659 mg, 2.17 mmol) in dichloromethane (10 ml) and N,N-dimethylformamide (5 ml) and ethyldiisopropylamine (0.56 ml, 3.26 mmol) were added successively. The reaction mixture was stirred for 16 h, while it was warming up to room temperature. It was diluted with ethyl acetate (100 ml) and washed with a saturated aqueous solution of sodium hydrogen carbonate (100 ml). The aqueous solution was extracted with ethyl acetate (3×50 ml). The combined organic layers were dried over magnesium sulfate. The solvent was removed in vacuo. The crude product was purified by flash chromatography 60 on silica (80 g), using ethyl acetate/heptane/triethylamine (1:1:0.08) as eluent, to give 1.05 g of N-((1R)-1-{N-[(1R)-1-benzyl-2-(4-(dimethylamino)methyl)piperidin-1-yl)-2-oxoethyl]-N-methylcarbamoyl}-2-(2-naphthyl)ethyl)-N-methylcarbamic acid tert-butyl ester.

¹H-NMR (CDCl₃, selected values): δ 1.24 and 1.42 (both s, together 9H); 5.04, 5.28, 5.44, 5.54, 5.73 (m, dd, dd, dd, and m, together 3H);

(2R)-N-[(1R)-1-Benzyl-2-(4-((dimethylamino)methyl)piperidin-1-yl)-2-oxoethyl]-N-methyl-2-(methylamino)-3-(2-naphthyl)propionamide

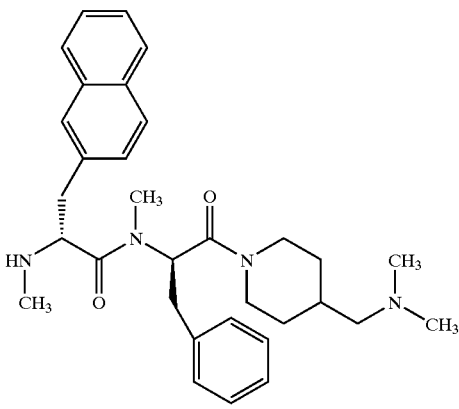

At 0° C., trifluoroacetic acid (18 ml) was added to a solution of N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylcarbamic acid tert-butyl ester (1.05 g, 1.71 mmol) in dichloromethane (18 ml). The reaction mixture was stirred for 50 min at 0° C. The solvents were removed in vacuo. The residue was dissolved in dichloromethane (50 ml) and the solvent was removed in vacuo. The latter procedure was repeated two times. The crude product was purified by flash chromatography on silica (80 g), using dichloromethane/methanol/25% aqueous ammonia as eluent, to give 846 mg of (2R)-N-[(1R)-1-benzyl-2-(4-((dimethylamino)methyl)piperidin-1-yl)-2-oxoethyl]-N-methyl-2-(methylamino)-3-(2-naphthyl)propionamide.

$^1$H-NMR (CDCl$_3$, selected values): δ 0.60 (m, 1H); 4.38 (t, 1H); 5.72 and 5.79 (both t, together 1H).

{(3E)-1-[N-((1R)-1-{N-[(1R)-1-Benzyl-2-(4-((dimethylamino)methyl)piperidin-1-yl)-2-oxoethyl]-N-methylcarbamoyl)-2-(2-naphthyl)ethyl)-N-methylcarbamoyl]-1,1-dimethylbut-3-enyl}carbamic acid tert-butyl ester At 0° C., N-(3-dimethylaminopropyl)-N'-ethylcarbodiimide hydrochloride (112 mg, 0.58 mmol) was added to a solution of (2E)-5-(tert-butoxycarbonylamino)-5-methylhex-2-enoic acid (142 mg, 0.58 mmol) and 1-hydroxy-7-azabenzotriazble (79 mg, 0.58 mmol) in dichloromethane (10 ml) and N,N-dimethylformamide (5 ml). The reaction mixture was stirred for 20 min at 0° C. A solution of (2R)-N-[(1R)-1-benzyl-2-(4-((dimethylamino)methyl)piperidin-1-yl)-2-oxoethyl]-N-methyl-2-(methylamino)-3-(2-naphthyl)propionamide (300 mg, 0.58 mmol) in dichloromethane (5 ml) and N,N-dimethylformamide (5 ml) and ethyldiisopropylamine 0.10 ml, 0.58 mmol) were added successively. The reaction mixture was stirred for 3 days, while it was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (70 g), using dichloromethane/methanol/25% aqueous ammonia (200:10:1) as eluent, to give 313 g of {(3E)-4-[N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester.

$^1$H-NMR (CDCl$_3$, selected values): δ 1.28 and 1.30 (both s, together 6H); 1.42 (s, 9H); 2.23, 2.27, 2.38, 2.43, 2.51, 2.52, 2.81, and 2.82 (all s, together 12H); 5.56, 5.76, and 5.90 (m, m, and dd, together 2H); 6.17 and 6.19 (both dd, together 1H); 6.94 (m, 1H).

At 0° C., trifluoroacetic acid (6 ml) was added to a solution of {(3E)-4-[N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester (212 mg, 0.29 mmol) in dichloromethane (6 ml). The reaction mixture was stirred for 20 min at 0° C. It was diluted with dichloromethane (30 ml). A saturated aqueous solution of sodium hydrogen carbonate (30 ml) was added dropwise. Solid sodium hydrogen carbonate was added, until pH 7 was obtained. The phases were separated. The aqueous phase was extracted with dichloromethane (3×50 ml). The combined organic layers were dried over magnesium sulfate. The solvent was removed in vacuo. The crude product was purified by flash chromatography on silica (20 g), using dichloromethane/methanol/25% aqueous ammonia (100:10:1) as eluent, to give 5 mg of the title compound.

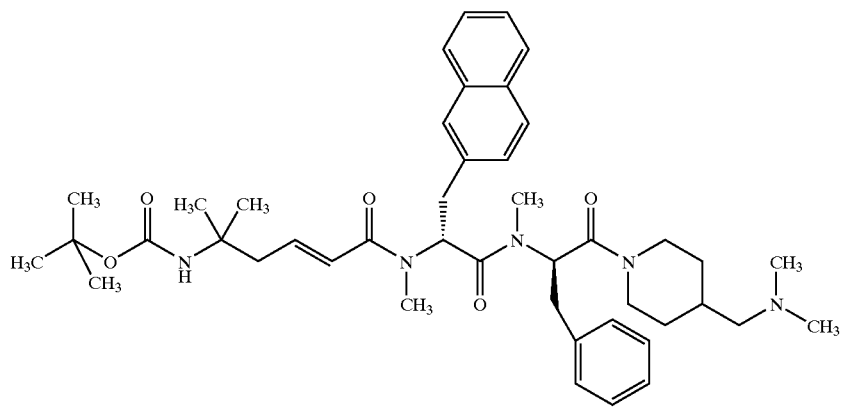

$^1$H-NMR (CDCl$_3$, selected values): δ 1.20 (s, 6H); 2.28, 2.32, 2.41, 2.49, 2.56, 2.57, 2.82, and 2.83 (all s, together 12H); 5.58, 5.78, and, 5.92 (m, m, and dd, together 2H); 6.16 and 6.19. (both d, together 1H); 7.00 (m, 1H).

HPLC: 39.23 min (A1). 41.55 min (B1).

MS: 640.4 [M+1]$^+$.

For biological testing, the title compound was transferred into its acetate salt by lyophilization with 0.5 M acetic acid (40 ml).

Example 2

(2E)-5-Amino-5-methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl)-2-(2-naphthyl)ethyl)-N-methylamide

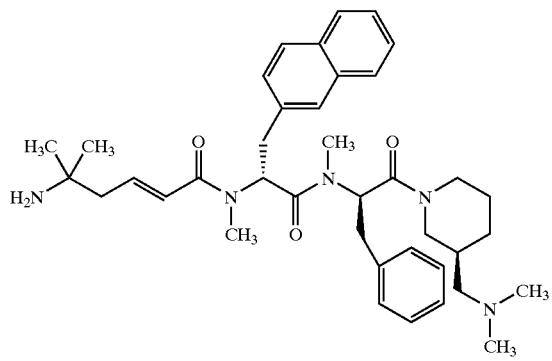

(3R)-Piperidine-1,3-dicarboxylic acid 1-tert-butyl ester 3-ethyl ester

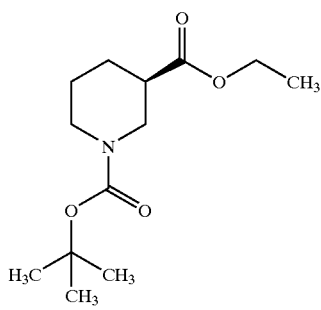

(R)-Ethyl nipetcotate tartrate (10.0 g, 32.5 mmol) were suspended in tetrahydrofuran (90 ml). An 1 N solution of sodium hydroxide in water (98 ml, 98 mmol) was added. A solution of di-tert-butyl dicarbonate (7.10 g, 32.5 mmol) in tetrahydrofuran (90 ml) was added. The reaction mixture was stirred for 16 h at room temperature. Ethyl acetate (400 ml) was added. The reaction mixture was washed with a 10% aqueous solution of sodium hydrogen sulfate (400 ml). The aqueous solution was extracted with ethyl acetate (2×200 ml). The combined organic layers were washed with a saturated aqueous solution of sodium hydrogen carbonate (200 ml) and dried over magnesium sulfate. The solvent was removed in vacuo. The crude product was purified by flash chromatography on silica (90 g), using ethyl acetate/heptane 1:4 as eluent, to give 4.13.g of (3R)-piperidine-1,3-dicarboxylic acid 1-tert-butyl ester 3-ethyl ester.

$^1$H-NMR (CDCl$_3$): δ 1.27 (t, 3H); 1.48 (s, 9H); 1.54 (m, 1H); 1.62 (m, 1H); 1.73 (m, 2H); 2.05 (m, 1H); 2.45 (m, 1H); 2.81 (m, 1H); 2.98 (br, 1H); 3.93 (m, 1H); 4.14 (q, 1H).

(3R)-3-Formylpiperidine-1-carboxylic acid tert-butyl ester

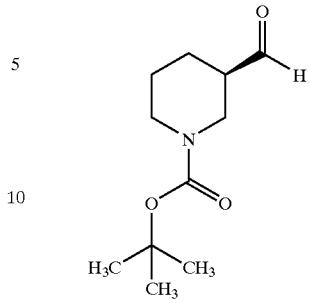

A 1.2 M solution of diisobutylaluminum hydride in toluene (30.8 ml, 36.9 mmol) was added at −78° C. to a solution of (3R)-piperidine-1,3-dicarboxylic acid 1-tert-butyl ester 3-ethyl ester (4.13 g, 16.1 mmol) in diethyl ether (30 ml). The reaction mixture was stirred for 2.5 h at −78° C. Water (9.6 ml) was added dropwise. The reaction mixture was warmed to room temperature. The precipitation was removed by filtration through a plug of celite. The celite was washed with tert-butyl methyl ether (3×100 ml). The liquids were combined and dried over magnesium sulfate. The solvent was removed in vacuo, to give 1.94 g of crude (3R)-3-formylpiperidine-1-carboxylic acid tert-butyl ester, which was used for the next step without further purification.

$^1$H-NMR (CDCl$_3$): δ 1.45 (s, 9H); 1.67 (m, 2H); 1.95 (m, 1H); 2.43 (m, 1H); 3.10 (m, 1H); 3.32 (dd, 1H); 3.52 (d, 1H); 3.66 (m, 1H); 3.95 (m, 1H); 9.69 (s, 1H).

(3S)-3-(Dimethylaminomethyl)piperidine-1-carboxylic acid tert-butyl ester

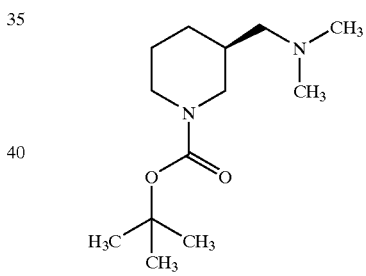

A solution of crude (3R)-3-formylpiperidine-1-carboxylic acid tert-butyl ester (1.94 g, 9.1 mmol) in dichloromethane (80 ml) was prepared. A 5.6 M solution of dimethylamine in ethanol (3.2 ml, 18.2 mmol) and mol sieves were added successively. Sodium triacetoxyborohydride (5.78 g, 27.3 mmol) was added to this mixture. Acetic acid (1.04 ml, 18.2 mmol) was added. The reaction mixture was stirred for 16 h at room temperature. An 1 N aqueous solution of sodium hydroxide (70 ml) and tert-butyl methyl ether (70 ml) were added. The phases were separated. The aqueous solution was extracted with tert-butyl methyl ether (3×70 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 866 mg of (3S)-3-(dimethylaminomethyl)piperidine-1-carboxylic acid tert-butyl ester.

$^1$H-NMR (CDCl$_3$): δ 1.10 (m, 1H); 1.45 (s, 9H), 1.45 (m, 1H); 1.64 (m, 2H); 1.85 (m, 1H); 2.10 (m, 2H); 2.20 (s, 6H); 2.50 (br, 1H); 2.79 (m, 1H); 3.95 (m, 2H).

N,N-Dimethyl-N-(((3R)-piperidin-3-yl)methyl)amine

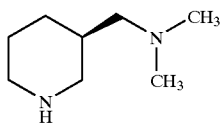

(3S)-3-(Dimethylaminomethyl)piperidine-1-carboxylic acid tert-butyl ester (1.25 g, 5.15 mmol) was dissolved in ethyl acetate (30 ml). A 2.7 M solution of hydrogen chloride in ethyl acetate (75 ml, 203 mmol) was added. The reaction mixture was stirred for 45 min at room temperature. The solvent was removed in vauco to give 976 mg of the crude dihydrochloride salt of N,N-dimethyl-N-(((3R)piperidin-3-yl)methyl)amine, which was used for the next step without further purification.

$^{1}$H-NMR (CD$_{3}$OD): δ 1.42 (m, 1H); 1.86 (m, 1H); 2.00 (m, 2H); 2.38 (m, 1H); 2.85 (t, 1H); 2.95 (s, 6H); 2.98 (m, 1H); 3.16 (m, 2H); 3.42 (m, 1H); 3.53 (m, 1H).

N-[(1R)-1-Benzyl-2-((3S)-3-(dimethylaminomethyl)piperidin-1-yl)-2-oxoethyl]-N-methylcarbamic acid tert-butyl ester

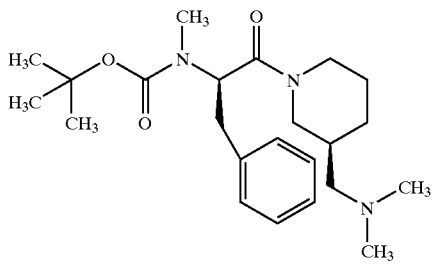

At 0° C. N-(3-dimethylaminopropyl)-N'-ethylcarbodiimide hydrochloride (870 mg, 4.54 mmol) was added to a solution (2R)-2-(N-(tert-butoxycarbonyl)-N-methylamino)-3-phenylpropionic acid (1.27 g, 4.54 mmol) and 1-hydroxy-7-azabenzotriazole (617 mg, 4.54 mmol) in dichloromethane (20 ml) and N,N-dimethylformamide (10 ml). The reaction mixture was stirred for 20 min at 0° C. A solution of the crude dihydrochloride salt of N,N-dimethyl-N-(((3R)-piperidin-3-yl)methyl)amine (976 mg, 4.54 mmol) in dichloromethane (20 ml) and N,N-dimethylformamide (10 ml) and ethyldiisopropylamine (3.9 ml, 22.7 mmol) were added successively. The reaction mixture was stirred for 3 days, while it was warming up to room temperature. Ethyl acetate (300 ml) was added. The solution was washed with a saturated aqueous solution of sodium hydrogen carbonate (300 ml). The aqueous phase was extracted with ethyl acetate (2×200 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 1.69 g of N-[(1R)-1-benzyl-2-((3S)-3-(dimethylaminomethyl)piperidin-1-yl)-2-oxoethyl]-N-methylcarbamic acid tert-butyl ester.

$^{1}$H-NMR (CDCl$_{3}$, selected values): δ 1.20, 1.24, 1.31, and 1.32 (all s, together 9H); 2.12. 2.13, and 2.18 (all s, together 6H); 2.81 (m, 3H); 4.97 and 5.30 (both m, together 1H); 7.05–7.35 (m, 5H).

(2R)-1-((3S)-3-((Dimethylamino)methyl)piperidin-1-yl)-2-methylamino-3-phenylpropan-1-one

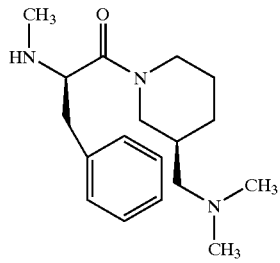

At 0° C., trifluoroacetic acid (25 ml) was added to a solution of N-[(1R)-1-benzyl-2-((3S)-3-(dimethylaminomethyl)piperidin-1-yl)-2-oxoethyl]-N-methylcarbamic acid tert-butyl ester (1.69 g, 4.2 mmol) in dichloromethane (25 ml). The reaction mixture was stirred for 30 min at 0° C. The solvent was removed in vacuo. The residue was dissolved in dichloromethane (100 ml) and the solvent was removed in vacuo. The latter procedure was repeated two times. The crude product was purified by flash chromatography on silica (90 g), using dichloromethane/methanol/25% aqueous ammonia (100:10:1) as eluent, to give 1.15 g of (2R)-1-((3S)-3-((dimethylamino)methyl)piperidin-1-yl)-2-methylamino-3-phenylpropan-1-one.

$^{1}$H-NMR (CDCl$_{3}$, selected values): δ 0.38, 1.11, 1.37, and 1.65 (all m, together 4H); 2.11, 2.19, 2.25, and 2.31 (all s, together 9H); 4.37 and 4.53 (both m, together 1H); 7.10–7.35 (m, 5H).

N-((1R)-1-{N-[(1R)-1-Benzyl-2-((3S)-3-((dimethylamino)methyl)piperidin-1-yl)-2-oxoethyl]-N-methylcarbamoyl}-2-(2-naphthyl)ethyl)-N-methylcarbamic acid tert-butyl ester

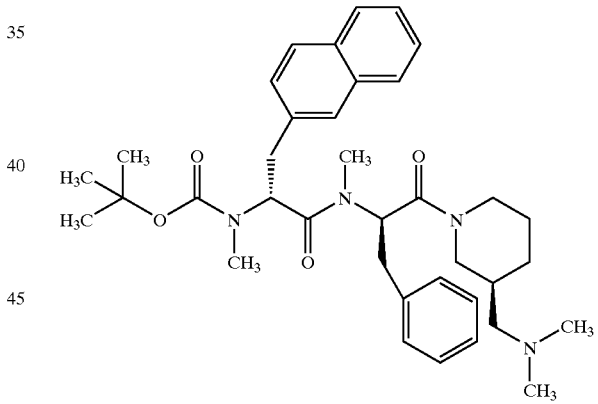

At 0° C. N-(3-dimethylaminopropyl)-N'-ethylcarbodiimide hydrochloride (379 mg, 1.98 mmol) was added to a solution of (2R)-2-(N-(tert-butoxycarbonyl)-N-methylamino)-3-(2-naphthyl)propionic acid (651 mg, 1.98 mmol) and 1-hydroxy-7-azabenzotriazole (269 mg, 1.98 mmol) in dichloromethane (10 ml) and N,N-dimethylformamide (5 ml). The reaction mixture was stirred for 20 min at 0° C. A solution of (2R)-1-((3S)-3-((dimethylamino)methyl)piperidin-1-yl)-2-methylamino-3-phenylpropan-1-one (600 mg, 1.98 mmol) in dichloromethane (10 ml) and ethyldiisopropylamine (0.51 ml, 2.97 mmol) were added successively. The reaction mixture was stirred for 3 days, while it was warming up to room temperature. Ethyl acetate (100 ml) was added. The solution was washed with a saturated aqueous solution of sodium hydrogen carbonate (100 ml). The aqueous phase was extracted with ethyl acetate (3×50 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 1.18 g of N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-phethylcarbamic acid tert-butyl ester.

¹H-NMR (CDCl₃, selected values): δ 0.45 and 0.71 (both m, together 1H); 1.03, 1.05, 1.15, 1.20, 1.28, 1.36, and 1.42 (all s, together 9H); 2.12, 2.15, 2.21, 2.26, 2.29, 2.85 (all s, together 6H); 5.05, 5.44, 5.58, 5.71, 5.85, and 6.00 (all s, together 2H); 7.10–7.80 (m, 12H).

(2R)-N-[(1R)-1-Benzyl-2-((3S)-3-((dimethylamino)methyl) piperidin-1-yl)-2-oxoethyl]-N-methyl-2-(methylamino)-3-(2-naphthyl)propionamide

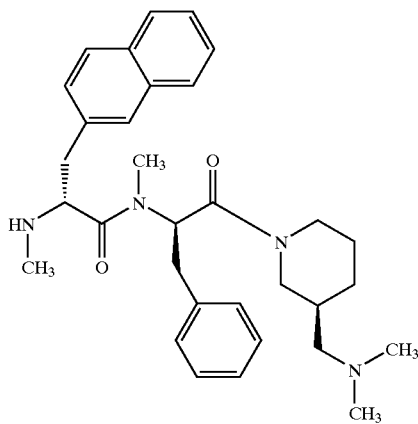

At 0° C., trifluoroacetic acid (20 ml) was added to a solution of N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-methylcarbamic acid tert-butyl ester (1.189, 1.92 mmol) in dichloromethane (20 ml). The reaction mixture was stirred for 50 min at 0° C. The solvent was removed in vacuo. The residue was dissolved in dichloromethane (80 ml) and the solvent was removed in vacuo. The latter procedure was repeated two times. The crude product was purified by flash chromatography on silica (40 g), using dichloromethane/methanol/25% aqueous ammonia (100:10:1) as eluent, to give 788 mg of (2R)-N-[(1R)-1-benzyl-2-((3S)-3-((dimethylamino)m ethyl) piperidin-1-yl)-2-oxoethyl]-N-methyl-2-(methylamino)-3-(2-naphthyl)propionamide.

¹H-NMR (CDCl₃, selected values): δ 2.01 and 2.25 (both s, together 9H); 3.72 (m, 2H); 3.95 and 4.27 (both m, together 1H); 5.77, 5.86, and 6.03 (t, m, and dd, together 1H); 7.10 and 7.85 (m, 12H).

{(3E)-4-[N-((1R)-1-{N-[(1R)-1-Benzyl-2-((3S)-3-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester

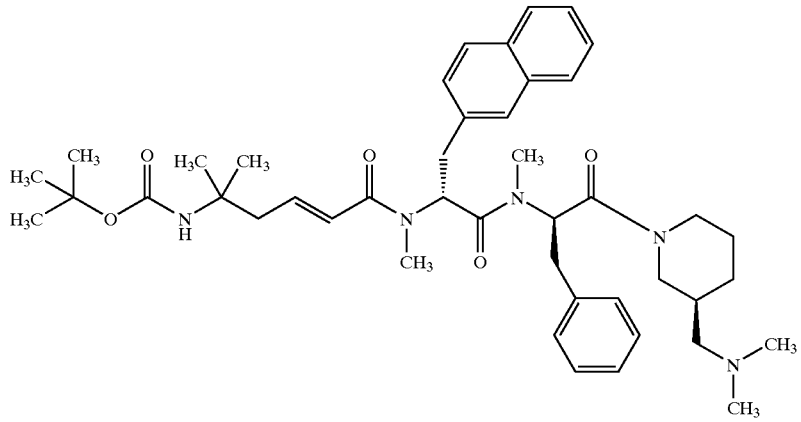

At 0° C., N-(3-dimethylaminopropyl)-N'-ethylcarbodiimide hydrochloride (105 mg, 0.55 mol) was added to a solution of (2E)-5-(tert-butoxycarbonylamino)-5-methylhex-2-enoic (136 mg, 0.55 mmol) and 1-hydroxy-7-azabenzotriazole (74 mg, 0.55 mmol) in dichloromethane (5 ml). The reaction mixture was stirred for 20 min at 0° C. A solution of (2R)-N-[(1R)-1-benzyl-2-((3S)-3-((dimethylamino)methyl)piperidin-1-yl)-2-oxoethyl]-N-methyl-2-(methylamino)-3-(2-naphthyl)propionamide (281 mg, 0.55 mmol) in dichloromethane (5 ml) and N,N-dimethylformamide (5 ml) and ethyldiisopropylamine (0.094 ml, 0.55 mmol) were added successively. The reaction mixture was stirred for 16 h, while it was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 398 mg of {(3E)-4-[N-((1R)-1-N-[(1R)-1-benzyl-2-((3S)-3-((dimethylamino)methyl) piperidin-1-yl)-2-oxoethyl]-N-methylcarbamoyl}-2-2-naphthyl)ethyl)-N-methylcarbamoyl]1,1-dimethylbut-3-enyl}carbamic acid tert-butyl ester.

¹H-NMR (CDCl₃, selected values): δ 1.44 (s, 9H); 5.58, 5.75, and 5.86 (all m, 2H); 6.09 and 6.17 (both d, together 1H); 6.84 (m, 1H); 7.10–7.80 (m, 12H).

At 0° C., trifluoroacetic acid (7 ml) was added to a solution of {(3E)-4-[N-((1R)-1-{N-[(1R)-1-benzyl-2-((3S)-3-((dimethylamino)methyl)piperidin-1-yl)-2-oxoethyl]-N-methylcarbamoyl)-2-(2-naphthyl)ethyl)-N-methylcarbamoyl]-1,1-dimethylbut-3-enyl}carbamic acid tert-butyl ester (398 mg, 0.54 mmol) in dichloromethane (7 ml). The reaction mixture was stirred for 40 min at 0° C. The solvent was removed in vacuo. The residue was dissolved in dichloromethane (20 ml) and the solvent was removed in vacuo. The latter procedure was repeated two times. The crude product was purified by flash chromatography on silica (40 g), using dichloromethane/methanol/25% aqueous ammonia (100:10:1) as eluent, to give 150 mg of the title compound.

$^1$H-NMR (CDCl$_3$, selected values): δ 1.08,1.12, 1.14, and 1.15 (all s, together 6H), 5.46, 5.59, 5.75, and 5.94 (all m, together 2H); 6.15 (m,1H); 6.93 (m, 1H).

HPLC 27.55 min (A1). 30.23 min (B1).

LC-MS: 640.4 [M+1]$^+$ at 8.54 min.

For biological testing, the title compound was transferred into its acetate salt, by lyophilization from 0.5 M acetic acid (40 ml).

Example 3

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

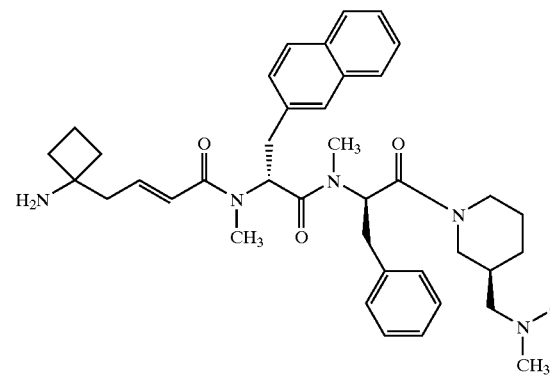

(1-{(2E)-3-[N-((1R)-1-{N-[(1R)-1-Benzyl-2-((3S)-3-((dimethylamino)methyl)piperidin-1-yl)-2-oxoethyl]-N-methylcarbamoyl}-2-(2-naphthyl)ethyl)-N-methylcarbamoyl]allyl}cyclobutyl)carbamic acid tert-butyl ester

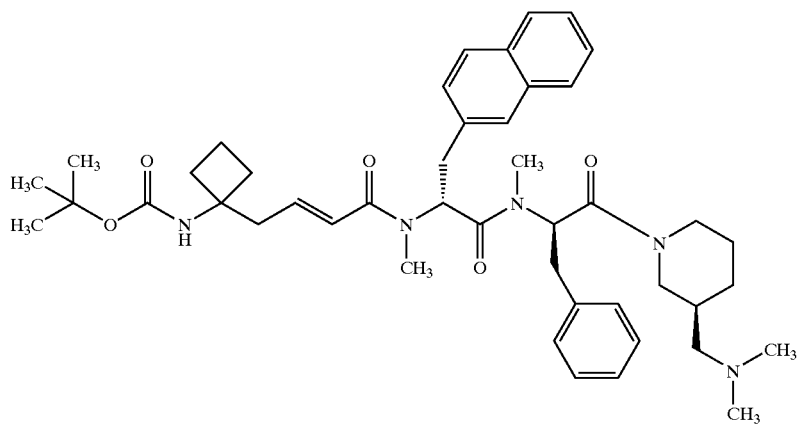

At 0° C., N-(3-dimethylaminopropyl)-N'-ethylcarbodiimide hydrochloride (85 mg, 0.44 mmol) was added to a solution of (2E)-5-(tert-butoxycarbonylamino)-5-methylhex-2-enoic acid (113 mg, 0.44 mmol) and 1-hydroxy-7-azabenzotriazole (60 mg, 0.44 mmol) in dichloromethane (5 ml) and N,N-dimethylformamide (5 ml). The reaction mixture was stirred for 20 min at 0° C. A solution of (2R)-N-[(1R)-1-benzyl-2-((3S)-3-((dimethylamino)methyl)piperidin-1-yl)-2-oxoethyl]-N-methyl-2-(methylamino)-(2-naphthyl)propionamide (228 mg, 0.44 mmol) in dichloromethane (10 ml) and ethyldiisopropylamine (0.07 ml, 0.44 mmol) were added successively. The reaction mixture was stirred for 16 h, while i was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 314 mg of (1((2E)-3-[N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-methylcarbamoyl]allyl}cyclobutyl)carbamic acid tert-butyl ester.

$^1$H-NMR (CDCl$_3$, selected values): δ 1.40 (m, 9H); 4.22 and 4.67 (both m, together 2H); 5.60, 5.75, 5.85, and 5.90 (dd, dd, m, and m, together 2H); 6.10 and 6.19 (both d, together 1H); 6.73 and 6.87 (both m, together 1H); 7.22, 7,42, and 7.76 (all m, together 12H).

At 0° C., trifluoroacetic acid (7 ml) was added to a solution of (1-{(2E)-3-[N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-methylcarbamoyl]allyl}cyclobutyl)carbamic acid tert-butyl ester (314 mg, 0.42 mmol) in dichloromethane (7 ml). The reaction mixture was stirred for 20 min at 0° C. The solvent was removed in vacuo without heating. The residue was dissolved in dichloro methane (20 ml) and the solvent was removed in vacuo. The latter procedure was repeated two times. The crude product was purified by flash chromatography on silica (40 g), using dichloromethane/methanol ammonia (100:10:1) as eluent, to give 180 mg of the title compound.

$^1$H-NMR (CDCl$_3$, selected values): δ 0.40 and 0.74 (both m, together 2H); 3.73 and 4.22 (both m, together 2H); 5.57, 5.77, and 5.91 (all m, together 2H); 6.15 and 6.24 (both d, together 1H); 6.85 and 6.96 (both m, together 1H); 7,22, 7,92, and 7.74 (all m, together 12H).

HPLC: 28.03 min (A1). 29.92 min (B1).

MS: 652.4 [M+1]$^+$.

For biological testing, the title compound was transferred into its diacetate salt, by lyophilization from 0.5 M acetic acid (40 ml).

Example 4

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

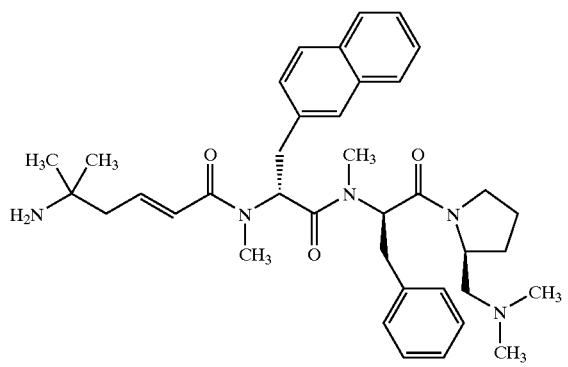

(2S)-Pyrrolidine-1,2-dicarboxylic acid 1-tert-butyl ester 2-ethyl ester

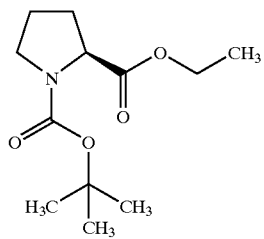

N-tert-Butoxycarbonylprolin (24.38 g, 113 mmol) was dissolved in dichloromethane (60 ml). Ethanol (7.9 ml, 135 mmol) and 4-dimethylaminopyridine (1.52 g, 12.5 mmol) were added. The solution was cooled to 0° C. N-(3-dimethylaminopropyl)-N'-ethylcarbodiimide hydrochloride (23.88 g, 125 mmol) was added. The reaction mixture was stirred for 16 h, while it was warming up to room temperature. Ethyl acetate (400 ml) was added. It was washed with a 10% aqueous solution of sodium hydrogen sulfate (300 ml). The aqueous phase was extracted with ethyl acetate (3×200 ml). The combined organic layers were washed with a saturated aqueous solution of sodium hydrogen carbonate (300 ml) and dried over magnesium sulfate. The solvent was removed in vacuo. The crude product was purified by flash chromatography on silica (400 g), using ethyl acetate (1:4) as eluent, to give 17.11 g of (2S)-pyrrolidine-1,2-dicarboxylic acid 1-tert-butyl ester 2-ethyl ester.

$^1$H-NMR (CDCl$_3$): δ 1.28 (m, 3H); 1.43 and 1.46 (both s, together 9H); 2.95 (m, 3H); 2.22 (m, 1H); 3.50 (m, 2H), 4.18 and 4.30 (m and dd, together 3H).

N-t-Butyloxycarbonyl-(S)-prolinal

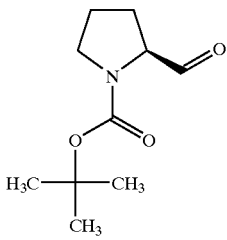

At −78° C., a 1.2 M solution of diisobutylaluminum hydride (31.7 ml, 38 mmol) in toluene was added dropwise to a solution of (2S)-pyrrolidine-1,2-dicarboxylic acid 1-tert-butyl ester 2-ethyl ester (4.02 g, 16.5 mmol) in diethyl ether (1.5 ml). The reaction mixture was stirred for 3 h at −78° C. Water (9.9 ml) was added dropwise. The reaction mixture was warmed to room temperature. The mixture was filtered through a plug of celite. The celite was washed with tert-butyl methyl ether (3×100 ml). The combined organic layers were dried over magnesium sulfate. The solvent was removed in vacuo, to give 2.34 g of crude N-t-butyloxycarbonyl-(S)-prolinal, which was used for the next step without further purification.

$^1$H-NMR (CDCl$_3$): δ 1.42 and 1.47 (both s, together 9H); 1.70–2.20 (m, 4H); 3.20–4.30 (m, 3H); 9.45 and 9.55 (both s, together 1H).

(2S)-2-((Dimethylamino)methyl)pyrrolidine-1-carboxylic acid tert-butyl ester

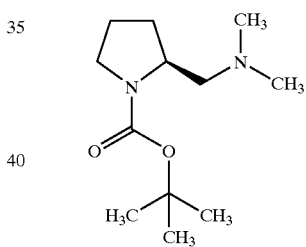

Crude N-t-butyloxycarbonyl-(S)-prolinal (2.34 g, 11.7 mmol) was dissolved in dichloromethane (90 ml). A 5.6 M solution of dimethylamine in ethanol (4.19 ml, 23.5 mmol) was added. 0.4 nm Mol sieves (10.0 g) was added. Sodium triacetoxyborohydride 7.47 g, 35.2 mmol) and glacial acetic acid (1.34 ml, 23.5 mmol) were added successively. The reaction mixture was stirred for 3 days. It was filtered through a plug of celite. The celite was washed with methanol (150 ml). An 1N aqueous solution of sodium hydroxide (150 ml) and tert-butyl methyl ether (150 ml) were added. The phases were separated. The aqueous phase was extracted with tert-butyl methyl ether (3×100 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 1.29 g of (2S)-2-((dimethylamino)methyl)pyrrolidine-1-carboxylic acid tert-butyl ester.

$^1$H-NMR (CDCl$_3$): δ 1.48 (s, 9H); 1.90 (m, 4H); 2.15 and 2.23 (AB, 2H); 2.26 (s, 6H); 3.31 (br, 2H); 3.85 (br, 1H).

N-Dimethyl-N-(((2S)-pyrrolidin-2-yl)methyl)amine

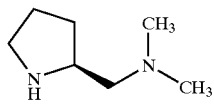

A 2.7 M solution of hydrogen chloride in ethyl acetate (75 ml, 202 mmol) was given to a solution of (2S)-2-((dimethylamino)methyl)pyrrolidine-1-carboxylic acid tert-butyl ester (1.29 g, 5.65 mmol) in ethyl acetate (30 ml). The reaction mixture was stirred for 30 min at room temperature. The solvent was removed in vacuo to give 1.36 g of the crude dihydrochloride salt of N-dimethyl-N-(((2S)-pyrrolidin-2-yl)methyl)amine, which was used for the next step without further purification.

$^1$H-NMR (CDCl$_3$): δ 1.90 (m, 2H); 2.17 (m, 1H); 2.40 (m, 1H); 2.90 (m, 2H); 3.14 (s, 6H); 3.55 (m, 2H); 4.35 (m, 1H).

N-[(1R)-1-Benzyl-2-(2S)-2-((dimethylamino)methyl)pyrrolidin-1-yl)-2-oxoethyl]-N-methylcarbamic acid tert-butyl ester

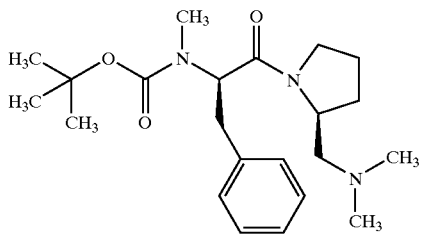

At 0° C., N-(3-dimethylaminopropyl)-N'-ethylcarbodiimide hydrochloride (1.30 g, 6.76 mmol) was added to a solution of (2R)-2-(N-tert-butoxycarbonyl)-N-methylamino)-3-phenylpropionic acid (1.89 g, 6.76 mmol) and 1-hydroxy-7-azabenzotriazole 0.92 g, 6.76 mmol) in dichloromethane (10 ml). The reaction mixture was stirred for 20 min at 0° C. A solution of the crude dihydrochloride salt of N-dimethyl-N-(((2S)-pyrrolidin-2-yl)methyl)amine (1.36 g, 6.76 mmol) in dichloromethane (10 ml) and N,N-dimethylformamide (10 ml) and ethyldiisopropylamine (5.75 ml, 33.8 mmol) were added successively. The reaction mixture was stirred for 16 h, while it was warming up to room temperature. It was diluted with ethyl acetate (100 ml) and washed with a saturated aqueous solution of sodium hydrogen carbonate (100 ml). The aqueous phase was extracted with ethyl acetate (3×80 ml). The combined organic layers were dried over magnesium sulfate. The solvent was removed in vacuo. The crude product was purified by flash chromatography on silica (90 g), using dichloromethane/methanol/25% aqueous ammonia (100.10:1) as eluent, to give 2.26 g of N-[(1R)-1-benzyl-2-((2S)-2-((dimethylamino)methyl)pyrrolidin-1-yl)-2-oxoethyl]-N-methylcarbamic acid tert-butyl ester.

$^1$H-NMR (CDCl$_3$, selected values): δ 1.20, 1.33, and 1.37 (all s, together 9H); 2.22 and 2.28 (both s, together 6H); 2.82 and 2.84 (both s, together 3H); 4.25 (m, 1H); 4.80, 5.1 1, and 5.30 (dd, t, and m, together 1H); 7.10–7.30 (m, 5H).

C$_{22}$H$_{35}$N$_3$O$_3$[389.5]; calc. C, 67.83; H, 9.06; N, 10.79; found C, 67.39; H, 9.13; N, 10.73.

(2R)-1-((2S)-2-((Dimethylamino)methyl)pyrrolidin-1-yl)-2-methylamino-3-phenylpropan-1-one

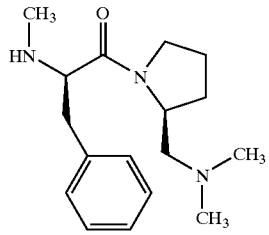

At 0° C., trifluoroacetic acid (8 ml) was added to a solution of N-[(1R)-1-benzyl-2-((2S)-2-((dimethylamino)methyl)pyrrolidin-1-yl}-2-oxoethyl]-N-methylcarbamic acid tert-butyl ester (2.26 g, 5.80 mmol) in dichloromethane (8 ml). The reaction mixture was stirred for 20 min at 20 0° C. The solvent was removed in vacuo. Dichloromethane (70 ml) was added, and the solvent was removed in vacuo. The latter procedure was repeated two times. The crude product was purified by flash chromatography on silica (90 g), using dichloromethane/methanol/25% aqueous ammonia (100:10:1) as eluent, to give 1.24 g of (2R)-1-((2S)-2-((dimethylamino)methyl)pyrrolidin-1-yl)-2-methylamino-3-phenylpropan-1-one.

$^1$H-NMR (CDCl$_3$, selected values): δ 2.33 (s, 3H); 2.43 (s, 6H); 3.25 (m, 3H); 4.17 (m, 1H); 7.25 (m, 5H).

N-((1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methylcarbamic acid tert-butyl ester

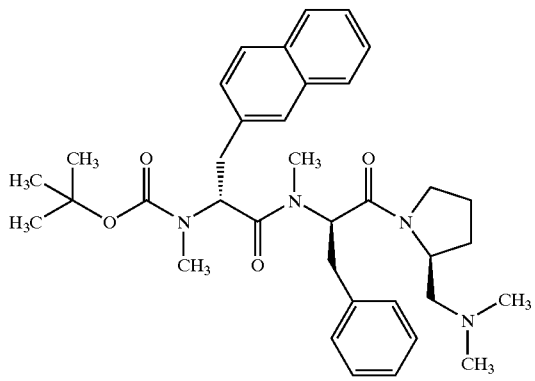

At 0° C., N-(3-dimethylaminopropyl)-N'-ethylcarbodiimide hydrochloride (530 mg, 2.76 mmol) was added to a solution of (2R)-2-(N-(tert-butoxycarbonyl)-N-methylamino)-3-(2-naphthyl)propionic acid (911 mg, 2.76 mmol) and 1-hydroxy-7-azabenzotriazole (376 mg, 2.76 mmol) in dichloromethane (5 ml). The reaction mixture was stirred for 20 min at 0° C. A solution of (2R)-1-((2S)-2-((dimethylamino)methyl)pyrrolidin-1-yl)-2-methylamino-3-phenylpropan-1-one (800 mg, 2.76 mmol) in dichloromethane (5 ml) and N,N-dimethylformamide (5 ml) and ethyldiisopropylamine (0.71 ml, 4.15 mmol) were added successively. The reaction mixture was stirred for 3 days, while it was warming up to room temperature, It was diluted with ethyl acetate (100 ml) and washed with a saturated aqueous solution of sodium hydrogen carbonate (100 ml). The aqueous solution was extracted with ethyl acetate (3×70 ml). The combined organic layers were dried over magnesium sulfate. The solvent was removed in vacuo. The crude product was purified by flash chromatography on silica (90 g), using dichloromethane/methanol/25% aqueous ammonia (200:10:1) as eluent, to give 1.37 g of N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamic acid tert-butyl ester.

¹H-NMR (CDCl₃, selected values): δ 0.64 (m, 1H); 1.10, 1.29, 1.36, and 1.47 (all s, together 9H); 4.99, 5.09, 5.45, and 5.53 (t, t, m, and t, together 2H); 7.10–7.90 (m, 12H).

(2R)-N-[(1R)-1-Benzyl-2-((2S)-2-((dimethylamino)methyl)pyrrolidin-1-yl)-2-oxoethyl]-N-methyl-2-(methylamino)-3-(2-naphthyl)propionamide

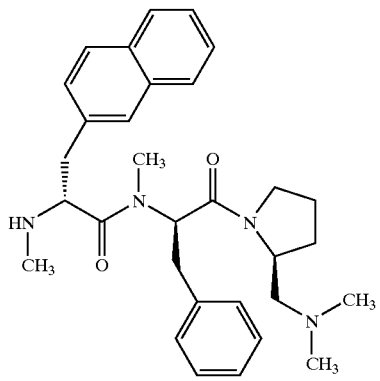

At 0° C., trifluoroacetic acid (10 ml) was added to a solution of N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamic acid tert-butyl ester.(1.37 g, 2.28 mmol) in dichloromethane (10 ml). The reaction mixture was stirred for 75 min at 0° C. The solvent was removed in vacuo. The residue was dissolved in dichloromethane (70 ml) and the solvent was removed in vacuo. The latter procedure was repeated two times. The crude product was purified by flash chromatography on silica (90 g), using dichloromethane/methanol/25% aqueous ammonia (100:10:1) as eluent, to give 692 mg of (2R)-N-[(1R)-1-benzyl-2-((2S)-2-((dimethylamino)methyl)pyrrolidin-1-yl)-2-oxoethyl]-N-methyl-2-(methylamino)-3-(2-naphthyl)propionamide.

¹H-NMR (CDCl₃, selected values): δ 1.85 and 2.01 (both s, together 3H); 2.20 and 2.31 (both s, together 6H); 3.65 and 3.80 (both t, 1H); 4.04 and 4.45 (both m, together 1H); 5.60 and 5.91 (t and dd, together 1H); 7.10–7.90 (m, 12H).

{(3E)-4-[N-((1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester

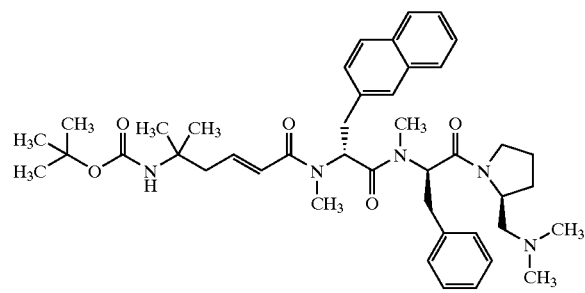

At 0° C., N-(3-dimethylaminopropyl)-N'-ethylcarbodiimide hydrochloride (132 mg, 0.69 mmol) was added to a solution of (2E)-5-(tert-butoxycarbonylamino)-5-methylhex-2-enoic acid (168 mg, 0.69 mmol) and 1-hydroxy-7-azabenzotriazole (94 mg, 0.69 mmol) in dichloromethane (5 ml). The reaction mixture was stirred for 20 min at 0° C. A solution of (2R)-N-[(1R)-1-benzyl-2-((2S)-2-((dimethylamino)methyl)pyrrolidin-1-yl)-2-oxoethyl]-N-methyl-2-(methylamino)-3-(2-naphthyl)propionamide (345 mg, 0.69 mmol) in dichloromethane (10 ml) and N,N-dimethylformamide (5 ml) and ethyldiisopropylamine were added successively. The reaction mixture was stirred for 16 h, while it was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 491 mg of {(3E)-4-[N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester.

¹H-NMR (CDCl₃, selected values): δ 1.30 and 1.32 (both s, together 6H); 1.45 (s, 9H); 1.60 (m, 2H); 4.00 (m, 1H); 4.48 (m, 1H); 5.48 (dd, 1H); 5.92 (dd, 1H); 6.11 and 6.20 (both d, together 1H); 6.82 and 6.92 (both m, together 1H); 7.10–7.90 (m, 12H).

At 0° C., trifluoroacetic acid (7 ml) was added to a solution of {(3E)-4-[N-((1R)-1-{N-[(1R)-1-benzyl-2-((2S)-2(dimethylamino)methyl)pyrrolidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester (491 mg, 0.68 mmol) in dichloromethane (7 ml). The reaction mixture was stirred for 60 min at 0° C. The solvent was removed in vacuo. The residue was dissolved in dichloromethane (100 ml) and the solvent was removed in vacuo. The latter procedure was repeated two times. The crude product was purified by flash chromatography on silica (40 g), using dichloromethane/methanol/25% ammonia (100:10:1) as eluent, to give 285 mg of the title compound.

¹H-NMR (CDCl₃, selected values): δ 0.55 (m, 1H); 1.11, 1.12, and 1.17 (all s, together 6H); 2.25 (s, 6H); 2.45 (s, 3H); 2.85 (s, 3H); 4.02 (m, 1H); 5.48 (dd, 1H); 5.80 and 5.93 (m, and dd, together 1H); 6.10 and 6.18 (both d, together 1H); 6.87 and 7.00 (both m, together 1H); 7.10–7.90 (m, 12H).

HPLC 27.97 min (A1). 27.80 min (B1).

MS: 626.4 [M+1]⁺.

For biological testing, the title compound was transferred into its diacetate salt by lyophilization from 0.5 acetic acid (40 ml).

Example 5

N-((1R)-1-{N-[(1R)-1-Benzyl-2-((2S)-2-((dimethylamino)methyl)pyrrolidin-1-yl)-2-oxoethyl]-N-methylcarbamoyl)-2-(2-naphthyl)ethyl)-N-methyl-3-((methylamino)methyl)benzamide

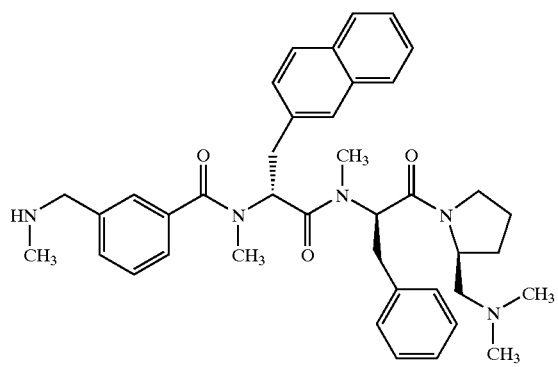

N-3-[N(1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]benzyl)-N-methylcarbamic acid tert-butyl ester

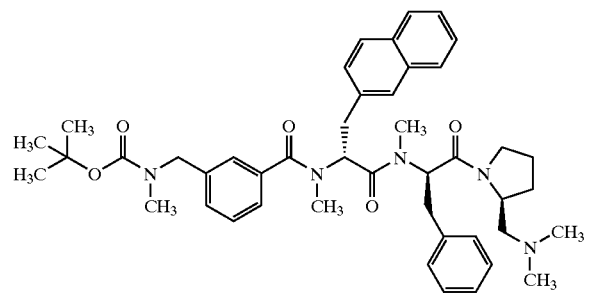

At 0° C. N-(dimethylaminopropyl)-N'-ethylcarbodiimide hydrochloride (132 mg, 0.69 mmol) was added to a solution of 3-(N-(tert-butoxycarbonyl)-N-methylamino)benzoic acid (183 mg, 0.69 mmol) and 1-hydroxy-7-azabenzotriazole (94 mg, 0.69 mmol) in dichloromethane (5 ml). The reaction mixture was stirred for 20 min at 0° C. A solution of (2R)-N-[(1R)-1-benzyl-2-((2S)-2-((dimethylamino)methyl)pyrrolidin-1-yl)-2-oxoethyl]-N-methyl-2-(methylamino)-3-(2-naphthyl)propionamide (345 mg, 0.69 mmol) in dichloromethane (10 ml) and N,N-dimethylformamide (5 ml) and ethyldiisopropylamine (0.118 ml) were added successively. The reaction mixture was stirred for 16 h, while it was warming up to room temperature. It was diluted with ethyl acetate and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 524 mg of N-{3-[N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]benzyl}-N-methylcarbamic acid tert-butyl ester.

$^1$H-NMR (CDCl$_3$, selected values): δ 0.72 (m, 1H); 1.45 (br, 9H); 3.18 (br, 6H); 4.05 (m, 1H); 4.32 and 4.40 (both br, together 2H); 5.60 (dd, 1H); 5.95 (m, 1H); 6.80–6.90 (m, 16H).

At 0° C., trifluoroacetic acid (7 ml) was added to a solution of N-(3-[N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]benzyl}-N-methylcarbamic acid tert-butyl ester (523 mg, 0.70 mmol) in dichloromethane (7 ml). The reaction mixture was stirred for 25 min at 0° C. The solvent was removed in vacuo. The residue was dissolved in dichloromethane (90 ml), and the solvent was removed in vacuo. The latter procedure was repeated two times. The crude product was purified by flash chromatography on silica (40 g), using dichloromethane/methanol/25% aqueous ammonia (100:10:1) as eluent, to give 436 mg of the title compound.

$^1$H-NMR (CDCl$_3$, selected values): δ 0.87 (m, 1H); 1.22 (m, 1H); 1.45 (m, 1H); 1.67 (m, 1); 4.09 (m, 1H); 5.53 and 5.90 (dd and m, together 2H); 6.80–7.90 (m, 16H).

HPLC 28.43 min (A1). 30.63 min (B1).

MS: 648.4 [M+1]$^+$.

For biological testing, the title compound was transferred into its diacetate salt by lyophilization from 0.5 M acetic add (40 ml).

Example 6

(2E)-5-Amino-5-methylhex-2-enoic acid N-((1R)-1-{N-[(1R)-1-benzyl-2-(4-(dimethylamino)piperidin-1-yl)-2-oxoethyl]N-methylcarbamoyl}-2-(2-naphthyl)ethyl)-N-methylamide

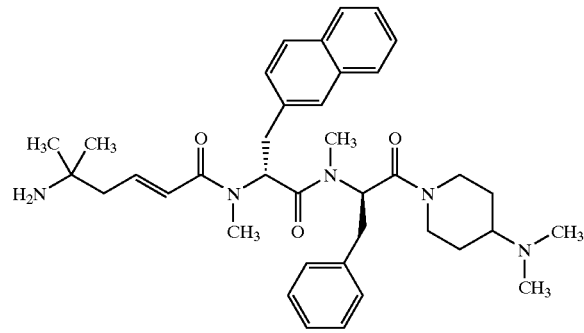

The title compound was prepared as in example 1 using 4-(dimethylamino)piperidine hydrochloride salt, (2R)-2-(N-(tert-butoxycarbonyl)-N-methylamino)-3-phenylpropionic add, (2R)-2-(N-(tert-butoxycarbonyl)-N-methylamino-3-(2-naphthyl))propionic acid, and (2E)-5-(butoxycarbonylamino)-5-methylhex-2-enoic acid.

$^1$H-NMR: (CDCl$_3$; selected values) δ 1.40 (s, 6H); 2.00 (s, 6H); 4.42–4,85 (2H); 5.45–5.90 (m, 2H); 6.28 (dd, 1H); 6.85(m, 1H); 7.10–7,85(m, 12H).

MS (ES): m/z 626.2 (M+H)$^+$.

Example 7

(2E)-5-Amino-5-methylhex-2-enoic acid N-methyl-N-[(1R)-1-(N-methyl-N-{(1R)-1-[N-methyl-N-(1-methylpiperidinyl)carbamoyl]-2-phenylethyl}carbamoyl)-2-(2-naphthyl)ethyl]amide

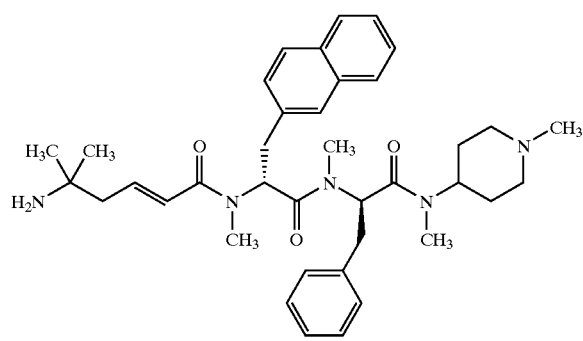

The title compound was prepared as in example 1 using 1-methyl-4-(methylamino)piperidine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-5-(butoxycarbonylamino)-5-methylhex-2-enoic acid.

$^1$H-NMR (CDCl$_3$; selected values) δ 5.50–6.08 (m, 2H); 6.20–6.70 (m, 2H); 7.10–7.85 (m, 12H).

Example 8

3-Aminomethyl-N-((1R)-1-{N-[(1R)-1-benzyl-2-(4-methylpiperazin-1-yl)-2-oxoethyl]-N-methylcarbamoyl}-2-(2-naphthyl)ethyl)-N-methylbenzamide

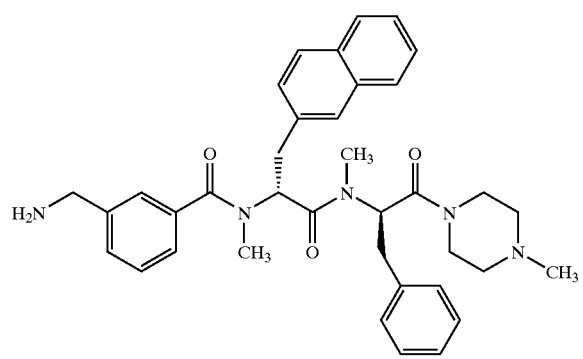

The title compound was prepared as in example 1 using N-methylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and 3-((tert-butoxycarbonylamino)methyl)benzoic acid.

$^1$H-NMR (CDCl$_3$; selected values) δ 3.30 (m, 1H); 3.50 (dd, 1H); 3.75 (m, 1H); 3.95 (s, 2H); 5.78 (t, 1H); 3.88 (m, 1H); 7.00–7.80 (16H).

HPLC: 24.55 min (A1). 26.52 min (B1).

MS (ES): m/z=606.4 [M+H]$^+$.

Example 9

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

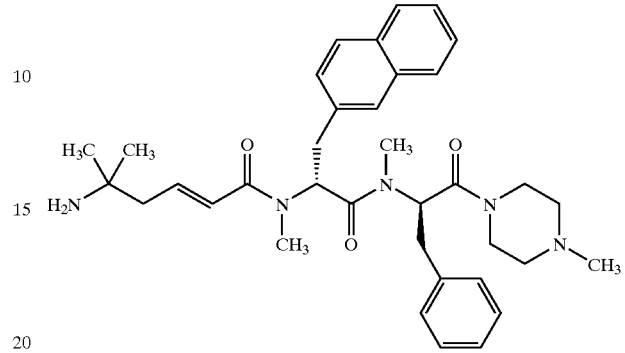

The title compound was prepared as in example 1 using N-methylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-5-(butoxycarbonylamino)-5-methylhex-2-enoic acid.

$^1$H-NMR (CDCl$_3$; selected values) δ 1.24 (s, 6H); 1.65 (s, 3H); 2.35 (s, 3H); 2.80 (s, 3H); 5.68 (dd, 1H); 5.78 (dd, 1H); 6.18 (dd, 1H); 6.95(m, 1H); 7.15–7.80 (m, 12H).

HPLC: 25.03 min (A1). 27.50 min (B1).

MS (ES): m/z=598.4 [M+H]$^+$.

Example 10

(2E)-5-Amino-5-methylhex-2-enoic acid N-methyl-N-((1R)-1-{N-methyl-N-[(1R)-2-phenyl-1-((2,2,6,6-tetramethylpiperidinyl)carbamoyl)ethyl]carbamoyl}-2-(2-naphthyl)ethyl)amide

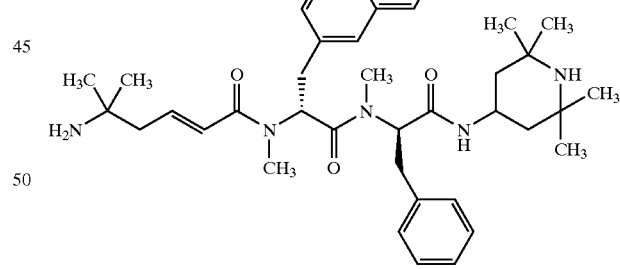

The title compound was prepared as in example 1 using 4-amino-2,2,6,6-tetramethylpiperidin, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-5-(butoxycarbonylamino)-5-methylhex-2-enoic acid.

$^1$H-NMR (CDCl$_3$; selected values) δ 1.25 (s, 6H); 1.40 (two s, 6H); 1.52 (two s, 6H); 2.92 (s, 3H); 3.02 (two s, 3H); 5.10 (dd, 1H); 5.50 (dd, 1H); 6.15 (d, 1H); 6.75 (m, 1H); 7.00–8.00 (m, 12H).

HPLC: 29.27 min (A1). 31.67 min (B1).

MS (ES): m/z=654.8 [M+H]$^+$.

Example 11

3-Aminomethyl-N-methyl-N-((1R)1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide

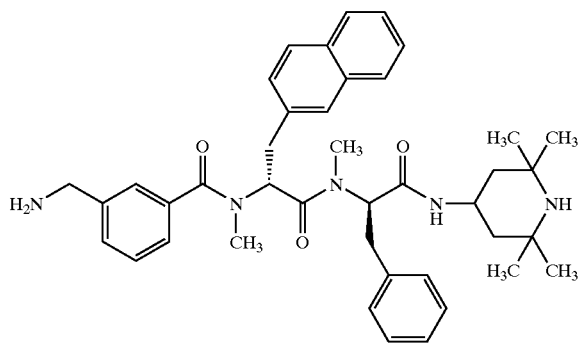

The title compound was prepared as in example 1 using 4-amino-2,2,6,6-tetramethylpiperidin, (2R)-2-(N(tert-butoxycarbonyl)-N-methylamino)-3-phenylpropionic acid, (2R)-2-(N-(tert-butoxycarbonyl)-N-methylamino-3-(2-naphthyl))propionic acid, and 3-((tert-butoxycarbonylamino)methyl)benzoic acid.

$^1$H-NMR (CDCl$_3$; selected values) δ 3.60–3.85 (m, 2H); 3.90–4.30 (m, 1H); 5.25–5.95 (m, 2H); 6.70–7.90 (m, 16H).

HPLC: 29.27 min (A1). 31.55 min (B1).

MS (ES): m/z=662.4 [M+H]$^+$.

Example 12

(2E)-5-Amino-3,5-dimethylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

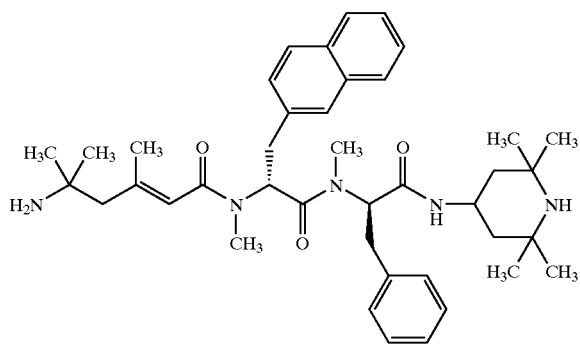

The title compound was prepared as in example 1 using 4-amino-2,2,6,6-tetramethylpiperidin, (2R)-2(N-(tert-butoxycarbonyl)-N-methylamino)-3-phenylpropionic acid, (2R)-2-(N--(tert-butoxycarbonyl)-N-methylamino-3-(2-naphthyl))propionic acid, and (2E)-S-(butoxycarbonylamino)-3,5-methylhex-2-enoic acid.

$^1$H-NMR (CDCl$_3$; selected values) δ 392–4.30 (m, 1H); 5.05–5.88 (m, 3H); 7.00–7.80 (m, 12H).

HPLC: 29.80 min (A1). 32.43 min (B1).

MS (ES): m/z=668.4 [M+H]$^+$.

Example 13

(2E)-4-(1-Aminocyclobutyl)but-2-enoic acid N-((1R)-1-{N-[(1R)1-benzyl-2-(4-methylpiperazin-1-yl)-2-oxoethyl]-N-methylcarbamoyl}2-(2-naphthyl)ethyl)-N-methylamide

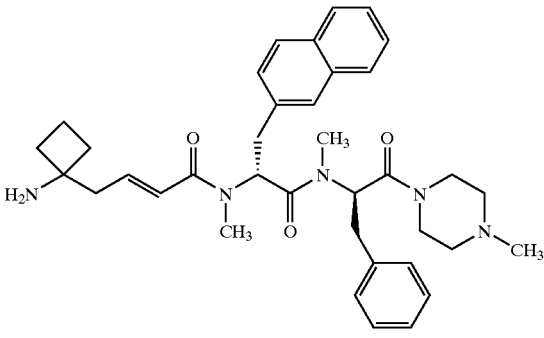

The title compound was prepared as in example 1 using N-methylpiperazine, (2R)-2-(N-(tert-butoxycarbonyl)-N-methylamino)-3-phenylproplonic acid, (2R)-2-(N-(tert-butoxycarbonyl)-N-methylamino-3-(2-naphthyl))propionic acid, and (2E)-4-(1-(butoxycarbonylamino)cyclobutyl)but-2-enoic acid.

$^1$H-NMR (CDCl$_3$; selected peaks) δ 1.62 (s, 3H); 2.35 (s, 3H); 2.80 (s, 3H); 5.70 (dd, 1H); 5.80 (dd, 1H); 6.22 (d, 1H); 6.98 (m, 1H); 7.15–7.80 (m, 12H).

HPLC: 25.88 min (A1). 28.65 min (B1).

MS (ES) m/z=610.4 [M+H]$^+$.

Example 14

(2E)-5-Amino-3,5-dimethylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

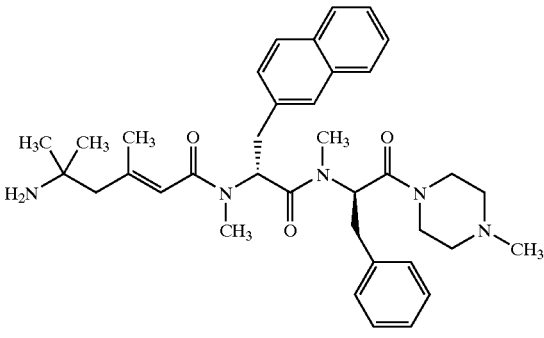

The title compound was prepared as in example 1 using N-methylpiperazine, (2R)-2-(N-(tert-butoxycarbonyl)-N-methylamino)-3-phenylpropionic acid, (2R)-2N-(tert-butoxycarbonyl)-N-methylamino-3-(2-naphthyl))proplonic acid, and (2E)-5-(butoxycarbonylamino)-3,5-methylhex-2-enoic acid.

$^1$H-NMR (CDCl$_3$; selected values) δ 1.18 (s, 6H); 1.68 (s, 3H); 1.95 (s, 3H); 2.30 (s, 3H); 2.85 (s, 3H); 3.40 (dd, 1H); 3.54–3.75 (m, 2H); 5.68–5.85 (m, 3H); 7.15–7.80 (m, 12H).

HPLC: 25.70 min (A1). 28.27 min (B1).

MS (ES) m/z=612.4 [M+H]$^+$.

Example 15

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

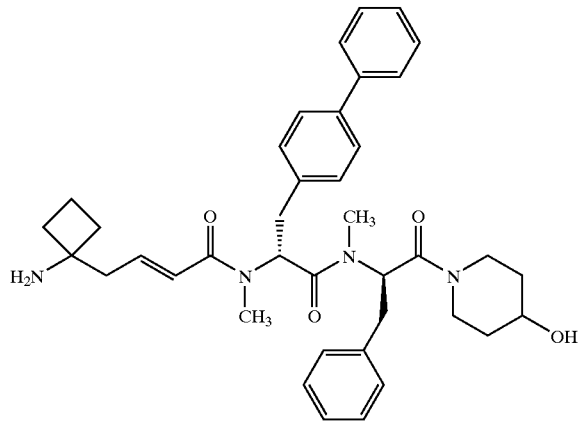

This compound was prepared as in example 1 but using 4-hydroxypiperidine, (2R)-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-4-(1-(tert-butoxycarbonylamino)cyclobutyl)but-2-enoic acid as starting materials.

ESMS: 637.4 (M+H)$^+$.
HPLC: $r_t$=33.58 min. (A1).
HPLC: $r_t$=34.95 min. (B1).

Example 16

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

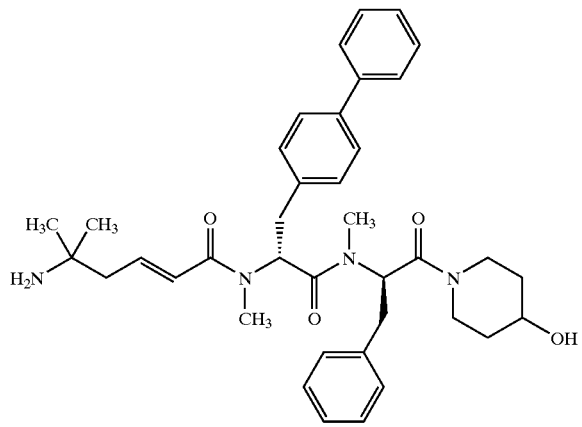

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-5-tert-Butoxycarbonylamino-5-methylhex-2-enoic acid as starting materials.

ESMS: 625.4 (M+H)$^+$.
HPLC: $r_t$=32.65 min. (A1).
HPLC: $r_t$=34.02 min. (B1).

Example 17

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

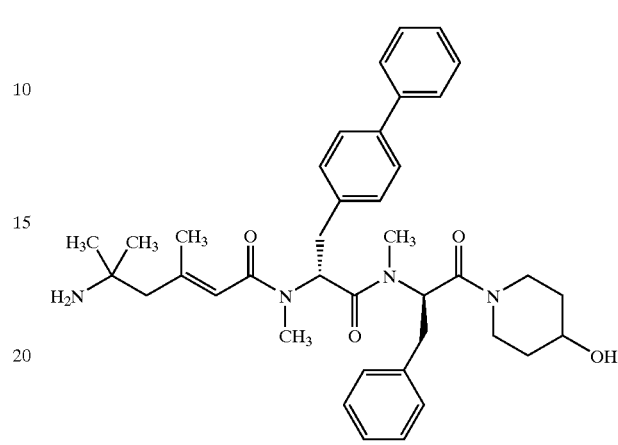

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-5-tert-butoxycarbonylamino-3,5-dimethylhex-2-enoic acid as starting materials.

ESMS: 639.4 (M+H)$^+$.
HPLC: $r_t$=33.29 min. (A1).
HPLC: $r_t$=36.40 min. (B1).

Example 18

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

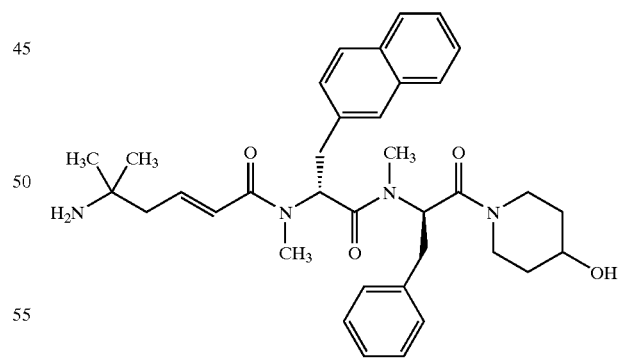

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(2-naphthyl)propionic acid and (2E)-5-tert-Butoxycarbonylamino-5-methylhex-2-enoic acid as starting materials.

ESMS: 599.4 (M+H)$^+$.
HPLC: $r_t$=29.88 min. (A1).

Example 19

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

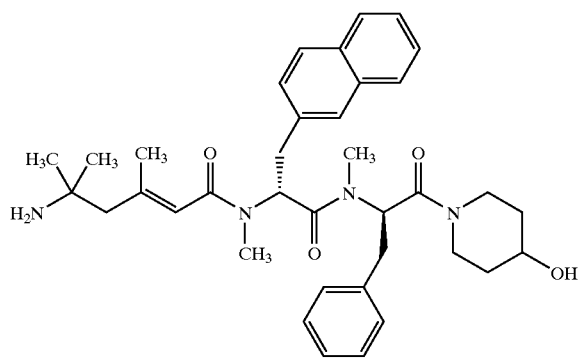

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(2-naphthyl)propionic acid and (2E)-5-tert-Butoxycarbonylamino-3,5-dimethylhex-2-enoic acid as starting materials.

ESMS; 613.4 (M+H)$^+$.

HPLC: r$_t$=30.58 min. (A1).

Example 20

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

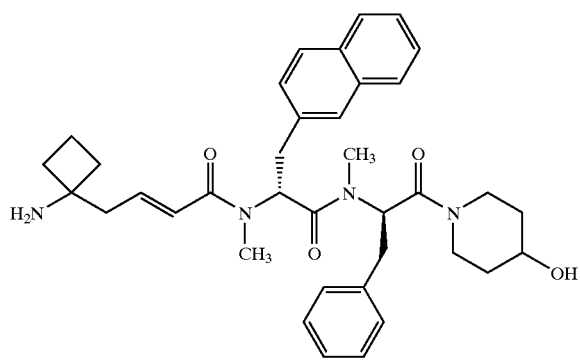

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(2-naphthyl)propionic acid and (2E)-4-(1-(tert-butoxycarbonylamino)cyclobutyl)but-2-enoic acid.

ESMS: 611.4 (M+H)$^+$.

HPLC: r$_t$=30.82 min. (A1).

Example 21

(2E)-5-Amino-5-methylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide This compound was prepared as in example 1 but using 4-hydroxypiperidine, (2R)-2-(N-tert-butoxycarbonyl-N-methylamino)-3-(4-fluorophenyl)propionic acid and (2R)-2-(N-tert-butoxycarbonyl-N-methylamino)-3-(2-naphthyl)propionic acid and (2E)-5-tert-butoxycarbonylamino-5-methylhex-2-enoic acid as starting materials.

ESMS: 617.4 (M+H)$^+$.

HPLC: r$_t$=30.27 min. (A1).

HPLC: r$_t$=31.60 min. (B1).

Example 22

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

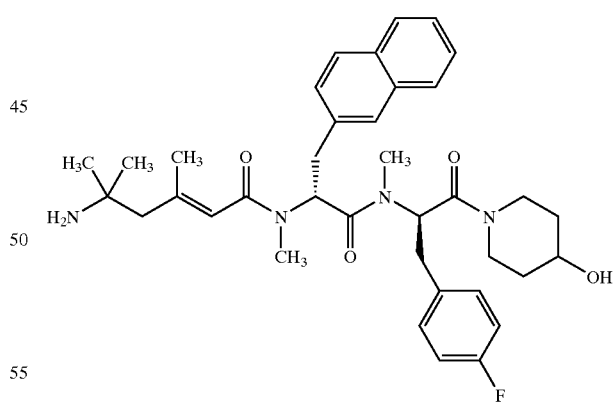

This compound was prepared as in example 1 but using 4-hydroxypiperidine, (2R)-2-(N-tert-butoxycarbonyl-N-methylamino)-3-(4-fluorophenyl)propionic acid and (2R)-2-(N-tert-butoxycarbonyl-N-methylamino)-3-(2-naphthyl)propionic acid and (2E)-5-tert-butoxycarbonylamino-3,5-dimethylhex-2-enoic acid as starting materials.

ESMS: 631.4 (M+H)$^+$.

HPLC: r$_t$=30.98 min. (A1).

HPLC: r$_t$=32.38 min. (B1).

Example 23

(2E)-4-(1-Aminocyclobutyl)but-2-enoic acid N-((1R)-1-{N-[(1R)-1-benzyl-2-(4-(dimethylamino)piperidin-1-yl)-2-oxoethyl]-N-methylcarbamoyl}-2-(2naphthyl)ethyl)-N-methylamide

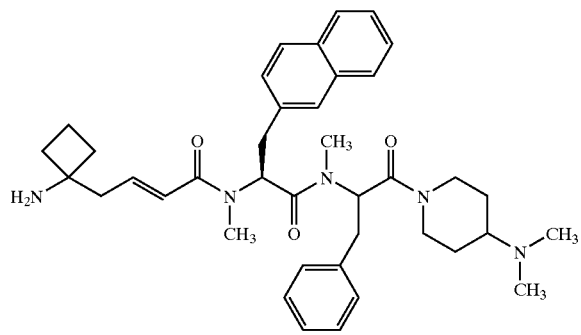

The title compound was prepared as in example 1 using 4-N,N-dimethylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-41-(butoxycarbonylamino)cyclobutyl)but-2-enoic acid.

$^1$H-NMR (CDCl$_3$; selected peaks) d 1.90 (s, 3H); 2.38 (s, 3H); 2.45 and 2.47 (two s, 3H); 2.78 and 2.80 (two s, 3H); 6.32 (dd, 1H); 6.90 (m, 1H); 7.15–7.84 (m, 12H).

HPLC: 26.72 min (A1).

MS (ES) m/z=638.4 [M+H]$^+$.

Example 24

(2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

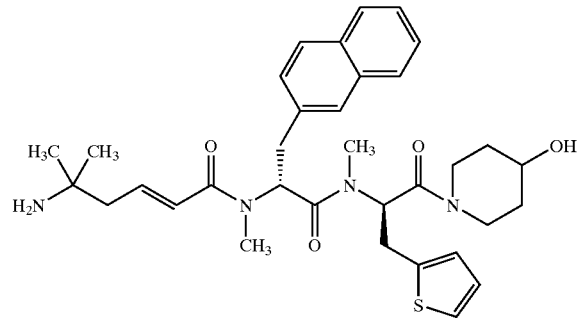

This compound was prepared as in example 1 but using 4-hydroxypiperidine, (2R)-2N-tert-butoxycarbonyl-N-methylamino)-3-(2-thienyl)propionic acid and (2R)-2-(N-tert-butoxycarbonyl-N-methylamino)-3-(2-naphthyl)propionic acid and (2E)-5-tert-butoxycarbonylaminomethylhex-2-enoic add as starting materials.

ESMS: 605.4 (M+H)$^+$.

HPLC: r$_t$=29.07 min. (A1).

Example 25

(2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

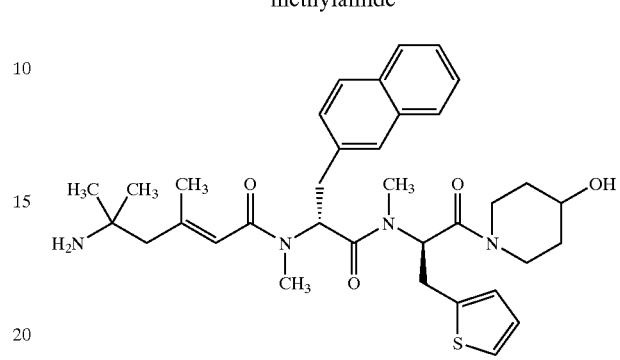

This compound was prepared as in example 1 but using 4-hydroxypiperidine, (2R)-2-(N-tert-butoxycarbonyl-N-methylamino)-3-(2-thienyl)proplonic acid and (2R)-2-(N-tert-butoxycarbonyl-N-methylamino)-3-(2-naphthyl)propionic acid and (2E)-5-tert-butoxycarbonylamino-3,5-dimethylhex-2-enoic acid as starting materials.

ESMS: 619.4 (M+H)$^+$.

HPLC: r$_t$=29.76 min. (A1).

Example 26

(2E)-5-Amino-5-methylhex-2-enoic acid N-((1R)-2-(biphenyl-4-yl)-1-{N-[(2R)-2-(4-hydroxypiperidin-1-yl)-2-oxo-((2-thienyl)methyl)ethyl]-N-methylcarbamoyl}ethyl)-N-methylamide

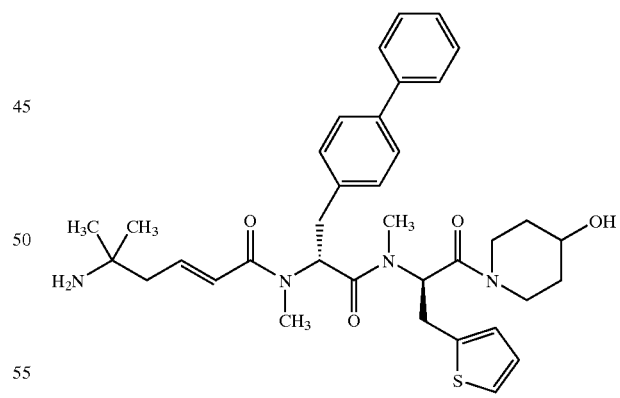

This compound was prepared as in example 1 but using 4-hydroxypiperidine, (2R)-2-(N-tert-butoxycarbonyl-N-methylamino)-3-(2-thienyl)propionic acid and (2R)-2-(N-tert-butoxycarbonyl-N-methylamino)-3-(biphenyl-4-yl)propionic acid and (2E)-5-tert-butoxycarbonylamino-5-methylhex-2-enoic acid as starting materials.

ESMS: 631.2 (M+H)$^+$.

HPLC: r$_t$=32.20 min. (A1).

Example 27

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide

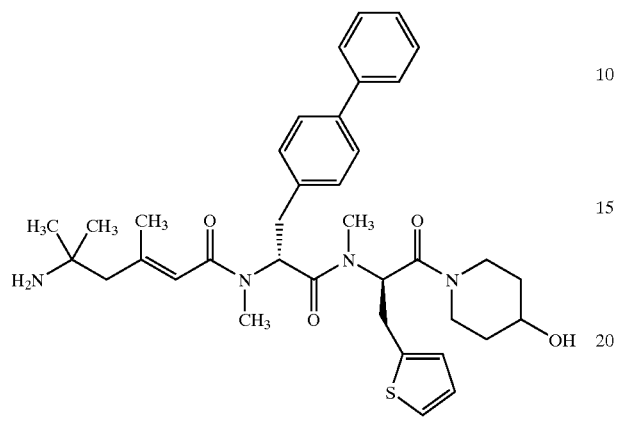

This compound was prepared as in example 1 but using 4-hydroxypiperidine, (2R)-2-(N-tert-butoxycarbonyl-N-methylamino)-3-(2-thienyl)propionic acid and (2R)-2-(N-tert-butoxycarbonyl-N-methylamino)-3-(biphenyl-4-yl)propionic acid and (2E)-5-tert-butoxycarbonylamino-3,5-dimethylhex-2-enoic acid as starting materials.

ESMS: 465.4 (M+H)$^+$.
HPLC: $r_t$=32.89 min. (A1).

Example 28

(2E)-5-Methyl-5-(methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

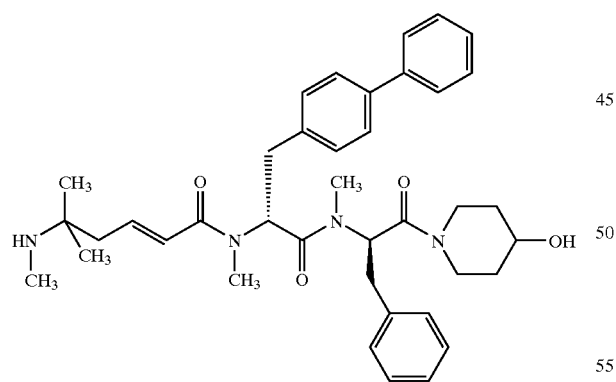

The title compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-5-(N-(tert Butoxycarbonyl)-N-methylamino)-5-methylhex-2-enoic acid as starting materials.

MS: m/z: 639.4 (M+H)$^+$.
HPLC: Method A1: $R_t$=32.94 min.

Example 29

(2E)-4-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide

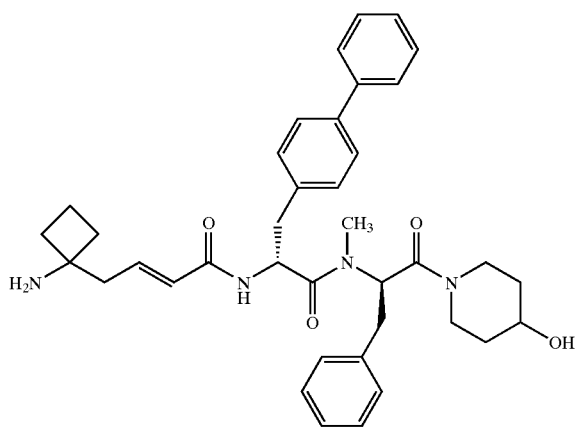

HPLC: Rt=31.55 min. (A1). Rt=31.11 min. (B1).
LC-MS: 623.6 [M+1]$^+$.

What is claimed is:
1. A compound of formula I

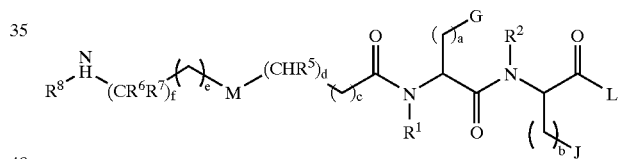

formula I wherein $R^1$ is hydrogen or $C_{1-6}$-alkyl;

$R^2$ is hydrogen or $C_{1-6}$alkyl;

L is

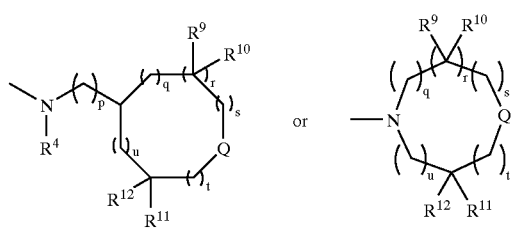

wherein $R^4$ is hydrogen or $C_{1-6}$ alkyl;

p is 0 or 1;

q, s, t, u are independently from each other 0, 1, 2, 3 or 4;

r is 0 or 1;

the sum q+r+s+1+u is 1, 2, 3, or 4;

$R^9$, $R^{10}$, $R^{11}$, and $R^{12}$ are independently from each other hydrogen or $C_{1-6}$ alkyl;

Q is >N—R$^{13}$ or

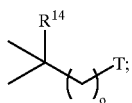

wherein o is 0, 1 or 2;

T is —N(R$^{15}$)(R$^{16}$) or hydroxyl;

R$^{13}$, R$^{15}$, and R$^{16}$ are independently from each other hydrogen or C$_{1-6}$ alkyl;

R$^{14}$ is hydrogen, aryl or hetaryl;

G is —O—(CH$_2$)$_k$—R$^{17}$,

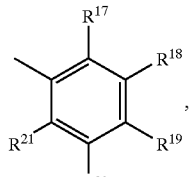 , 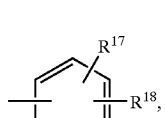 ,

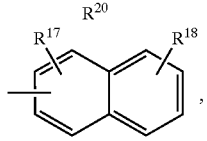 , 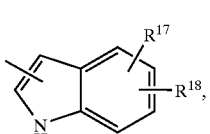 ,

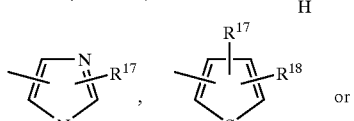 or

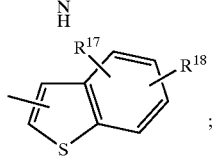 ;

wherein R$^{17}$, R$^{18}$, R$^{19}$, R$^{20}$ and R$^{21}$ independently from each other are hydrogen, halogen, aryl, hetaryl, C$_{1-6}$-alkyl or C$_{1-6}$-alkoxy;

k is 0, 1 or 2;

J is —O—(CH$_2$)$_l$—R$^{22}$,

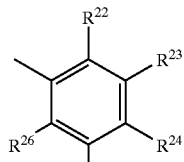 , 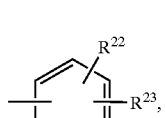 ,

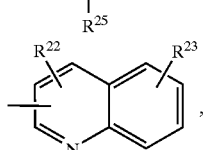 , 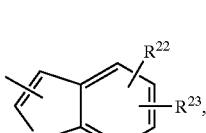 ,

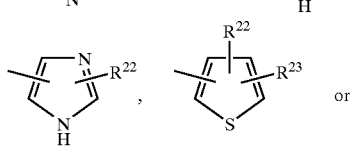 or

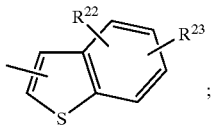 ;

wherein R$^{22}$, R$^{23}$, R$^{24}$, R$^{25}$ and R$^{26}$ independently from each other are hydrogen, halogen, aryl, hetaryl, C$_{1-6}$-alkyl or C$_{1-6}$-alkoxy;

l is 0, 1 or 2;

a is 0, 1 or 2;

b is 0, 1 or 2;

c is 0 1, or 2;

d is 0 or 1;

e is 0, 1, 2, or 3;

f is 0 or 1;

R$^5$ is hydrogen or C$_{1-6}$-alkyl optionally substituted with one or more hydroxyl, aryl or hetaryl;

R$^6$ and R$^7$ are independently from each other hydrogen or C$_{1-6}$-alkyl, optionally substituted with one or more halogen, amino, hydroxyl, aryl, or hetaryl;

R$^8$ is hydrogen or C$_{1-6}$-alkyl, optionally substituted with one or more halogen, amino, hydroxyl, aryl, or hetaryl;

R$^6$ and R$^7$ or R$^6$ and R$^8$ or R$^7$ and R$^8$ may optionally form —(CH$_2$)$_i$—U—(CH$_2$)$_j$—, wherein i and j independently from each other are 1, 2 or 3 and U is —O—, —S—, or a valence bond;

M is arylene, hetarylene, —O—, —S— or —CR$^{27}$=CR$^{28}$—;

R$^{27}$ and R$^{28}$ are independently from each other hydrogen or C$_{1-6}$-alkyl, optionally substituted with one or more aryl or hetaryl;

or a pharmaceutically acceptable salt thereof.

2. The compound of claim 1 wherein R$^1$ is C$_{1-6}$-alkyl.

3. The compound of claim 1 wherein R$^2$ is C$_{1-6}$-alkyl.

4. The compound of claim 1 wherein L is

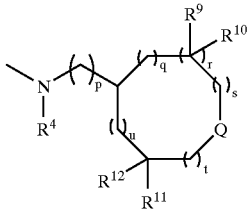

wherein R$^4$ is hydrogen or C$_{1-6}$ alkyl;

p is 0 or 1;

q, s, t, u are independently from each other 0, 1, 2, 3 or 4;

r is 0 or 1;

the sum q+r+s+t+u is 1, 2, 3, or 4;

R$^9$, R$^{10}$, R$^{11}$, and R$^{12}$ are independently from each other hydrogen or C$_{1-6}$ alkyl;

Q is >N—$R^{13}$ or

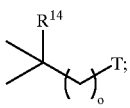

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl; and $R^{14}$ is hydrogen, aryl or hetaryl.

5. The compound of claim 1 wherein L is

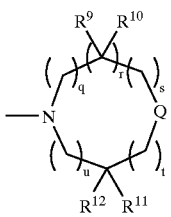

wherein q, s, t, u are independently from each other 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

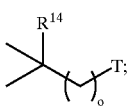

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl; and $R^{14}$ is hydrogen, aryl or hetaryl.

6. The compound of claim 1 wherein G is

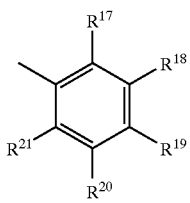

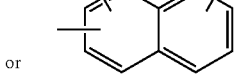

wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy.

7. The compound of claim 1 wherein J is

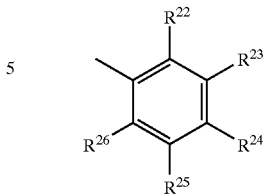

or

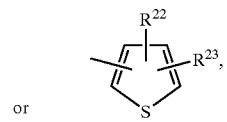

wherein $R^{22}$, $R^{23}$, $R^{24}$, $R^{25}$ and $R^{26}$ independently are hydrogen, halogen, aryl, hetaryl, $C_{1-6}$-alkyl or $C_{1-6}$-alkoxy.

8. The compound of claim 1 wherein M is arylene or —$CR^{28}$=$CR^{28}$—, wherein $R^{27}$ and $R^{28}$ independently are hydrogen or $C_{1-6}$-alkyl, optionally substituted with aryl or hetaryl.

9. The compound of claim 1 wherein $R^6$ and $R^7$ independently from each other are hydrogen or $C_{1-6}$-alkyl.

10. The compound of claim 1 wherein $R^6$ and $R^7$ form —(CH$_2$)$_i$—U—(CH$_2$)$_j$—, wherein i and j independently from each other are 1, 2 or 3 and U is —O—, —S—, or a valence bond.

11. The compound of claim 1 wherein $R^8$ is hydrogen or $C_{1-6}$-alkyl.

12. The compound of claim 1 selected from (2E)-5-Amino-5-methylhex-2-enoic acid N-((1R)-1-{N-[(1R)-1-benzyl-2-(4-(dimethylamino)methyl)piperidin-1-yl)-2-oxoethyl]-N-methylcarbamoyl}-2-(2-naphthyl)ethyl)-N-methylamide

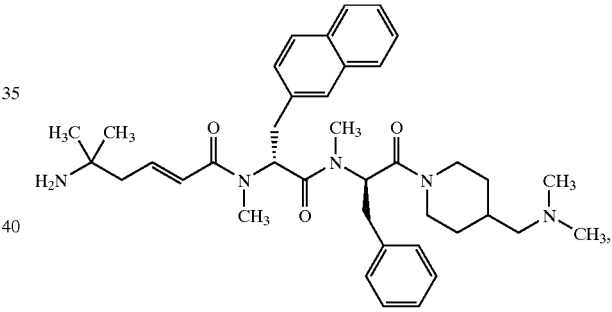

(2E)-5-Amino-5-methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

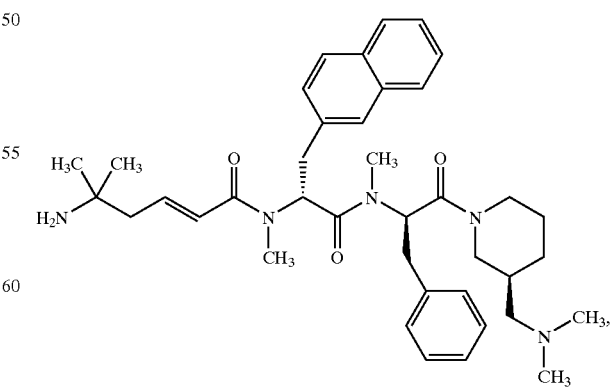

(2E)-4-(1-Aminocyclobutyl)but-2-enoic acid N-((1R)-1-{N-[(1R)-1-benzyl-2-((3S)-3-(dimethylaminomethyl)

piperidin-1-yl)-2-oxoethyl]-N-methylcarbamoyl}-2-(2-naphthyl)ethyl)-N-methylamide 2-oxoethyl]-N-methylcarbamoyl}-2-(2-naphthyl)ethyl)-N-methylamide

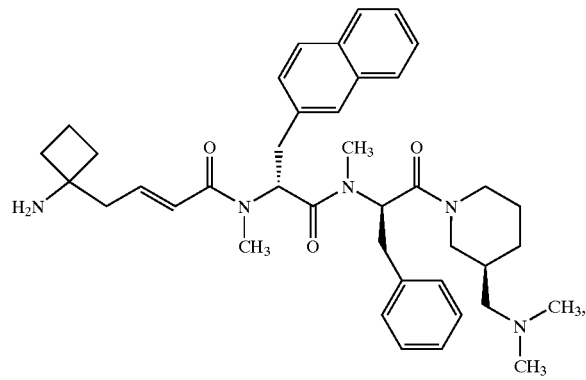

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

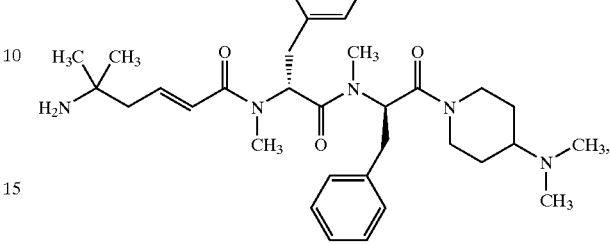

(2E)-5-Amino-5-methylhex-2-enoic acid N-methyl-N-[(1R)-1-(N-methyl-N-{(1R)-1-[N-methyl-N-(1-methylpiperidin-4-yl)carbamoyl]-2-phenylethyl}carbamoyl)-2-(2-naphthyl)ethyl]amide

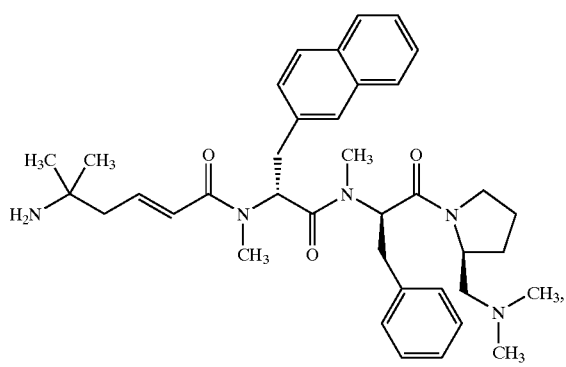

N-((1R)-1-{N-[(1R)-1-Benzyl-2-((2S)-2-(dimethylamino)methyl)pyrrolidin-1-yl)-2-oxoethyl]-N-methylcarbamoyl}-2-(2-naphthyl)ethyl)-N-methyl-3-((methylamino)methyl)benzamide 3-Aminomethyl-N-((1R)-1-{N-[(1R)-1-benzyl-2-(4-methylpiperazin-1-yl)-2-oxoethyl]-N-methylcarbamoyl}-2-(2-naphthyl)ethyl)-N-methylbenzamide

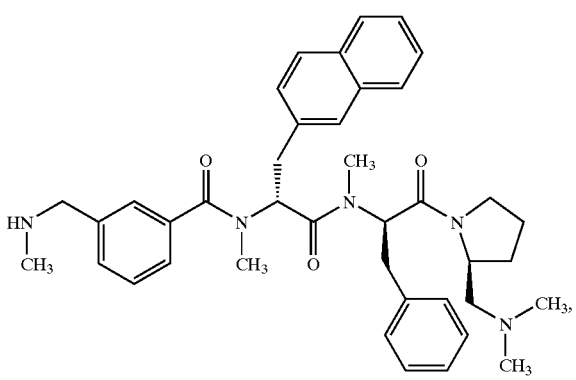

(2E)-5-Amino-5-methylhex-2-enoic acid N-((R)-1-{N-[(1R)-1-benzyl-2-(4-(dimethylamino)piperidin-1-yl)-

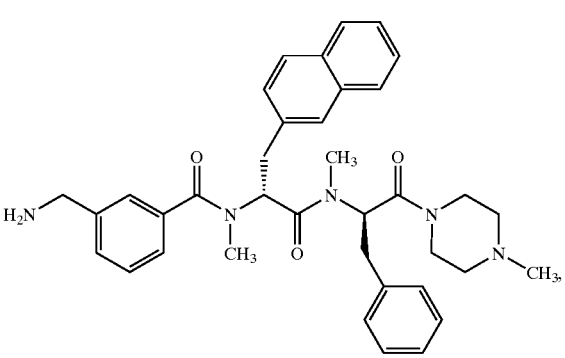

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

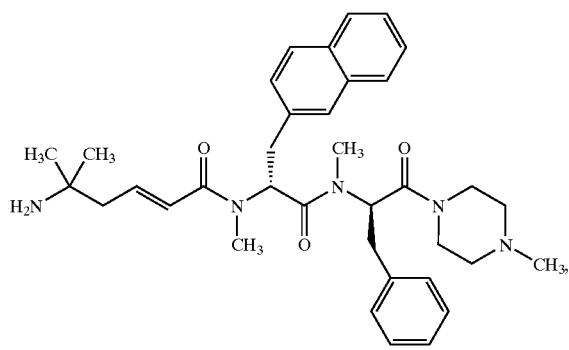

(2E)-5-Amino-5-methylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

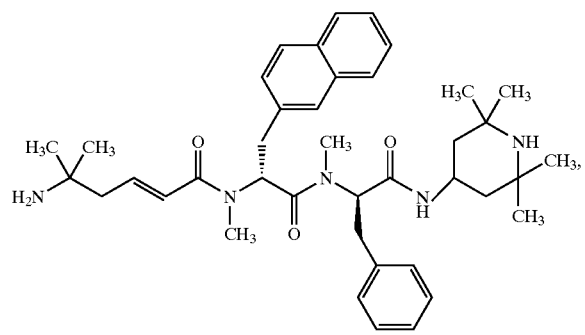

3-Aminomethyl-N-methyl-N-((1R)1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide

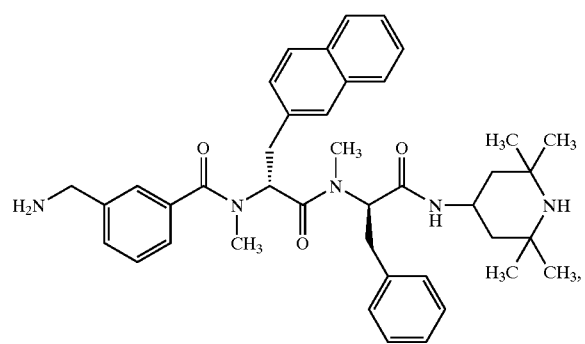

(2E)-5-Amino-3,5-dimethylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide (2E)-4-(1-Aminocyclobutyl)but-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide (2E)-5-Amino-3,5-dimethylhex-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

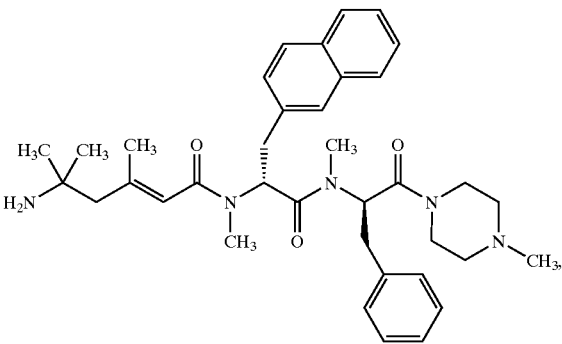

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

81

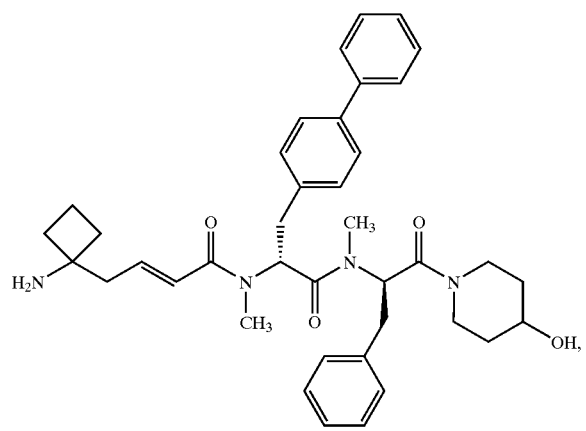

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

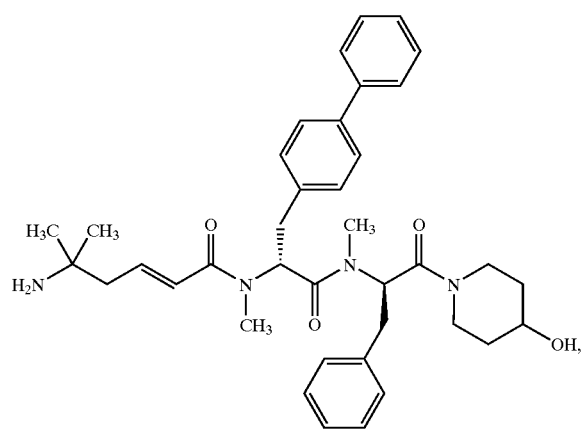

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

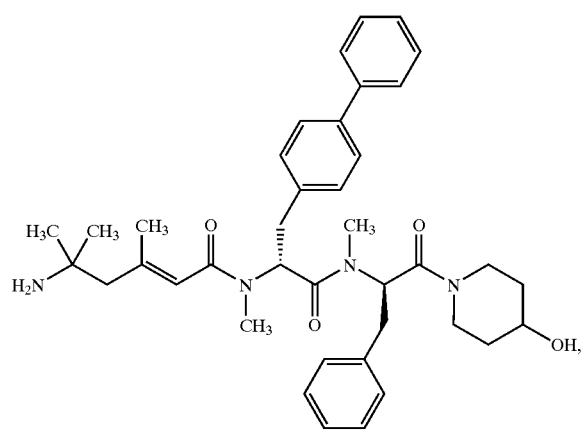

(2E)-5-Amino-5-methylhex-2-enoic acid N-((1R)-1-{N-[(1R)-1-benzyl-2-(4-hydroxypiperidin-1-yl)-2-

82 oxoethyl]-N-methylcarbamoyl}-2-(2-naphthyl)ethyl)-N-methylamide

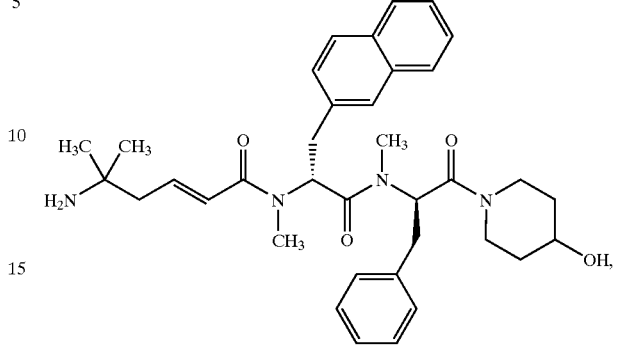

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

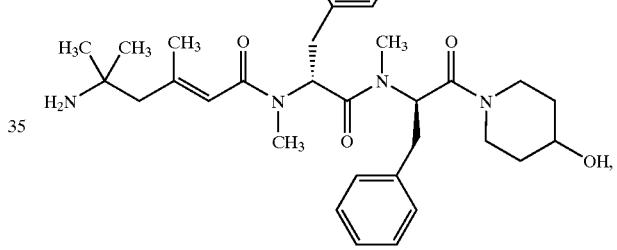

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

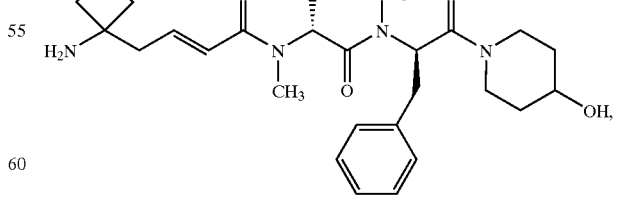

(2E)-5-Amino-5-methylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide phenylethyl]-N-methylcarbamoyl}-2-(2-naphthyl)ethyl)-N-methylamide

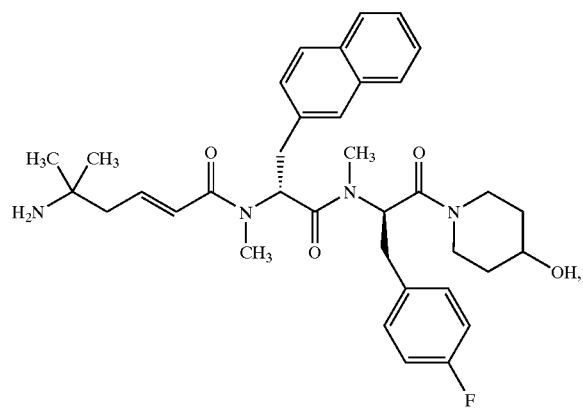

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

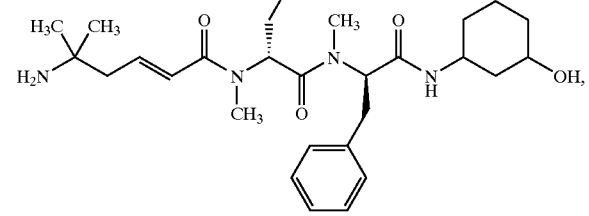

(2E)4-(1-Aminocyclobutyl)but-2-enoic acid N(1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide

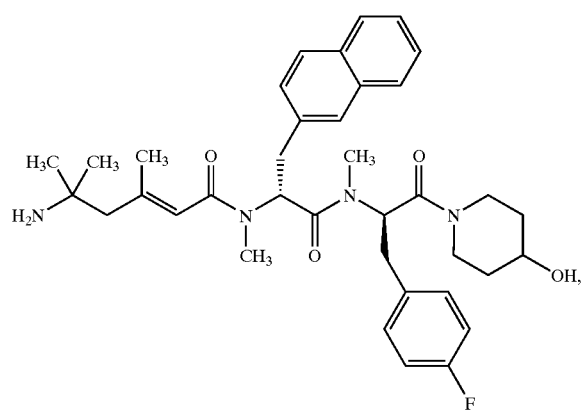

(2E)-5-Amino-5-methylhex-2-enoic acid N-((1R)-1-{N-[(1R)-1-benzyl-2-(4-hydroxy-4-(2-thienyl)piperidin-1-yl)-2-oxoethyl]-N-methylcarbamoyl}-2-(2-naphthyl)ethyl)-N-methylamide

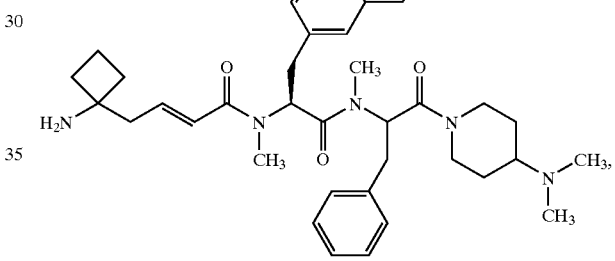

(2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

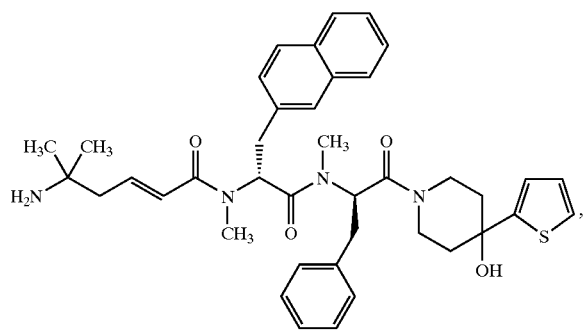

(2E)-5-Amino-5-methylhex-2-enoic acid N-((1R)-1-{N-[(1R)-1-(3-hydroxycyclohexylcarbamoyl)-2-

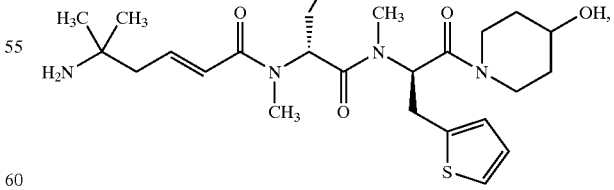

(2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

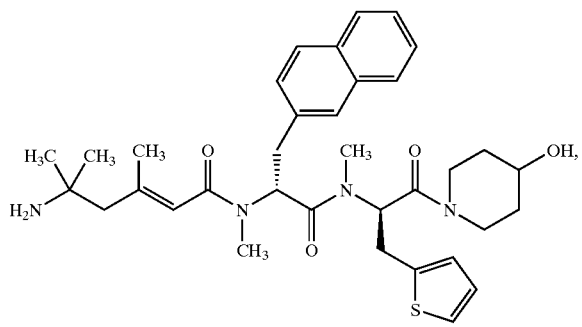

(2E)-5-Amino-5-methylhex-2-enoic acid N-((1R)-2-(biphenyl-4-yl)-1-{N-[(2R)-2-(4-hydroxypiperidin-1-yl)-2-oxo-1-((2-thienyl)methyl)ethyl]-N-methylcarbamoyl}ethyl)-N-methylamide

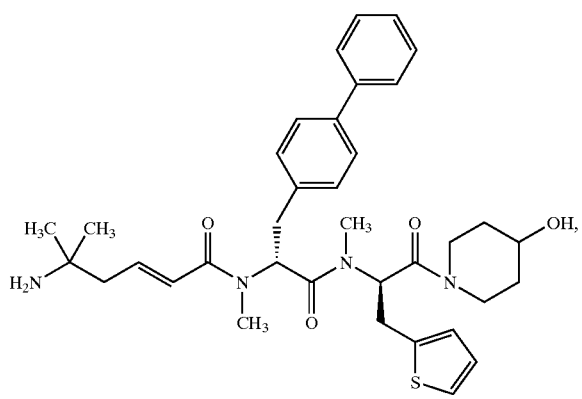

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide

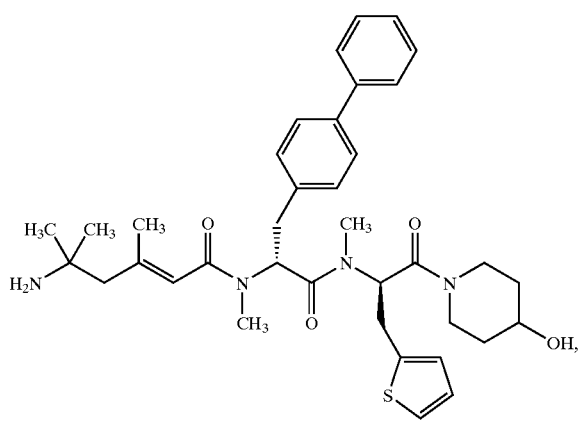

(2E)-5-Methyl-5-methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

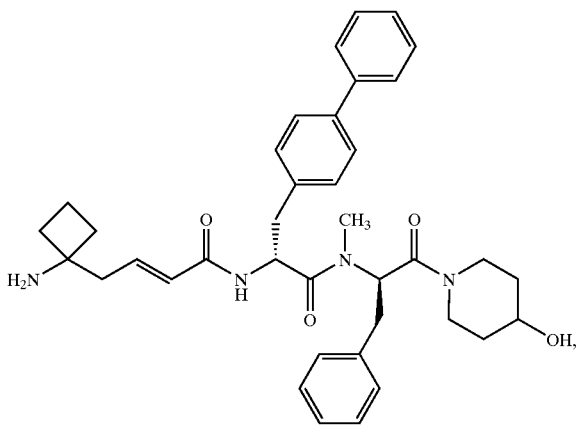

(2E)-4-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide, or and pharmaceutically acceptable salts thereof.

13. A method of treating growth retardation in connection with asthma, the method comprising administering to a subject in need thereof an effective amount of a compound of claim 1.

14. The method of claim 13, wherein the compound is a growth hormone secretagogue.

15. A composition comprising, as an active ingredient, a compound of claim 1 together with a pharmaceutically acceptable carrier or diluent.

16. A method of stimulating the release of growth hormone from the pituitary of a mammal, the method comprising administering to the mammal an effective amount of a compound of claim 1 or a composition of claim 15.

17. A method of treating growth retardation in connection with juvenile rheumatic arthritis or systic fibrosis, the method comprising administering to a subject in need thereof an effective amount of a compound of claim 1.

* * * * *

UNITED STATES PATENT AND TRADEMARK OFFICE
CERTIFICATE OF CORRECTION

| | | |
|---|---|---|
| PATENT NO. | : 6,919,315 B1 | Page 1 of 45 |
| APPLICATION NO. | : 09/356313 | |
| DATED | : July 19, 2005 | |
| INVENTOR(S) | : Peschke et al. | |

It is certified that error appears in the above-identified patent and that said Letters Patent is hereby corrected as shown below:

Please delete Patent 6,919,315 in its entirety and insert Patent 6,919,315 as attached.

Signed and Sealed this
Twenty-ninth Day of November, 2011

David J. Kappos
*Director of the United States Patent and Trademark Office*

United States Patent
Peschke et al.

(12) 
(10) Patent No.: US 6,919,315 B1
(45) Date of Patent: Jul. 19, 2005

(54) COMPOUNDS WITH GROWTH HORMONE RELEASING PROPERTIES

(75) Inventors: Bernd Peschke, Malov (DK); Lutz Richter, deceased, late of St. James (JM); by Birgit Richter, legal representative, St. James (JM); Thomas Hansen Kruse, Herlev (DK); Michael Ankersen, Frederiksberg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/356,313

(22) Filed: Jul. 16, 1999

Related U.S. Application Data

(63) Continuation-in-part of application No. 09/337,809, filed on Jun. 21, 1999, now abandoned.
(60) Provisional application No. 60/108,369, filed on Nov. 13, 1998, and provisional application No. 60/091,786, filed on Jul. 6, 1998.

(30) Foreign Application Priority Data

Jun. 30, 1998 (DK) .................................. 1998 00857
Nov. 9, 1998 (DK) .................................. 1998 01440

(51) Int. Cl.$^7$ .................................................. C07K 5/06
(52) U.S. Cl. .................... 514/19; 514/18; 514/183; 530/331
(58) Field of Search ........................................ 514/18, 19

(56) References Cited

U.S. PATENT DOCUMENTS

| | | | |
|---|---|---|---|
| 5,767,085 A | 6/1998 | Johansen et al. | 514/17 |
| 5,798,337 A | 8/1998 | Somers et al. | 514/19 |
| 6,127,354 A | * 10/2000 | Peschke et al. | 514/183 |
| 6,127,391 A | 10/2000 | Hansen et al. | 514/343 |

FOREIGN PATENT DOCUMENTS

| | | |
|---|---|---|
| EP | 18072 | 10/1980 |
| EP | 83864 | 5/1987 |
| WO | WO 8302272 | 7/1983 |
| WO | WO 09780 | 12/1988 |
| WO | WO 8901711 | 2/1989 |
| WO | WO 8907110 | 10/1989 |
| WO | WO 8910933 | 11/1989 |
| WO | WO 9118016 | 11/1991 |
| WO | WO 9201711 | 2/1992 |
| WO | WO 9304081 | 3/1993 |
| WO | WO 9413696 | 6/1994 |
| WO | WO 9514666 | 6/1995 |
| WO | WO 9517423 | 6/1995 |
| WO | WO 9615148 | 5/1996 |
| WO | WO 9622997 | 8/1996 |
| WO | WO 9635713 | 11/1996 |
| WO | WO 9700894 | 1/1997 |
| WO | WO 9722620 | 6/1997 |
| WO | WO 97/23508 | 7/1997 |
| WO | WO 9740023 | 10/1997 |
| WO | WO 98/03473 | 1/1998 |
| WO | WO 9810653 | 3/1998 |
| WO | WO 98/58950 | 12/1998 |

* cited by examiner

*Primary Examiner*—Christopher S. F. Low
*Assistant Examiner*—David Lukton
(74) *Attorney, Agent, or Firm*—Rosemarie R. Wilk-Drescan; Reza Green; Richard W. Bork

(57) ABSTRACT

Disclosed are compounds of formula I formula I

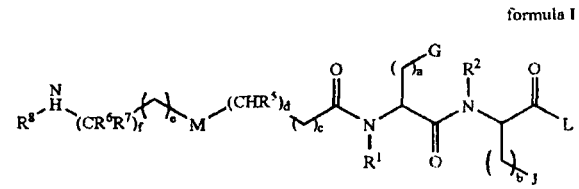

wherein $R^1$, $R^2$, $R^5$, $R^6$, $R^7$, $R^8$, G, J, L, M, a, b, c, d, e, and f are as defined in the specification, and compositions containing them. These compounds are useful for treating medical disorders resulting from a deficiency in growth hormone.

17 Claims, No Drawings

COMPOUNDS WITH GROWTH HORMONE RELEASING PROPERTIES

CROSS REFERENCE TO RELATED APPLICATIONS

This application is a continuation-in-part of U.S. Application No. 09/337,809, filed on Jun. 21, 1999, now abandoned, which claims the benefit under 35 U.S.C. 119 of U.S. Provisional Application No. 60/091,786, filed Jul. 6, 1998, and U.S. Provisional Application No. 60/108,369, filed Nov. 13, 1998, and which claims priority of Danish Application No. PA 1998 00857, filed Jun. 30, 1998, and Danish Application No. PA 1998 01440, filed Nov. 9, 1998, the contents of which are fully incorporated herein by reference.

FIELD OF INVENTION

The present invention relates to novel compounds, compositions containing them, and their use for treating medical disorders resulting from a deficiency in growth hormone.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilisation and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthetic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration non-viable. Furthermore, other directly acting natural secretagogues, e.g., GHRH and PACAP, are longer polypeptides for which reason parenteral administration is preferred.

The use of certain compounds for increasing the levels of growth hormone in mammals has previously been proposed, e.g. in EP 18 072, EP 83 864, WO 8302272, WO 8907110, WO 8901711, WO 8910933, WO 8809780, WO 9118016, WO 9201711, WO 9304081, WO 9413698, WO 9517423, WO 9514666, WO 9615148, WO 9622997, WO 9635713, WO 9700894, WO 9722620, WO 9723508, WO 9740023, and WO 9810653.

The composition of growth hormone releasing compounds is important for their growth hormone releasing potency as well as their bioavailability. It is therefore an object of the present invention to provide novel compounds with growth hormone releasing properties. Moreover, it is an object to provide novel growth hormone releasing compounds (growth hormone secretagogues) which are specific and/or selective and have no or substantially no side-effects, such as e.g. release of LH, FSH, TSH, ACTH, vasopressin, oxytocin, cortisol and/or prolactin. It is also an object to provide compounds which have good oral bioavailability.

SUMMARY OF THE INVENTION

In accordance with the present invention there is provided novel compounds which act directly on the pituitary cells under normal experimental conditions in vitro to release growth hormone therefrom.

These growth hormone releasing compounds can be utilized in vitro as unique research tools for understanding, inter alia, how growth hormone secretion is regulated at the pituitary level.

Moreover, the growth hormone releasing compounds of the present invention can also be administered in vivo to increase endogenous growth hormone release.

DESCRIPTION OF THE INVENTION

Accordingly, the present invention relates to a compound of the general formula I

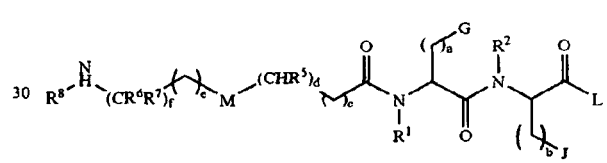

formula I wherein $R^1$ is hydrogen or $C_{1-6}$-alkyl;

$R^2$ is hydrogen or $C_{1-6}$-alkyl;

L is

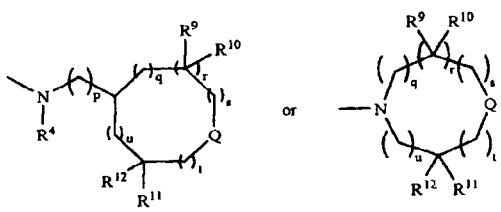

wherein $R^4$ is hydrogen or $C_{1-6}$ alkyl;

p is 0 or 1;

q, s, t, u are independently from each other 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

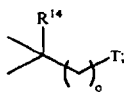

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl;

$R^{14}$ is hydrogen, aryl or hetaryl;

G is —O—(CH$_2$)$_k$—R$^{17}$,

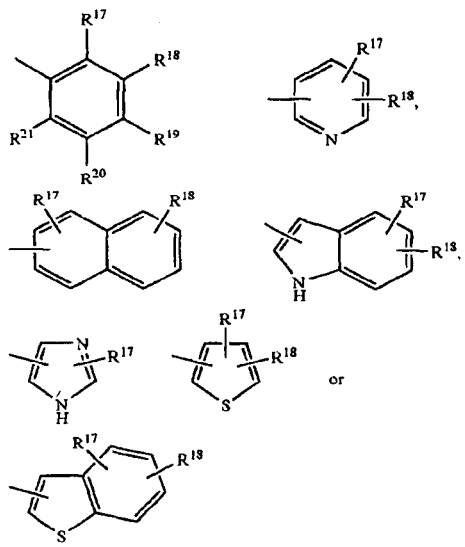

wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy;

k is 0, 1 or 2;

J is —O—(CH$_2$)$_l$—R$^{22}$,

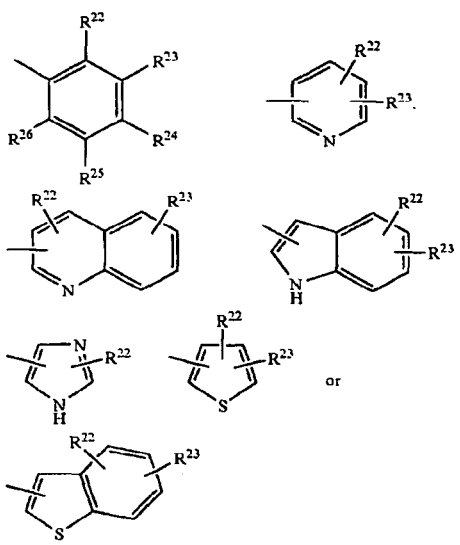

wherein $R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy;

l is 0, 1 or 2;

a is 0, 1, or 2;

b is 0, 1, or 2;

c is 0, 1, or 2;

d is 0 or 1;

e is 0, 1, 2, or 3;

f is 0 or 1;

$R^5$ is hydrogen or $C_{1-6}$-alkyl optionally substituted with one or more hydroxyl, aryl or hetaryl;

$R^6$ and $R^7$ are independently from each other hydrogen or $C_{1-6}$-alkyl, optionally substituted with one or more halogen, amino, hydroxyl, aryl, or hetaryl;

$R^8$ is hydrogen or $C_{1-6}$-alkyl, optionally substituted with one or more halogen, amino, hydroxyl, aryl, or hetaryl;

$R^6$ and $R^7$ or $R^6$ and $R^8$ or $R^7$ and $R^8$ may optionally form —(CH$_2$)$_i$—U—(CH$_2$)$_j$—, wherein i and j independently from each other are 1, 2 or 3 and U is —O—, —S—, or a valence bond;

M is arylene, hetarylene, —O—, —S— or —CR$^{27}$=CR$^{28}$—;

$R^{27}$ and $R^{28}$ are independently from each other hydrogen or $C_{1-6}$-alkyl, optionally substituted with one or more aryl or hetaryl;

or a pharmaceutically acceptable salt thereof.

Moreover, the compounds of formula I may comprise any optical isomers thereof, in the form of separated, pure or partially purified optical isomers or racemic mixtures thereof. Whenever one or more chiral carbon atoms are present such chiral center or centers may be in the R- and/or S-configuration, or a mixture of R and S.

Furthermore, the compounds of formula I may have one or more carbon-carbon double bonds with the possibility of geometric isomer, and it is intended that possible stereoisomers (E or Z isomers) are included in the scope of the invention, unless a special geometric isomer is specified.

In one embodiment of the compound of formula I $R^1$ is $C_{1-6}$-alkyl, such as $C_{1-6}$-alkyl, in particular methyl. In a second embodiment $R^1$ is hydrogen.

In a further embodiment of the compound of formula I $R^2$ is $C_{1-6}$-alkyl, such as $C_{1-6}$-alkyl, in particular methyl.

In a still further embodiment of the compound of formula I L is

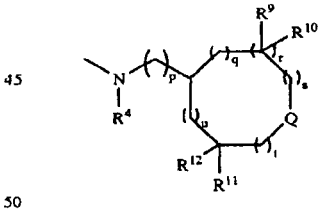

wherein $R^1$ is hydrogen or $C_{1-6}$ alkyl;

p is 0 or 1;

q, s, t, u are independently from each other 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—R$^{13}$ or

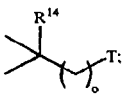

wherein o is 0, 1 or 2;

T is —N(R$^{15}$)(R$^{16}$) or hydroxyl;

R$^{13}$, R$^{15}$, and R$^{16}$ are independently from each other hydrogen or C$_{1-6}$ alkyl;

R$^{14}$ is hydrogen, aryl or hetaryl. In one embodiment R$^4$ is hydrogen. In a second embodiment R$^4$ is C$_{1-6}$-alkyl, such as C$_{1-4}$-alkyl, in particular methyl. In a third embodiment p is 0. In a further embodiment q is 0. In a still further embodiment q is 1. In a further embodiment s is 0. In a still further embodiment s is 1. In a further embodiment t is 0. In a still further embodiment t is 1. In a further embodiment u is 0. In a still further embodiment u is 1. In a further embodiment r is 0. In a still further embodiment r is 1. In a further embodiment R$^9$ is hydrogen. In a still further embodiment R$^9$ is C$_{1-6}$-alkyl, such as C$_{1-4}$-alkyl, in particular methyl. In a further embodiment R$^{10}$ is hydrogen. In a still further embodiment R$^{10}$ is C$_{1-6}$-alkyl, such as C$_{1-4}$-alkyl, in particular methyl. In a further embodiment R$^{11}$ is hydrogen. In a still further embodiment R$^{11}$ is C$_{1-6}$-alkyl, such as C$_{1-4}$-alkyl, in particular methyl. In a further embodiment R$^{12}$ is hydrogen. In a still further embodiment R$^{12}$ is C$_{1-6}$-alkyl, such as C$_{1-4}$-alkyl, in particular methyl. In a further embodiment Q is >N—R$^{13}$. In a still further embodiment R$^{13}$ is hydrogen. In a further embodiment R$^{13}$ is C$_{1-6}$-alkyl, such as C$_{1-4}$-alkyl, in particular methyl. In a still further embodiment Q is

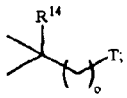

In a still further embodiment R$^{14}$ is hetaryl, In particular thiazolyl. In a further embodiment R$^{14}$ is hydrogen. In a still further embodiment o is 0. In a further embodiment o is 1. In a still further embodiment T is hydroxyl. In a further embodiment T is —N(R$^{15}$)(R$^{16}$). In a still further embodiment R$^{15}$ is C$_{1-6}$-alkyl, such as C$_{1-4}$-alkyl, in particular methyl. In a further embodiment R$^{16}$ is C$_{1-6}$-alkyl, such as C$_{1-4}$-alkyl, in particular methyl.

In a further embodiment of the compound of formula I L is

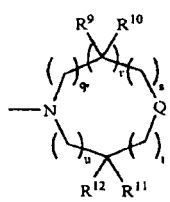

wherein q, s, t, u independently from each other are 0, 1, 2, 3 or 4;

r is 0 or 1;

the sum q+r+s+t+u is 0, 1, 2, 3, or 4;

R$^9$, R$^{10}$, R$^{11}$, and R$^{12}$ are independently from each other hydrogen or C$_{1-6}$ alkyl;

Q is >N—R$^{13}$ or

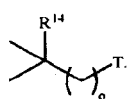

wherein o is 0, 1 or 2;

T is —N(R$^{15}$)(R$^{16}$) or hydroxyl;

R$^{13}$, R$^{15}$, and R$^{16}$ are independently from each other hydrogen or C$_{1-6}$ alkyl;

R$^{14}$ is hydrogen, aryl or hetaryl. In one embodiment q is 0. In a second embodiment q is 1. In a third embodiment s is 0. In a further embodiment s is 1. In a still further embodiment t is 0. In a further embodiment t is 1. In a still further embodiment u is 0. In a further embodiment u is 1. In a still further embodiment r is 0. In a further embodiment r is 1. In a still further embodiment R$^9$ is hydrogen. In a still further embodiment R$^9$ is C$_{1-6}$-alkyl, such as C$_{1-4}$-alkyl, in particular methyl. In a further embodiment R$^{10}$ is hydrogen. In a still further embodiment R$^{10}$ is C$_{1-6}$-alkyl, such as C$_{1-4}$-alkyl, in particular methyl. In a further embodiment R$^{11}$ is hydrogen. In a still further embodiment R$^{11}$ is C$_{1-6}$-alkyl, such as C$_{1-4}$-alkyl, in particular methyl. In a further embodiment R$^{12}$ is hydrogen. In a still further embodiment R$^{12}$ is C$_{1-6}$-alkyl, such as C$_{1-4}$-alkyl, in particular methyl. In a further embodiment Q is >N—R$^{13}$. In a still further embodiment R$^{13}$ is hydrogen. In a still further embodiment R$^{13}$ is C$_{1-6}$-alkyl, such as C$_{1-4}$-alkyl, in particular methyl. In a further embodiment Q is

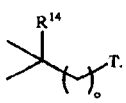

In a still further embodiment R$^{14}$ is hetaryl, in particular thiazolyl. In a further embodiment R$^{14}$ is hydrogen. In a still further embodiment o is 0. In a further embodiment o is 1. In a still further embodiment T is hydroxyl. In a further embodiment T is —N(R$^{15}$)(R$^{16}$). In a still further embodiment R$^{15}$ is C$_{1-6}$-alkyl, such as C$_{1-4}$-alkyl, in particular methyl. In a further embodiment R$^{16}$ is C$_{1-6}$-alkyl, such as C$_{1-4}$-alkyl, in particular methyl.

In the compound of the above formula I L is preferably 4-hydroxy-4-(2-thienyl)piperidino, (3-hydroxycyclohexyl) amino, 4-(N,N-dimethylamino)piperidino, N-methyl-N-(1-methylpiperidin-4-yl)amino), 4-((N,N-dimethylamino) methyl)piperidino, 4-methylpiperazino, (2,2,6,6-tetramethylpiperidine-4-yl)amino, 4-hydroxypiperidino, (3S)-3-((N,N-dimethylamino)methyl)piperidino, (2S)-2-((N,N-dimethylamino)methyl)pyrrolidino.

In a still further embodiment of the compound of formula I G is

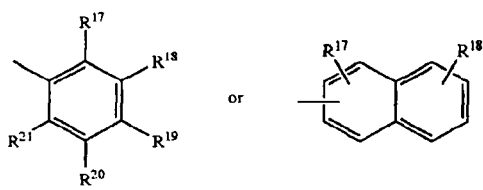

wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy. In one embodiment $R^{17}$ is hydrogen. In a second embodiment $R^{18}$ is hydrogen. In a third embodiment $R^{19}$ is hydrogen. In a further embodiment $R^{19}$ is aryl, in particular phenyl. In a still further embodiment $R^{20}$ is hydrogen. In a further embodiment $R^{21}$ is hydrogen. In the compound of the above formula I G is preferably 2-naphthyl or biphenyl-4-yl.

In a further embodiment of the compound of formula I J is

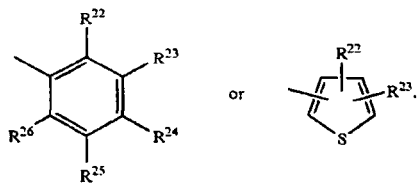

wherein $R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy. In one embodiment $R^{22}$ is hydrogen. In a second embodiment $R^{23}$ is hydrogen. In a third embodiment $R^{24}$ is hydrogen. In a further embodiment $R^{24}$ is halogen, in particular fluorine. In a still further embodiment $R^{25}$ is hydrogen. In a further embodiment $R^{26}$ is hydrogen. In the compound of the above formula I J is preferably phenyl, 4-fluorophenyl or 2-thienyl.

In a still further embodiment of the compound of formula I a is 1.

In a further embodiment of the compound of formula I b is 1.

In a still further embodiment of the compound of formula I c is 0.

In a further embodiment of the compound of formula I d is 0.

In a still further embodiment of the compound of formula I M is arylene or —$CR^{27}$=$CR^{28}$—, wherein $R^{27}$ and $R^{28}$ independently from each other are hydrogen or $C_{1-6}$-alkyl, optionally substituted with aryl or hetaryl. In one embodiment M is arylene, in particular phenylene. In another embodiment M is —$CR^{27}$=$CR^{28}$—, wherein $R^{27}$ and $R^{28}$ are independently hydrogen or $C_{1-6}$-alkyl. In a further embodiment $R^{27}$ is hydrogen. In a still further embodiment $R^{27}$ is $C_{1-6}$-alkyl, in particular methyl. In a further embodiment $R^{28}$ is hydrogen. In a further embodiment M is the E-isomer of $CR^{27}$=$CR^{28}$—. In the compound of the above formula I M is preferably ethenylene, 1,3-phenylene or 1,2-propenylene.

In a further embodiment of the compound of formula I e is 0.

In a still further embodiment of the compound of formula I e is 0.

In a further embodiment of the compound of formula I f is 0.

In a still further embodiment of the compound of formula I f is 1.

In a further embodiment of the compound of formula I $R^6$ and $R^7$ are independently from each other hydrogen or $C_{1-6}$-alkyl. In one embodiment $R^6$ is hydrogen. In a second embodiment $R^6$ is $C_{1-6}$-alkyl, in particular methyl. In a third embodiment $R^7$ is hydrogen. In a further embodiment $R^7$ is $C_{1-6}$-alkyl, in particular methyl.

In a still further embodiment of the compound of formula I $R^6$ and $R^7$ or $R^6$ and $R^8$ or $R^7$ and $R^8$ may optionally form —$(CH_2)_i$—U—$(CH_2)_j$—, wherein i and j independently from each other are 1 or 2 and U is —O—, —S—, or a valence bond.

In a further embodiment of the compound of formula I $R^6$ and $R^7$ form —$(CH_2)_i$—U—$(CH_2)_j$—, wherein i and j independently from each other are 1, 2 or 3 and U is —O—, —S—, or a valence bond. In one embodiment the sum i+j is 3. In a second embodiment U is a valence bond. In a particular embodiment $(CR^6R^7)$ is cyclobutyl.

In a still further embodiment of the compound of formula I $R^6$ and $R^7$ form —$(CH_2)_i$—U—$(CH_2)_j$—, wherein i and j independently from each other are 1 or 2 and U is —O—, —S—, or a valence bond. In one embodiment the sum i+j is 3. In a second embodiment U is a valence bond. In a particular embodiment $(CR^6R^7)$ is cyclobutyl.

In a further embodiment of the compound of formula I $R^8$ is hydrogen. In a second embodiment $R^8$ is $C_{1-6}$-alkyl, in particular methyl.

In a special embodiment the present invention relates to a compound of the general formula I formula I

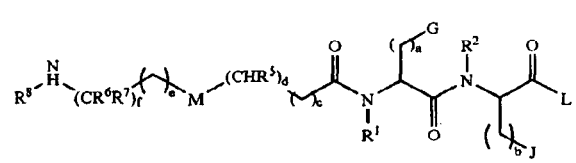

wherein $R^1$ is hydrogen or $C_{1-6}$-alkyl;

$R^2$ is $C_{1-6}$-alkyl;

L is

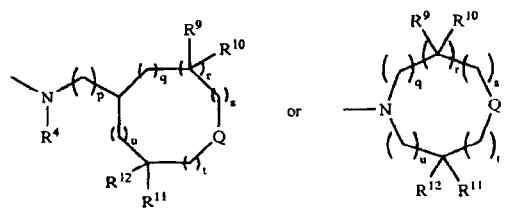

wherein $R^4$ is hydrogen or $C_{1-6}$ alkyl;

p is 0 or 1;

q, s, t, u are independently from each other 0, 1, 2, 3 or 4;

r is 0 or 1;

the sum q+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

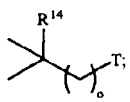

wherein o is 0, 1 or 2;

T is —N($R^{15}$)($R^{16}$) or hydroxyl;

$R^{13}$, $R^{15}$, and $R^{16}$ are independently from each other hydrogen or $C_{1-6}$ alkyl;

$R^{14}$ is hydrogen, aryl or hetaryl;

G is

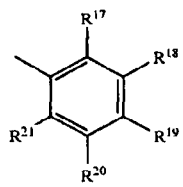 or 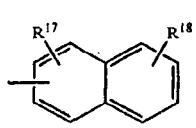

wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy;

J is

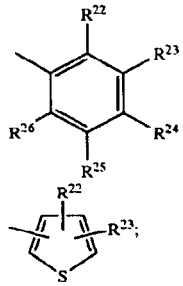 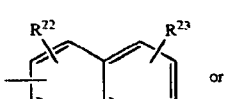

wherein $R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy;

a is 0, 1, or 2;

b is 0, 1, or 2;

c is 0, 1, or 2;

d is 0 or 1;

e is 0, 1, 2, or 3;

f is 0 or 1;

$R^5$ is hydrogen or $C_{1-6}$-alkyl optionally substituted with one or more hydroxyl, aryl or hetaryl;

$R^6$ and $R^7$ are independently from each other hydrogen or $C_{1-6}$-alkyl, optionally substituted with one or more halogen, amino, hydroxyl, aryl, or hetaryl;

$R^8$ is hydrogen or $C_{1-6}$-alkyl, optionally substituted with one or more halogen, amino, hydroxyl, aryl, or hetaryl;

$R^6$ and $R^7$ or $R^6$ and $R^8$ or $R^7$ and $R^8$ may optionally form —(CH$_2$)$_i$—U—(CH$_2$)$_j$—, wherein i and j independently from each other are 1, 2 or 3 and U is —O—, —S—, or a valence bond;

M is arylene or —C$R^{27}$=C$R^{28}$—;

$R^{27}$ and $R^{28}$ are independently from each other hydrogen or $C_{1-6}$-alkyl, optionally substituted with one or more aryl or hetaryl;

or a pharmaceutically acceptable salt thereof.

Preferred compounds of formula I of the invention are:

(2E)-5-Amino-5-methylhex-2-enoic acid N-((1R)-1-{N-[(1R)-1-benzyl-2-(4-(dimethylamino)methyl)piperidin-1-yl)-2-oxoethyl]-N-methylcarbamoyl}-2-(2-naphthyl)ethyl)-N-methylamide

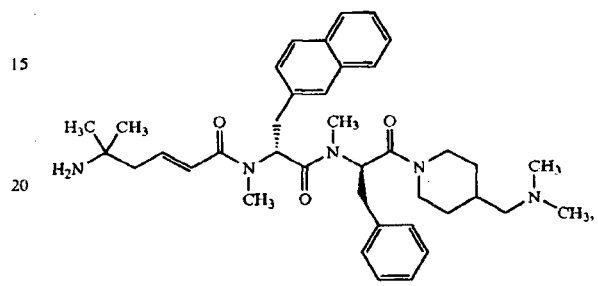

(2E)-5-Amino-5-methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

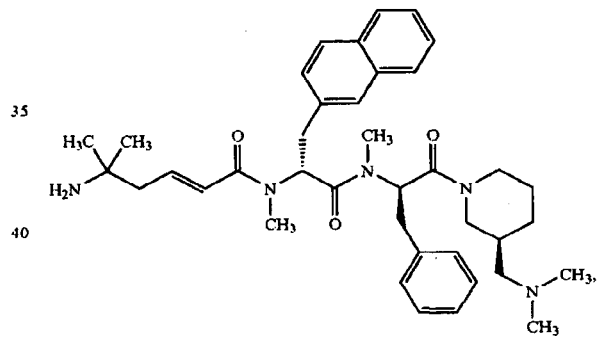

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

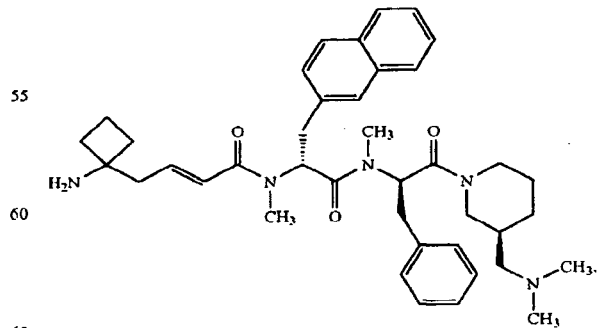

11

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

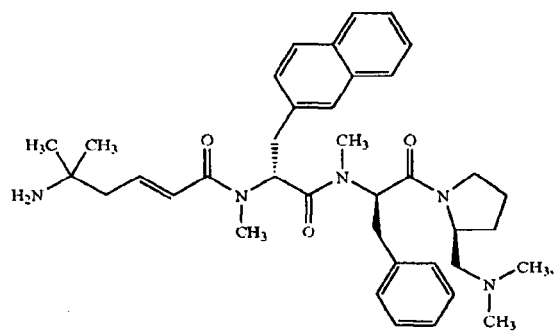

N-((1R)-1-{N-[(1R)-1-Benzyl-2-((2S)-2-(dimethylamino)methyl)pyrrolidin-1-yl)-2-oxoethyl]-N-methylcarbamoyl}-2-(2-naphthyl)ethyl)-N-methyl-3-((methylamino)methyl)benzamide

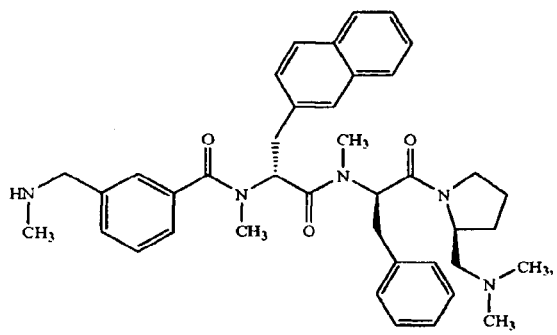

(2E)-5-Amino-5-methylhex-2-enoic acid N-((1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide.

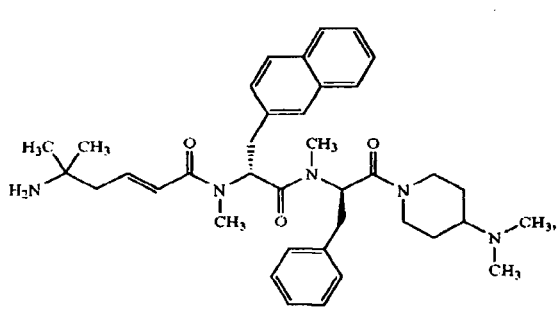

12

(2E)-5-Amino-5-methylhex-2-enoic acid N-methyl-N-[(1R)-1-(N-methyl-N-{(1R)-1-[N-methyl-N-(1-methylpiperidin-4-yl)carbamoyl]-2-phenylethyl}carbamoyl)-2-(2-naphthyl)ethyl]amide

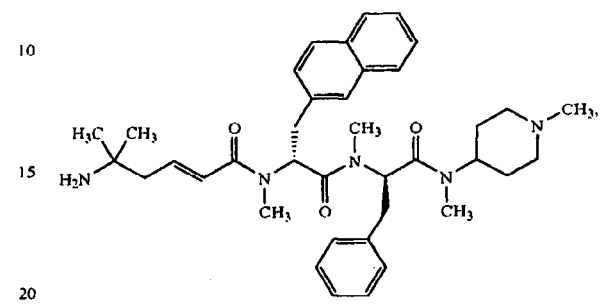

3-Aminomethyl-N-((1R)-1-{N-[(1R)-1-benzyl-2-(4-methylpiperazin-1-yl)-2-oxoethyl]-N-methylcarbamoyl}-2-(2-naphthyl)ethyl)-N-methylbenzamide

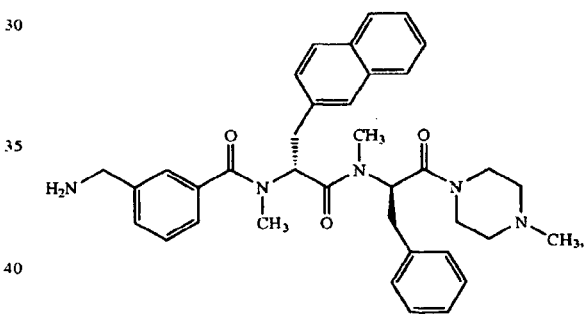

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

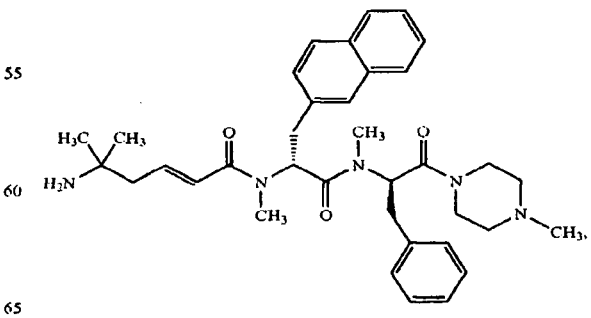

13

(2E)-5-Amino-5-methylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

14

(2E)4-(1-Aminocyclobutyl)but-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

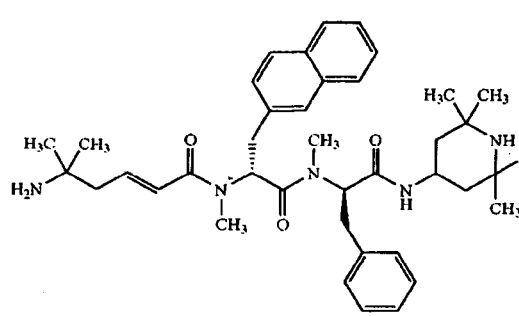

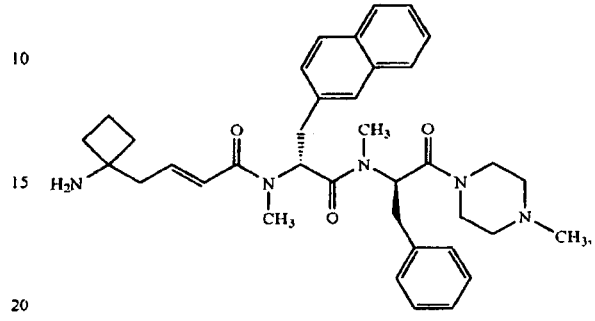

3-Aminomethyl-N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide (2E)-5-Amino-3,5-dimethylhex-2-enoic acid N-((1R)1-{N-[(1R)1-benzyl-2-(4-methylpiperazin-1-yl)-2-oxoethyl]-N-methylcarbamoyl}-2-(2-naphthyl)ethyl)-N-methylamide

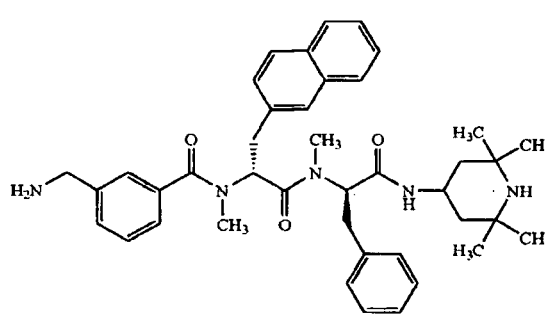

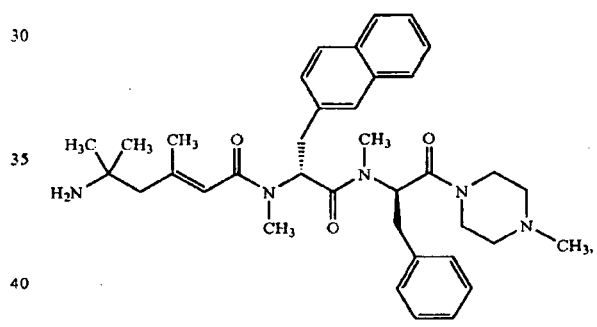

(2E)-5-Amino-3,5-dimethylhex-2-enoic acid N-methyl-N-((1R)-1-{N-methyl-N-[(1R)-2-phenyl-1-((2 2,6,6-tetramethylpiperdin-4-yl)carbamoyl)ethyl]carbamoyl}-2-(2-naphthyl)ethyl)amide (2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

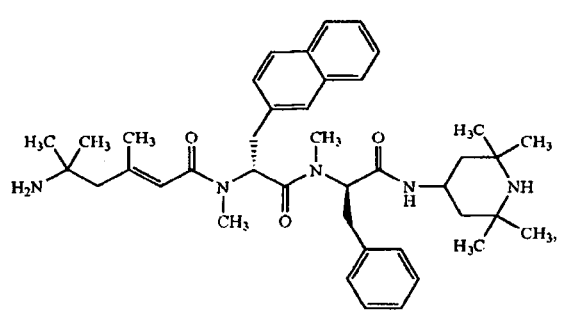

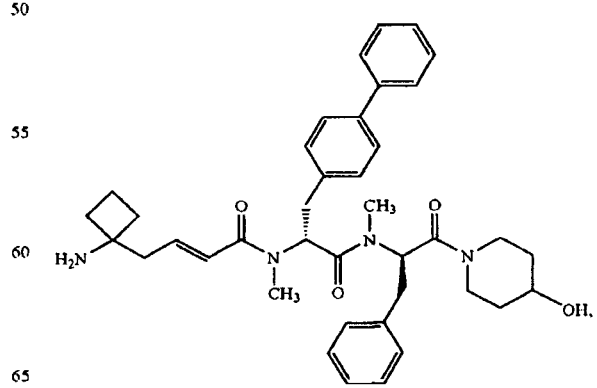

15

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

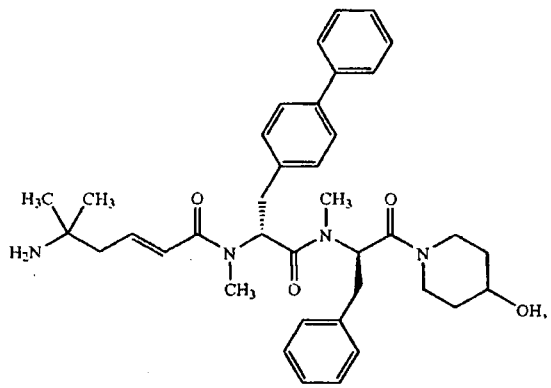

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

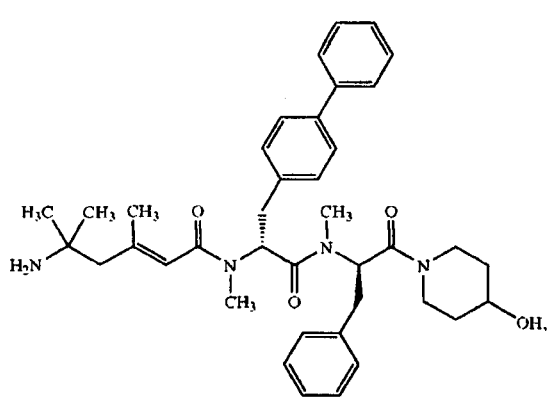

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

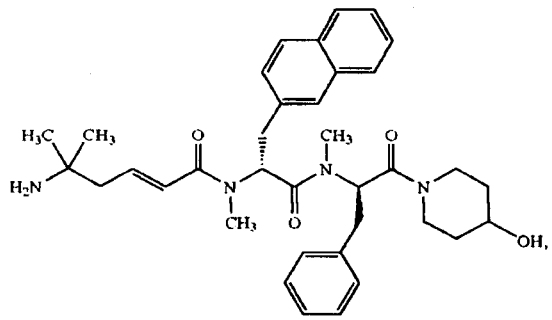

16

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

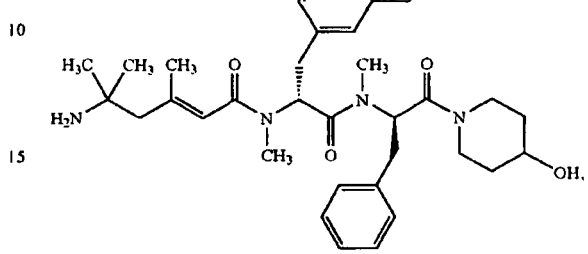

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

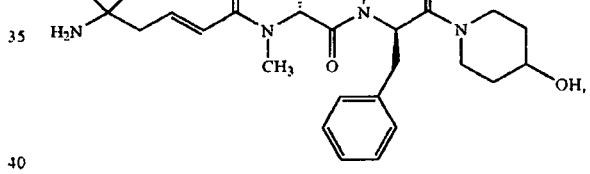

(2E)-5-Amino-5-methylhex-2-enoic acid N-((1R)-1-{N [(1R)-1-(4-fluorobenzyl)-2-(4-hydroxypiperidin-1-yl)-2-oxoethyl]-N-methylcarbamoyl}-2-(2-naphthyl)ethyl)-N-methylamide

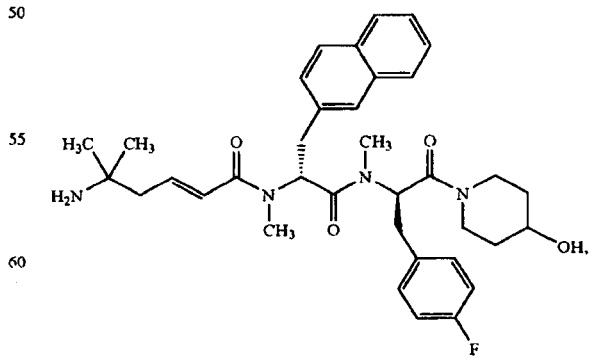

17

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

18

(2E)4-(1-Aminocyclobutyl)but-2-enoic acid N-((1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide

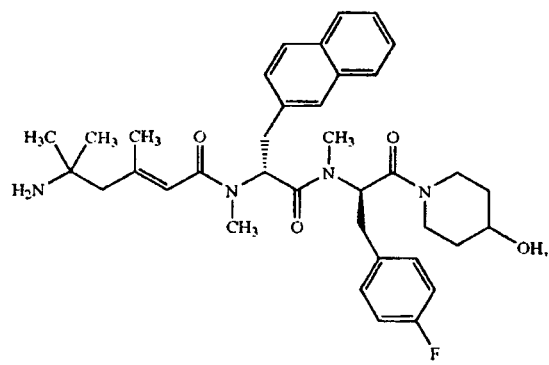
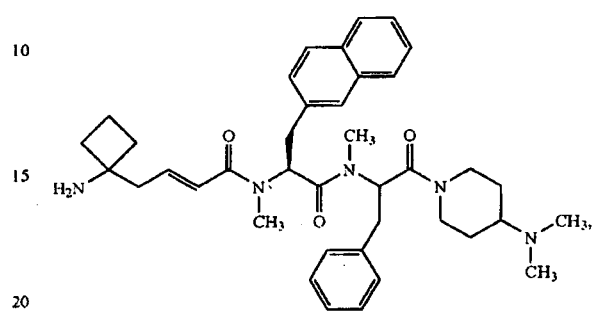

(2E)-5-Amino-5-methylhex-2-enoic acid N-((1R)-1-{N-[(1R)-1-benzyl-2-(4-hydroxy-4-(2-thienyl)piperidin-1-yl)-2-oxoethyl]-N-methylcarbamoyl}-2-(2-naphthyl)ethyl)-N-methylamide (2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

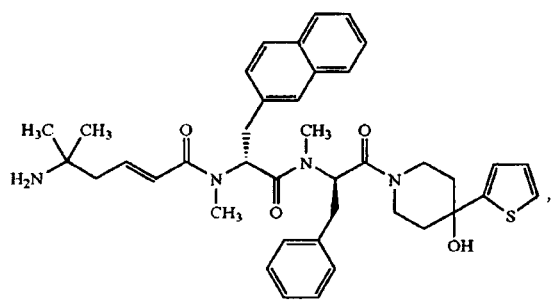
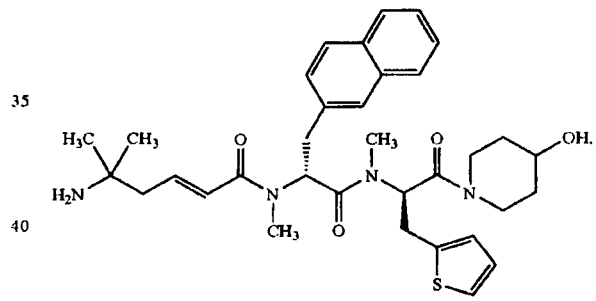

(2E)5-Amino-5-methylhex-2-enoic acid N-((1R)-1-{N-[(1R)-1-(3-hydroxycyclohexylcarbamoyl)-2-phenylethyl]-N-methylcarbamoyl}-2-(2-naphthyl)ethyl)-N-methylamide (2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

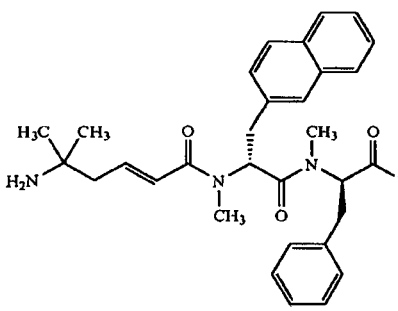
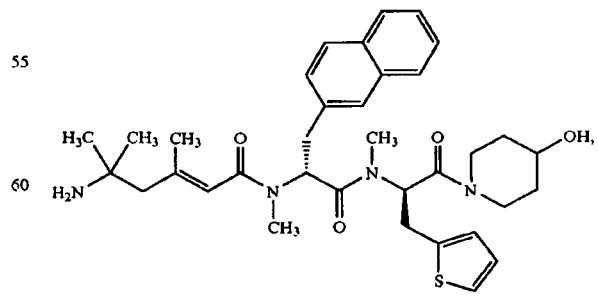

19

(2E)-5-Amino-5-methylhex-2-enoic acid N-((1R)-2-(biphenyl-4-yl)-1-{N-[(2R)-2-(4-hydroxypiperidin-1-yl)-2-oxo-1-((2-thienyl)methyl)ethyl]-N-methylcarbamoyl}ethyl)-N-methylamide

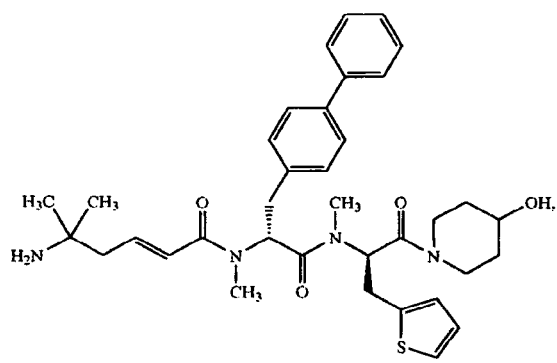

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide

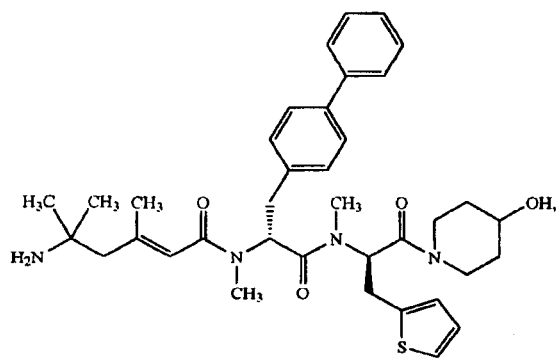

(2E)-5-Methyl-5-methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

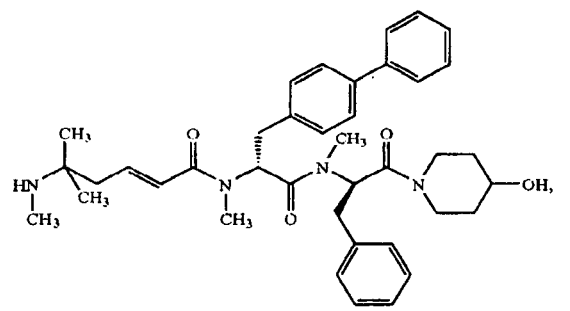

20

(2E)74-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide

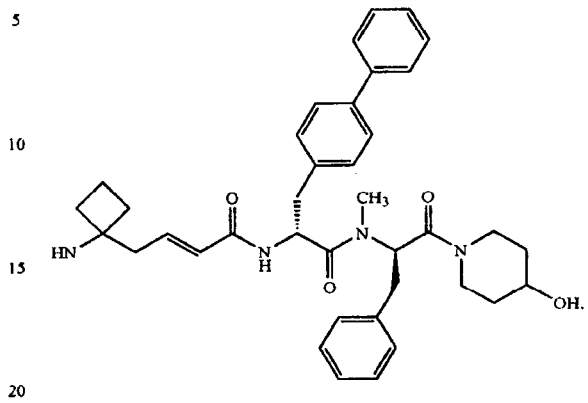

and pharmaceutically acceptable salts thereof.

General Methods

The methods illustrated in below schemes I–III are by no mean intended to limit the present invention in any aspect, but should only be seen as a guidance for how the present compounds may be prepared.

Scheme I

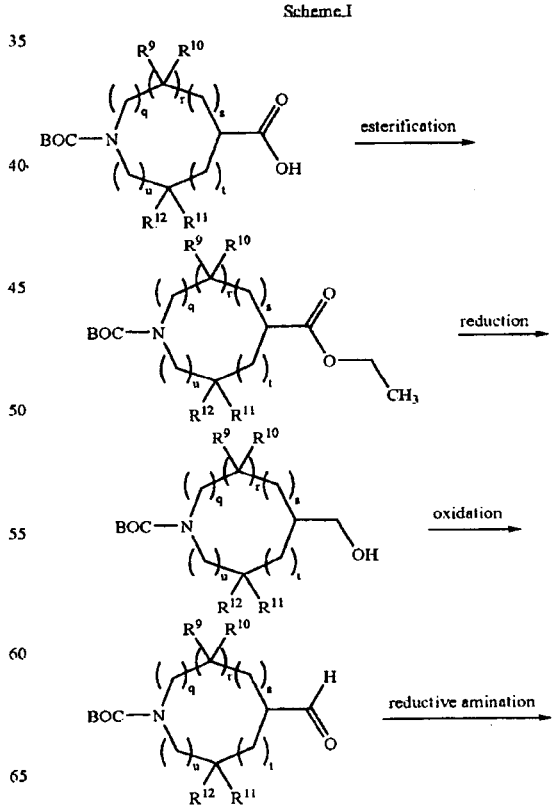

21

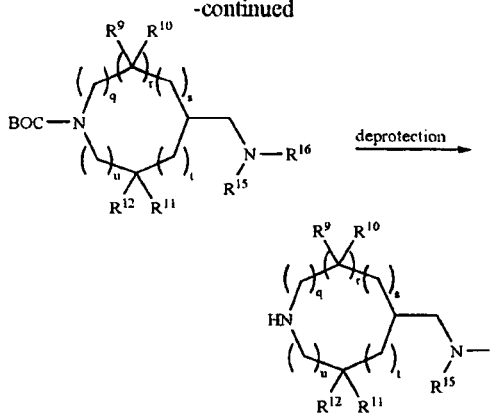

Amines of Type

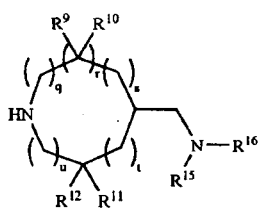

22 may be synthesized from a BOC-protected amino acid (cf. scheme I). The acid is transformed into an ester by reaction with or without a reagent such as e. g. 1-hydroxybenzotriazole, 1-hydroxy-7-azabenzotriazole, or 3-hydroxy-1,2,3-benzotriazole-4(3H)-one and a reagent such e.g. as N-3-dimethylaminopropyl)-N'-ethylcarbodiimide hydrochloride or diisopropylcarbodiimide and a catalyst such as N,N-dimethylaminopyridine. The ester may be reduced by a suitable reagent, such as diisobutylaluminum hydride in a appropriate solvent such as e.g. toluene, dichloromethane, ether, or tetrahydrofuran to give the BOC-protected aldehyde or alcohol. If the alcohol is obtained, the alcohol may be oxidized to the corresponding aldehyde, by a suitable method, such as e.g. dimethylsulfoxide/oxalyl chloride/triethylamine or dimethylsufloxide/sulfotrioxide/pyridine, pyridinium dichromate, or pyridinium chlorochromate. A reductive amination with an appropriate amine $N(R^{15})(R^{16})$ and a suitable reagent, such as sodium cyanoborohydride or sodium triacetoxyborohydride in a suitable solvent such as e.g. alcohols may yield the BOC-protected amine. If at least one of $R^{15}$ or $R^{16}$ is hydrogen, the amino group may be protected by a method known to those skilled in the art and described in the literature as e.g. T. W. Greene, P. G. M. Wuts Protective groups in organic synthesis, $2^{nd}$ edition, Wiley, New York, before carrying out the following steps. The removal of the BOC-protection group can be achieved by a method known to those skilled in the art as described in T. W. Greene, P. G. M. Wuts Protective groups in organic synthesis, $2^{nd}$ edition, Wiley, New York, such as e.g. hydrogen chloride in ethyl acetate, or trifluoroacetic acid in dichloromethane.

Scheme II

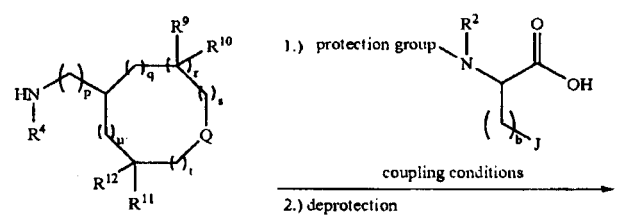

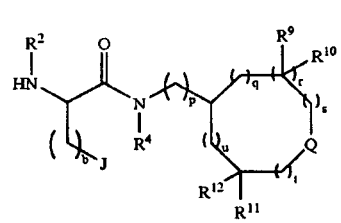

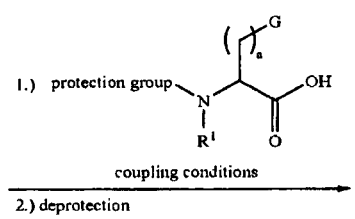

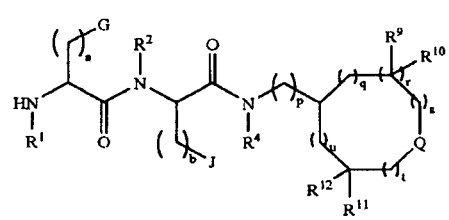

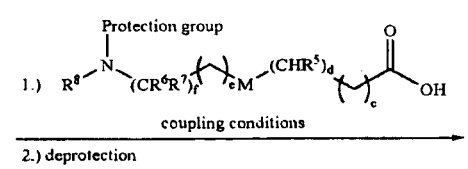

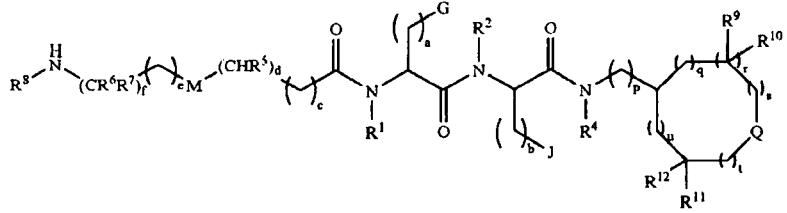

Compounds of the type of formula I may be synthesized by coupling of an amine of type

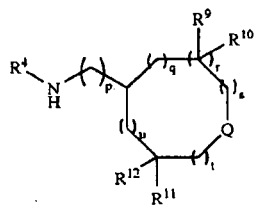

and a suitable protected acid with or without a coupling reagent such as e.g. 1-hydroxybenzotriazole, 1 hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane (cf. scheme II). The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York.

The product is coupled with a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. All protection groups may be removed by a method known for a person skilled in the art and described in the literature e.g. in T. W. Greene, P. G. M. Wuts Protective groups in organic synthesis, $2^{nd}$ edition, Wiley, New York.

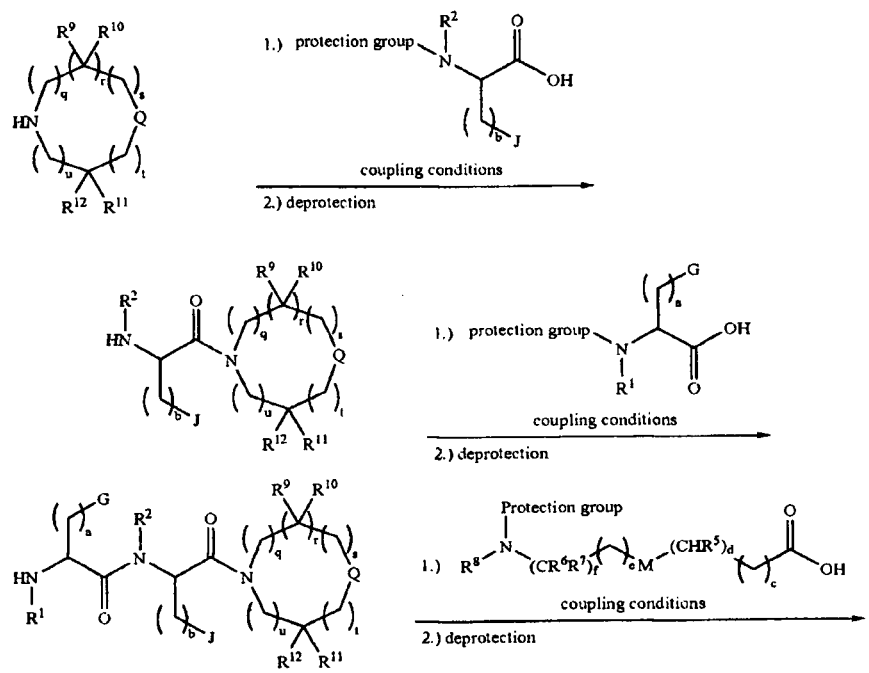

Scheme III

-continued

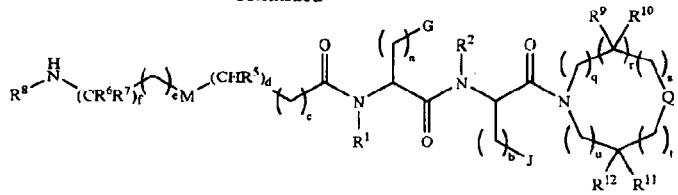

Compounds of the type of formula I may be synthesized by coupling of an amine of type

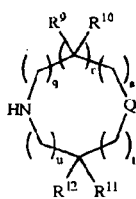

and a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane (cf. scheme III). The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with a suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as (3-dimethylaminopropyl)-N'-ethylcarbodiimide hydrochloride or diisopropylcarbodiimide in a suitable solvent, such as N,N-dimethylformamide or dichloromethane. The product may be deprotected at the nitrogen of the acid by a method known for a person skilled in the art and described in the literature e.g. in T. W. Greene, P. G. M. Wuts Protective groups in organic synthesis, $2^{nd}$ edition, Wiley, New York. The product is coupled with suitable protected acid with or without a coupling reagent such as e.g. 1-hydroxybenzotriazole, 1-hydroxy-7-azabenzotriazole, or 3-hydroxy-1,2,3-benzotriazole-4(3H)-one and a reagent such e.g. as N-(3-dimethylaminopropyl)-N'-ethylcarbodiimide hydrochloride or diisopropylcarbodiimide in a suitable solvent, such as N,N-dimethylformamide or dichloromethane. All protection groups may be removed by a method known for a person skilled in the art and described in the literature e.g. in T. W. Greene, P. G. M. Wuts Protective groups in organic synthesis, $2^{nd}$ edition, Wiley, New York.

The compounds of formula I exhibit an improved resistance to proteolytic degradation by enzymes because they are non-natural, in particular because the natural amide bonds are replaced by non-natural amide bond mimetics. The increased resistance to proteolytic degradation of the compounds of the invention in comparison with known hormone releasing peptides is expected to improve their bioavailability compared to that of the peptides suggested in the prior literature.

In the above structural formulas and throughout the present specification, the following terms have the indicated meanings:

The $C_{1-6}$-alkyl, $C_{1-6}$-alkylene, $C_{1-4}$-alkyl or $C_{1-4}$-alkylene groups specified above are intended to include those alkyl or alkylene groups of the designated length in either a linear or branched or cyclic configuration. Examples of linear alkyl are methyl, ethyl, propyl, butyl, pentyl, and hexyl and their corresponding divalent moieties, such as ethylene. Examples of branched alkyl are isopropyl, sec-butyl, tert-butyl, isopentyl, and isohexyl and their corresponding divalent moieties, such as isopropylene. Examples of cyclic alkyl are $C_{3-6}$ cycloalkyl such as cyclopropyl, cyclobutyl, cyclopentyl and cyclohexyl and their corresponding divalent moieties, such as cyclopropylene.

The $C_{1-6}$-alkoxy groups specified above are intended to include those alkoxy groups of the designated length in either a linear or branched or cyclic configuration. Examples of linear alkoxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are $C_{3-6}$-cycloalkoxy such as cyclopropyloxy, cyclobutyloxy, cyclopentyloxy and cyclohexyloxy.

In the present context, the term "aryl" is intended to include monovalent carbocyclic aromatic ring moieties, being either monocyclic, bicyclic or polycyclic, e.g. selected from the group consisting of phenyl and naphthyl, optionally substituted with one or more $C_{1-6}$-alkyl, $C_{1-6}$-alkoxy, halogen, amino or aryl.

In the present context, the term "arylene" is intended to include divalent carbocyclic aromatic ring moieties, being either monocyclic, bicyclic or polycyclic, e.g. selected from the group consisting of phenylene and naphthylene, optionally substituted with one or more $C_{1-6}$-alkyl, $C_{1-6}$-alkoxy, halogen, amino or aryl.

In the present context, the term "hetaryl" is intended to Include monovalent heterocyclic aromatic ring moieties, being either monocyclic, bicyclic or polycyclic, e.g. selected from the group consisting of pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thienyl, quinolinyl, pyrazinyl, or isothiazolyl, optionally substituted with one or more $C_{1-6}$-alkyl, $C_{1-6}$-alkoxy, halogen, amino or aryl.

In the present context, the term "hetarylene" is intended to include divalent heterocyclic aromatic ring moieties, being either monocyclic, bicyclic or polycyclic, e.g. selected from the group consisting of pyridinediyl, 1-H-tetrazolediyl, thiazoldiyl, imidazolediyl, indolediyl, pyrimidinediyl, thiadiazolediyl, pyrazolediyl, oxazolediyl, isoxazolediyl, oxadiazolediyl, thiophenediyl, quinolinediyl, pyrazinediyl, or isothiazolediyl, optionally substituted with one or more $C_{1-6}$-alkyl, $C_{1-6}$-alkoxy, halogen, amino or aryl.

In the present context, the term "heterocyclic system" is intended to include aromatic as well as non-aromatic ring moieties, which may be monocyclic, bicyclic or polycyclic, and contain in their ring structure at least one, such as one, two or three, nitrogen atom(s), and optionally one or more, such as one or two, other hetero atoms, e.g. sulpher or oxygen atoms. The heterocyclic system is preferably selected from pyrazole, pyridazine, triazine, indazole, phthalazine, cinnoline, pyrazolidine, pyrazoline, aziridine, dithiazine, pyrrol, imidazol, pyrazole, isoindole, indole, indazole, purine, pyrrolidine, pyrroline, imidazolidine, imidazoline, pyrazolidine, pyrazoline, piperidine, piperazine, indoline, isoindoline, or morpholine, optionally substituted with one or more $C_{1-6}$-alkyl, $C_{1-6}$-alkoxy, halogen, amino, oxy or aryl.

The term "halogen" is intended to include chlorine (Cl), fluorine (F), bromine (Br) and iodine (I).

In the context of the present application, the term "growth hormone secretagogue" is intended to include any compound which has the capacity, directly or indirectly, of inducing (i.e. stimulating or increasing) the release of growth hormone from the pituitary gland. The term "growth hormone secretagogue" includes growth hormone releasing peptides, growth hormone releasing peptidomimetics, and growth hormone releasing compounds of a nonpeptidyl nature.

The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, malic, maleic, mandelic phthalic, citric, glutaric, gluconic, methanesulfonic, salicylic, succinic, tartaric, toluenesulfonic, trifluoracetic, sulfamic or fumaric acid and/or water.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in Remington's Pharmaceutical Sciences, 1985 or in Remington: The Science and Practice of Pharmacy, 19th Edition (1995). The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 10 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacet: 940 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to a method of treating growth retardation in connection with asthma, the method comprising administering to a subject in need thereof an effective amount of a growth hormone secretagogue or a pharmaceutically acceptable salt thereof. In a particular embodiment, the present invention relates to a method of treating growth retardation in connection with asthma, the method comprising administering to a subject in need thereof an effective amount of a compound of the general formula I or a pharmaceutically acceptable salt thereof.

In a still further aspect, the present invention relates to a method of treating growth retardation in connection with juvenile rheumatic arthritis or systic fibrosis, the method comprising administering to a subject in need thereof an effective amount of a growth hormone secretagogue or a pharmaceutically acceptable salt thereof. In one embodiment, the present invention relates to a method of treating growth retardation in connection with juvenile rheumatic arthritis, the method comprising administering to a subject in need thereof an effective amount of a growth hormone secretagogue or a pharmaceutically acceptable salt thereof. In a second embodiment, the present invention relates to a method of treating growth retardation in connection with systic fibrosis, the method comprising administering to a subject in need thereof an effective amount of a growth hormone secretagogue or a pharmaceutically acceptable salt thereof. In a particular embodiment, the present invention relates to a method of treating growth retardation in connection with Juvenile rheumatic arthritis, the method comprising administering to a subject in need thereof an effective amount of a compound of the general formula I or a pharmaceutically acceptable salt thereof. In another particular embodiment, the present invention relates to a method of treating growth retardation In connection with systic fibrosis, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. Compounds of formula I are useful for stimulation of growth hormone release in the elderly, prevention of catabolic side effects of glucocorticoids, prevention and treatment of osteoporosis, treatment of chronic fatigue syndrom (CFS), treatment of acute fatigue syndrom and muscle loss following elective surgery, stimulation of the immune system, acceleration of wound healing, accelerating bone fracture repair, accelerating complicated fractures, e.g. disctraction osteogenesis, treatment of wasting secondary to fractures, treatment of growth retardation, treating growth retardation resulting from renal failure or insufficiency, treatment of cardiomyopathy, treatment of wasting in connection with chronic liver disease, treatment of thrombocytopenia, treatment of growth retardation in connection with Crohn's disease, treatment of short bowel syndrome, treatment of wasting in connection with chronic obstructive pulmonary disease (COPD), treatment of complications associated with transplantation, treatment of physiological short stature including growth hormone deficient children and short stature associated with chronic illness, treatment of obesity and growth retardation associated with obesity, treatment of anorexia, treatment of growth retardation associated with the Prader-Willi syndrome and Turner's syndrome; increasing the growth rate of a patient having partial growth hormone insensitive syndrome, accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patents, treatment of osteochondrodysplasias, Noonan's syndrome, schizophrenia, depressions, Alzheimer's disease, delayed wound healing and psychosocial deprivation, treatment of catabolism in connection with pulmonary dysfunction and ventilator dependency; treatment of cardiac failure or related vascular dysfunction, treatment of impaired cardiac function, treatment or prevention of myocardial infarction, lowering blood pressure, protection against ventricular dysfunction or prevention of reperfusion events; treatment of adults in chronic dialysis; attenuation of protein catabolic responses after major surgery, reducing cachexia and protein loss due to chronic illness such as cancer or AIDS; treatment of hyperihsulinemia including nesidioblastosis, adjuvant treatment for ovulation induction; stimulation of thymic development and prevention of the age related decline of thyme function, treatment of immunosuppressed patients; treatments of sarcopenia, treatment of wasting in connection with AIDS; improvement in muscle strength, mobility, maintenance of skin thickness, treatment of metabolic homeostasis and renal homeostasis in the frail elderly, stimulation of osteoblasts, bone remodelling and cartilage growth; regulation of food intake; stimulation of the immune system in companion animals and treatment of disorder of aging in companion animals, promoting growth in livestock and stimulation of wool growth in sheep, increasing milk production in livestock, treatment of metabolic syndrom (syndrome X), treatment of insulin resistance, including NIDDM, in mammals, e.g. humans, treatment of insulin resistance in the heart, improvement of sleep quality and correction of the relative hyposomatotropism of senescence due to high increase in REM sleep and a decrease in REM latency, treatment of hypothermia, treatment of frailty associated with aging, treatment of congestive heart failure, treatment of hip fractures, treatment of immune deficiency in individuals with a depressed T4/T8 cell ratio, treatment of muscular atrophy, treatment of musculoskeletal impairment in elderly, enhancing the activity of protein kinase B (PKB), improvement of the overall pulmonary function, and treatment of sleep disorders.

Within the context of the present application, the term "treatment" is also intended to include prophylactic treatment.

In a further aspect the present invention relates to the use of a growth hormone secretagogue or a pharmaceutically acceptable salt thereof for the preparation of a medicament for the treatment of growth retardation in connection with asthma. In one particular embodiment the invention relates to the use of a compound of the general formula I or a pharmaceutically acceptable salt thereof for the treatment of growth retardation in connection with asthma. In a second particular embodiment the invention relates to the use of growth hormone releasing peptides, growth hormone releasing peptidomimetics, or growth hormone releasing compounds of a nonpeptidyl nature or a pharmaceutically acceptable salt thereof for the treatment of growth retardation in connection with asthma.

In a still further aspect the present invention relates to the use of a growth hormone secretagogue or a pharmaceutically acceptable salt thereof for the preparation of a medicament for the treatment of growth retardation in connection with juvenile rheumatic arthritis or systic fibrosis. In one embodiment the invention relates to the use of a growth hormone secretagogue or a pharmaceutically acceptable salt thereof for the preparation of a medicament for the treatment of growth retardation in connection with juvenile rheumatic arthritis. In a second embodiment the invention relates to the use of a growth hormone secretagogue or a pharmaceutically acceptable salt thereof for the preparation of a medicament for the treatment of growth retardation in connection with systic fibrosis. In one particular embodiment the invention relates to the use of a compound of the general formula or a pharmaceutically acceptable salt thereof for the treatment of growth retardation in connection with juvenile rheumatic arthritis. In another particular embodiment the invention relates to the use of a compound of the general formula I or a pharmaceutically acceptable salt thereof for the treatment of growth retardation in connection with systic fibrosis. In a further particular embodiment the invention relates to the use of growth hormone releasing peptides, growth hormone releasing peptidomimetics, or growth hormone releasing compounds of a nonpeptidyl nature or a pharmaceutically acceptable salt thereof for the treatment of growth retardation in connection with juvenile rheumatic arthritis. In a still further particular embodiment the invention relates to the use of growth hormone releasing peptides, growth hormone releasing peptidomimetics, or growth hormone releasing compounds of a nonpeptidyl nature or a pharmaceutically acceptable salt thereof for the treatment of growth retardation in connection with systic fibrosis.

For the above indications the dosage will vary depending on the growth hormone secretagogue employed, e.g. on the compound of formula I employed, on the mode of administration and on the therapy desired. However, generally dosage levels between 0.0001 and 100 mg/kg body weight daily are administered to patients and animals to obtain effective release of endogenous growth hormone. Moreover the compounds of formula I have no or substantially no side-effects, when administered in the above dosage levels, such side-effects being e.g. release of LH, FSH, TSH, ACTH, vasopressin, oxytocin, cortisol and/or prolactin. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

The dosage of the compounds according to this invention is suitably 0.01–500 mg/day, e.g. from about 5 to about 50 mg, such as about 10 mg per dose, when administered to patients, e.g. humans, as a drug.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula I, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals to increase their rate and extent of growth, and to increase milk and wool production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures, and such evaluation may be performed as described below.

The isolation of rat pituitary cells is a modification of O. Sartor et al. *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium: DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/l dexamethasone (Sigma D-4902) pH 7.3, to a density of $2 \times 10^5$ cells/ml. The cells were seeded into microtiter plates (Nunc, Denmark), 200 ml/well, and cultured for 3 days at 37° C. and 8% $CO_2$.

Compound Testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability using the procedure described below:

Compounds is dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, MO, USA).

Enzymes (trypsin, chymotrypsin, elastase aminopeptidase M and carboxypeptidase Y and B) were all purchased from Boehringer Mannheim GmbH (Mannheim, Germany).

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0.

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass spectrometry (PDMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative | MW/SIM ion (amu) | Carboxy-peptidase mix | Pan. enzyme mix |
|---|---|---|---|
| Standards | | | |
| ACTH 4–10 | 1124.5/562.8 | + | − |
| Glucagon | 3483/871.8 | − | − |
| Insulin (B23–29) | 859.1/430.6 | | |
| Angiotensin 1–14 | 1760.1/881.0 | − | − |
| GHRP-2 | 817.4/409.6 | | |
| GHRP-6 | 872.6/437.4 | − | − |

+: Stable (less than 20% decrease in SIM signal after 24 h in degradation solution)
−: Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. mp is melting point and is given in °C. Column chromatography was carried out using the technique described by W. C. Still et al, J. Org. Chem. 1978, 43, 2923–2925 on silica gel 60. Compounds used as starting materials are either known compounds or compounds which can readily be prepared by methods known per se.

HPLC-Analysis:
Method A1.

The RP-analysis was performed using UV detections at 214, 254, 276, and 301 nm on a 218TP54 4.6 mm×250 mm 5 m C-18 silica column (The Seperations Group, Hesperia), a which was eluted at 1 mL/min at 42° C. The column was equilibrated with 5% acetonitrile in a buffer consisting of 0.1 M ammonium sulfate, which was adjusted to pH 2.5 with 4M sulfuric acid. After injection the sample was eluted by a gradient of 5% to 60% acetonitrile in the same buffer during 50 min.

Method B1.

The RP-analysis was performed using UV detections at 214, 254, 276, and 301 nm on a 218TP54 4.6 mm×250 mm 5 m C-18 silica column (The Seperations Group, Hesperia), which was eluted at 1 mL/min at 42° C. The column was equilibrated with 5% (acetonitrile+0.1% TFA) in an aqueous solution of TFA in water (0.1%). After injection the sample was eluted by a gradient of 5% to 60% (acetonitrile+0.1% TFA) in the same aqueous buffer during 50 min.

Abbreviations:

| TLC: | thin layer chromatography |
| DMSO: | dimethylsulfoxide |
| min: | minutes |
| h: | hours |

Boc: tert butyloxycarbonyl
DMF: dimethylformamide
THF: tetrahydrofuran
EDAC: N-ethyl-N'-dimethylaminopropylcarbodiimide hydrochloride
HOAt: 1-hydroxy-7-azabenzotrazole
DIEA: diisopropylethylamine
TFA: trifluoroacetic acid Buildingblocks:
N-methylated amino acids used in the following examples were prepared as in Can. J. Chem. 1977, 55, 906.
3-Hydroxy-1,1-dimethylpropylcarbamic acid tert-butyl ester:

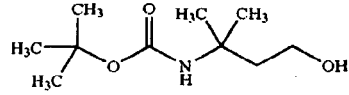

At 0° C., ethyl chloroformate (1.10 mL, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature over a period of 4 h. It was cooled to 0° C. Methanol (5 mL) was added carefully. 1N Hydrochloric acid (100 mL) was added. The solution was extracted with ethyl acetate (2×100 mL, 3×50 mL). The combined organic layers were washed with saturated sodium hydrogen carbonate solution (100 mL) and dried over magnesium sulfate. The solvent was removed in vacuo. The crude product was chromatographed on silica (110 g) with ethyl acetate/heptane 1:2 to give 1.84 g of 3hydroxy-1,1-dimethylpropylcarbamic acid tert-butyl ester.

¹H-NMR (CDCl₃): d 1.33 (s, 6H); 1.44 (s, 9H); 1.88 (t, 2H); 1.94 (br, 1H); 3.75 (q, 2H); 4.98 (br, 1H).

3-(tert-Butoxycarbonylamino)-3-methylbutanal:

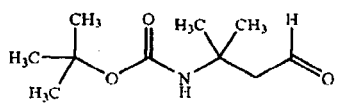

DMSO (1.22 mL, 17.2 mmol) was added to a solution of oxalyl chloride (1.1 mL, 12.9 mmol) at −78° C. in dichloromethane (15 mL). The mixture was stirred for 15 min at −78° C. A solution of 3-hydroxy-1,1-dimethylpropylcarbamic acid tert-butyl ester (1.75 g, 8.6 mmol) in dichloromethane (10 mL) was added dropwise over a period of 15 min. The solution was stirred at −78° C. for another 15 min. Triethylamine (6.0 mL, 43 mmol) was added. The solution was stirred at −78° C. for 5 min and then warmed to room temperature. The solution was diluted with dichloromethane (100 mL) and extracted with 1 N hydrochloric acid (100 mL). The aqueous phase was extracted with dichloromethane (50 mL). The combined organic layers were washed with saturated sodium hydrogen carbonate solution (100 mL) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

MHz-¹H-NMR (CDCl₃): d 1.39 (s, 6H); 1.45 (s, 9H); 2.85 (d, 2H); 4.73 (br, 1H); 9.80 (t, 1H).

Ethyl (2E)-5-(tert-Butoxycarbonylamino)-5-methylhex-2-enoate:

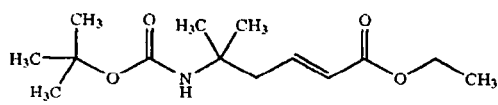

Triethylphoshonoacetate (1.96 ml, 9.8 mmol) was dissolved in tetrahydrofuran (30 ml). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 ml) was added. The solution was stirred at room temperature for 75 min. It was diluted with ethyl acetate (100 ml) and 1N hydrochloric acid (100 ml). The phases were separated. The aqueous phase was extracted with ethyl acetate (2×50 ml). The combined organic phases were washed with saturated sodium hydrogen carbonate solution (60 ml) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

¹H-NMR (CDCl₃): d 1.30 (s, 6H); 1.30 (t, 3H); 1.46 (s, 9H); 2.62 (d, 2H); 4.27 (q, 2H); 4.42 (br, 1H); 5.88 (d, 1H); 6.94 (td, 1H).

(2E)-5-(tert-Butoxycarbonylamino)-5-methylhex-2-enoic acid:

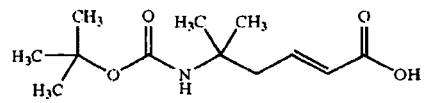

Ethyl (2E)-5-(tert-butoxycarbonylamino)-5-methylhex-2-enoate (1.233 g, 4.54 mmol) was dissolved in dioxane (20 ml). Lithium hydroxide (0.120 g, 5.00 mmol) was added as a solid. Water (10 ml) was added, until a clear solution was reached. The solution was stirred 16 h at room temperature. The solution was diluted with water (70 ml) and was extracted with tert-butyl methyl ether (2×100 ml). The aqueous phase was acidified with 1N sodium hydrogensulfate solution (pH=1) and was extracted with tert-butylmethylether (3×70 ml). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.

¹H-NMR (DMSO d₆): d 1.15 (s, 6H); 1.35 (s, 9H); 2.53 (d, 2H); 5.75 (d, 1H); 6.57 (br, 1H); 6.75 (td, 1H); 12.15 (s, 1H).

1-Aza-spiro[3.3]heptan-2-one:

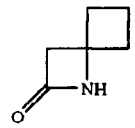

Methylenecyclobutane (40.0g, 0.587 mol) was dissolved in diethylether (250 ml). At −40° C. chlorosulfonylisocyanate (26 ml, 0.294 mol) was added dropwise. The reaction mixture was warmed to 10° C., An exothermic reaction was observed, and precipitation was formed. The reaction mixture was cooled to −20° C. It was stirred for 16 h, while it was warming up to room temperature. A saturated aqueous solution of sodium sulfite (100 ml) was added dropwise. The reaction mixture was stirred vigorously for 1 h. Another saturated aqueous solution of sodium sulfite (100 ml) was added dropwise. Solid sodium hydrogen carbonate was added, until pH 7. Dichloromethane (500 ml) was added. The phases were separated. The organic layer was dried over magnesium sulfate. The solvent was removed in vacuo, to give 23.59 g of 1-aza-spiro[3.3]heptan-2-one.

¹H-NMR (CDCl₃): d 1.75 (m, 2H); 2.26 (m, 2H); 2.39 (m, 2H); 2.96 (s, 2H); 6.55 (br, 1H).

2-Oxo-1-azaspiro[3.3]heptane-1-carboxylic acid tert-butylester

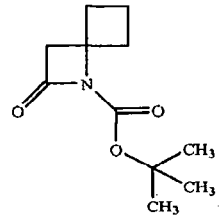

A solution of di-tert-butyl dicarbonate (55.7 g, 0.211 mol) in dichloromethane (100 ml) was added dropwise to a solution of 1-aza-spiro[3.3]heptan-2-one, triethylamine (36 ml, 0.255 mol), and 4-dimethylaminopyridiene (2.6 g, 0.021 mol) in dichloromethane (100 ml). The reaction mixture was stirred for 16 h at room temperature. It was washed with a 10% aqueous solution of ammonium chloride (100 ml), water (100 ml) and a saturated aqueous solution of sodium hydrogen carbonate (100 ml). The organic layer was dried over magnesium sulfate. The solvent was removed in vacuo to give 48.24 g of crude 2-oxo-1-azaspiro[3.3]heptane-1-carboxylic acid tert-butylester, which was used for the next step without purification.

¹H-NMR (CDCl₃): d 1.55 (s, 9H); 1.78 (m, 1H); 1.92 (m, 1H); 2.18 (m, 2H); 2.90 (m, 2H); 3,04 (s, 1H).

(1-(tert-Butoxycarbonylamino)cyclobutyl)acetic acid:

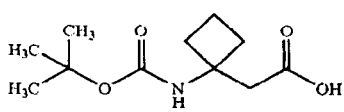

An 1 N aqueous solution of lithium hydroxide (227 ml, 227 mmol) was added to a solution of 2-oxo-1-azaspiro[3.3]heptane-1-carboxylic acid tert-butylester (48 g, 0.227 mmol) in tetrahydrofuran (200 ml). The reaction mixture was stirred for 2 h. Diethyl ether (200 ml) and water (200 ml) were added. The mixture was stirred for 16 h. The organic layer was isolated. The aqueous phase was extracted with diethyl ether (200 ml). The aqueous phase was acidified with a 10% aqueous solution of sodium hydrogen sulfate until pH 3. The formed precipitation was filtered off, washed with water, and dried in vacuo, to give 38.84 g of (1-(tert-butoxycarbonylamino)cyclobutyl)acetic acid.

¹H-NMR (CDCl₃): d 1.45 (s, 9H); 1.85 (m, 1H); 1.95 (m, 1H); 2.25 (m, 4H); 2.87 (m, 2H); 5.15 and 6.20 (both br, together 1H).

(2E)-4-(1-(tert-Butoxycarbonylamino)cyclobutyl)but-2-enoic acid:

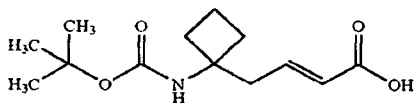

(2E)4-(1-(tert-Butoxycarbonylamino)cyclobutyl)but-2-enoic acid was synthesized starting with (1-tert-butoxycarbonylamino)cyclobutyl)acetic acid analogously to the synthesis of (2E)-5-(tert-butoxycarbonylamino)-5-methylhex-2-enoic acid starting with of 3-tert-butoxycarbonylamino-3-methylbutanoic acid.

¹H-NMR (CDCl₃): d 1.43 (s, 9H); 1.84 (m, 1H); 1.95 (m, 1H); 2.10 (m, 2H); 2.20 (m, 2H); 2.70 (m, 2H); 4.75 (br, 0.5H); 5.90 (m, 1H); 6.35 (br, 0.5H); 6.95 (m, 1H).

(2E)-5-tert-Butoxycarbonylamino-3,5-dimethylhex-2-enoic acid ethyl ester

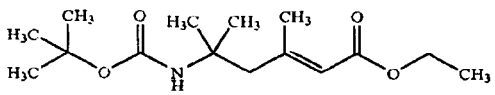

Diacetonamine hydrogen oxalate (30.0 g; 146 mmol) was suspended in tetrahydrofuran (400 ml). An aqueous solution of sodium hydroxide (1 N; 146 ml) was added. Di-tert-butyl dicarbonate (38.3 g; 175 mmol) was dissolved in tetrahydrofuran (100 ml) and added dropwise to the reaction mixture. The reaction mixture was stirred for 2 h at room temperature. Sodium hydroxide (1 N; 146 ml) was added and the reaction mixture was stirred for 12 h at room temperature. Water (200 ml) and ethyl acetate (200 ml) were added. The aqueous phase was extracted with ethyl acetate (4×200 ml). The combined organic phases were dried over magnesium sulfate, and the solvent was removed in vacuo. The residue was purified by flash chromatography on silica (200 g), using ethyl acetate/heptane (1:3) as eluent, to afford 28.4 g of (1,1-dimethyl-3-oxobutyl)carbamic acid tert-butyl ester.

Triethyl phosphonoacetate (4.7 g; 20.9 mmol) was dissolved in tetrahydrofuran (36 ml). Potassium tert-butoxide (2.3 g; 20.9 mmol) was added and the reaction mixture was stirred for 40 min at room temperature. (1,1-Dimethyl-3-oxobutyl)carbamic acid tert-butyl ester (2.5 g; 11.6 mmol) was dissolved in tetrahydrofuran (15 ml) and added dropwise to the reaction mixture which was heated to reflux for 12 h. Ethyl acetate (100 ml) and hydrochloric acid (1 N; 100 ml) were added and the phases were separated. The aqueous phase was extracted with ethyl acetate (3×50 ml). The combined organic phases were washed with an aqueous solution of sodium hydrogen carbonate (saturated; 100 ml), dried (magnesium sulfate) and evaporated in vacuo. The residue was purified by flash chromatography on silica (120 g) using ethyl acetate/heptane (1:2) as eluent to afford 2.0 g of (2E)-5-tert-butoxycarbonylamino-3,5-dimethylhex-2-enoic acid ethyl ester.

¹H-NMR (CDCl₃) d 1.25 (t, 3H); 1.30 (s, 6H); 1.44 (s, 9H); 2.21 (s, 3H); 2.58 (s, 2H); 4.14 (q, 2H); 4.48 (s, 1H); 5.65 (s, 1H).

(2E)-5-tert-Butoxycarbonylamino-3,5-dimethylhex-2-enoic acid:

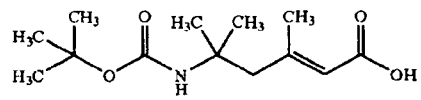

(2E)-5-tert-Butoxycarbonylamino-3,5-dimethylhex-2-enoic acid ethyl ester (1.95 g; 6.83 mmol) was dissolved in 1,4-dioxane (25 ml) and water (15 ml). Lithium hydroxide (0.18 g; 7.52 mmol) was added and the reaction mixture was stirred for 12 h at room temperature. Water (150 ml) and tert-butyl methyl ether (150 ml) was added. The aqueous phase was diluted with a 10% aqueous solution of sodium hydrogensulfate until pH 2.5 and extracted with tert-butyl methyl ether (3×100 ml). The combined organic phases were dried over magnesium sulfate and evaporated in vacuo. The residue was recrystallized from heptane (20 ml) to afford 0.6 g of (2E)-tert-Butoxycarbonylamino-3,5-dimethylhex-2-enoic acid.

¹H-NMR (CDCl₃) d 1.29 (s, 6H); 1.44 (s, 9H); 2.23 (s, 3H); 2.62 (s, 2H); 4.45 (s, 1H); 5.66 (s, 1H).

(2E)-5-(N-(tert Butoxycarbonyl)-N-methylamino)-5-methylhex-2-enoic acid.

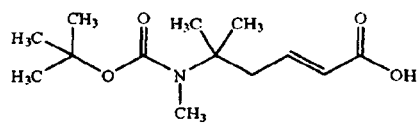

(2E)-5-(tert-Butyloxycarbonylamino)-5-methylhex-2-enoic acid (5.00 g; 20.6 mmol) was dissolved in tetrahydrofuran (70 ml). Methyliodide (10.3 ml; 164 mmol) was added and the solution was cooled to 0° C. Sodium hydride (60% in oil) (2.07 g; 61.6 mmol) was added in portions and the solution was stirred at room temperature for four days. Ethyl acetate (70 ml) and water (60 ml) was added dropwise and the solvent was removed in vacuo. The crude product was dissolved in water (40 ml) and ether (40 ml). The organic phase was washed with a saturated aqueous solution of sodium hydrogencarbonate (30 ml). The aqueous phases were mixed and 5% aqueous citric acid was added to pH 3. The aqueous phase was extracted with ethylacetate (4×50 ml). The organic phase was washed with water (2×40 ml), an aqueous solution of sodium thiosulfate (5%; 40 ml), water (40 ml), dried over MgSO₄ and the solvent was removed in vacuo. The residue was dissolved in ethylacetate (45 ml) and washed with an aqueous solution of sodium hydrogensulfate (10%; 3×30 ml), dried over MgSO₄ and concentrated in vacuo to give 4.00 g of (2E)-5-(N-(tert Butoxycarbonyl)-N-methylamino)-5-methylhex-2-enoic acid.

¹H-NMR (CDCl₃) δ 1.38 (s, 6H), 1.45 (s, 9H); 2.80 (d, 2H); 2.85 (s, 3H); 5.88 (d, 1H); 7.01 (q, 1H).

Example 1

(2E)-5-Amino-5-methylhex-2-enoic acid N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylamide

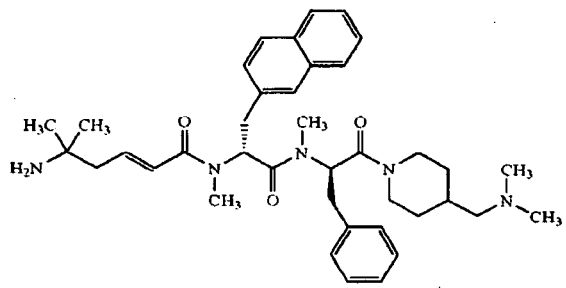

4-(Dimethylcarbamoyl)piperidine-1-carboxylic acid tert-butyl ester

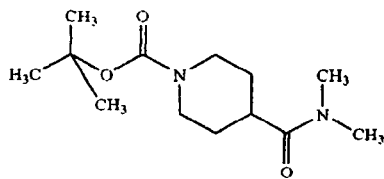

1-(tert-Butoxycarbonyl)piperidine-4-carboxylic acid (8.0 g, 35 mmol) was dissolved in dichloromethane (70 ml) and N,N-dimethylformamide (35 ml). 1-Hydroxy-7-azabenzotriazole (4.75 g, 35 mmol) was added. The solution was cooled to 0° C. N-3-dimethylaminopropyl)-N'-ethylcarbodiimide hydrochloride (6.69 g, 35 mmol) was added. The reaction mixture was stirred for 20 min at 0° C. A 5.6 M solution of dimethylamine in ethanol (37 ml, 209 mmol) was added. The reaction mixture was stirred for 3 days, while it was warming up to room temperature. It was diluted with ethyl acetate (400 ml) and washed with a 10% aqueous solution of sodium hydrogen sulfate (400 ml). The aqueous phase was extracted with ethyl acetate (2×200 ml). The combined organic layers were washed with a saturated aqueous solution of sodium hydrogen carbonate (300 ml) and dried over magnesium sulfate. The solvent was removed in vacua. The crude product was purified by flash chromatography on silica (300 g), using dichloromethane/methanol 20:1 as eluent, to give 4.56 g of 4-(dimethylcarbamoyl)piperidine-1-carboxylic acid tert-butyl ester.

¹H-NMR (CDCl₃): δ 1.47 (s, 9H); 1.70 (m, 4H); 2.60–2.90 (m, 3H); 2.96 (s, 3H); 3.08 (s, 3H); 4.17(m, 2H).

4-((Dimethylamino)methyl)piperidine-1-carboxylic acid tert-butyl ester

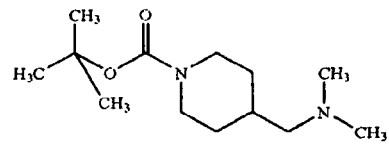

At 0° C. a solution of 4-((dimethylamino)methyl) piperidine-1-carboxylic acid tert-butyl ester (4.56 g, 18 mmol) in tetrahyrofuran (80 ml) was added dropwise to a suspension of sodium borohydride (1.61 g, 43 mmol) in tetrahydrofuran (80 ml). The reaction mixture was stirred for 20 min at 0° C. A solution of iodine 4.51 g, 18 mmol) in tetrahydrofuran (80 ml) was added dropwise at 0° C. The reaction mixture was heated to reflux for 16 h. It was cooled to 4° C. Methanol (200 ml) was added dropwise. The solvent was removed in vacuo. The residue was dissolved in a 20% aqueous solution of sodium hydroxide (200 ml) and tert-butyl methyl ether (150 ml). The phases were separated. The aqueous phase was extracted with tert-butyl methyl ether (3×100 ml). The combined organic layers were dried over magnesium sulfate. The solvent was removed in vacua. The crude product was purified by flash chromatography on silica (100 g), using dichloromethane/methanol/25% aqueous ammonia (100:10:1) as eluent, to give 4.07 g of 4-((dimethylamino)methyl)piperidine-1-carboxylic acid tert-butyl ester.

¹H-NMR (CDCl₃): δ 1.22 (m, 2H); 1.44 (s, 9H); 1.85 (d, 2H); 2.09 (m, 1H); 2.61 (s, 6H); 2.65 (m, 2H); 2.78 (t, 2H); 4.05 (d, 2H).

N,N-Dimethyl-N-((piperidin-4-yl)methyl)amine

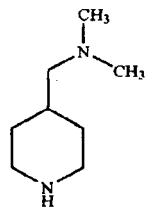

A 3 M solution of hydrogen chloride in ethyl acetate (120 ml, 360 mmol) was added to a solution of 4-((dimethylamino)methyl)piperidine-1-carboxylic acid tert-butyl ester (2.0 g, 14 mmol) in ethyl acetate (50 ml). The reaction mixture was stirred for 30 min at room temperature. The solvent was removed in vacuo to give 2.3 g of the crude dihydrochloride salt of N,N-dimethyl-N-((piperidin-4-yl) methyl)amine, which was used without purification for the next step.

¹H-NMR (CDCl₃, selected values): δ 1.48 (m, 2H); 1.92 (s, 6H); 3.22 (d, 2H).

41

N-[(1R)-1-Benzyl-2-(4-((dimethylamino)methyl)piperidin-1-yl)-2-oxoethyl]-N-methylcarbamic acid tert-butyl ester

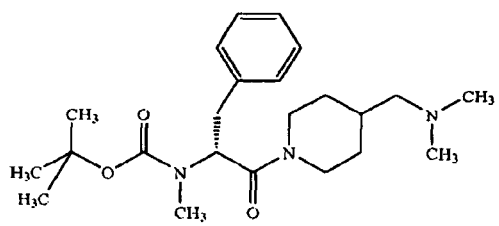

At 0° C., N-(3-dimethylaminopropyl)-N'-ethylcarbodiimide hydrochloride (1.158,g, 6.04 mmol) was added to a solution of (2R)-2-(N-(tert-butoxycarbonyl)-N-methylamino)-3-phenylpropionic acid (149 g, 6.04 mmol) and 1-hydroxy-7-azabenzotriazole (0.822 g, 6.04 mmol) in dichloromethane (25 ml) and N,N-dimethylformamide (12 ml). The reaction mixture was stirred for 20 min at 0° C. A solution of the crude dihydrochloride salt of N,N-dimethyl-N-((piperidin-4-yl)methyl)amine (1.3 g, 6.04 mmol) in N,N-dimethylformamide (10 ml) and dichloromethane (5 ml) and ethyldiisopropylamine (6.2 ml, 36.25 mmol) were added successively. The reaction mixture was stirred for 16 h, while it was warming up to room temperature. It was diluted with ethyl acetate (100 ml) and washed with a saturated aqueous solution of sodium hydrogen carbonate (100 ml). The organic layer was dried over magnesium sulfate. The solvent was removed in vacuo. The crude product was purified by flash chromatography on silica (100 g), using dichloromethane/methanol/25% aqueous ammonia (200:10:1) as eluent, to give 1.22 g of N-[(1R)-1-benzyl-2-(4-((dimethylamino)methyl)piperidin-1-yl)-2-oxoethyl]-N-methylcarbamic acid tert-butyl ester.

$^1$H-NMR (CDCl$_3$, selected values): δ 1.28, 1.11, 1.37, and 1.38 (all s, together 9H); 4.00 (m, 1H); 4.57 (m, 1H); 4.97 and 5.28 (both t, together 1H); 7.10–7.40 (m, 5H).

MS: 404 [M+1]$^+$.

(2R)-1-(4-((Dimethylamino)methyl)piperidin-1-yl)-2-(methylamino)-3-phenylpropan-1-one

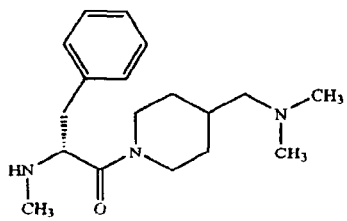

At 0° C., trifluoroacetic acid (20 ml) was added to a solution of N-[(1R)-1-benzyl-2-(4-((dimethylamino)methyl)piperidin-1-yl)-2-oxoethyl]-N-methylcarbamic acid tert-butyl ester (1.22 g, 3.02 mmol) in dichloromethane (20 ml). The reaction mixture was stirred for 1 h at 0° C. The solvents were removed in vacuo. The residue was dissolved in dichloromethane (70 ml) and the solvent was removed in vacuo. The latter procedure was repeated two times. The crude product was purified by flash chromatography on silica (100 g), using dichloromethane/methanol/25% aqueous ammonia (100:10:1), to give 659 mg of (2R)-1-(4-((dimethylamino)methyl)piperidin-1-yl)-2-(methylamino)-3-phenylpropan-1-one.

$^1$H-NMR (CDCl$_3$, selected values): δ 0.91 and 1.47 (m and d, together 1H); 1.27 (m, 1H); 4.62 (t, 1H).

42

N-((1R)-1-{N-[(1R)-1-Benzyl-2-(4-((dimethylamino)methyl)piperidin-1-yl)-2-oxoethyl]-N-methylcarbamoyl}-2-(2-naphthyl)ethyl)-N-methylcarbamic acid tert-butyl ester

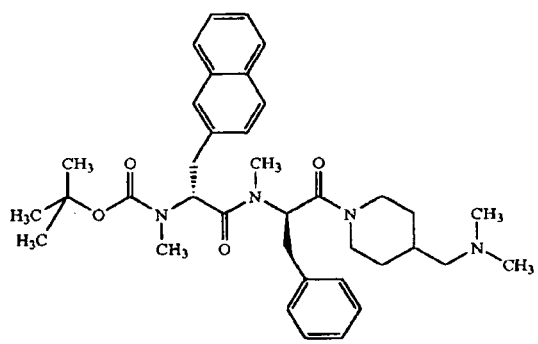

At 0° C., N-3-dimethylaminopropyl)-N'-ethylcarbodiimide hydrochloride (416 mg, 2.17 mmol) was added to a solution of (2R)-2-(N-(tert-butoxycarbonyl)-N-methylamino)-3-(2-naphthyl)-propioni acid (715 mg, 2.17 mmol) and 1-hydroxy-7-azabenzotriazole (296 mg, 2.17 mmol) in dichloromethane (20 ml) and N,N-dimethylformamide (10 ml). The reaction mixture was stirred for 20 min at 0° c. A solution of (2R)-1-(4-((dimethylamino)methyl)piperidin-1-yl)-2-(methylamino)-3-phenylpropan-1-one (659 mg, 2.17 mmol) in dichloromethane (10 ml) and N,N-dimethylformamide (5 ml) and ethyldiisopropylamine (0.56 ml, 3.26 mmol) were added successively. The reaction mixture was stirred for 16 h, while it was warming up to room temperature. It was diluted with ethyl acetate (100 ml) and washed with a saturated aqueous solution of sodium hydrogen carbonate (100 ml). The aqueous solution was extracted with ethyl acetate (3×50 ml). The combined organic layers were dried over magnesium sulfate. The solvent was removed in vacuo. The crude product was purified by flash chromatography 60 on silica (80 g), using ethyl acetate/heptane/triethylamine (1:1:0.08) as eluent, to give 1.05 g of N-((1R)-1-{N-[(1R)-1-benzyl-2-(4-(dimethylamino)methyl)piperidin-1-yl)-2-oxoethyl]-N-methylcarbamoyl}-2-(2-naphthyl)ethyl)-N-methylcarbamic acid tert-butyl ester.

$^1$H-NMR (CDCl$_3$, selected values): δ 1.24 and 1.42 (both s, together 9H); 5.04, 5.28, 5.44, 5.54, 5.73 (m, dd, dd, dd, and m, together 3H);

43

(2R)-N-[(1R)-1-Benzyl-2-(4-((dimethylamino)methyl)piperidin-1-yl)-2-oxoethyl]-N-methyl-2-(methylamino)-3-(2-naphthyl)propionamide

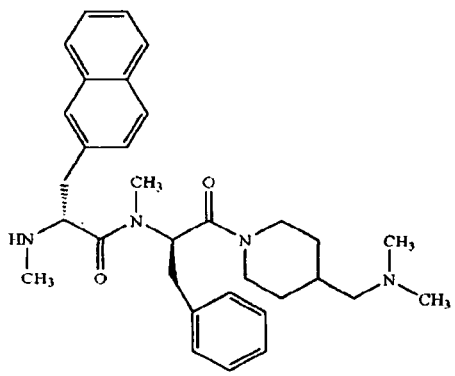

At 0° C., trifluoroacetic acid (18 ml) was added to a solution of N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylcarbamic acid tert-butyl ester (1.05 g, 1.71 mmol) in dichloromethane (18 ml). The reaction mixture was stirred for 50 min at 0° C. The solvents were removed in vacuo. The residue was dissolved in dichloromethane (50 ml) and the solvent was removed in vacuo. The latter procedure was repeated two times. The crude product was purified by flash chromatography on silica (80 g), using dichloromethane/methanol/25% aqueous ammonia as eluent, to give 846 mg of (2R)-N-[(1R)-1-benzyl-2-(4-((dimethylamino)methyl)piperidin-1-yl)-2-oxoethyl]-N-methyl-2-(methylamino)-3-(2-naphthyl)propionamide.

$^1$H-NMR (CDCl$_3$, selected values): δ 0.60 (m, 1H); 4.38 (t, 1H); 5.72 and 5.79 (both t, together 1H).

{(3E)-1-[N-((1R)-1-{N-[(1R)-1-Benzyl-2-(4-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester

44

(methylamino)-3-(2-naphthyl)propionamide (300 mg, 0.58 mmol) in dichloromethane (5 ml) and N,N-dimethylformamide (5 ml) and ethyldiisopropylamine 0.10 ml, 0.58 mmol) were added successively. The reaction mixture was stirred for 3 days, while it was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (70 g), using dichloromethane/methanol/25% aqueous ammonia (200:10:1) as eluent, to give 313 g of {(3E)-4-[N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester.

$^1$H-NMR (CDCl$_3$, selected values): δ 1.28 and 1.30 (both s, together 6H); 1.42 (s, 9H); 2.23, 2.27, 2.38, 2.43, 2.51, 2.52, 2.81, and 2.82 (all s, together 12H); 5.56, 5.76, and 5.90 (m, m, and dd, together 2H); 6.17 and 6.19 (both dd, together 1H); 6.94 (m, 1H).

At 0° C., trifluoroacetic acid (6 ml) was added to a solution of {(3E)-4-[N-((1R)-1-{N-[(1R)-1-benzyl-2-(4-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester (212 mg, 0.29 mmol) in dichloromethane (6 ml). The reaction mixture was stirred for 20 min at 0° C. It was diluted with dichloromethane (30 ml). A saturated aqueous solution of sodium hydrogen carbonate (30 ml) was added dropwise. Solid sodium hydrogen carbonate was added, until pH 7 was obtained. The phases were separated. The aqueous phase was extracted with dichloromethane (3×50 ml). The combined organic layers were dried over magnesium sulfate. The solvent was removed in vacuo. The crude product was purified by flash chromatography on silica (20 g), using dichloromethane/methanol/25% aqueous ammonia (100:10:1) as eluent, to give 5 mg of the title compound.

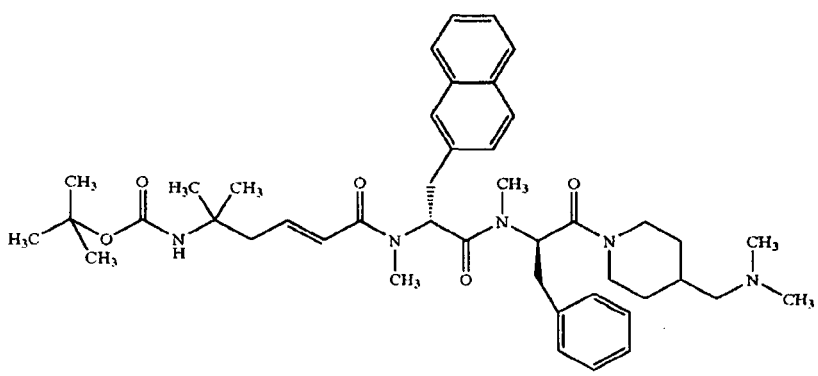

At 0° C., N-(3-dimethylaminopropyl)-N'-ethylcarbodiimide hydrochloride (112 mg, 0.58 mmol) was added to a solution of (2E)-5-(tert-butoxycarbonylamino)-5-methylhex-2-enoic acid (142 mg, 0.58 mmol) and 1-hydroxy-7-azabenzotriazble (79 mg, 0.58 mmol) in dichloromethane (10 ml) and N,N-dimethylformamide (5 ml). The reaction mixture was stirred for 20 min at 0° C. A solution of (2R)-N-[(1R)-1-benzyl-2-(4-((dimethylamino)methyl)piperidin-1-yl)-2-oxoethyl]-N-methyl-2-

$^1$H-NMR (CDCl$_3$, selected values): δ 1.20 (s, 6H); 2.28, 2.32, 2.41, 2.49, 2.56, 2.57, 2.82, and 2.83 (all s, together 12H); 5.58, 5.78, and, 5.92 (m, m, and dd, together 2H); 6.16 and 6.19. (both d, together 1H); 7.00 (m, 1H).

HPLC: 39.23 min (A1). 41.55 min (B1).

MS: 640.4 [M+1]$^+$.

For biological testing, the title compound was transferred into its acetate salt by lyophilization with 0.5 M acetic acid (40 ml).

Example 2

(2E)-5-Amino-5-methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl)-2-(2-naphthyl)ethyl)-N-methylamide

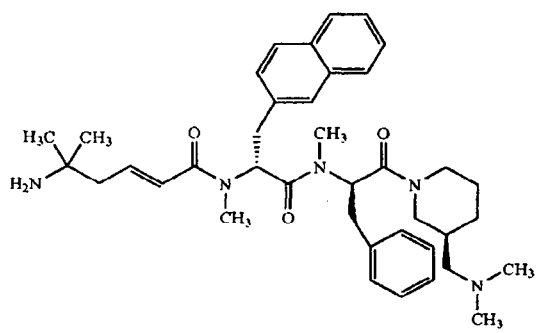

(3R)-Piperidine-1,3-dicarboxylic acid 1-tert-butyl ester 3-ethyl ester

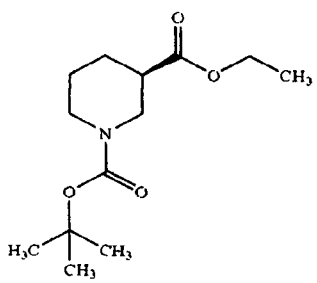

(R)-Ethyl nipecotate tartrate (10.0 g, 32.5 mmol) were suspended in tetrahydrofuran (90 ml). An 1 N solution of sodium hydroxide in water (98 ml, 98 mmol) was added. A solution of di-tert-butyl dicarbonate (7.10 g, 32.5 mmol) in tetrahydrofuran (90 ml) was added. The reaction mixture was stirred for 16 h at room temperature. Ethyl acetate (400 ml) was added. The reaction mixture was washed with a 10% aqueous solution of sodium hydrogen sulfate (400 ml). The aqueous solution was extracted with ethyl acetate (2×200 ml). The combined organic layers were washed with a saturated aqueous solution of sodium hydrogen carbonate (200 ml) and dried over magnesium sulfate. The solvent was removed in vacuo. The crude product was purified by flash chromatography on silica (90 g), using ethyl acetate/heptane 1:4 as eluent, to give 4.13 g of (3R)-piperidine-1,3-dicarboxylic acid 1-tert-butyl ester 3-ethyl ester.

$^1$H-NMR (CDCl$_3$): δ 1.27 (t, 3H); 1.48 (s, 9H); 1.54 (m, 1H); 1.62 (m, 1H); 1.73 (m, 2H); 2.05 (m, 1H); 2.45 (m, 1H); 2.81 (m, 1H); 2.98 (br, 1H); 3.93 (m, 1H); 4.14 (q, 1H).

(3R)-3-Formylpiperidine-1-carboxylic acid tert-butyl ester

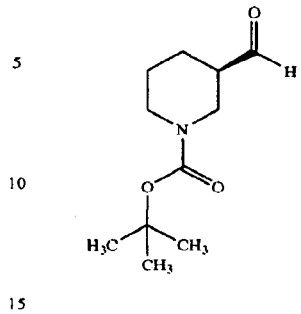

A 1.2 M solution of diisobutylaluminum hydride in toluene (30.8 ml, 36.9 mmol) was added at −78° C. to a solution of (3R)-piperidine-1,3-dicarboxylic acid 1-tert-butyl ester 3-ethyl ester (4.13 g, 16.1 mmol) in diethyl ether (30 ml). The reaction mixture was stirred for 2.5 h at −78° C. Water (9.6 ml) was added dropwise. The reaction mixture was warmed to room temperature. The precipitation was removed by filtration through a plug of celite. The celite was washed with tert-butyl methyl ether (3×100 ml). The liquids were combined and dried over magnesium sulfate. The solvent was removed in vacuo, to give 1.94 g of crude (3R)-3-formylpiperidine-1-carboxylic acid tert-butyl ester, which was used for the next step without further purification.

$^1$H-NMR (CDCl$_3$): δ 1.45 (s, 9H); 1.67 (m, 2H); 1.95 (m, 1H); 2.43 (m, 1H); 3.10 (m, 1H); 3.32 (dd, 1H); 3.52 (d, 1H); 3.66 (m, 1H); 3.95 (m, 1H); 9.69 (s, 1H).

(3S)-3-(Dimethylaminomethyl)piperidine-1-carboxylic acid tert-butyl ester

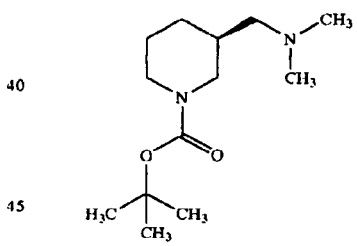

A solution of crude (3R)-3-formylpiperidine-1-carboxylic acid tert-butyl ester (1.94 g, 9.1 mmol) in dichloromethane (80 ml) was prepared. A 5.6 M solution of dimethylamine in ethanol (3.2 ml, 18.2 mmol) and mol sieves were added successively. Sodium triacetoxyborohydride (5.78 g, 27.3 mmol) was added to this mixture. Acetic acid (1.04 ml, 18.2 mmol) was added. The reaction mixture was stirred for 16 h at room temperature. An 1 N aqueous solution of sodium hydroxide (70 ml) and tert-butyl methyl ether (70 ml) were added. The phases were separated. The aqueous solution was extracted with tert-butyl methyl ether (3×70 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 866 mg of (3S)-3-(dimethylaminomethyl)piperidine-1-carboxylic acid tert-butyl ester.

47

¹H-NMR (CDCl₃): δ 1.10 (m, 1H); 1.45 (s, 9H), 1.45 (m, 1H); 1.64 (m, 2H); 1.85 (m, 1H); 2.10 (m, 2H); 2.20 (s, 6H); 2.50 (br, 1H); 2.79 (m, 1H); 3.95 (m, 2H).

N,N-Dimethyl-N-(((3R)-piperidin-3-yl)methyl)amine

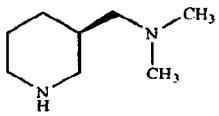

(3S)-3-(Dimethylaminomethyl)piperidine-1-carboxylic acid tert-butyl ester (1.25 g, 5.15 mmol) was dissolved in ethyl acetate (30 ml). A 2.7 M solution of hydrogen chloride in ethyl acetate (75 ml, 203 mmol) was added. The reaction mixture was stirred for 45 min at room temperature. The solvent was removed in vauco to give 976 mg of the crude dihydrochloride salt of N,N-dimethyl-N-(((3R)piperidin-3-yl)methyl)amine, which was used for the next step without further purification.

¹H-NMR (CD₃OD): δ 1.42 (m, 1H); 1.86 (m, 1H); 2.00 (m, 2H); 2.38 (m, 1H); 2.85 (t, 1H); 2.95 (s, 6H); 2.98 (m, 1H); 3.16 (m, 2H); 3.42 (m, 1H); 3.53 (m, 1H).

N-[(1R)-1-Benzyl-2-((3S)-3-(dimethylaminomethyl)piperidin-1-yl)-2-oxoethyl]-N-methylcarbamic acid tert-butyl ester

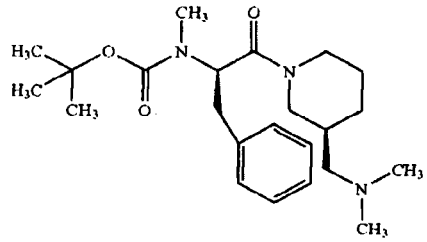

At 0° C. N-(3-dimethylaminopropyl)-N'-ethylcarbodiimide hydrochloride (870 mg, 4.54 mmol) was added to a solution (2R)-2-(N-(tert-butoxycarbonyl)-N-methylamino)-3-phenylpropionic acid (1.27 g, 4.54 mmol) and 1-hydroxy-7-azabenzotriazole (617 mg, 4.54 mmol) in dichloromethane (20 ml) and N,N-dimethylformamide (10 ml). The reaction mixture was stirred for 20 min at 0° C. A solution of the crude dihydrochloride salt of N,N-dimethyl-N-(((3R)-piperidin-3-yl)methyl)amine (976 mg, 4.54 mmol) in dichloromethane (20 ml) and N,N-dimethylformamide (10 ml) and ethyldiisopropylamine (3.9 ml, 22.7 mmol) were added successively. The reaction mixture was stirred for 3 days, while it was warming up to room temperature. Ethyl acetate (300 ml) was added. The solution was washed with a saturated aqueous solution of sodium hydrogen carbonate (300 ml). The aqueous phase was extracted with ethyl acetate (2×200 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 1.69 g of N-[(1R)-1-benzyl-2-((3S)-3-(dimethylaminomethyl)piperidin-1-yl)-2-oxoethyl]-N-methylcarbamic acid tert-butyl ester.

¹H-NMR (CDCl₃, selected values): δ 1.20, 1.24, 1.31, and 1.32 (all s, together 9H); 2.12, 2.13, and 2.18 (all s, together 6H); 2.81 (m, 3H); 4.97 and 5.30 (both m, together 1H); 7.05–7.35 (m, 5H).

48

(2R)-1-((3S)-3-((Dimethylamino)methyl)piperidin-1-yl)-2-methylamino-3-phenylpropan-1-one

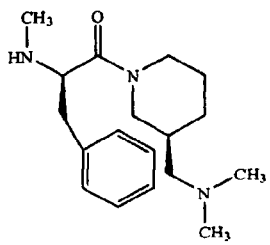

At 0° C., trifluoroacetic acid (25 ml) was added to a solution of N-[(1R)-1-benzyl-2-((3S)-3-(dimethylaminomethyl)piperidin-1-yl)-2-oxoethyl]-N-methylcarbamic acid tert-butyl ester (1.69 g, 4.2 mmol) in dichloromethane (25 ml). The reaction mixture was stirred for 30 min at 0° C. The solvent was removed in vacuo. The residue was dissolved in dichloromethane (100 ml) and the solvent was removed in vacuo. The latter procedure was repeated two times. The crude product was purified by flash chromatography on silica (90 g), using dichloromethane/methanol/25% aqueous ammonia (100:10:1) as eluent, to give 1.15 g of (2R)-1-((3S)-3-((dimethylamino)methyl)piperidin-1-yl)-2-methylamino-3-phenylpropan-1-one.

¹H-NMR (CDCl₃, selected values): δ 0.38, 1.11,,1.37, and 1.65 (all m, together 4H); 2.11, 2.19, 2.25, and 2.31 (all s, together 9H); 4.37 and 4.53 (both m, together 1H); 7.10–7.35 (m, 5H).

N-((1R)-1-{N-[(1R)-1-Benzyl-2-((3S)-3-((dimethylamino)methyl)piperidin-1-yl)-2-oxoethyl]-N-methylcarbamoyl}-2-(2-naphthyl)ethyl)-N-methylcarbamic acid tert-butyl ester

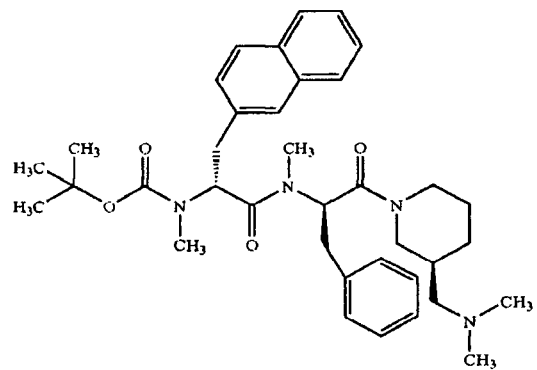

At 0° C. N-(3-dimethylaminopropyl)-N'-ethylcarbodiimide hydrochloride (379 mg, 1.98 mmol) was added to a solution of (2R)-2-(N-(tert-butoxycarbonyl)-N-methylamino)-3-(2-naphthyl)propionic acid (651 mg, 1.98 mmol) and 1-hydroxy-7-azabenzotriazole (269 mg, 1.98 mmol) in dichloromethane (10 ml) and N,N-dimethylformamide (5 ml). The reaction mixture was stirred for 20 min at 0° C. A solution of (2R)-1-((3S)-3-((dimethylamino)methyl)piperidin-1-yl)-2-methylamino-3-phenylpropan-1-one (600 mg, 1.98 mmol) in dichloromethane (10 ml) and ethyldiisopropylamine (0.51 ml, 2.97 mmol) were added successively. The reaction mixture was stirred for 3 days, while it was warming up to room temperature. Ethyl acetate (100 ml) was added. The solution was washed with a saturated aqueous solution of sodium hydrogen carbonate (100 ml). The aqueous phase was extracted with ethyl acetate (3×50 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 1.18 g of N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-phethylcarbamic acid tert-butyl ester.

$^1$H-NMR (CDCl$_3$, selected values): δ 0.45 and 0.71 (both m, together 1H); 1.03, 1.05, 1.15, 1.20, 1.28, 1.36, and 1.42 (all s, together 9H); 2.12, 2.15, 2.21, 2.26, 2.29, 2.85 (all s, together 6H); 5.05, 5.44, 5.58, 5.71, 5.85, and 6.00 (all s, together 2H); 7.10–7.80 (m, 12H).

(2R)-N-[(1R)-1-benzyl-2-((3S)-3-((dimethylamino)m ethyl)piperidin-1-yl)-2-oxoethyl]-N-methyl-2-(methylamino)-3-(2-naphthyl)propionamide.

$^1$H-NMR (CDCl$_3$, selected values): δ 2.01 and 2.25 (both s, together 9H); 3.72 (m, 2H); 3.95 and 4.27 (both m, together 1H); 5.77, 5.86, and 6.03 (t, m, and dd, together 1H); 7.10 and 7.85 (m, 12H).

{(3E)-4-[N-((1R)-1-{N-[(1R)-1-Benzyl-2-((3S)-3-((dimethylamino)methyl)piperidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester

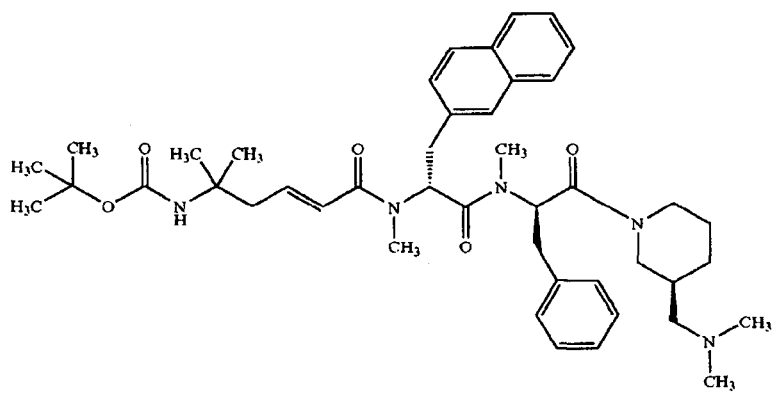

(2R)-N-[(1R)-1-Benzyl-2-((3S)-3-((dimethylamino)methyl)piperidin-1-yl)-2-oxoethyl]-N-methyl-2-(methylamino)-3-(2-naphthyl)propionamide

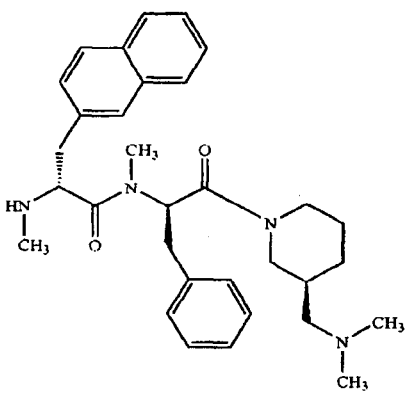

At 0° C., trifluoroacetic acid (20 ml) was added to a solution of N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-methylcarbamic acid tert-butyl ester (1.189, 1.92 mmol) in dichloromethane (20 ml). The reaction mixture was stirred for 50 min at 0° C. The solvent was removed in vacuo. The residue was dissolved in dichloromethane (80 ml) and the solvent was removed in vacuo. The latter procedure was repeated two times. The crude product was purified by flash chromatography on silica (40 g), using dichloromethane/methanol/25% aqueous ammonia (100:10:1) as eluent, to give 788 mg of At 0° C., N-(3-dimethylaminopropyl)-N'-ethylcarbodiimide hydrochloride (105 mg, 0.55 mol) was added to a solution of (2E)-5-(tert-butoxycarbonylamino)-5-methylhex-2-enoic (136 mg, 0.55 mmol) and 1-hydroxy-7-azabenzotriazole (74 mg, 0.55 mmol) in dichloromethane (5 ml). The reaction mixture was stirred for 20 min at 0° C. A solution of (2R)-N-[(1R)-1-benzyl-2-((3S)-3-((dimethylamino)methyl)piperidin-1-yl)-2-oxoethyl]-N-methyl-2-(methylamino)-3-(2-naphthyl)propionamide (281 mg, 0.55 mmol) in dichloromethane (5 ml) and N,N-dimethylformamide (5 ml) and ethyldiisopropylamine (0.094 ml, 0.55 mmol) were added successively. The reaction mixture was stirred for 16 h, while it was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 398 mg of {(3E)-4-[N-((1R)-1-N-[(1R)-1-benzyl-2-((3S)-3-((dimethylamino)methyl)piperidin-1-yl)-2-oxoethyl]-N-methylcarbamoyl}-2-2-naphthyl)ethyl)-N-methylcarbamoyl]1,1-dimethylbut-3-enyl}carbamic acid tert-butyl ester.

$^1$H-NMR (CDCl$_3$, selected values): δ 1.44 (s, 9H); 5.58, 5.75, and 5.86 (all m, 2H); 6.09 and 6.17 (both d, together 1H); 6.84 (m, 1H); 7.10–7.80 (m, 12H).

At 0° C., trifluoroacetic acid (7 ml) was added to a solution of {(3E)-4-[N-((1R)-1-{N-[(1R)-1-benzyl-2-((3S)-3-((dimethylamino)methyl)piperidin-1-yl)-2-oxoethyl]-N-methylcarbamoyl)-2-(2-naphthyl)ethyl)-N-methylcarbamoyl]-1,1-dimethylbut-3-enyl}carbamic acid tert-butyl ester (398 mg, 0.54 mmol) in dichloromethane (7 ml). The reaction mixture was stirred for 40 min at 0° C. The solvent was removed in vacuo. The residue was dissolved in dichloromethane (20 ml) and the solvent was removed in vacuo. The latter procedure was repeated two times. The crude product was purified by flash chromatography on silica (40 g), using dichloromethane/methanol/25% aqueous ammonia (100:10:1) as eluent, to give 150 mg of the title compound.

$^1$H-NMR (CDCl$_3$, selected values): δ 1.08,1.12, 1.14, and 1.15 (all s, together 6H), 5.46, 5.59, 5.75, and 5.94 (all m, together 2H); 6.15 (m, 1H); 6.93 (m, 1H).

HPLC 27.55 min (A1). 30.23 min (B1).

LC-MS: 640.4 [M+1]$^+$ at 8.54 min.

For biological testing, the title compound was transferred into its acetate salt, by lyophilization from 0.5 M acetic acid (40 ml).

Example 3

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

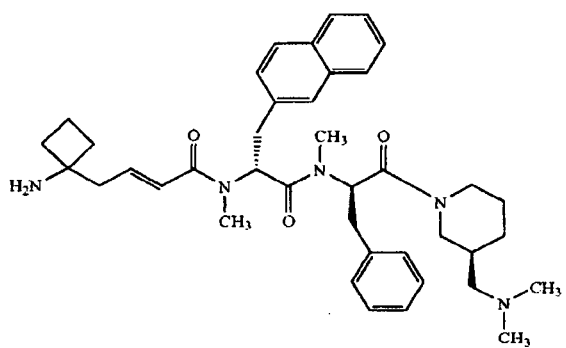

(1-{(2E)-3-[N-((1R)-1-{N-[(1R)-1-Benzyl-2-((3S)-3-((dimethylamino)methyl)piperidin-1-yl)-2-oxoethyl]-N-methylcarbamoyl}-2-(2-naphthyl)ethyl)-N-methylcarbamoyl]allyl}cyclobutyl)carbamic acid tert-butyl ester At 0° C., N-(3-dimethylaminopropyl)-N'-ethylcarbodiimide hydrochloride (85 mg, 0.44 mmol) was added to a solution of (2E)-5-(tert-butoxycarbonylamino)-5-methylhex-2-enoic acid (113 mg, 0.44 mmol) and 1-hydroxy-7-azabenzotriazole (60 mg, 0.44 mmol) in dichloromethane (5 ml) and N,N-dimethylformamide (5 ml). The reaction mixture was stirred for 20 min at 0° C. A solution of (2R)-N-[(1R)-1-benzyl-2-((3S)-3-((dimethylamino)methyl)piperidin-1-yl)-2-oxoethyl]-N-methyl-2-(methylamino)-(2-naphthyl)propionamide (228 mg, 0.44 mmol) in dichloromethane (10 ml) and ethyldiisopropylamine (0.07 ml, 0.44 mmol) were added successively. The reaction mixture was stirred for 16 h, while i was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 314 mg of (1-{(2E)-3-[N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-methylcarbamoyl]allyl}cyclobutyl)carbamic acid tert-butyl ester.

$^1$H-NMR (CDCl$_3$, selected values): δ 1.40 (m, 9H); 4.22 and 4.67 (both m, together 2H); 5.60, 5.75, 5.85, and 5.90 (dd, dd, m, and m, together 2H); 6.10 and 6.19 (both d, together 1H); 6.73 and 6.87 (both m, together 1H); 7.22, 7.42, and 7.76 (all m, together 12H).

At 0° C., trifluoroacetic acid (7 ml) was added to a solution of (1-{(2E)-3-[N-((1R)-1-{N-[(1R)-1-benzyl-2-((3S)-3-((dimethylamino)methyl)piperidin-1-yl)-2-oxoethyl]-N-methylcarbamoyl}-2-(2-naphthyl)ethyl)-N-methylcarbamoyl]allyl}cyclobutyl)carbamic acid tert-butyl ester (314 mg, 0.42 mmol) in dichloromethane (7 ml). The reaction mixture was stirred for 20 min at 0° C. The solvent was removed in vacuo without heating. The residue was dissolved in dichloro methane (20 ml) and the solvent was removed in vacuo. The latter procedure was repeated two times. The crude product was purified by flash chromatography on silica (40 g), using dichloromethane/methanol ammonia (100:10:1) as eluent, to give 180 mg of the title compound.

$^1$H-NMR (CDCl$_3$, selected values): δ 0.40 and 0.74 (both m, together 2H); 3.73 and 4.22 (both m, together 2H); 5.57, 5.77, and 5.91 (all m, together 2H); 6.15 and 6.24 (both d, together 1H); 6.85 and 6.96 (both m, together 1H); 7.22, 7.92, and 7.74 (all m, together 12H).

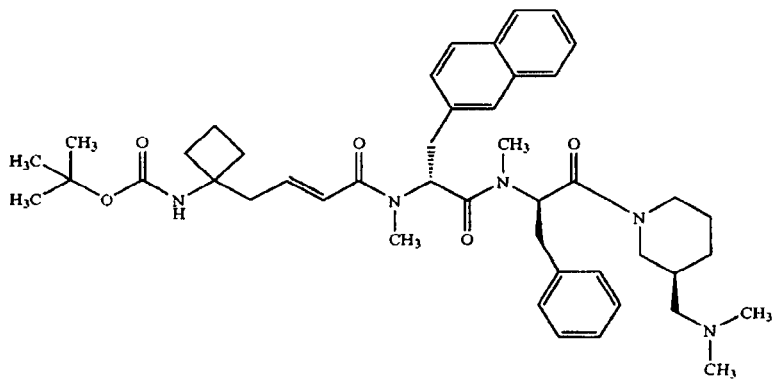

Example 4

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

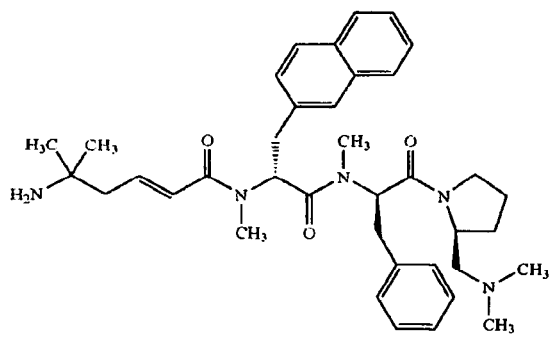

HPLC: 28.03 min (A1). 29.92 min (B1).
MS: 652.4 [M+1]⁺.

For biological testing, the title compound was transferred into its diacetate salt, by lyophilization from 0.5 M acetic acid (40 ml).

(2S)-Pyrrolidine-1,2-dicarboxylic acid 1-tert-butyl ester 2-ethyl ester

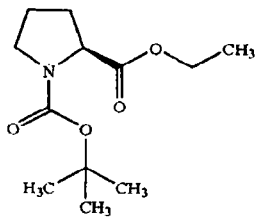

N-tert-Butoxycarbonylprolin (24.38 g, 113 mmol) was dissolved in dichloromethane (60 ml). Ethanol (7.9 ml, 135 mmol) and 4-dimethylaminopyridine (1.52 g, 12.5 mmol) were added. The solution was cooled to 0° C. N-(3-dimethylaminopropyl)-N'-ethylcarbodiimide hydrochloride (23.88 g, 125 mmol) was added. The reaction mixture was stirred for 16 h, while it was warming up to room temperature. Ethyl acetate (400 ml) was added. It was washed with a 10% aqueous solution of sodium hydrogen sulfate (300 ml). The aqueous phase was extracted with ethyl acetate (3×200 ml). The combined organic layers were washed with a saturated aqueous solution of sodium hydrogen carbonate (300 ml) and dried over magnesium sulfate. The solvent was removed in vacuo. The crude product was purified by flash chromatography on silica (400 g), using ethyl acetate (1:4) as eluent, to give 17.11 g of (2S)-pyrrolidine-1,2-dicarboxylic acid 1-tert-butyl ester 2-ethyl ester.

¹H-NMR (CDCl₃): δ 1.28 (m, 3H); 1.43 and 1.46 (both s, together 9H); 2.95 (m, 3H); 2.22 (m, 1H); 3.50 (m, 2H); 4.18 and 4.30 (m and dd, together 3H).

N-t-Butyloxycarbonyl-(S)-prolinal

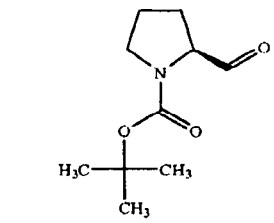

At −78° C., a 1.2 M solution of diisobutylaluminum hydride (31.7 ml, 38 mmol) in toluene was added dropwise to a solution of (2S)-pyrrolidine-1,2-dicarboxylic acid 1-tert-butyl ester 2-ethyl ester (4.02 g, 16.5 mmol) in diethyl ether (1.5 ml). The reaction mixture was stirred for 3 h at −78° C. Water (9.9 ml) was added dropwise. The reaction mixture was warmed to room temperature. The mixture was filtered through a plug of celite. The celite was washed with tert-butyl methyl ether (3×100 ml). The combined organic layers were dried over magnesium sulfate. The solvent was removed in vacuo, to give 2.34 g of crude N-t-butyloxycarbonyl-(S)-prolinal, which was used for the next step without further purification.

¹H-NMR (CDCl₃): δ 1.42 and 1.47 (both s, together 9H); 1.70–2.20 (m, 4H); 3.20–4.30 (m, 3H); 9.45 and 9.55 (both s, together 1H).

(2S)-2-((Dimethylamino)methyl)pyrrolidine-1-carboxylic acid tert-butyl ester

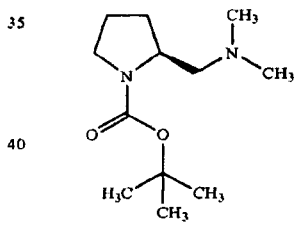

Crude N-t-butyloxycarbonyl-(S)-prolinal (2.34 g, 11.7 mmol) was dissolved in dichloromethane (90 ml). A 5.6 M solution of dimethylamine in ethanol (4.19 ml, 23.5 mmol) was added. 0.4 nm Mol sieves (10.0 g) was added. Sodium triacetoxyborohydride 7.47 g, 35.2 mmol) and glacial acetic acid (1.34 ml, 23.5 mmol) were added successively. The reaction mixture was stirred for 3 days. It was filtered through a plug of celite. The celite was washed with methanol (150 ml). An 1N aqueous solution of sodium hydroxide (150 ml) and tert-butyl methyl ether (150 ml) were added. The phases were separated. The aqueous phase was extracted with tert-butyl methyl ether (3×100 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 1.29 g of (2S)-2-((dimethylamino)methyl)pyrrolidine-1-carboxylic acid tert-butyl ester.

¹H-NMR (CDCl₃): δ 1.48 (s, 9H); 1.90 (m, 4H); 2.15 and 2.23 (AB, 2H); 2.26 (s, 6H); 3.31 (br, 2H); 3.85 (br, 1H).

55

N-Dimethyl-N-(((2S)-pyrrolidin-2-yl)methyl)amine

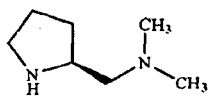

A 2.7 M solution of hydrogen chloride in ethyl acetate (75 ml, 202 mmol) was given to a solution of (2S)-2-((dimethylamino)methyl)pyrrolidine-1-carboxylic acid tert-butyl ester (1.29 g, 5.65 mmol) in ethyl acetate (30 ml). The reaction mixture was stirred for 30 min at room temperature. The solvent was removed in vacuo to give 1.36 g of the crude dihydrochloride salt of N-dimethyl-N-(((2S)-pyrrolidin-2-yl)methyl)amine, which was used for the next step without further purification.

¹H-NMR (CDCl₃): δ 1.90 (m, 2H); 2.17 (m, 1H); 2.40 (m, 1H); 2.90 (m, 2H); 3.14 (s, 6H); 3.55 (m, 2H); 4.35 (m, 1H).

N-[(1R)-1-Benzyl-2-(2S)-2-((dimethylamino)methyl) pyrrolidin-1-yl)-2-oxoethyl]-N-methylcarbamic acid tert-butyl ester

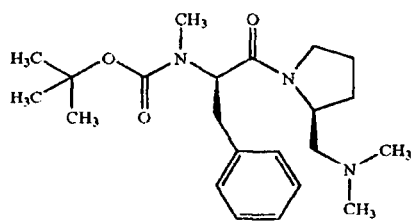

At 0° C., N-(3-dimethylaminopropyl)-N'-ethylcarbodiimide hydrochloride (1.30 g, 6.76 mmol) was added to a solution of (2R)-2-(N-tert-butoxycarbonyl)-N-methylamino)-3-phenylpropionic acid (1.89 g, 6.76 mmol) and 1-hydroxy-7-azabenzotriazole 0.92 g, 6.76 mmol) in dichloromethane (10 ml). The reaction mixture was stirred for 20 min at 0° C. A solution of the crude dihydrochloride salt of N-dimethyl-N-(((2S)-pyrrolidin-2-yl)methyl)amine (1.36 g, 6.76 mmol) in dichloromethane (10 ml) and N,N-dimethylformamide (10 ml) and ethyldiisopropylamine (5.75 ml, 33.8 mmol) were added successively. The reaction mixture was stirred for 16 h, while it was warming up to room temperature. It was diluted with ethyl acetate (100 ml) and washed with a saturated aqueous solution of sodium hydrogen carbonate (100 ml). The aqueous phase was extracted with ethyl acetate (3×80 ml). The combined organic layers were dried over magnesium sulfate. The solvent was removed in vacuo. The crude product was purified by flash chromatography on silica (90 g), using dichloromethane/methanol/25% aqueous ammonia (100:10:1) as eluent, to give 2.26 g of N-[(1R)-1-benzyl-2-((2S)-2-((dimethylamino)methyl)pyrrolidin-1-yl)-2-oxoethyl]-N-methylcarbamic acid tert-butyl ester.

¹H-NMR (CDCl₃, selected values): δ 1.20, 1.33, and 1.37 (all s, together 9H); 2.22 and 2.28 (both s, together 6H); 2.82 and 2.84 (both s, together 3H); 4.25 (m, 1H); 4.80, 5.11, and 5.30 (dd, t, and m, together 1H); 7.10–7.30 (m, 5H).

C₂₂H₃₅N₃O₃[389.5]; calc. C, 67.83; H, 9.06; N, 10.79; found C, 67.39; H, 9.13; N, 10.73.

56

(2R)-1-((2S)-2-((Dimethylamino)methyl)pyrrolidin-1-yl)-2-methylamino-3-phenylpropan-1-one

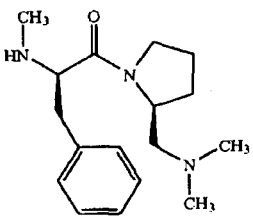

At 0° C., trifluoroacetic acid (8 ml) was added to a solution of N-[(1R)-1-benzyl-2-((2S)-2-((dimethylamino) methyl)pyrrolidin-1-yl}-2-oxoethyl]-N-methylcarbamic acid tert-butyl ester (2.26 g, 5.80 mmol) in dichloromethane (8 ml). The reaction mixture was stirred for 20 min at 20 0° C. The solvent was removed in vacuo. Dichloromethane (70 ml) was added, and the solvent was removed in vacuo. The latter procedure was repeated two times. The crude product was purified by flash chromatography on silica (90 g), using dichloromethane/methanol/25% aqueous ammonia (100:10:1) as eluent, to give 1.24 g of (2R)-1-((2S)-2-((dimethylamino)methyl)pyrrolidin-1-yl)-2-methylamino-3-phenylpropan-1-one.

¹H-NMR (CDCl₃, selected values): δ 2.33 (s, 3H); 2.43 (s, 6H); 3.25 (m, 3H); 4.17 (m, 1H); 7.25 (m, 5H).

N-((1R)-1-{N-[(1R)-1-Benzyl-2-((2S)-2-((dimethylamino) methyl)pyrrolidin-1-yl)-2-oxoethyl]-N-methylcarbamoyl}-2-(2-naphthyl)ethyl)-N-methylcarbamic acid tert-butyl ester

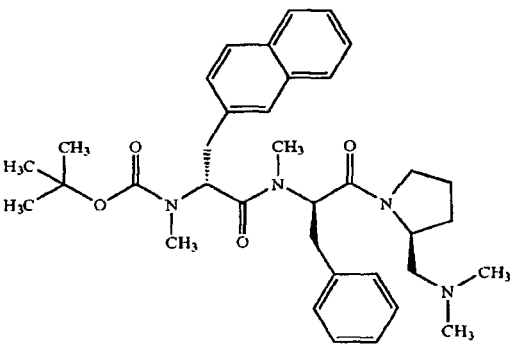

At 0° C., N-(3-dimethylaminopropyl)-N'-ethylcarbodiimide hydrochloride (530 mg, 2.76 mmol) was added to a solution of (2R)-2-(N-(tert-butoxycarbonyl)-N-methylamino)-3-(2-naphthyl)propionic acid (911 mg, 2.76 mmol) and 1-hydroxy-7-azabenzotriazole (376 mg, 2.76 mmol) in dichloromethane (5 ml). The reaction mixture was stirred for 20 min at 0° C. A solution of (2R)-1-((2S)-2-((dimethylamino)methyl)pyrrolidin-1-yl)-2-methylamino-3-phenylpropan-1-one (800 mg, 2.76 mmol) in dichloromethane (5 ml) and N,N-dimethylformamide (5 ml) and ethyldiisopropylamine (0.71 ml, 4.15 mmol) were added successively. The reaction mixture was stirred for 3 days, while it was warming up to room temperature, It was diluted with ethyl acetate (100 ml) and washed with a saturated aqueous solution of sodium hydrogen carbonate (100 ml). The aqueous solution was extracted with ethyl acetate (3×70 ml). The combined organic layers were dried over magnesium sulfate. The solvent was removed in vacuo. The crude product was purified by flash chromatography on silica (90 g), using dichloromethane/methanol/25% aqueous ammonia (200:10:1) as eluent, to give 1.37 g of N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamic acid tert-butyl ester.

¹H-NMR (CDCl₃, selected values): δ 0.64 (m, 1H); 1.10, 1.29, 1.36, and 1.47 (all s, together 9H); 4.99, 5.09, 5.45, and 5.53 (t, t, m, and t, together 2H); 7.10–7.90 (m, 12H).

(2R)-N-[(1R)-1-Benzyl-2-((2S)-2-((dimethylamino)methyl)pyrrolidin-1-yl)-2-oxoethyl]-N-methyl-2-(methylamino)-3-(2-naphthyl)propionamide

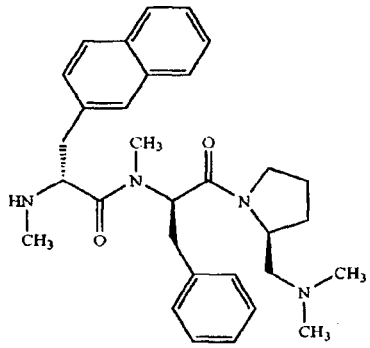

At 0° C., trifluoroacetic acid (10 ml) was added to a solution of N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamic acid tert-butyl ester.(1.37 g, 2.28 mmol) in dichloromethane (10 ml). The reaction mixture was stirred for 75 min at 0° C. The solvent was removed in vacuo. The residue was dissolved in dichloromethane (70 ml) and the solvent was removed in vacuo. The latter procedure was repeated two times. The crude product was purified by flash chromatography on silica (90 g), using dichloromethane/methanol/25% aqueous ammonia (100:10:1) as eluent, to give 692 mg of (2R)-N-[(1R)-1-benzyl-2-((2S)-2-((dimethylamino)methyl)pyrrolidin-1-yl)-2-oxoethyl]-N-methyl-2-(methylamino)-3-(2-naphthyl)propionamide.

¹H-NMR (CDCl₃, selected values): δ 1.85 and 2.01 (both s, together 3H); 2.20 and 2.31 (both s, together 6H); 3.65 and 3.80 (both t, 1H); 4.04 and 4.45 (both m, together 1H); 5.60 and 5.91 (t and dd, together 1H); 7.10–7.90 (m, 12H).

{(3E)-4-[N-((1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester

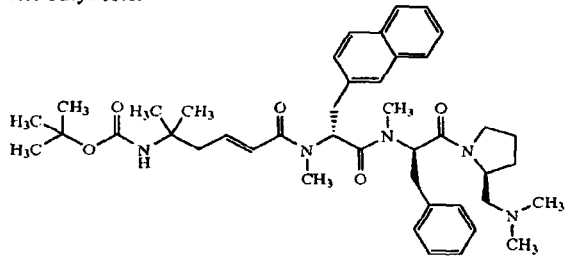

At 0° C., N-(3-dimethylaminopropyl)-N'-ethylcarbodiimide hydrochloride (132 mg, 0.69 mmol) was added to a solution of (2E)-5-(tert-butoxycarbonylamino)-5-methylhex-2-enoic acid (168 mg, 0.69 mmol) and 1-hydroxy-7-azabenzotriazole (94 mg, 0.69 mmol) in dichloromethane (5 ml). The reaction mixture was stirred for 20 min at 0° C. A solution of (2R)-N-[(1R)-1-benzyl-2-((2S)-2-((dimethylamino)methyl)pyrrolidin-1-yl)-2-oxoethyl]-N-methyl-2-(methylamino)-3-(2-naphthyl)propionamide (345 mg, 0.69 mmol) in dichloromethane (10 ml) and N,N-dimethylformamide (5 ml) and ethyldiisopropylamine were added successively. The reaction mixture was stirred for 16 h, while it was warming up to room temperature. It was diluted with ethyl acetate (70 ml) and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 491 mg of {(3E)-4-[N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester.

¹H-NMR (CDCl₃, selected values): δ 1.30 and 1.32 (both s, together 6H); 1.45 (s, 9H); 1.60 (m, 2H); 4.00 (m, 1H); 4.48 (m, 1H); 5.48 (dd, 1H); 5.92 (dd, 1H); 6.11 and 6.20 (both d, together 1H); 6.82 and 6.92 (both m, together 1H); 7.10–7.90 (m, 12H).

At 0° C., trifluoroacetic acid (7 ml) was added to a solution of {(3E)-4-[N-((1R)-1-{N-[(1R)-1-benzyl-2-((2S)-2-(dimethylamino)methyl)pyrrolidin-1-yl)-2-oxoethyl]-N-methylcarbamoyl}-2-(2-naphthyl)ethyl)-N-methylcarbamoyl]-1,1-dimethylbut-3-enyl}carbamic acid tert-butyl ester (491 mg, 0.68 mmol) in dichloromethane (7 ml). The reaction mixture was stirred for 60 min at 0° C. The solvent was removed in vacuo. The residue was dissolved in dichloromethane (100 ml) and the solvent was removed in vacuo. The latter procedure was repeated two times. The crude product was purified by flash chromatography on silica (40 g), using dichloromethane/methanol/25% ammonia (100:10:1) as eluent, to give 285 mg of the title compound.

¹H-NMR (CDCl₃, selected values): δ 0.55 (m, 1H); 1.11, 1.12, and 1.17 (all s, together 6H); 2.25 (s, 6H); 2.45 (s, 3H); 2.85 (s, 3H); 4.02 (m, 1H); 5.48 (dd, 1H); 5.80 and 5.93 (m, and dd, together 1H); 6.10 and 6.18 (both d, together 1H); 6.87 and 7.00 (both m, together 1H); 7.10–7.90 (m, 12H).

HPLC 27.97 min (A1). 27.80 min (B1).

MS: 626.4 [M+1]⁺.

For biological testing, the title compound was transferred into its diacetate salt by lyophilization from 0.5 acetic acid (40 ml).

Example 5

N-((1R)-1-{N-[(1R)-1-Benzyl-2-((2S)-2-((dimethylamino)methyl)pyrrolidin-1-yl)-2-oxoethyl]-N-methylcarbamoyl}-2-(2-naphthyl)ethyl)-N-methyl-3-((methylamino)methyl)benzamide

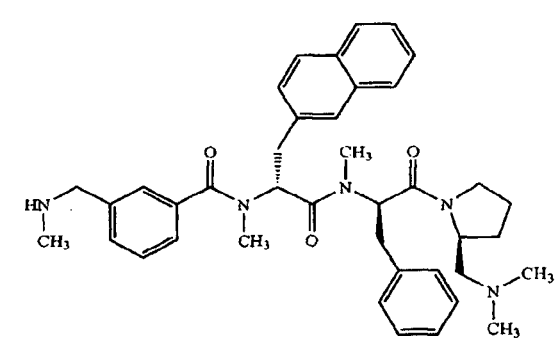

N-3-[N(1R)-1-{N-[(1R)-1-Benzyl-2-((2S)-2-((dimethylamino)methyl)pyrrolidin-1-yl)-2-oxoethyl]-N- methylcarbamoyl}-2-(2-naphthyl)ethyl)-N-methylcarbamoyl]benzyl)-N-methylcarbamic acid tert-butyl ester

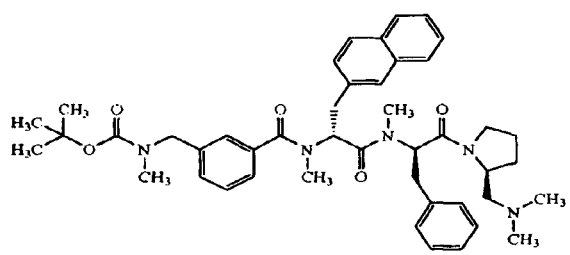

At 0° C. N-(dimethylaminopropyl)-N'-ethylcarbodiimide hydrochloride (132 mg, 0.69 mmol) was added to a solution of 3-(N-(tert-butoxycarbonyl)-N-methylamino)benzoic acid (183 mg, 0.69 mmol) and 1-hydroxy-7-azabenzotriazole (94 mg, 0.69 mmol) in dichloromethane (5 ml). The reaction mixture was stirred for 20 min at 0° C. A solution of (2R)-N-[(1R)-1-benzyl-2-((2S)-2-((dimethylamino)methyl)pyrrolidin-1-yl)-2-oxoethyl]-N-methyl-2-methylamino)-3-(2-naphthyl)propionamide (345 mg, 0.69 mmol) in dichloromethane (10 ml) and N,N-dimethylformamide (5 ml) and ethyldiisopropylamine (0.118 ml) were added successively. The reaction mixture was stirred for 16 h, while it was warming up to room temperature. It was diluted with ethyl acetate and washed with a saturated aqueous solution of sodium hydrogen carbonate (70 ml). The aqueous phase was extracted with ethyl acetate (3×50 ml). The combined organic layers were dried over magnesium sulfate. The solvent was removed in vacuo. The crude product was purified by flash chromatography on silica (40 g), using dichloromethane/methanol/25% aqueous ammonia (100:10:1) as eluent, to give 524 mg of N-{3-[N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]benzyl}-N-methylcarbamic acid tert-butyl ester.

¹H-NMR (CDCl₃, selected values): δ 0.72 (m, 1H); 1.45 (br, 9H); 3.18 (br, 6H); 4.05 (m, 1H); 4.32 and 4.40 (both br, together 2H); 5.60 (dd, 1H); 5.95 (m, 1H); 6.80–6.90 (m, 16H).

At 0° C., trifluoroacetic acid (7 ml) was added to a solution of N-(3-[N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylcarbamoyl]benzyl}-N-methylcarbamic acid tert-butyl ester (523 mg, 0.70 mmol) in dichloromethane (7 ml). The reaction mixture was stirred for 25 min at 0° C. The solvent was removed in vacuo. The residue was dissolved in dichloromethane (90 ml), and the solvent was removed in vacuo. The latter procedure was repeated two times. The crude product was purified by flash chromatography on silica (40 g), using dichloromethane/methanol/25% aqueous ammonia (100:10:1) as eluent, to give 436 mg of the title compound.

¹H-NMR (CDCl₃, selected values): δ 0.87 (m, 1H); 1.22 (m, 1H); 1.45 (m, 1H); 1.67 (m, 1); 4.09 (m, 1H); 5.53 and 5.90 (dd and m, together 2H); 6.80–7.90 (m, 16H).

HPLC 28.43 min (A1). 30.63 min (B1).

MS: 648.4 [M+1]⁺.

For biological testing, the title compound was transferred into its diacetate salt by lyophilization from 0.5 M acetic acid (40 ml).

Example 6

(2E)-5-Amino-5-methylhex-2-enoic acid N-((1R)-1-{N-[(1R)-1-benzyl-2-(4-(dimethylamino)piperidin-1-yl)-2-oxoethyl]N-methylcarbamoyl}-2-(2-naphthyl)ethyl)-N-methylamide

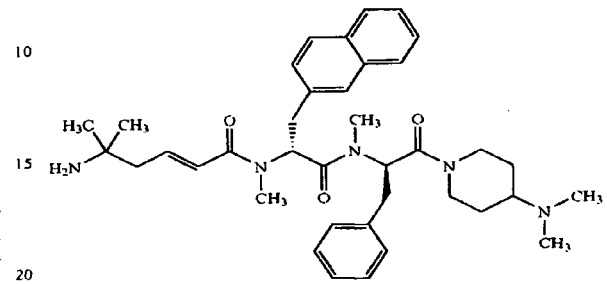

The title compound was prepared as in example 1 using 4-(dimethylamino)piperidine hydrochloride salt, (2R)-2-(N-(tert-butoxycarbonyl)-N-methylamino)-3-phenylpropionic add, (2R)-2-(N-(tert-butoxycarbonyl)-N-methylamino-3-(2-naphthyl))propionic acid, and (2E)-5-(butoxycarbonylamino)-5-methylhex-2-enoic acid.

¹H-NMR: (CDCl₃; selected values) δ 1.40 (s, 6H); 2.00 (s, 6H); 4.42–4,85 (2H); 5.45–5.90 (m, 2H); 6.28 (dd, 1H); 6.85 (m, 1H); 7.10–7,85(m, 12H).

MS (ES): m/z 626.2 (M+H)⁺.

Example 7

(2E)-5-Amino-5-methylhex-2-enoic acid N-methyl-N-[(1R)-1-(N-methyl-N-{(1R)-1-[N-methyl-N-(1-methylpiperidinyl)carbamoyl]-2-phenylethyl}carbamoyl)-2-(2-naphthyl)ethyl]amide

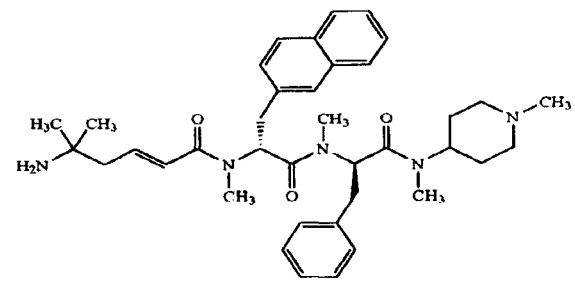

The title compound was prepared as in example 1 using 1-methyl-4-(methylamino)piperidine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-5-(butoxycarbonylamino)-5-methylhex-2-enoic acid.

¹H-NMR (CDCl₃; selected values) δ 5.50–6.08 (m, 2H); 6.20–6.70 (m, 2H); 7.10–7.85 (m, 12H).

61

Example 8

3-Aminomethyl-N-((1R)-1-{N-[(1R)-1-benzyl-2-(4-methylpiperazin-1-yl)-2-oxoethyl]-N-methylcarbamoyl}-2-(2-naphthyl)ethyl)-N-methylbenzamide

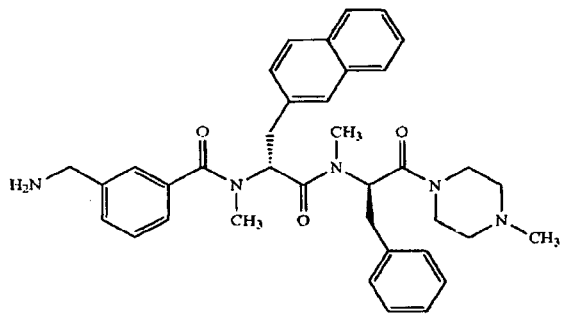

The title compound was prepared as in example 1 using N-methylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and 3-((tert-butoxycarbonylamino)methyl)benzoic acid.

$^1$H-NMR (CDCl$_3$; selected values) δ 3.30 (m, 1H); 3.50 (dd, 1H); 3.75 (m, 1H); 3.95 (s, 2H); 5.78 (t, 1H); 3.88 (m, 1H); 7.00–7.80 (16H).

HPLC: 24.55 min (A1). 26.52 min (B1).
MS (ES): m/z=606.4 [M+H]$^+$.

Example 9

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

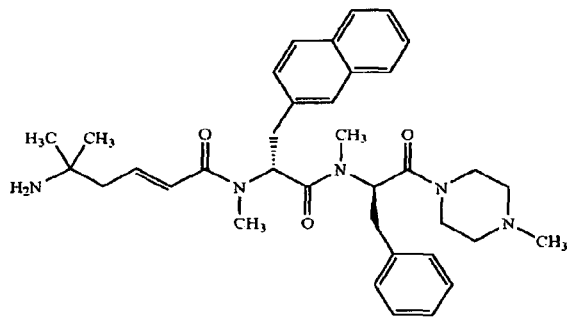

The title compound was prepared as in example 1 using N-methylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-5-(butoxycarbonylamino)-5-methylhex-2-enoic acid.

$^1$H-NMR (CDCl$_3$; selected values) δ 1.24 (s, 6H); 1.65 (s, 3H); 2.35 (s, 3H); 2.80 (s, 3H); 5.68 (dd, 1H); 5.78 (dd, 1H); 6.18 (dd, 1H); 6.95(m, 1H); 7.15–7.80 (m, 12H).

HPLC: 25.03 min (A1). 27.50 min (B1)
MS (ES): m/z=598.4 [M+H]$^+$.

62

Example 10

(2E)-5-Amino-5-methylhex-2-enoic acid N-methyl-N-((1R)-1-{N-methyl-N-[(1R)-2-phenyl-1-((2,2,6,6-tetramethylpiperidinyl)carbamoyl)ethyl]carbamoyl}-2-(2-naphthyl)ethyl)amide

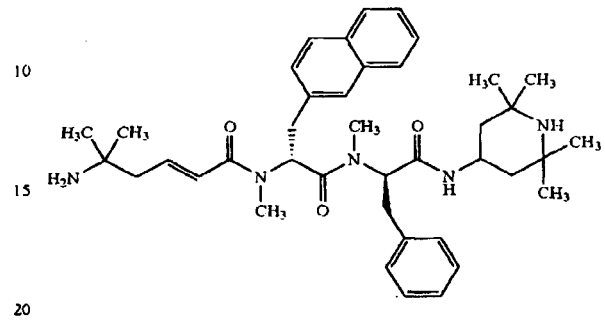

The title compound was prepared as in example 1 using 4-amino-2,2,6,6-tetramethylpiperidin, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-5-(butoxycarbonylamino)-5-methylhex-2-enoic acid.

$^1$H-NMR (CDCl$_3$; selected values) δ 1.25 (s, 6H); 1.40 (two s, 6H); 1.52 (two s, 6H); 2.92 (s, 3H); 3.02 (two s, 3H); 5.10 (dd, 1H); 5.50 (dd, 1H); 6.15 (d, 1H); 6.75 (m, 1H); 7.00–8.00 (m, 12H).

HPLC: 29.27 min (A1). 31.67 min (B1).
MS (ES): m/z=654.8 [M+H]$^+$.

Example 11

3-Aminomethyl-N-methyl-N-((1R)1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide

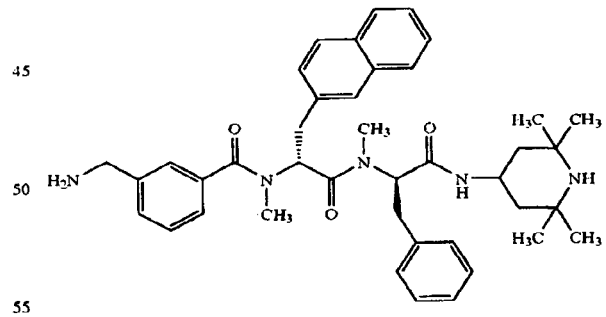

The title compound was prepared as in example 1 using 4-amino-2,2,6,6-tetramethylpiperidin, (2R)-2-(N(tert-butoxycarbonyl)-N-methylamino)-3-phenylpropionic acid, (2R)-2-(N-(tert-butoxycarbonyl)-N-methylamino-3-(2-naphthyl))propionic acid, and 3-((tert-butoxycarbonylamino)methyl)benzoic acid.

$^1$H-NMR (CDCl$_3$; selected values) δ 3.60–3.85 (m, 2H); 3.90–4.30 (m, 1H); 5.25–5.95 (m, 2H); 6.70–7.90 (m, 16H).

HPLC: 29.27 min (A1). 31.55 min (B1).
MS (ES): m/z=662.4 [M+H]$^+$.

Example 12

(2E)-5-Amino-3,5-dimethylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

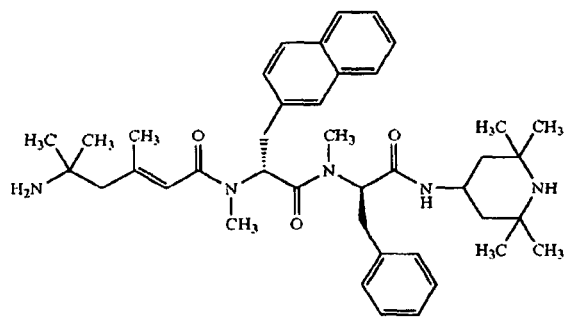

The title compound was prepared as in example 1 using 4-amino-2,2,6,6-tetramethylpiperidin, (2R)-2(N-(tert-butoxycarbonyl)-N-methylamino)-3-phenylpropionic acid, (2R)-2-(N--(tert-butoxycarbonyl)-N-methylamino-3-(2-naphthyl))propionic acid, and (2E)-S-(butoxycarbonylamino)-3,5-methylhex-2-enoic acid.

$^1$H-NMR (CDCl$_3$; selected values) δ 392–4.30 (m, 1H); 5.05–5.88 (m, 3H); 7.00–7.80 (m, 12H).

HPLC: 29.80 min (A1). 32.43 min (B1).

MS (ES): m/z=668.4 [M+H]$^+$.

Example 13

(2E)-4-(1-Aminocyclobutyl)but-2-enoic acid N-((1R)-1-{N-[(1R)1-benzyl-2-(4-methylpiperazin-1-yl)-2-oxoethyl]-N-methylcarbamoyl}2-(2-naphthyl)ethyl)-N-methylamide

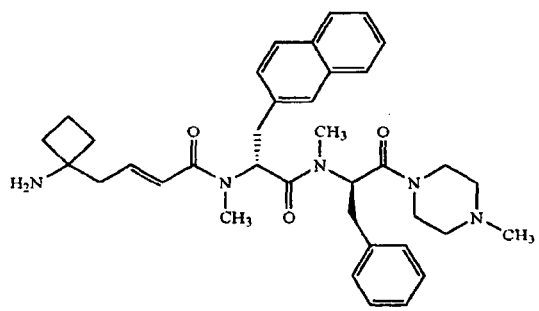

The title compound was prepared as in example 1 using N-methylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-4-(1-(butoxycarbonylamino)cyclobutyl)but-2-enoic acid.

$^1$H-NMR (CDCl$_3$; selected peaks) δ 1.62 (s, 3H); 2.35 (s, 3H); 2.80 (s, 3H); 5.70 (dd, 1H); 5.80 (dd, 1H); 6.22 (d, 1H); 6.98 (m, 1H); 7.15–7.80 (m, 12H).

HPLC: 25.88 min (A1). 28.65 min (B1).

MS (ES) m/z=610.4 [M+H]$^+$.

Example 14

(2E)-5-Amino-3,5-dimethylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

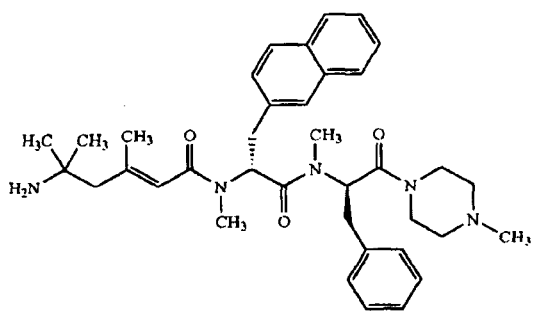

The title compound was prepared as in example 1 using N-methylpiperazine, (2R)-2-(N-(tert-butoxycarbonyl)-N-methylamino)-3-phenylpropionic acid, (2R)-2N-(tert-butoxycarbonyl)-N-methylamino-3-(2-naphthyl))propionic acid, and (2E)-5-(butoxycarbonylamino)-3,5-methylhex-2-enoic acid.

$^1$H-NMR (CDCl$_3$; selected values) δ 1.18 (s, 6H); 1.68 (s, 3H); 1.95 (s, 3H); 2.30 (s, 3H); 2.85 (s, 3H); 3.40 (dd, 1H); 3.54–3.75 (m, 2H); 5.68–5.85 (m, 3H); 7.15–7.80 (m, 12H).

HPLC: 25.70 min (A1). 28.27 min (B1).

MS (ES) m/z=612.4 [M+H]$^+$.

Example 15

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

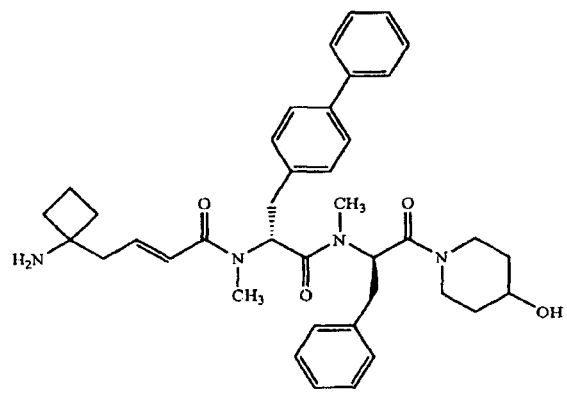

This compound was prepared as in example 1 but using 4-hydroxypiperidine, (2R)-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-4-(1-(tert-butoxycarbonylamino)cyclobutyl)but-2-enoic acid as starting materials.

ESMS: 637.4 (M+H)⁺.
HPLC: r$_t$=33.58 min. (A1).
HPLC: r$_t$=34.95 min. (B1).

Example 16

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

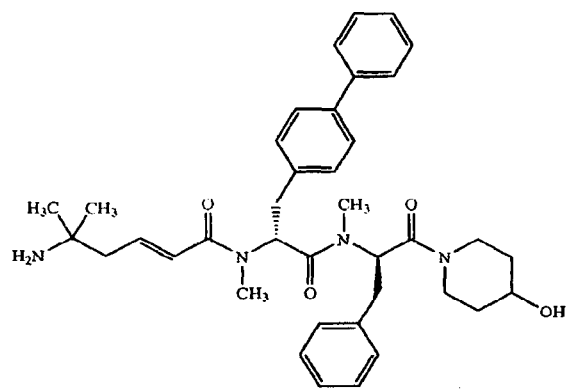

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-5-tert-Butoxycarbonylamino-5-methylhex-2-enoic acid as starting materials.

ESMS: 625.4 (M+H)⁺.
HPLC: r$_t$=32.65 min. (A1).
HPLC: r$_t$=34.02 min. (B1).

Example 17

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

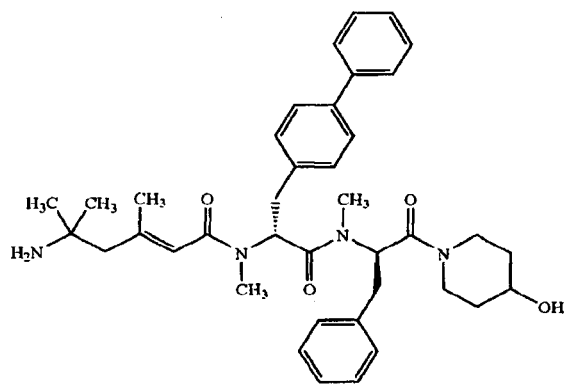

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(biphenyl-4-yl)propionic acid and (2E)-5-tert-butoxycarbonylamino-3,5-dimethylhex-2-enoic acid as starting materials.

ESMS: 639.4 (M+H)⁺.
HPLC: r$_t$=33.29 min. (A1).
HPLC: r$_t$=36.40 min. (B1).

Example 18

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

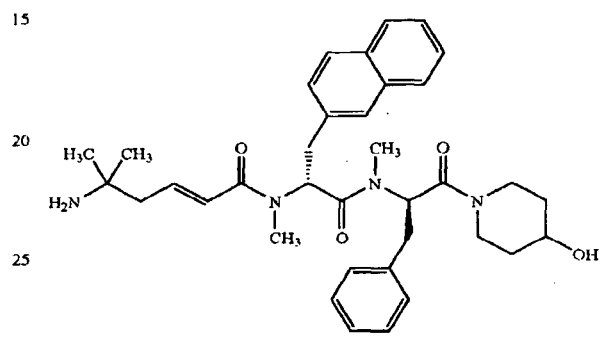

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(2-naphthyl)propionic acid and (2E)-5-tert-Butoxycarbonylamino-5-methylhex-2-enoic acid as starting materials.

ESMS: 599.4 (M+H)⁺.
HPLC: r$_t$=29.88 min. (A1).

Example 19

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

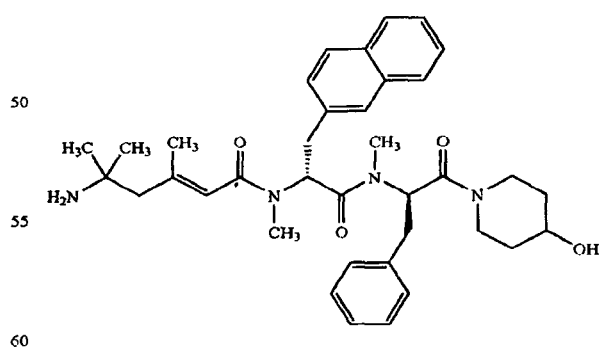

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(2-naphthyl)propionic acid and (2E)-5-tert-Butoxycarbonylamino-3,5-dimethylhex-2-enoic acid as starting materials.

ESMS; 613.4 (M+H)+.
HPLC: r_t=30.58 min. (A1).

Example 20

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

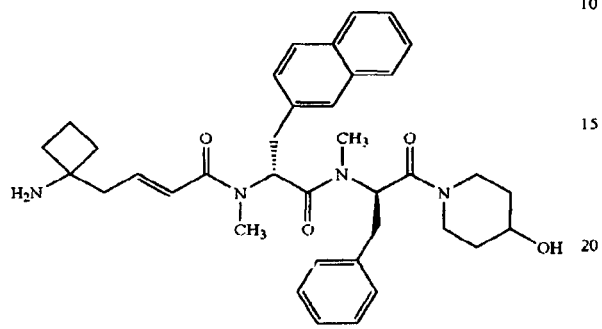

This compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(2-naphthyl)propionic acid and (2E)-4-(1-(tert-butoxycarbonylamino)cyclobutyl)but-2-enoic acid.

ESMS: 611.4 (M+H)+.
HPLC: r_t=30.82 min. (A1).

Example 21

(2E)-5-Amino-5-methylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

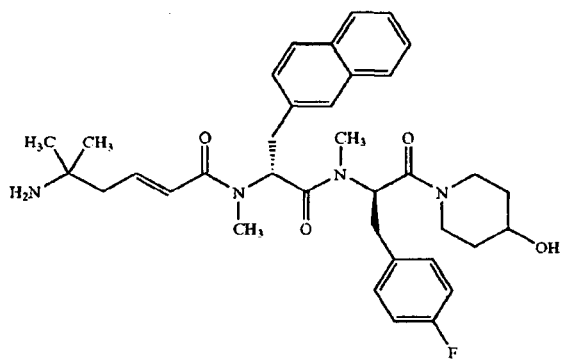

This compound was prepared as in example 1 but using 4-hydroxypiperidine, (2R)-2-(N-tert-butoxycarbonyl-N-methylamino)-3-(4-fluorophenyl)propionic acid and (2R)-2-(N-tert-butoxycarbonyl-N-methylamino)-3-(2-naphthyl) propionic acid and (2E)-5-tert-butoxycarbonylamino-5-methylhex-2-enoic acid as starting materials.

ESMS: 617.4 (M+H)+.
HPLC: r_t=30.27 min. (A1).
HPLC: r_t=31.60 min. (B1).

Example 22

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

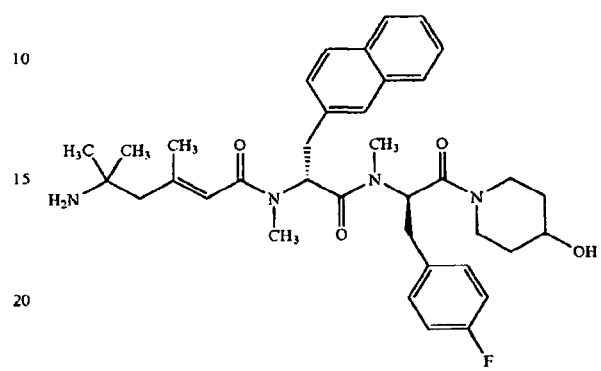

This compound was prepared as in example 1 but using 4-hydroxypiperidine, (2R)-2-(N-tert-butoxycarbonyl-N-methylamino)-3-(4-fluorophenyl)propionic acid and (2R)-2-(N-tert-butoxycarbonyl-N-methylamino)-3-(2-naphthyl) propionic acid and (2E)-5-tert-butoxycarbonylamino-3,5-dimethylhex-2-enoic acid as starting materials.

ESMS: 631.4 (M+H)+.
HPLC: r_t=30.98 min. (A1).
HPLC: r_t=32.38 min. (B1).

Example 23

(2E)-4-(1-Aminocyclobutyl)but-2-enoic acid N-((1R)-1-{N-[(1R)-1-benzyl-2-(4-(dimethylamino)piperidin-1-yl)-2-oxoethyl]-N-methylcarbamoyl}-2-(2naphthyl)ethyl)-N-methylamide

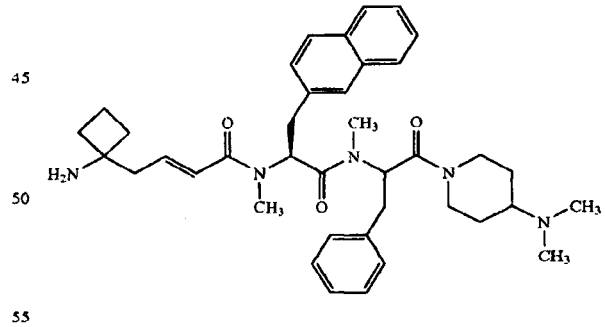

The title compound was prepared as in example 1 using 4-N,N-dimethylpiperazine, (2R)-2-(N-(tert-butoxycarbonyl)-N-methylamino)-3-phenylpropionic acid, (2R)-2-(N-(tert-butoxycarbonyl)-N-methylamino-3-(2-naphthyl))propionic acid, and (2E)-4-1-(butoxycarbonylamino)cyclobutyl)but-2-enoic acid.

$^1$H-NMR (CDCl$_3$; selected peaks) d 1.90 (s, 3H); 2.38 (s, 3H); 2.45 and 2.47 (two s, 3H); 2.78 and 2.80 (two s, 3H); 6.32 (dd, 1H); 6.90 (m, 1H); 7.15–7.84 (m, 12H).
HPLC: 26.72 min (A1).
MS (ES) m/z=638.4 [M+H]+.

Example 24

(2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

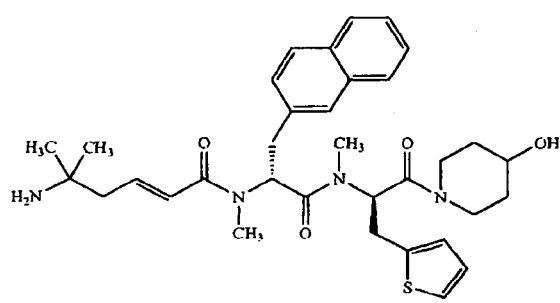

This compound was prepared as in example 1 but using 4-hydroxypiperidine, (2R)-2N-tert-butoxycarbonyl-N-methylamino)-3-(2-thienyl)propionic acid and (2R)-2-(N-tert-butoxycarbonyl-N-methylamino)-3-(2-naphthyl)propionic acid and (2E)-5-tert-butoxycarbonylaminomethylhex-2-enoic add as starting materials.

ESMS: 605.4 (M+H)$^+$.

HPLC: r$_t$=29.07 min. (A1).

Example 25

(2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

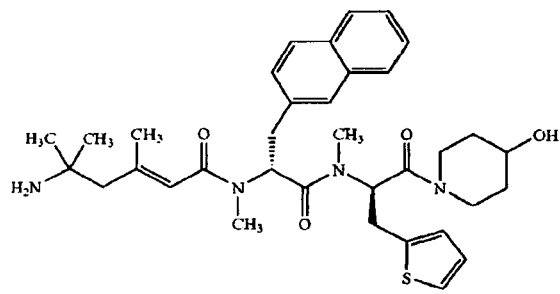

This compound was prepared as in example 1 but using 4-hydroxypiperidine, (2R)-2-(N-tert-butoxycarbonyl-N-methylamino)-3-(2-thienyl)propionic acid and (2R)-2-(N-tert-butoxycarbonyl-N-methylamino)-3-(2-naphthyl)propionic acid and (2E)-5-tert-butoxycarbonylamino-3,5-dimethylhex-2-enoic acid as starting materials.

ESMS: 619.4 (M+H)$^+$.

HPLC: r$_t$=29.76 min. (A1).

Example 26

(2E)-5-Amino-5-methylhex-2-enoic acid N-((1R)-2-(biphenyl-4-yl)-1-{N-[(2R)-2-(4-hydroxypiperidin-1-yl)-2-oxo-((2-thienyl)methyl)ethyl]-N-methylcarbamoyl}ethyl)-N-methylamide

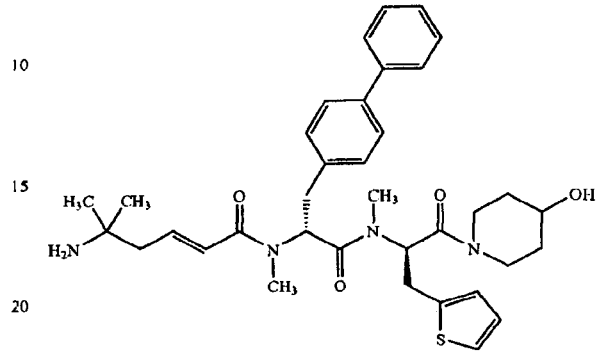

This compound was prepared as in example 1 but using 4-hydroxypiperidine, (2R)-2-(N-tert-butoxycarbonyl-N-methylamino)-3-(2-thienyl)propionic acid and (2R)-2-(N-tert-butoxycarbonyl-N-methylamino)-3-(biphenyl-4-yl)propionic acid and (2E)-5-tert-butoxycarbonylamino-5-methylhex-2-enoic acid as starting materials.

ESMS: 631.2 (M+H)$^+$.

HPLC: r$_t$=32.20 min. (A1).

Example 27

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide

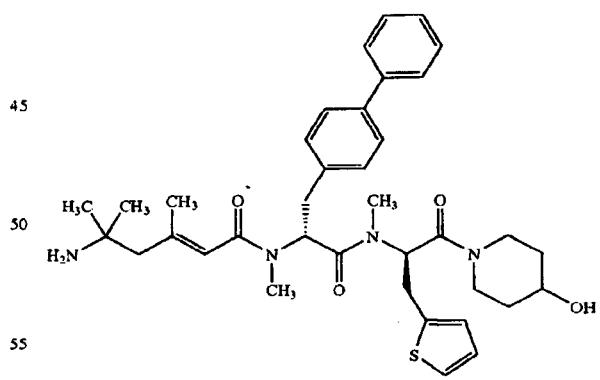

This compound was prepared as in example 1 but using 4-hydroxypiperidine, (2R)-2-(N-tert-butoxycarbonyl-N-methylamino)-3-(2-thienyl)propionic acid and (2R)-2-(N-tert-butoxycarbonyl-N-methylamino)-3-(biphenyl-4-yl)propionic acid and (2E)-5-tert-butoxycarbonylamino-3,5-dimethylhex-2-enoic acid as starting materials.

ESMS: 465.4 (M+H)$^+$.

HPLC: r$_t$=32.89 min. (A1).

Example 28

(2E)-5-Methyl-5-(methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

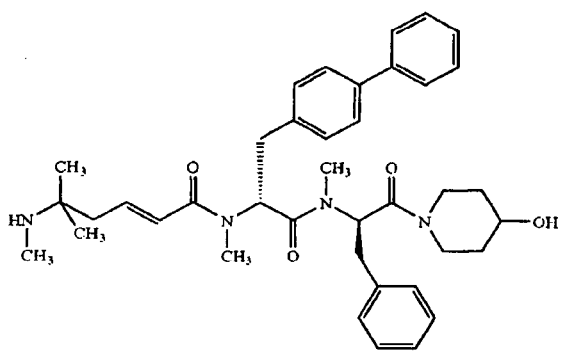

The title compound was prepared as in example 1 but using 4-hydroxypiperidine, (2R)-2-(N-tert-butoxycarbonyl-N-methylamino)-3-phenylpropionic acid and (2R)-2-(N-tert-butoxycarbonyl-N-methylamino)-3-(biphenyl-4-yl) propionic acid and (2E)-5-(N-(tert Butoxycarbonyl)-N-methylamino)-5-methylhex-2-enoic acid as starting materials.

MS: m/z: 639.4 (M+H)$^+$.

HPLC: Method A1: $R_t$=32.94 min.

Example 29

(2E)-4-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide

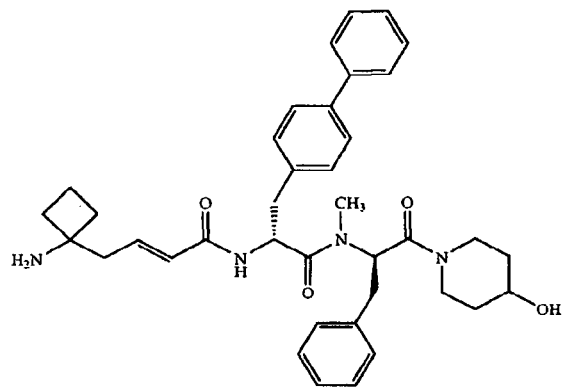

HPLC: Rt=31.55 min. (A1). Rt=31.11 min. (B1).

LC-MS: 623.6 [M+1]$^+$.

What is claimed is:

1. A compound of formula I

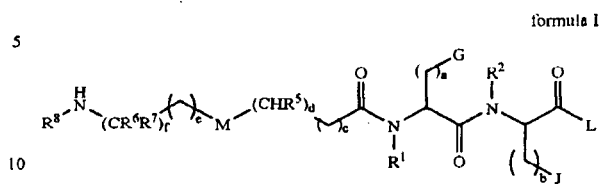

formula I wherein $R^1$ is hydrogen or $C_{1-6}$-alkyl;
$R^2$ is hydrogen or $C_{1-6}$-alkyl;
L is

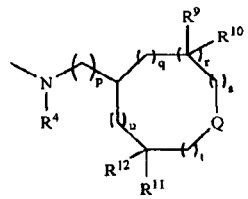

wherein $R^4$ is hydrogen or $C_{1-6}$ alkyl;
p is 0 or 1;
q, s, t, u are independently from each other 0, 1, 2, 3 or 4;
r is 1;
the sum q+r+s+t+u is 1, 2, 3, or 4;
$R^9$, $R^{10}$, $R^{11}$, and $R^{12}$ are independently from each other hydrogen or $C_{1-6}$ alkyl;
Q is >N—$R^{13}$ or

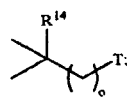

wherein o is 0, 1 or 2;
T is —N($R^{15}$)($R^{16}$) or hydroxyl;
$R^{13}$, $R^{15}$, and $R^{16}$ are independently from each other hydrogen or $C_{1-6}$ alkyl;
$R^{14}$ is hydrogen, aryl or hetaryl;
or L is

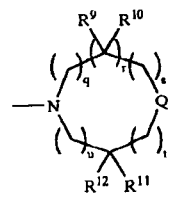

p is 0 or 1;
q, s, t, u are independently from each other 0, 1, 2, 3 or 4;
r is 0 or 1;
the sum 1+r+s+t+u is 0, 1, 2, 3, or 4;

$R^9$, $R^{10}$, $R^{11}$, and $R^{12}$ are independently from each other hydrogen or $C_{1-6}$ alkyl;

Q is >N—$R^{13}$ or

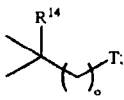

wherein o is 0, 1 or 2;
T is —N($R^{15}$)($R^{16}$) or hydroxyl;
$R^{13}$, $R^{15}$, $R^{16}$ are independently from each other hydrogen or $C_{1-6}$ alkyl;
$R^{14}$ is hydrogen, aryl or hetaryl;
G is —O—(CH$_2$)$_k$R$^{17}$,

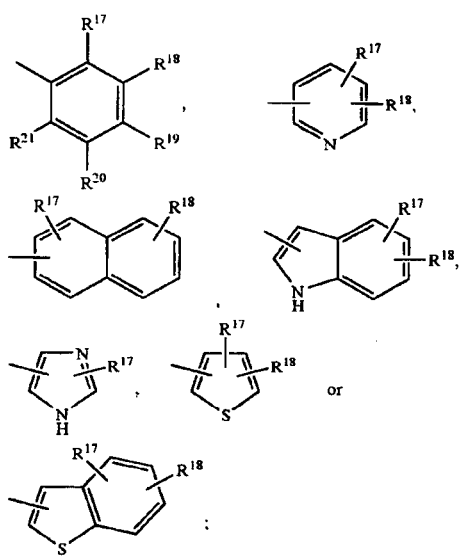

wherein $R^{17}$, $R^{18}$, $R^{19}$, $R^{20}$ and $R^{21}$ independently from each other are hydrogen, halogen, aryl, hetaryl, $C_{1-6}$-alkyl or $C_{1-6}$-alkoxy;
k is 0, 1 or 2;
J is —O—(CH$_2$)$_l$—R$^{22}$,

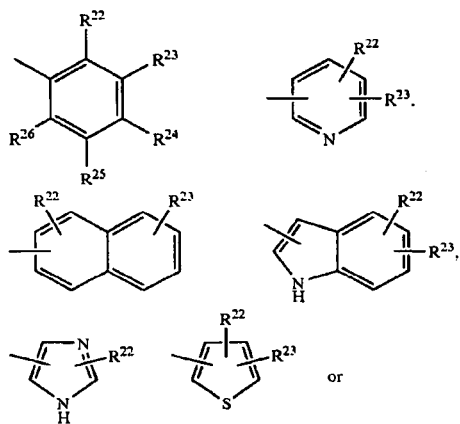

wherein $R^{22}$, $R^{23}$, $R^{24}$, $R^{25}$ and $R^{26}$ independently from each other are hydrogen, halogen, aryl, hetaryl, $C_{1-6}$-alkyl or $C_{1-6}$-alkoxy;
l is 0, 1, or 2;
a is 0, 1, or 2;
b is 0, 1, or 2;
c is 0, 1, or 2;
d is 0 or 1;
e is 0, 1, 2, or 3;
f is 0 or 1;
$R^5$ is hydrogen or $C_{1-6}$-alkyl optionally substituted with one or more hydroxyl, aryl or hetaryl;
$R^6$ and $R^7$ are independently from each other hydrogen or $C_{1-6}$-alkyl, optionally substituted with one or more halogen, amino, hydroxyl, aryl, or hetaryl;
$R^8$ is hydrogen or $C_{1-6}$-alkyl, optionally substituted with one or more halogen, amino, hydroxyl, aryl, or hetaryl;
$R^6$ and $R^7$ or $R^6$ and $R^8$ or $R^7$ and $R^8$ may optionally form —(CH$_2$)$_i$—U—(CH$_2$)$_j$—, wherein i and j independently from each other are 1, 2 or 3 and U is —O—, —S—, or a valence bond;
M is arylene, hetarylene, —O—, —S— or —CR$^{27}$=CR$^{28}$—;
$R^{27}$ and $R^{28}$ are independently from each other hydrogen or $C_{1-6}$-alkyl, optionally substituted with one or more aryl or hetaryl;
or a pharmaceutically acceptable salt thereof.

2. The compound of claim 1 wherein $R^1$ is $C_{1-6}$-alkyl.
3. The compound of claim 1 wherein $R^2$ is $C_{1-6}$-alkyl.
4. The compound of claim 1 wherein L is

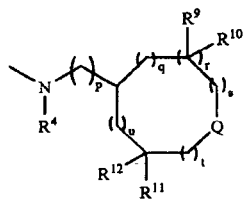

wherein $R^4$ is hydrogen or $C_{1-6}$ alkyl;
p is 0 or 1;
q, s, t, u are independently from each other 0, 1, 2, 3 or 4;
r is 1;
the sum q+r+s+t+u is 1, 2, 3, or 4;
$R^9$, $R^{10}$, $R^{11}$, and $R^{12}$ are independently from each other hydrogen or $C_{1-6}$ alkyl;
Q is >N—$R^{13}$ or

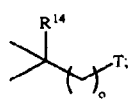

75 wherein o is 0, 1 or 2;
T is —N(R$^{15}$)(R$^{16}$) or hydroxyl;
R$^{13}$, R$^{15}$, and R$^{16}$ are independently from each other hydrogen or C$_{1-6}$ alkyl; and
R$^{14}$ is hydrogen, aryl or hetaryl.

5. The compound of claim 1 wherein L is

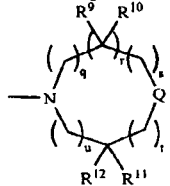

wherein q, s, t, u are independently from each other 0, 1, 2, 3 or 4;
r is 0 or 1;
the sum q+r+s+t+u is 0, 1, 2, 3, or 4;
R$^9$, R$^{10}$, R$^{11}$, and R$^{12}$ are independently from each other hydrogen or C$_{1-6}$ alkyl;
Q is >N—R$^{13}$ or

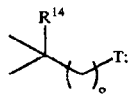

wherein o is 0, 1 or 2;
T is —N(R$^{15}$)(R$^{16}$) or hydroxyl;
R$^{13}$, R$^{15}$, and R$^{16}$ are independently from each other hydrogen or C$_{1-6}$ alkyl; and
R$^{14}$ is hydrogen, aryl or hetaryl.

6. The compound of claim 1 wherein G is

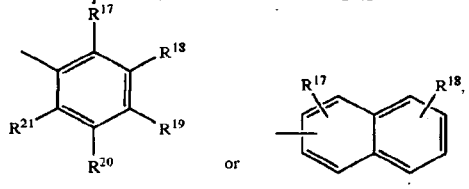

wherein R$^{17}$, R$^{18}$, R$^{19}$, R$^{20}$ and R$^{21}$ independently from each other are hydrogen, halogen, aryl, hetaryl, C$_{1-6}$-alkyl or C$_{1-6}$-alkoxy.

7. The compound of claim 1 wherein J is

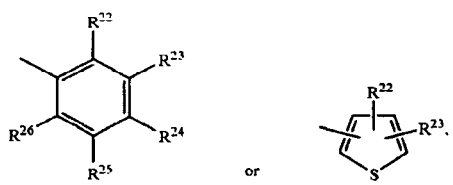

wherein R$^{22}$, R$^{23}$, R$^{24}$, R$^{25}$ and R$^{26}$ independently are hydrogen, halogen, aryl, hetaryl, C$_{1-6}$-alkyl or C$_{1-6}$-alkoxy.

8. The compound of claim 1 wherein M is arylene or —CR$^{28}$=CR$^{28}$—, wherein R$^{27}$ and R$^{28}$ independently are hydrogen or C$_{1-6}$-alkyl, optionally substituted with aryl or hetaryl.

9. The compound of claim 1 wherein R$^6$ and R$^7$ independently from each other are hydrogen or C$_{1-6}$-alkyl.

76

10. The compound of claim 1 wherein R$^6$ and R$^7$ form —(CH$_2$)$_i$—U—(CH$_2$)$_j$—, wherein i and j independently from each other are 1, 2 or 3 and U is —O—, —S—, or a valence bond.

11. The compound of claim 1 wherein R$^8$ is hydrogen or C$_{1-6}$-alkyl.

12. The compound of claim 1 selected from (2E)-5-Amino-5-methylhex-2-enoic acid N-((1R)-1-{N-[(1R)-1-benzyl-2-(4-(dimethylamino)methyl)piperidin-1-yl)-2-oxoethyl]-N-methylcarbamoyl}-2-(2-naphthyl)ethyl)-N-methylamide

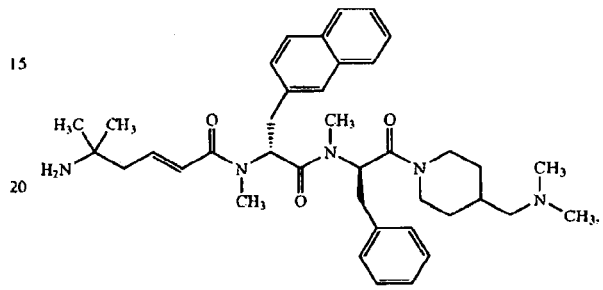

(2E)-5-Amino-5-methylhex-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

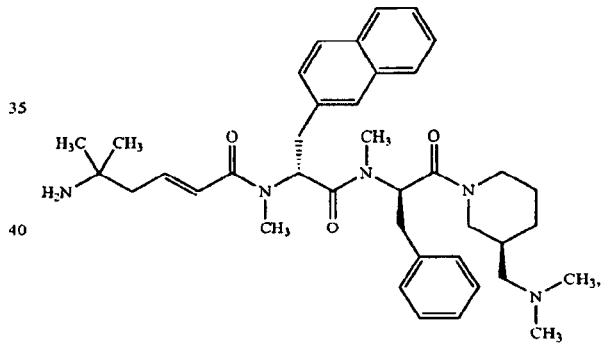

(2E)-4-(1-Aminocyclobutyl)but-2-enoic acid N-((1R)-1-{N-[(1R)-1-benzyl-2-((3S)-3-(dimethylaminomethyl)piperidin-1-yl)-2-oxoethyl]-N-methylcarbamoyl}-2-(2-naphthyl)ethyl)-N-methylamide

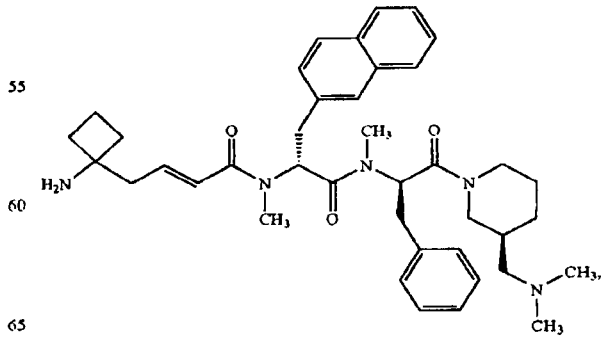

77

(2E)-5-Amino-5-methylhex-2-enoic acid N-((1R)-1-{N-[(1R)-1-benzyl-2-((2S)-2-((dimethylamino)methyl)pyrrolidin-1-yl)-2-oxoethyl]-N-methylcarbamoyl}-2-(2-naphthyl)ethyl)-N-methylamide

78

(2E)-5-Amino-5-methylhex-2-enoic acid N-methyl-N-[(1R)-1-(N-methyl-N-{(1R)-1-[N-methyl-N-(1-methylpiperidin-4-yl)carbamoyl]-2-phenylethyl}carbamoyl)-2-(2-naphthyl)ethyl]amide

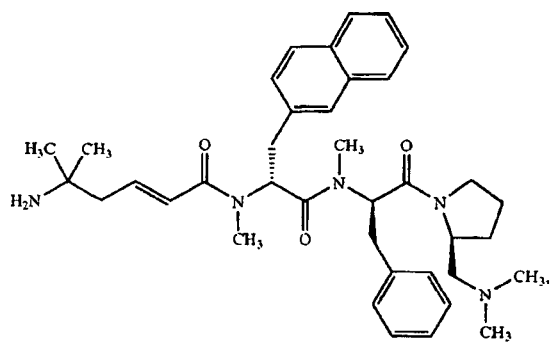

N-((1R)-1-{N-[(1R)-1-Benzyl-2-((2S)-2-(dimethylamino)methyl)pyrrolidin-1-yl)-2-oxoethyl]-N-methylcarbamoyl}-2-(2-naphthyl)ethyl)-N-methyl-3-((methylamino)methyl)benzamide

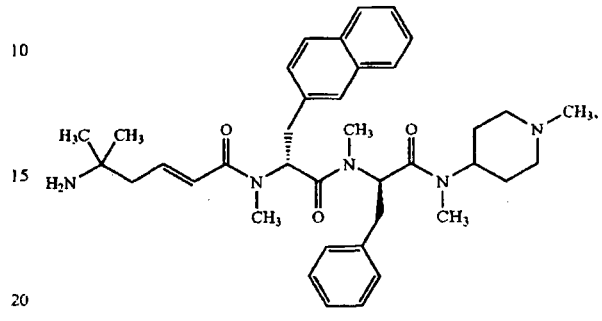

3-Aminomethyl-N-((1R)-1-{N-[(1R)-1-benzyl-2-(4-methylpiperazin-1-yl)-2-oxoethyl]-N-methylcarbamoyl}-2-(2-naphthyl)ethyl)-N-methylbenzamide

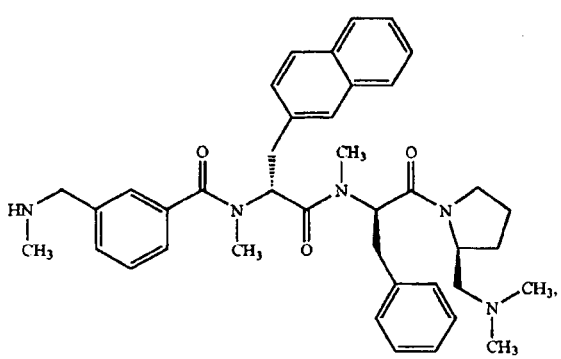

(2E)-5-Amino-5-methylhex-2-enoic acid N-((R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide

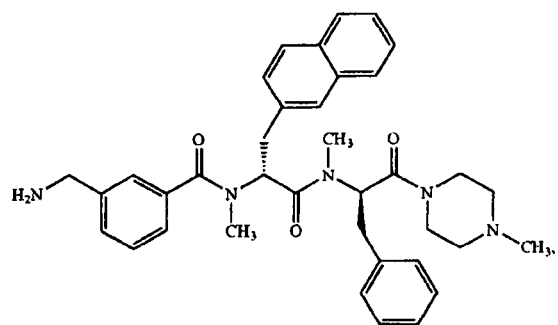

(2E)-5-Amino-5-methylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

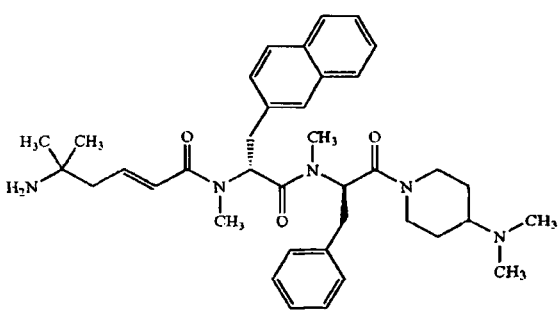

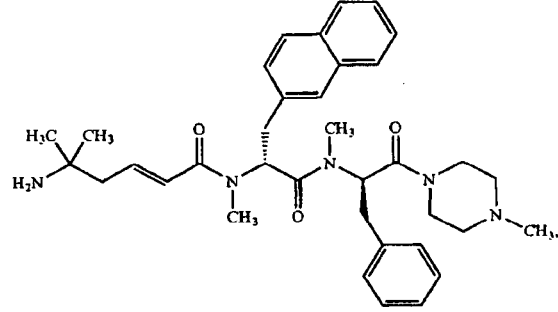

79

(2E)-5-Amino-5-methylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

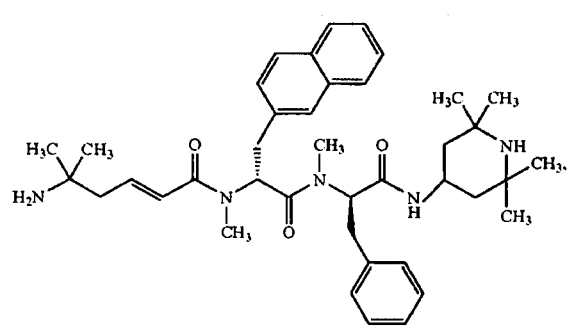

3-Aminomethyl-N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)benzamide

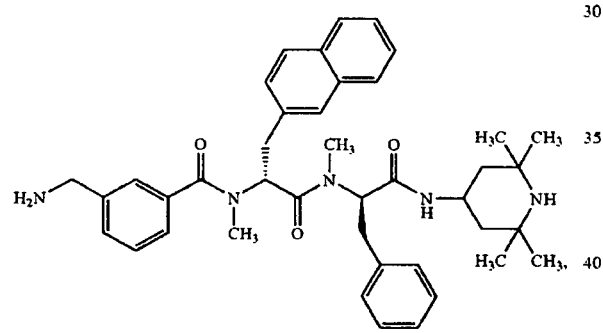

(2E)-5-Amino-3,5-dimethylhex-2-enoic acid N-methyl-N-((1R)-1-{N-methyl-N-[(1R)-2-phenyl-1-((2,2,6,6-tetramethylpiperidin-4-yl)carbamoyl)ethyl]carbamoyl}-2-(2-naphthyl)ethyl)amide

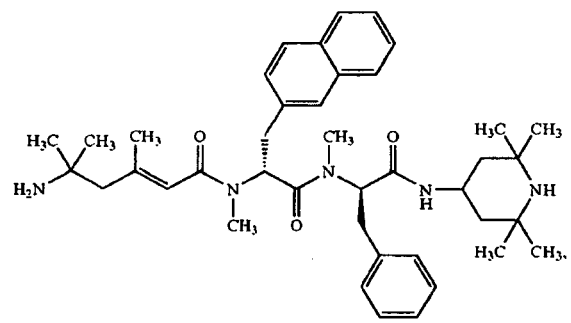

80

(2E)-4-(1-Aminocyclobutyl)but-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

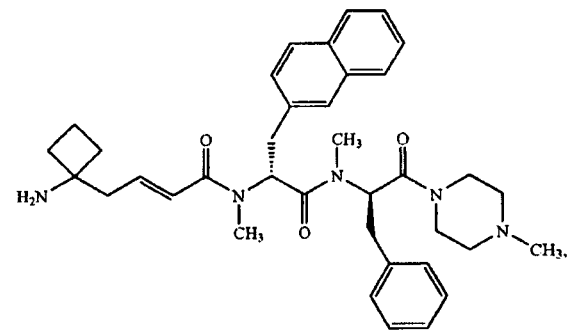

(2E)-5-Amino-3,5-dimethylhex-2-enoic acid N-((1R)-1-{N-[(1R)-1-benzyl-2-(4-methylpiperazin-1-yl)-2-oxoethyl]-N-methylcarbamoyl}-2-(2-naphthyl)ethyl)-N-methylamide

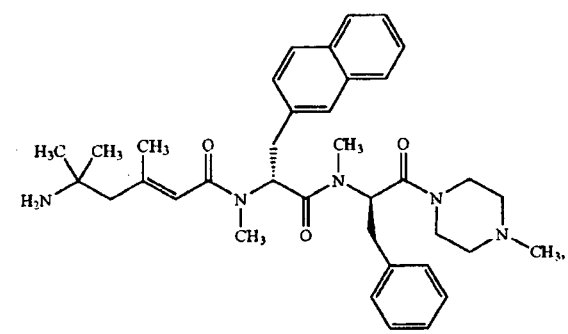

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

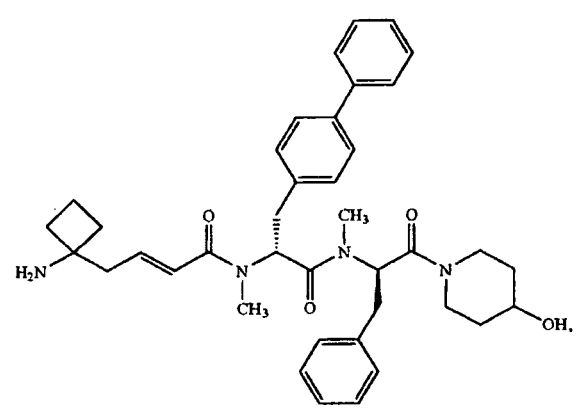

81

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

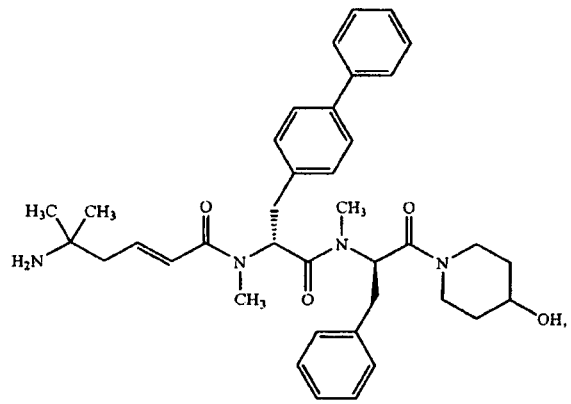

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

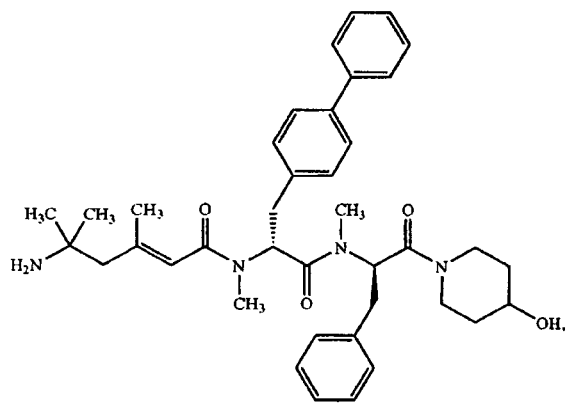

(2E)-5-Amino-5-methylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

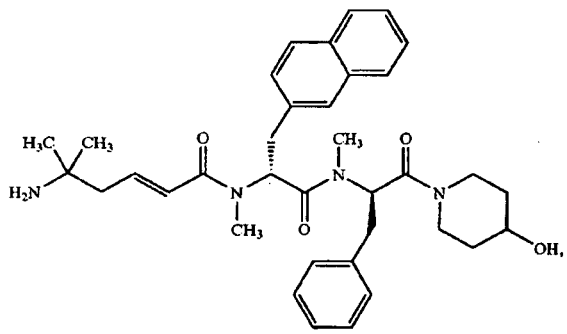

82

(2E)-5-Amino-3,5-dimethylhex-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

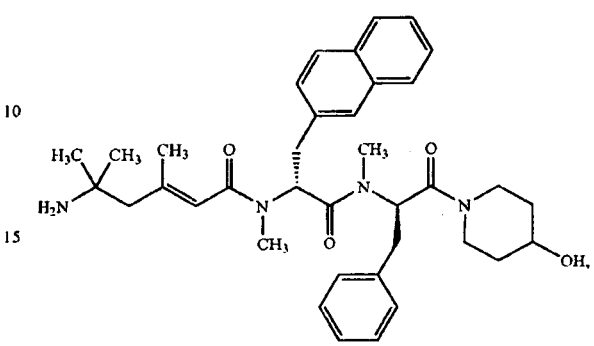

(2E)-4-(1-Aminocyclobutyl)but-2-enoic acid N-((1R)-1-{N-[(1R)-1-benzyl-2-(4-hydroxypiperidin-1-yl)-2-oxoethyl]-N-methylcarbamoyl}-2-(2-naphthyl)ethyl)-N-methylamide

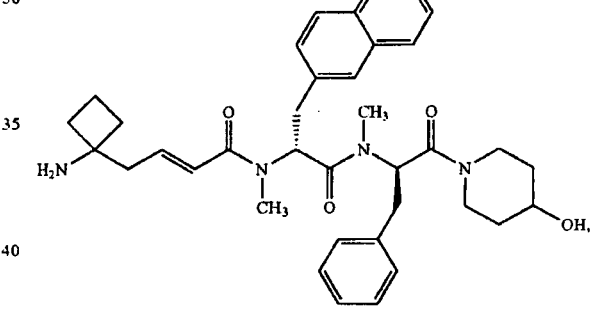

(2E)-5-Amino-5-methylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

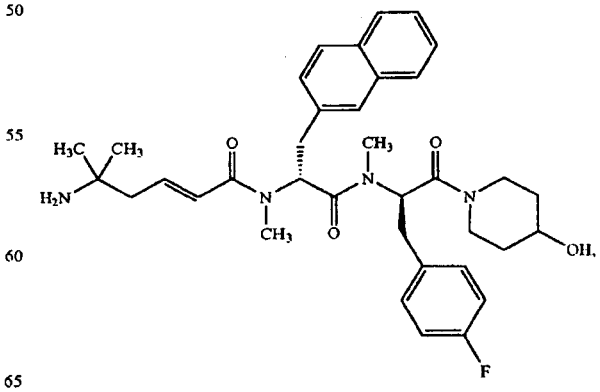

83

(2E)-5-Amino-3,5-dimethylhex-2-enoic acid N-((1R)-1-{N-[(1R)-1-(4-fluorobenzyl)-2-(4-hydroxypiperidin-1-yl)-2-oxoethyl]-N-methylcarbamoyl}-2-(2-naphthyl)ethyl)-N-methylamide

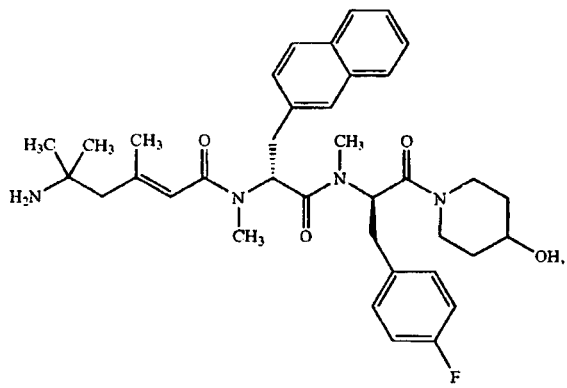

(2E)-5-Amino-5-methylhex-2-enoic acid N-((1R)-1-{N-[(1R)-1-benzyl-2-(4-hydroxy-4-(2-thienyl)piperidin-1-yl)-2-oxoethyl]-N-methylcarbamoyl}-2-(2-naphthyl)ethyl)-N-methylamide

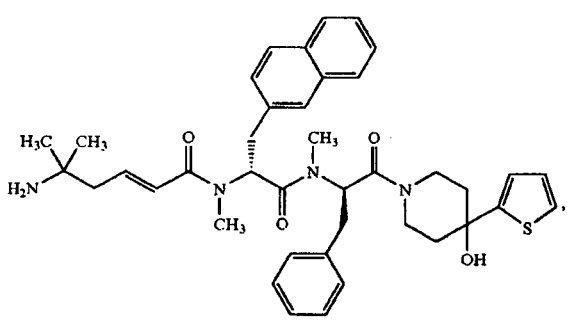

(2E)-5-Amino-5-methylhex-2-enoic acid N-((1R)-1-{N-[(1R)-1-(3-hydroxycyclohexylcarbamoyl)-2-phenylethyl]-N-methylcarbamoyl}-2-(2-naphthyl)ethyl)-N-methylamide

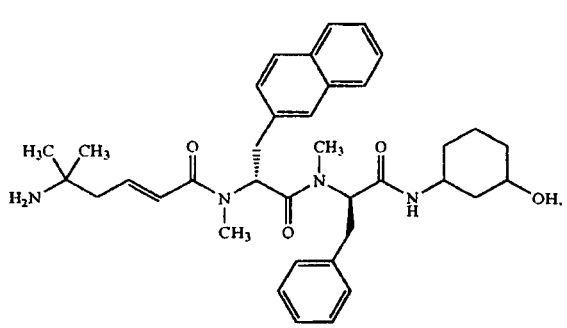

84

(2E)4-(1-Aminocyclobutyl)but-2-enoic acid N(1R)-1-{N-[(1R)-1-benzyl-2-(4-(dimethylamino)piperidin-1-yl)-2-oxoethyl]-N-methylcarbamoyl}-2-(2-naphthyl)ethyl)-N-methylamide

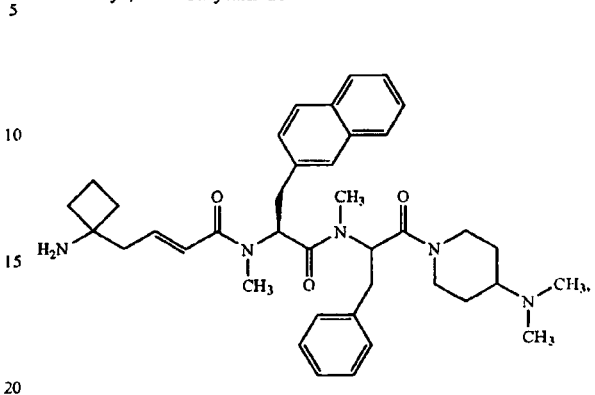

(2E)-5-Amino-5-methylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

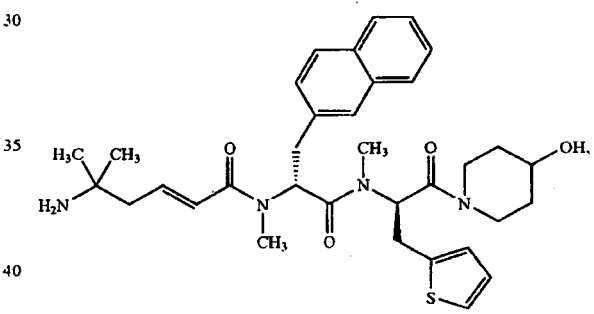

(2E)-5-Amino-3,5-dimethylhex-2-enoic acid N-((1R)-1-{N-[(2R)-2-(4-hydroxypiperidin-1-yl)-2-oxo-1-((2-thienyl)methyl)ethyl]-N-methylcarbamoyl}-2-(2-naphthyl)ethyl)-N-methylamide

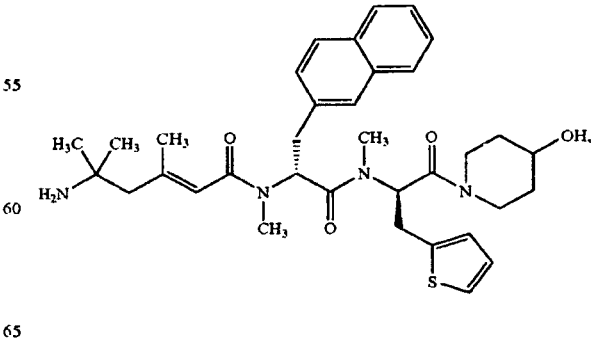

85

(2E)-5-Amino-5-methylhex-2-enoic acid N-((1R)-2-(biphenyl-4-yl)-1-{N-[(2R)-2-(4-hydroxypiperidin-1-yl)-2-oxo-1-((2-thienyl)methyl)ethyl]-N-methylcarbamoyl}ethyl)-N-methylamide

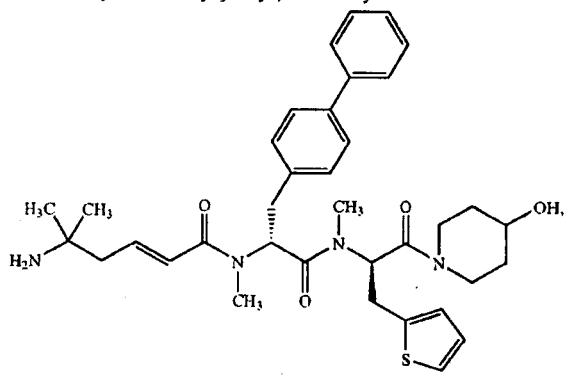

(2E)-5-Amino-3,5-dimethylhex-2-enoic acid N-((1R)-2-(biphenyl-4-yl)-1-{N-[(1R)-2-(4-hydroxypiperidin-1-yl)-2-oxo-1-((2-thienyl)methyl)ethyl]-N-methylcarbamoyl}ethyl)-N-methylamide

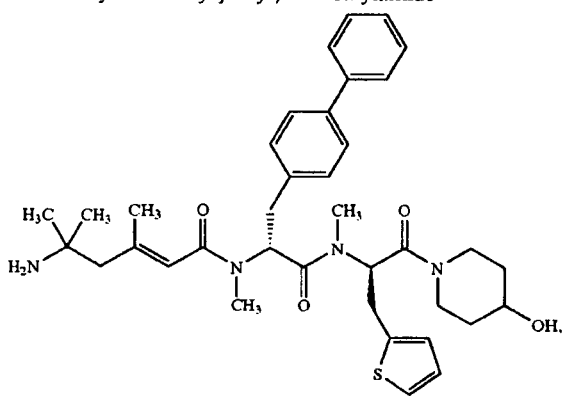

(2E)-5-Methyl-5-methylamino)hex-2-enoic acid N-((1R)-1-{N-[(1R)-1-benzyl-2-(4-hydroxypiperidin-1-yl)-2-oxoethyl]-N-methylcarbamoyl}-2-(biphenyl-4-yl)ethyl)-N-methylamide

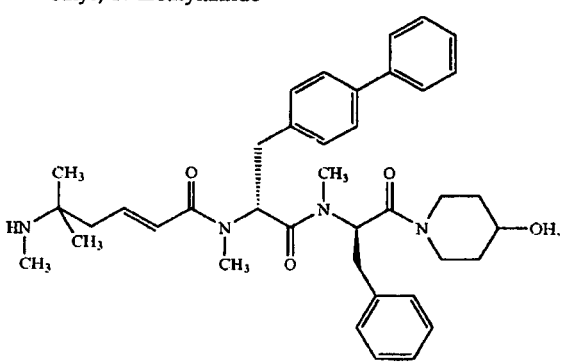

86

(2E)-4-(1-Aminocyclobutyl)but-2-enoic acid ((1R)-1-{N-[(1R)-1-benzyl-2-(4-hydroxypiperidin-1-yl)-2-oxoethyl]-N-methylcarbamoyl}-2-(biphenyl-4-yl)ethyl)amide, or

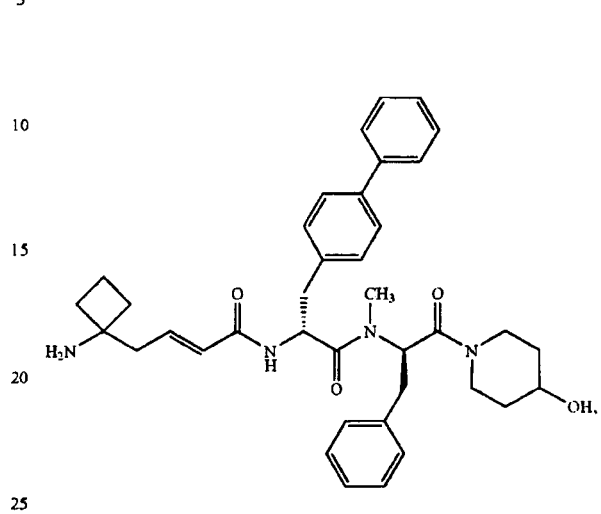

and pharmaceutically acceptable salts thereof.

13. A method of treating growth retardation in connection with asthma, the method comprising administering to a subject in need thereof an effective amount of a compound of claim 1.

14. The method of claim 13, wherein the compound is a growth hormone secretagogue.

15. A composition comprising, as an active ingredient, a compound of claim 1 together with a pharmaceutically acceptable carrier or diluent.

16. A method of stimulating the release of growth hormone from the pituitary of a mammal, the method comprising administering to the mammal an effective amount of a compound of claim 1 or a composition of claim 15.

17. A method of treating growth retardation in connection with juvenile rheumatic arthritis or systic fibrosis, the method comprising administering to a subject in need thereof an effective amount of a compound of claim 1.

* * * * *